US007247302B1

(12) United States Patent
Rosok et al.

(10) Patent No.: US 7,247,302 B1
(45) Date of Patent: Jul. 24, 2007

(54) METHOD FOR INHIBITING IMMUNOGLOBULIN-INDUCED TOXICITY RESULTING FROM THE USE OF IMMUNOGLOBULINS IN THERAPY AND IN VIVO DIAGNOSIS

(75) Inventors: Mae Joanne Rosok, Seattle, WA (US); Dale E. Yelton, Seattle, WA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 08/905,293

(22) Filed: Aug. 1, 1997

Related U.S. Application Data

(60) Provisional application No. 60/023,033, filed on Aug. 2, 1996.

(51) Int. Cl.
*A61K 39/40* (2006.01)
*A61K 39/395* (2006.01)
*A61K 49/00* (2006.01)

(52) U.S. Cl. .............................. 424/133.1; 424/130.1; 424/174.1; 424/141.1; 424/142.1; 424/178.1; 424/9.2

(58) Field of Classification Search .............. 426/174.1, 426/130.1, 133.1, 9.1, 9.2, 142.1, 178.1; 514/8
See application file for complete search history.

(56) References Cited

U.S. PATENT DOCUMENTS

| 5,338,669 | A | * | 8/1994 | Gillies ........................ 435/69.1 |
| 5,648,260 | A | * | 7/1997 | Winter et al. ............. 435/252.3 |
| 5,714,350 | A | * | 2/1998 | Co et al. .................... 435/69.6 |
| 5,728,821 | A | * | 3/1998 | Yelton et al. ............. 536/23.53 |
| 5,792,456 | A | * | 8/1998 | Yelton et al. ............. 424/133.1 |
| 5,872,222 | A | * | 2/1999 | Chang ...................... 530/391.1 |
| 6,020,145 | A | * | 2/2000 | Hellstrom et al. .......... 435/7.23 |
| 6,180,377 | B1 | * | 1/2001 | Morgan et al. ........... 435/172.3 |
| 2006/0134709 | A1 | * | 6/2006 | Stavenhagen et al. ..... 435/7.23 |

FOREIGN PATENT DOCUMENTS

| EP | 0 699 756 A1 | | 3/1996 |
| EP | 0699756 | * | 3/1996 |
| JP | 03128330 A | * | 5/1991 |
| WO | WO 91/00295 | * | 1/1991 |
| WO | WO 93/02702 | * | 2/1993 |
| WO | WO 94/29351 | | 12/1994 |
| WO | WO 94/29451 | * | 12/1994 |

OTHER PUBLICATIONS

Eghtedarzadeh-Kondri et al. BioTechniques 23: 830-834, 1997.*
Comereski et al. Toxicol. Pathol. 22: 473-488, 1994.*
Muroi et al. Blood 79: 713-719, abstract, 1992.*
Goldenberg DM. Ca 44: 43(22), 1994.*
Dorai et al. Hybridoma 10: 211-217, abstract, 1991.*
Lo et al. Human Antibodies Hybridoma 3: 123-138, abstract, 1991.*
Chiorini et al. Int. J. Cancer 53: 97-103, abstract, 1993.*
Calvo et al. Cancer Biother. 8: 95-109, abstract, 1993.*
Chiorini et al. Cancer Res. 55: 5957s-5967s, abstract, 1995.*
Robinson et al. Human Antibodies Hybridoma 2: 84-93, abstract, 1991.*
Siegall et al. Bioconjugate Chem. 3: 302-307, 1992.*
Slavin-Chiorini et al. Cancer Res. 55: 5957s-5967s, Dec. 1, 1995.*
Carlin et al. J. Nucl. Med. 44: 1827-1838, 2003 (abstract)*
Cook et al. Cancer Biother. Radiopharm. 11: 415-422, 1996 (abstract).*
D. Yelton, et al., "Mutant Monoclonal Antibodies With Alterations in Biological Functions," *J. Exp. Medicine*, vol. 56, pp. 1131-1148, Oct. 1982 (Exhibit 3).
Mueller, et al., "Serum Half-Life and Tumor Localization of a Chimeric Antibody Delected of the $C_H2$ Domain and Directed Against the Disialoganglioside GD2," *P.N.A.S.*, vol. 87, pp. 5702-5705, Aug. 1990 (Exhibit 4).
H. Garrigues, et al., Detection of a Human Melanoma-Associated Antigen, p97, in Histological Sections of Primary Human Melanomas, *Int. J. Cancer*, vol. 29, pp. 511-515, 1982 (Exhibit 5).
Alexander R. Duncan, et al., "The Binding Site for Clq on IgG" *Nature*, vol. 332, pp. 738-740, Apr. 1988 (Exhibit 6).
Mi-Hua Tao, et al., "Structural Features of Human Immunoglobulin G That Determine Isotype-Specific Differences in Complement Activation" *J. Exp. Med.*, vol. 178, No. 2, pp. 661-667, Aug. 1993 (Exhibit 7).
Yuanyuan. Xu, et al., "Residue at Position 331 in the IgG1 and IgG4 Domains Contributes to Their Differential Ability to Bind and Activate Complement" *J. Biol. Chem.*, vol. 269, No. 5, pp. 3469-3474, Feb. 1994 (Exhibit 8).
A. Morgan, et al., "The N-Terminal End of the $C_H2$ Domain of Chimeric Human IgG1 Anti-HLA-DR is Necessary for Clq, FcγRI and FcγRIII Binding" *Immunology*, vol. 86, pp. 319-324, 1995 (Exhibit 9).
Mae Joanne Rosok, et al. "A Combinatorial Library Strategy for the Rapid Humanization of Anticarcinoma BR96 Fab," *J. Biol. Chem.*, vol. 271, No. 37, pp. 22611-22618, Sep. 1996 (Exhibit 10).
Mi-Hua Tao, et al., "the Differential Ability of Human IgG1 and IgG4 to Activate Complement is Determined by the COOH-Terminal Sequence of the $C_H2$ Domain," *J. Exp. Med.*, vol. 173, pp. 1025-1028, Apr. 1991 (Exhibit 11).
I. Hellström, et al., "Strong Antitumor Activities of IgG3 Antibodies to a Human Melanoma-Associated Ganglioside," *P.N.A.S.*, vol. 82, pp. 1499-1502, Mar. 1985 (Exhibit 12).
Stephen D. Gillies, et al., "Antigen Binding And Biological Activites of Engineered Mutant Chimeric Antibodies With Human Tumor Specificities," *Hum. Antibod. Hybridomas*, vol. 1, No. 1, pp. 47-54, 1990.

(Continued)

*Primary Examiner*—S. Devi

(57) ABSTRACT

The present invention provides a method for inhibiting immunoglobulin-induced toxicity resulting from immunotherapy in a subject comprising administering an immunoglobulin or Ig fusion protein molecule to the subject, the immunoglobulin molecule having a variable region and a constant region, the immunoglobulin molecule being modified prior to administration by inactivation of at least a portion of the constant region.

22 Claims, 53 Drawing Sheets

OTHER PUBLICATIONS

George J. Schreiber, et al., "An Unmodified Anticarninoma Antibody, BR96, Localizes to And Inhibits The Outgrowth of Human Tumors in Nude Mice," *Cancer Research*, vol. 52, pp. 3262-3266, Jun. 15, 1992.

L. Tan et al., Influence Of The Hinge Region On Complement Activation, Clg Binding, And Segmental Flexibility In Chimeric Human Immunoglobulins, *Proceedings of the National Academy of Sciences Of The USA*, 1990, vol. 8, No. 1, pp. 162-166.

J. Lund et al., Human FcγRI and FcγRII Interact With Distinct But Overlapping Sites On Human IgG, *The Journal Of Immunology*, 1991, vol. 147, No. 8, pp. 2657-2662.

T. Michaelson et al., One Disulfide Bond In Front Of The Second Heavy Chain Constant Region Is Necessary And Sufficient For Effector Functions Of Humans IgG3 Without A Genetic Hinge, *Proceedings Of The National Academy Of Sciences Of The USA*, 1994, vol. 91, No. 20, pp. 9243-9247.

Weiner et al. (1994), Journal of Immunology, "The Role of T Cell Activation in Anti-CD3 x Antitumor Bispecific Antibody Therapy" 152:2385-2392.

Canfield, et al., "The Binding Affinity of Human IgG for its High Affinity Fc Receptor Is Determined by Multiple Amino Acids in the $C_H2$ Domain and Is Modulated by the Hinge Region", J. Exp. Med., vol. 173, pp. 1483-1491 (1991).

* cited by examiner

A.-HINGE + CH2 + CH3 DOMAINS WERE REMOVED FROM BR96 IgG1 CONSTRUCT BY E.CO.47-III RESTRICTION DIGESTION.

B.-HINGE+CH3 DOMAINS AMPLIFIED BY PCR FROM L6 IgG1 CONSTRUCT LACKING THE CH2 DOMAIN.

C-HINGE+CH3 PCR FRAGMENT CLONED BY HOMOLOGOUS RECOMBINATION INTO E.CO.47-III SITE OF BR96 IgG1 MOLECULE.

1.- INTRODUCTION OF MUTATIONS BY SITE DIRECTED MUTAGENESIS ON DOUBLE-STRANDED PLASMID DNA.

FIG. 10A

A.- MUTATIONS INTRODUCED INTO SYNTHETIC OLIGONUCLEOTIDES USED FOR THE PCR AMPLIFICATION OF CH2 DOMAIN

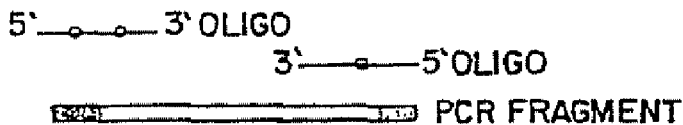

FIG. 10B

B.- PLASMID DNA LINEARIZED INSIDE CH2 DOMAIN AND CO-TRANSFORMED WITH PCR FRAGMENT INTO COMPETENT DH5α

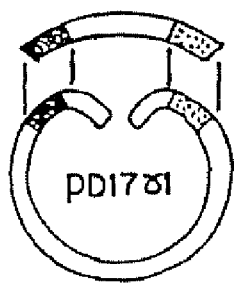

FIG. 10C

C.- CLONING MEDIATED BY HOMOLOGOUS RECOMBINATION YIELDS TRANSFORMANTS HARBOURING RECOMBINANT PLASMIDS.

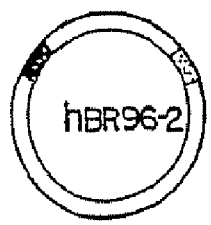

FIG. 14A
Primary Sequence = SEQ ID NO:10
Complementary Sequence = SEQ ID NO:28 pD17-cJ-dCH2.H1

```
         10         20         30         40         50         60         70         80         90
GACGGATCGG GAGATCTGCT AGGTGACCTG AGGCGCGCCG GCTTCGAATA GCCAGAGTAA CCTTTTTTT TAATTTATT TTATTTATT
CTGCCTAGCC CTCTAGACGA TCCACTGGAC TCCGCGCGGC CGAAGCTTAT CGGTCTCATT GGAAAAAAAA ATTAAAATAA AATAAAATAA 100        110        120        130        140        150        160        170        180
TTTGAGATGG AGTTTGGCGC CGATCTCCCG ATCCCCTATG GTCGACTCTC AGTACAATCT GCTCTGATGC CGCATAGTTA AGCCAGTATC
AAACTCTACC TCAAACCGCG GCTAGAGGGC TAGGGGATAC CAGCTGAGAG TCATGTTAGA CGAGACTACG GCGTATCAAT TCGGTCATAG 190        200        210        220        230        240        250        260        270
TGCTCCCTGC TTGTGTGTTG GAGGTCGCTG AGTAGTGCGC GAGCAAAATT TAAGCTACAA CAAGGCAAGG CTTGACCGAC AATTGCATGA
ACGAGGGACG AACACACAAC CTCCAGCGAC TCATCACGCG CTCGTTTTAA ATTCGATGTT GTTCCGTTCC GAACTGGCTG TTAACGTACT 280        290        300        310        320        330        340        350        360
AGAATCTGCT TAGGGTTAGG CGTTTGCGC TGCTTCGCGA TGTACGGGCC AGATATACGC GTTGACATTG ATTATTGACT AGTTATTAAT
TCTTAGACGA ATCCCAATCC GCAAACGCG ACGAAGCGCT ACATGCCCGG TCTATATGCG CAACTGTAAC TAATAACTGA TCAATAATTA 370        380        390        400        410        420        430        440        450
AGTAATCAAT TACGGGGTCA TTAGTTCATA GCCCATATAT GGAGTTCCGC GTTACATACA TTACGGTAAA TGGCCCGCCT GGCTGACCGC
TCATTAGTTA ATGCCCCAGT AATCAAGTAT CGGGTATATA CCTCAAGGCG CAATGTATGT AATGCCATTT ACCGGGCGGA CCGACTGGCG 460        470        480        490        500        510        520        530        540
CCAACGACCC ACGTCAATTG TGACGTATGT TCCCATAGTA ACGCCAATAG GGACTTTCCA TTGACGTCAA TGGGTGGACT
GGTTGCTGGG GGCGGGTAAC TGCAGTTATT ACTGCATACA AGGGTATCAT TGCGGTTATC CCTGAAAGGT AACTGCAGTT ACCCACCTGA 550        560        570        580        590        600        610        620        630
ATTTACGGTA AACTGCCCAC TTGGCAGTAC ATCAAGTGTA TCATATGCCA AGTACGCCCC CTATTGACGT CAATGACGGT AAATGCCCG
TAAATGCCAT TTGACGGGTG AACCGTCATG TAGTTCACAT AGTATACGGT TCATGCGGGG GATAACTGCA GTTACTGCCA TTTACGGGC 640        650        660        670        680        690        700        710        720
CCTGGCATTA TGCCCAGTAC ATGACCTTAT GGGACTTTCC TACTTGGCAG TACATCTACG TATTAGTCAT CGCTATTACC ATGGTGATGC
GGACCGTAAT ACGGGTCATG TACTGGAATA CCCTGAAAGG ATGAACCGTC ATGTAGATGC ATAATCAGTA GCGATAATGG TACCACTACG 730        740        750        760        770        780        790        800        810
GGTTTTGGCA GTACATCAAT GGGCGTGGAT AGCGGTTTGA CTCACGGGGA TTTCCAAGTC TCCACCCCAT TGACGTCAAT GGAGTTTGT
CCAAAACCGT CATGTAGTTA CCCGCACCTA TCGCCAAACT GAGTGCCCCT AAAGGTTCAG AGGTGGGGTA ACTGCAGTTA CCCTCAAACA 820        830        840        850        860        870        880        890        900
TTTGGCACCA AAATCAACGG GACTTTCCAA AATGTCGTAA CAACTCCGCC CCATTGACGC AAATGGGCGG TAGGCGTGTA CGGTGGGAGG
AAACCGTGGT TTTAGTTGCC CTGAAAGGTT TTACAGCATT GTTGAGGCGG GGTAACTGCG TTTACCCGCC ATCCGCACAT GCCACCCTCC
```

FIG. 14B
Primary Sequence = SEQ ID NO:10
Complementary Sequence = SEQ ID NO:28 pD17-cJ-dCH2.H1

```
       910        920        930        940        950        960        970        980        990
TCTATATAAG CAGAGCTCTC TGGCTAACTA GAGAACCCAC TGCTTACTGG CTTATCGAAA TTAATCGAC TCACTATAGG GAGACCCAAG
AGATATATTC GTCTCGAGAG ACCGATTGAT CTCTTGGGTG ACGAATGACC GAATAGCTTT AATTATGCTG AGTGATATCC CTCTGGGTTC 1000       1010       1020       1030       1040       1050       1060       1070       1080
CTTGGTACCA ATTTAAATTG ATATCTCCTT AGGTCTCGAG TCTCTAGATA ACCGGTCAAT CGATTGGAAT TCTTGCGGCC GCTGCTAGC
GAACCATGGT TAAATTTAAC TATAGAGGAA TCCAGAGCTC AGAGATCTAT TGGCCAGTTA GCTAACCTTA AGAACGCCGG CGAACGATCG 1090       1100       1110       1120       1130       1140       1150       1160       1170
CACCATGGAG TTGTGGTTAA GCTTGGTCCT TCCTTGTCCT TGTTTTAAAA GGTGTCCAGT GTGAAGTGAA TCTGGTGGAG TCTGGGGGAG
GTGGTACCTC AACACCAATT CGAACCAGGA AGGAACAGGA ACAAAATTTT CCACAGGTCA CACTTCACTT AGACCACCTC AGACCCCCTC 1180       1190       1200       1210       1220       1230       1240       1250       1260
GCTTAGTGCA GCCTGGAGGG TCCCTGAAAG TCTCCTGTGT AACCCTCTGA TTCACTTTCA GTGACTATTA CATGTATTGG GTTCGCCAGA
CGAATCACGT CGGACCTCCC AGGGACTTTC AGAGGACACA TTGGAGACCT AAGTGAAAGT CACTGATAAT GTACATAACC CAAGCGGTCT 1270       1280       1290       1300       1310       1320       1330       1340       1350
CTCCAGAGAA GAGGCTGGAG TGGGTCGCAT ACATTAGTCA AGTGGTGAT ATAACCGACT ATCCAGACAC TGTAAAGGGT CGATTCACCA
GAGGTCTCTT CTCCGACCTC ACCCAGCGTA TGTAATCAGT TCCACCACTA TATTGGCTGA TAGGTCTGTG ACATTTCCCA GCTAAGTGGT 1360       1370       1380       1390       1400       1410       1420       1430       1440
TCTCCAGAGA CAATGCCAAG AACACCCTGT ACCTGCAAAT GAGCCGTCTG AAGTCTGAGG ACACAGCCAT GTATTACTGT GCAAGAGGCC
AGAGTCTCTT GTTACGGTTC TTGTGGGACA TGGACGTTTA CTCGGCAGAC TTCAGACTCC TGTGTCGGTA CATAATGACA CGTTCTCCGG 1450       1460       1470       1480       1490       1500       1510       1520       1530
TGGACGACGG GGCCTGGTTT GCTTACTGGG GCCAAGGGAC TCTGGTCACG GTCTCTGTAG CAGTGTGGTT GGGCCCATCG GTCTTCCCCC
ACCTGCTGCC CCGGACCAAA CGAATGACCC CGGTTCCCTG AGACCAGTGC CAGAGACATC GTCACACCAA CCCGGGTAGC CAGAAGGGGG 1540       1550       1560       1570       1580       1590       1600       1610       1620
TGGCACCCTC CTCCAAGAGC ACCTCTGGGG GCACAGCGGC CCTGGGCTGC CTGGTCAAGG ACTACTTCCC CGAACCGGTG ACGGTGTCGT
ACCGTGGGAG GAGGTTCTCG TGGAGACCCC CGTGTCGCCG GGACCCGACG GACCAGTTCC TGATGAAGGG GCTTGGCCAC TGCCACAGCA 1630       1640       1650       1660       1670       1680       1690       1700       1710
GGAACTCAGG CGCCCTGACC AGCGGCGTGC ACACCTTCCC GGCTGTCCTA CAGTCCTCAG GACTCTACTC CCTCAGCAGC GTGGTCACCG
CCTTGAGTCC GCGGGACTGG TCGCCGCACG TGTGGAAGGG CCGACAGGAT GTCAGGAGTC CTGAGATGAG GGAGTCGTCG CACCAGTGGC 1720       1730       1740       1750       1760       1770       1780       1790       1800
TGCCCTCCAG CAGCTTGGGC ACCCAGACCT ACATCTGCAA CGTGAATCAC AAGCCCAGCA ACACCAAGGT GGACAAGAAA GTTGGTGAGA
ACGGGAGGTC GTCGAACCCG TGGGTCTGGA TGTAGACGTT GCACTTAGTG TTCGGGTCGT TGTGGTTCCA CCTGTTCTTT CAACCACTCT
```

FIG. 14C
Primary Sequence = SEQ ID NO:10
Complementary Sequence = SEQ ID NO:28 pD17-cJ-dCH2.H1

```
         1810       1820       1830       1840       1850       1860       1870       1880       1890
GGCAGCACA  GGGAGGAGG  GTGTCTGCTG  GAAGCCAGGC  TCAGCGCTCC  TGCCTGGACG  CATCCCGGCT  ATGCAGCCCC  AGTCCAGGGC
CCGGTCGTGT  CCCTCCTCC  CACAGACGAC  CTTCGGTCCG  AGTCGCGAGG  ACGGACCTGC  GTAGGGCCGA  TACGTCGGGG  TCAGGTCCCG 1900       1910       1920       1930       1940       1950       1960       1970       1980
AGCAAGGCAG  GCCCGTCTG  CCTCTTCACC  CGGAGGCCTC  TGCCCGCCCC  ACTCATGCTC  AGGGAGAGGG  TCTTCTGGCT  TTTTCCCCAG
TCGTTCCGTC  CGGGGCAGAC  GGAGAAGTGG  GCCTCCGGAG  ACGGGCGGGG  TGAGTACGAG  TCCCTCTCCC  AGAAGACCGA  AAAAGGGGTC 1990       2000       2010       2020       2030       2040       2050       2060       2070
GCTCTGGGCA  GGCACAGGCT  AGGTGCCCCT  AACCCAGGCC  CTGCACACAA  AGGGGCAGGT  GCTGGGCTCA  GACCTGCCAA  GAGCCATATC
CGAGACCCGT  CCGTGTCCGA  TCCACGGGGA  TTGGGTCCGG  GACGTGTGTT  TCCCCGTCCA  CGACCCGAGT  CTGGACGGTT  CTCGGTATAG 2080       2090       2100       2110       2120       2130       2140       2150       2160
CGGGAGGACC  CTGCCCCTGA  CCTAAGCCCA  CCCCAAAGGC  CAAACTCTCC  ACTCCCTCAG  CTCGGACACC  TTTCTCTCTC  CCAGATTCCA
GCCCTCCTGG  GACGGGGACT  GGATTCGGGT  GGGGTTTCCG  GTTTGAGAGG  TGAGGGAGTC  GAGCCTGTGG  AAGAGAGGAG  GGTCTAAGGT 2170       2180       2190       2200       2210       2220       2230       2240       2250
GTAACTCCCA  ATCTTCTCTC  TGCAGAGCCC  AAATCTTGTG  ACAAAACTCA  CACATGCCCA  CCGTGCCCAG  GTAAGCCAGC  CCAGGCCTCG
CATTGAGGGT  TAGAAGAGAG  ACGTCTCGGG  TTTAGAACAC  TGTTTTGAGT  GTGTACGGGT  GGCACGGGTC  CATTCGGTCG  GGTCCGGAGC 2260       2270       2280       2290       2300       2310       2320       2330       2340
CCCTCCAGCT  CAAGGCGGGA  CAGGTGCCCT  AGAGTAGCCT  GCATCCAGGG  ACACCACCTG  CCGTGTACCAA  TGGGTACCACG  GCCACATGGA
GGGAGGTCGA  GTTCCGCCCT  GTCCACGGGA  TCTCATCGGA  CGTAGGTCCC  TGTGTGGTGC  ACCCATGGTT  ACCCATGTGTC  CGGTGTACCT 2350       2360       2370       2380       2390       2400       2410       2420       2430
CAGAGGCCGG  CTCGGGCCAC  CCTCTGCCCT  GAGAGTGACC  GCTGTACCAA  CCTCTGTCCC  TACAGGGCAG  CCCGAGAAC  CACAGGTGTA
GTCTCCGGCC  GAGCCCGGGTG  GGAGACGGGA  CTCTCACTGG  CGACATGGTT  GGAGACAGGG  ATGTCCCGTC  GGGGCTCTTG  GTGTCCACAT 2440       2450       2460       2470       2480       2490       2500       2510       2520
CACCCTGCCC  CCATCCGGG  ATGAGCTGAC  CAAGAACCAG  GTCAGCCTGA  CCTGCCTGGT  CAAAGGCTTC  TATCCCAGCG  ACATCGCCGT
GTGGGACGGG  GGTAGGGCCC  TACTCGACTG  GTTCTTGGTC  CAGTCGGACT  GGACGGACCA  GTTTCCGAAG  ATAGGGTCGC  TGTAGCGGCA 2530       2540       2550       2560       2570       2580       2590       2600       2610
GGAGTGGGAG  AGCAATGGGC  AGCCGGAGAA  CAACTACAAG  ACCACGCCTC  CGTGCTGGA  CTCCGACGGC  TCCTTCTTCC  TCTACAGCAA
CCTCACCCTC  TCGTTACCCG  TCGGCCTCTT  GTTGATGTTC  TGGTGCGGAG  GGCACGACCT  GAGGCTGCCG  AGGAAGAAGG  AGATGTCGTT 2620       2630       2640       2650       2660       2670       2680       2690       2700
GCTCACCGTG  GACAAGAGCA  GGTGGCAGCA  GGGGAACGTC  TTCTCATGCT  CCGTGATGCA  TGAGGCTCTG  CACAACCACT  ACACGCAGAA
CGAGTGGCAC  CTGTTCTCGT  CCACCGTCGT  CCCCTTGCAG  AAGAGTACGA  GGCACTACGT  ACTCCGAGAC  GTGTTGGTGA  TGTGCGTCTT
```

FIG. 14D
Primary Sequence = SEQ ID NO:10
Complementary Sequence = SEQ ID NO:28 pD17-cJ-dCH2.H1

```
        2710       2720       2730       2740       2750       2760       2770       2780       2790
GAGCCTCTCC CTGTCTCCGG GTAAATGAGT GCGACGGCCG GCAAGCCCCC GCTCCCCGGG CTCTCGCGGT CGCACGAGGA TGCTTGGCAC
CTCGGAGAGG GACAGAGGCC CATTTACTCA CGCTGCCGGC CGTTCGGGCC CGAGGGGCCC GAGAGCGCCA GCGTGCTCCT ACGAACCGTG 2800       2810       2820       2830       2840       2850       2860       2870       2880
GTACCCCCTG TACATACTTC CCGGGCGCCC AGCATGGAAA TAAAGCACCC AGGCTGCCCC TGGGCCCCTG CGAGACTGTG ATGGTTCTTT
CATGGGGGAC ATGTATGAAG GGCCCGCGGG TCGTACCTTT ATTTCGTGGG TCCGACGGG  ACCCGGGGAC GCTCTGACAC TACCAAGAAA 2890       2900       2910       2920       2930       2940       2950       2960       2970
CCACGGGTCA GGCCGAGTCT GAGGCTGAGG TGGCATGAGG GAGGCAGAGC GGGTCCCACT GTCCCCACAC TGGCCCAGGC TGTGCAGGTG
GGTGCCCAGT CCGGCTCAGA CTCCGACTC  ACCGTACTCC CTCCGTCTCG CCCAGGGTGA CAGGGGTGTG ACCGGGTCCG ACACGTCCAC 2980       2990       3000       3010       3020       3030       3040       3050       3060
TGCCTGGGCC CCCTAGGGTG GGGCTCAGCC AGGGGCTGCC CTCGGCAGGG TGGGGGATTT GCCAGCGTGG CCCTCCCTCC AGCAGCACCT
ACGGACCCGG GGGATCCCAC CCCGAGTCGG TCCCCGACGG GAGCCCGTCC ACCCCCTAAA CGGTCGCACC GGGAGGGAGG TCGTCGTGGA 3070       3080       3090       3100       3110       3120       3130       3140       3150
GCCCTGGGCT GGGCCACGGG AAGCCCTAGG TTCGGGATCC AGCCCCTGCC CAGGACACA  CTCTGTAGGA GACTGTCCTG TTCTGTGAGC
CGGGACCCGA CCCGGTGCCC TTCGGGATCC AAGCCCTAGG TCGGGGACGG GTCGTGTGT  GAGACATCCT CTGACAGGAC AAGACACTCG 3160       3170       3180       3190       3200       3210       3220       3230       3240
GCCCCTGTCC TCCCGACCTC CATGCCCACT CGGGGGCATG CCTAGTCCAT GTGCGTAGGG ACAGCCCTC  CCTCACCCAT CTACCCCCAC
CGGGACAGG  AGGGCTGGAG GTACGGGTGA GCCCCCGTAC GGATCAGGTA CACGCATCCC TGTCGGGAG  GGAGTGGGTA GATGGGGGTG 3250       3260       3270       3280       3290       3300       3310       3320       3330
GGCACTAACC CCTGGCTGCC CTGCCCAGCC TCGCACCCGC ATGGGGACAC AACCGACTCC GGGGACATGC ACTCTCGGGC CCTGTGGAGG
CCGTGATTGG GGACCGACGG GACGGGTCGG AGCGTGGGCG TACCCCTGTG TTGGCTGAGG CCCCTGTACG TGAGAGCCCG GGACACCTCC 3340       3350       3360       3370       3380       3390       3400       3410       3420
GACTGGTGCA GATGCCCACA CACACACTCA GCCCAGAGCC GTTCAACAAA CCCGCACTG  AGGTTGGCCG GCCACACGGC CACCACACAC
CTGACCACGT CTACGGGTGT GTGTGTGAGT CGGGTCTCGG CAAGTTGTTT GGGCGTGAC  TCCAACCGGC CGGTGTGCCG GTGGTGTGTG 3430       3440       3450       3460       3470       3480       3490       3500       3510
ACACGTGCAC GCCTCACACA CGGAGCCTCA CCCGGGCGAA CTGCACAGCA CCCAGACCAG AGCAAGGTCC TCGCACACGT GAACACTCCT
TGTGCACGTG CGGAGTGTGT GCCTCGGAGT GGGCCCGCTT GACGTGTCGT GGGTCTGGTC TCGTTCCAGG AGCGTGTGCA CTTGTGAGGA 3520       3530       3540       3550       3560       3570       3580       3590       3600
CGGACACAGG CCCCACGCAG CCCCACGCGG CACCTCAAGG CCCACGAGCC TCTCGGCAGC TTCTCCACAT GCTGACCTGC TCAGACAAAC
GCCTGTGTCC GGGGTGCGTC GGGGTGCGCC GTGGAGTTCC GGGTGCTCGG AGAGCCGTCG AAGAGGTGTA CGACTGGACG AGTCTGTTTG
```

FIG. 14E
Primary Sequence = SEQ ID NO:10
Complementary Sequence = SEQ ID NO:28 pD17-cJ-dCH2.H1

```
       3610       3620       3630       3640       3650       3660       3670       3680       3690
CCAGCCCTCC TCTCACAAGG GTGCCCCTGC AGCCGCCACA CACACACAGG GGATCACACA CCACGTCACG TCCCTGGCCC TGGCCCACTT
GGTCGGGAGG AGAGTGTTCC CACGGGGACG TCGGCGGTGT GTGTGTGTCC CCTAGTGTGT GGTGCAGTGC AGGGACCGGG ACCGGGTGAA 3700       3710       3720       3730       3740       3750       3760       3770       3780
CCCAGTGCCG CCCTTCCCTG CAGGACGGAT CAGCCTCGAC TGTGCCTTCT AGTTGCCAGC CATCTGTTGT TTGCCCCTCC CCCGTGCCTT
GGGTCACGGC GGGAAGGGAC GTCCTGCCTA GTCGGAGCTG ACACGGAAGA TCAACGGTCG GTAGACAACA AACGGGGAGG GGGCACGGAA 3790       3800       3810       3820       3830       3840       3850       3860       3870
CCTTGACCCT GGAAGGTGCC ACTCCCACTG TCCTTTCCTA ATAAAATGAG GAAATTGCAT CGCATTGTCT GAGTAGGTGT CATTCTATTC
GGAACTGGGA CCTTCCACGG TGAGGGTGAC AGGAAAGGAT TATTTTACTC CTTTAACGTA GCGTAACAGA CTCATCCACA GTAAGATAAG 3880       3890       3900       3910       3920       3930       3940       3950       3960
TGGGGGTGG GGTGGGGCAG GACAGCAAGG GGGAGGATTG GGAAGACAAT AGCAGGCATG CTGGGGATGC GGTGGGCTCT ATGGCTTCTG
ACCCCCCACC CCACCCCGTC CTGTCGTTCC CCCTCCTAAC CCTTCGTTTA TCGTCCGTAC GACCCCTACG CCACCCGAGA TACCGAAGAC 3970       3980       3990       4000       4010       4020       4030       4040       4050
AGGGGAAAG AACCAGCTGG GGCTCTAGGG GGTATCCCCA CGGCCCTGT AGCGGCGCAT TAAGCGCGGC GGGTGTGGTG GTTACGCGCA
TCCGCCTTTC TTGGTCGACC CCGAGATCC CCATAGGGGT GCCGGGACA TCGCCGCGTA ATTCGCGCCG CCCACACCAC CAATGCGCGT 4060       4070       4080       4090       4100       4110       4120       4130       4140
GCGTGACGGC TACACTTGCC AGCGCCCTAG CGCCCGCTCC TTTCGCTTTC TTCCCTTCCT TTCTCGCCAC GTTCGCCGGG CCTCTCAAAA
CGCACTGCCG ATGTGAACGG TCGCGGGATC GCGGGCGAGG AAAGCGAAAG AAGGGAAGGA AAGAGCGGTG CAAGCGGCCC GGAGAGTTTT 4150       4160       4170       4180       4190       4200       4210       4220       4230
AAGGGAAAA AAGCATGCAT CTCAATTAGT CAGCAACCAT AGTCCCGCCC CTAACTCCGC CCATCCCGCC CCTAACTCCG CCCAGTTCCG
TTCCCTTTTT TTCGTACGTA GAGTTAATCA GTCGTTGGTA TCAGGGCGGG GATTGAGGCG GGTAGGGCGG GGATTGAGGC GGGTCAAGGC 4240       4250       4260       4270       4280       4290       4300       4310       4320
CCCATTCTCC GCCCATGGC TGACTAATTT TTTTTATTTA TGCAGAGGCC CGGCCTCTGA GAGGCCGCCT GCTATTCCAG AAGTAGTGAG
GGGTAAGAGG CGGGTACCG ACTGATTAAA AAAATAAAT ACGTCTCCGG GCCGGAGACT CTCCGGCGGA GCCGGAGACT CGATAAGGTC TTCATCACTC 4330       4340       4350       4360       4370       4380       4390       4400       4410
GAGGCTTTTT TGGAGGCCTA GGCTTTTGCA AAAAGCTTGG ACAGCTCAGG GCTGCGATTT CGGCCAAAC TTGACGGCAA TCCTAGCGTG
CTCCGAAAAA ACCTCCGGAT CCGAAAACGT TTTTCGAACC TGTCGAGTCC CGACGCTAAA CGCCGGTTTG AACTGCCGTT AGGATCGCAC 4420       4430       4440       4450       4460       4470       4480       4490       4500
AAGGCTGGTA GGATTTATC CCCGCTGCCA TCATGGTTCG CCATTGAAC TGCATCGTCG CCGTGTCCCA AAATATGGGG ATTGGCAAGA
TTCCGACCAT CCTAAATAG GGGCGACGGT AGTACCAAGC GGTAACTTG ACGTAGCAGC GGCACAGGGT TTTATACCCC TAACCGTTCT
```

FIG. 14F
Primary Sequence = SEQ ID NO:10
Complementary Sequence = SEQ ID NO:28 pD17-cJ-dCH2.H1

```
        4510       4520       4530       4540       4550       4560       4570       4580       4590
ACGGAGACCT ACCCTGGCCT CCGCTCAGGA ACGAGTTCAA GTACTTCCAA AGAATGACCA CAACCTCTTC AGTGGAAGGT AAACAGAATC
TGCCTCTGGA TGGGACCGGA GGCGAGTCCT TGCTCAAGTT CATGAAGGTT TCTTACTGGT GTTGGAGAAG TCACCTTCCA TTTGTCTTAG 4600       4610       4620       4630       4640       4650       4660       4670       4680
TGGTGATTAT GGGTAGGAAA ACCTGGTTCT CCATTCCTGA GAAGAATCGA CCTTTAAAGG ACAGAATTAA TATAGTTCTC AGTAGAGAAC
ACCACTAATA CCCATCCTTT TGGACCAAGA GGTAAGGACT CTTCTTAGCT GGAAATTTCC TGTCTTAATT ATATCAAGAG TCATCTCTTG 4690       4700       4710       4720       4730       4740       4750       4760       4770
TCAAAGAACC ACCACGAGGA GCTCATTTTC TTGCCAAAAG TTTGGATGAT GCCTTAAGAC TTATTGAACA ACCGGAATTG GCAAGTAAAG
AGTTTCTTGG TGGTGCTCCT CGAGTAAAAG AACGGTTTTC AAACCTACTA CGGAATTCTG AATAACTTGT TGGCCTTAAC CGTTCATTTC 4780       4790       4800       4810       4820       4830       4840       4850       4860
TAGACATGGT TTGGATAGTC GGAGGCAGTT CTGTTACCA AATCAACCAG GCCACCTTAG ACTCTTGTG ACAAGGATCA
ATCTGTACCA AACCTATCAG CCTCCGTCAA GACAAATGGT CCTTCGGTAC TTAGTTGGTC CGGTGGAATC TGAGAAACAC TGTTCCTAGT 4870       4880       4890       4900       4910       4920       4930       4940       4950
TGCAGGAATT TGAAAGTGAC ACGTTTTTC CAGAAATTGA TTTGGGGAAA TATAAACTTC TCCCAGAATA CCCAGGCGTC CTCTCTGAGG
ACGTCCTTAA ACTTTCACTG TGCAAAAAAG GTCTTTAACT AAACCCCTTT ATATTTGAAG AGGGTCTTAT GGGTCCGCAG GAGAGACTCC 4960       4970       4980       4990       5000       5010       5020       5030       5040
TCCAGGAGGA AAAAGGCATC AAGTATAAGT TTGAAGTCTA CGAGAAGAAA GACTAACAGG AAGATGCTTT CAAGTTCTCT GCTCCCCTCC
AGGTCCTCCT TTTTCCGTAG TTCATATTCA AACTTCAGAT GCTCTTCTTT CTGATTGTCC TTCTACGAAA GTTCAAGAGA CGAGGGGAGG 5050       5060       5070       5080       5090       5100       5110       5120       5130
TAAAGCTATG CATTTTTATA AGACCATGGG ACTTTGCTG GCTTAGATC TCTTTGTGAA GGAACCTTAC TTCTGTGGTG TGACATAATT
ATTTCGATAC GTAAAAATAT TCTGGTACCC TGAAACGAC CGAAATCTAG AGAACACTT CCTTGGAATG AAGACACCAC ACTGTATTAA 5140       5150       5160       5170       5180       5190       5200       5210       5220
GGACAAACTA CCTACAGAGA TTTAAAGCTC TAAGGTAAAT ATAAAATTTT TAAGTGTATA ATGTGTTAAA CTACTGATTC TAATTGTTTG
CCTGTTTGAT GGATGTCTCT AAATTTCGAG ATTCCATTTA TATTTTAAAA ATTCACATAT TACACAATTT GATGACTAAG ATTAACAAAC 5230       5240       5250       5260       5270       5280       5290       5300       5310
TGTATTTTAG ATTCCAACCT ATGGAACTGA TGAATGGGAG CAGTGGTGGA ATGCCTTTAA TGAGGAAAAC CTGTTTTGCT CAGAAGAAAT
ACATAAAATC TAAGGTTGGA TACCTTGACT ACTTACCCTC GTCACCACCT TACGGAAATT ACTCCTTTTG GACAAAACGA GTCTTCTTTA 5320       5330       5340       5350       5360       5370       5380       5390       5400
GCCATCTAGT GATGATGAGG CTACTGCTGA CTCTCAACAT TCTACTCCTC CAAAAAAGAA GTTTTTTCTT CAGAAGGTA GAAGACCCCA AGGACTTTCC
CGGTAGATCA CTACTACTCC GATGACGACT GAGAGTTGTA AGATGAGGAG GTTTTTTCTT CTCTTCCAT CTTCTGGGGT TCCTGAAAGG
```

FIG. 14G
Primary Sequence = SEQ ID NO:10
Complementary Sequence = SEQ ID NO:28 pD17-cJ-dCH2.H1

```
         5410       5420       5430       5440       5450       5460       5470       5480       5490
TTCAGAATTG CTAAGTTTTT TGAGTCATGC TGTGTTTAGT AATAGAACTC TTGCTTGCTT TGCTATTTAC ACCACAAAGG AAAAAGCTGC
AAGTCTTAAC GATTCAAAAA ACTCAGTACG ACACAAATCA TTATCTTGAG AACGAACGAA ACGATAAATG TGGTGTTTCC TTTTTCGACG 5500       5510       5520       5530       5540       5550       5560       5570       5580
ACTGCTATAC AAGAAAATTA TGGAAAAATA TTCTGTAACC TTTATAAGTA GGCATAACAG TTATAATCAT AACATACTGT TTTTTCTTAC
TGACGATATG TTCTTTTAAT ACCTTTTTAT AAGACATTGG AAATATTCAT CCGTATTGTC AATATTAGTA TTGTATGACA AAAAGAATG 5590       5600       5610       5620       5630       5640       5650       5660       5670
TCCACACAGG CATAGAGTGT CTGCTATTAA TAACTATGCT CAAAAATTGT GTACCTTTAG CTTTTTAATT TGTAAGGGGG TTAATAAGGA
AGGTGTGTCC GTATCTCACA GACGATAATT ATTGATACGA GTTTTTAACA CATGGAAATC GAAAAATTAA ACATTTCCCC AATTATTCCT 5680       5690       5700       5710       5720       5730       5740       5750       5760
ATATTTGATG TATAGTGCCT TGACTAGAGA TCATAATCAG CCATACCACA TTTGTAGAGG TTTTACTTGC TTTAAAAAAC CTCCCACACC
TATAACTAC ATATCACGGA ACTGATCTCT AGTATTAGTC GGTATGGTGT AAACATCTCC AAAATGAACG AAATTTTTTG GAGGGTGTGG 5770       5780       5790       5800       5810       5820       5830       5840       5850
TCCCCCTGAA CCTGAAACAT AAAATGAATG CAATTGTGT TGTTAACTTG TTTATTGCAG TTTATTAATGG TTACAATAA AGCAATAGCA
AGGGGGACTT GGACTTTGTA TTTTACTTAC GTTAACAACA ACAATTGAAC ACAATGAAGTC AAATAACGTC AATGTTATT TCGTTATCGT 5860       5870       5880       5890       5900       5910       5920       5930       5940
TCACAAATTT CACAAATAAA GCATTTTTT CACTGCATTC TAGTGTGGT TTGTCCAAAC TCATCAATGT ATCTTATCAT GTCTGGATCG
AGTGTTTAAA GTGTTTATT CGTAAAAAA GTGACGTAAG ATCAACACCA AACAGGTTTG AGTAGTACA TAGAATAGTA CAGACCTAGC 5950       5960       5970       5980       5990       6000       6010       6020       6030
GCTGGATGAT CCTCCAGCGC GGGGATCTCA TGCTGGAGTT CTTCGCCCAC CCCAACTTGT TTATTGCAGC TTATAATGGT TACAAATAA
CGACCTACTA GGAGGTCGCG CCCCTAGAGT ACGACCTCAA GAAGCGGGTG GGGTTGAACA AATAACGTCG AATATTACCA ATGTTTATTT 6040       6050       6060       6070       6080       6090       6100       6110       6120
GCAATAGCAT CACAAATTC ACAAATAAAG CATTTTTTC ACTGCATTCT AGTTGTGGTT TGTCCAAACT CATCAATGTA TCTTATCATG
CGTTATCGTA GTGTTTAAG TGTTTATTTC GTAAAAAAG TGACGTAAGA TCAACACCAA ACAGGTTTGA GTAGTTACAT AGAATAGTAC 6130       6140       6150       6160       6170       6180       6190       6200       6210
TCTGTATACC GTCGACCCTCT AGCTAGAGCT TGGCGTAATC ATGGTCATAG CTGTTTCCTG TGTGAAATTG TTATCCGCTC ACAATTCCAC
AGACATATGG CAGCTGGAGA TCGATCTCGA ACCGCATTAG TACCAGTATC GACAAGGAC GACACTTTAAC ACACTTTAAC AATAGGCGAG TGTTAAGGTG 6220       6230       6240       6250       6260       6270       6280       6290       6300
ACAACATACG AGCCGGAAGC ATAAAGTGTA AAGCCTGGGG TGCCTAATGA GTGAGCTAAC TCACATTAAT TGCGTTGCGC TCACTGCCCG
TGTTGTATGC TCGGCCTTCG TATTTCACAT TTCGGACCCC ACGGATTACT CACTCGATTG CACTCGATTG ACGCAACGCG AGTGACGGGC
```

FIG. 14H
Primary Sequence = SEQ ID NO:10
Complementary Sequence = SEQ ID NO:28 pD17-cJ-dCH2.H1

```
        6310       6320       6330       6340       6350       6360       6370       6380       6390
CTTTCCAGTC GGGAAACCTG TCGTGCCAGC TGCATTAATG AATCGGCCAA CGCGGGGGGA GAGGCGGTTT GGCTATTGGG CGCTCTTCCG
GAAAGGTCAG CCCTTTGGAC AGCACGGTCG ACGTAATTAC TTAGCCGGTT GCGCCCCCCT CTCCGCCAAA CCGATAACCC GCGAGAAGGC 6400       6410       6420       6430       6440       6450       6460       6470       6480
CTTCCTCGCT CACTGACTCG CTGCGCTCGG TCGTTCGGCT GCGGCGAGCG GTATCAGCTC ACTCAAAGGC GGTAATACGG TTATCCACAG
GAAGGAGCGA GTGACTGAGC GACGCGAGCC AGCAAGCCGA CGCCGCTCGC CATAGTCGAG TGAGTTTCCG CCATTATGCC AATAGGTGTC 6490       6500       6510       6520       6530       6540       6550       6560       6570
AATCAGGGGA TAACGCAGGA AAGAACATGT GAGCAAAAGG CCAGCAAAAG GCCAGGAACC GTAAAAAGGC CGCGTTGCTG GCGTTTTTCC
TTAGTCCCCT ATTGCGTCCT TTCTTGTACA CTCGTTTTCC GGTCGTTTTC CGGTCCTTGG CATTTTTCCG GCGCAACGAC CGCAAAAAGG 6580       6590       6600       6610       6620       6630       6640       6650       6660
ATAGGCTCCG CCCCCCTGAC GAGCATCACA AAAATCGACG CTCAAGTCAG AGGTGGCGAA ACCCGACAGG ACTATAAAGA TACCAGGCGT
TATCCGAGGC GGGGGGACTG CTCGTAGTGT TTTTAGCTGC GAGTTCAGTC TCCACCGCTT TGGGCTGTCC TGATATTTCT ATGGTCCGCA 6670       6680       6690       6700       6710       6720       6730       6740       6750
TTCCCCCTGG AAGCTCCCTC GTGCGCTCTC CTGTTCCGAC CCTGCCGCTT ACCGGATACC TGTCCGCCCTT TCTCCCTTCG GGAAGCGTGG
AAGGGGGACC TTCGAGGGAG CACGCGAGAG GACAAGGCTG GGACGGCGAA TGGCCTATGG ACAGGCGGGA AGAGGGAAGC CCTTCGCACC 6760       6770       6780       6790       6800       6810       6820       6830       6840
CGCTTTCTCA ATGCTCACGC TGTAGGTATC TCAGTTCGGT GTAGGTCGTT CGCTCCAAGC TGGGCTGTGT GCACGAACCC CCCGTTCAGC
GCGAAAGAGT TACGAGTGCG ACATCCATAG AGTCAAGCCA CATCCAGCAA CGCGAGGTTCG ACCCGACACA CGTGCTTGGG GGGCAAGTCG 6850       6860       6870       6880       6890       6900       6910       6920       6930
CCGACCGCTG CGCCTTATCC GGTAACTATC GTCTTGAGTC CAACCCGGTA AGACACGACT TATCGCCACT GGCAGCAGCC ACTGGTAACA
GGCTGGCGAC GCGGAATAGG CCATTGATAG CAGAACTCAG GTTGGGCCAT TCTGTGCTGA ATAGCGGTGA CCGTCGTCGG TGACCATTGT 6940       6950       6960       6970       6980       6990       7000       7010       7020
GGATTAGCAG AGCGAGGTAT GTAGGCGGTG CTACAGAGTT CTTGAAGTGG TGGCCTAACT ACGGCTACAC TAGAAGGACA GTATTGGTA
CCTAATCGTC TCGCTCCATA CATCCGCCAC GATGTCTCAA GAACTTCACC ACCGGATTGA TGCCGATGTG ATCTCCTGT CATAAACCAT 7030       7040       7050       7060       7070       7080       7090       7100       7110
TCTGGCTCT GCTGAAGCCA GTTACCTTCG GAAAAAGAGT TGGTAGCTCT TGATCCGGCA AACAAACCAC CGCTGGTAGC GGTGGTTTTT
AGACCGAGA CGACTTCGGT CAATGGAAGC CTTTTTCTCA ACCATCGAGA ACTAGGCCGT TTGTTTGGTG GCGACCATCG CCACCAAAAA 7120       7130       7140       7150       7160       7170       7180       7190       7200
TTGTTTGCAA GCAGCAGATT ACGGCGCAGAA AAAAGGATCT TCAAGAAGAT CCTTTGATCT TTTCTACGGG GTCTGACGCT CAGTGGAACG
AACAAACGTT CGTCGTCTAA TGCCGCGTCTT TTTTTCCTAG AGTTCTTCTA GGAAACTAGA AAAGATGCCC CAGACTGCGA GTCACCTTGC
```

FIG. 14I
Primary Sequence = SEQ ID NO:10
Complementary Sequence = SEQ ID NO:28 pD17-cJ-dCH2.H1

```
         7210       7220       7230       7240       7250       7260       7270       7280       7290
    AAAACTCACG TTAAGGGATT TTGGTCATGA GATTATCAAA AAGGATCTTC ACCTAGATCC TTTTAAATTA AAAATGAAGT TTTAAATCAA
    TTTGAGTGC AATTCCCTAA AACCAGTACT CTAATAGTTT TTCCTAGAAG TGGATCTAGG AAAATTTAAT TTTTACTTCA AAATTTAGTT
         7300       7310       7320       7330       7340       7350       7360       7370       7380
    TCTAAAGTAT ATATGAGTAA ACTTGGTCTG ACAGTTACCA ATGCTTAATC AGTGAGGCAC CTATCTCAGC GATCTGTCTA TTTCGTTCAT
    AGATTTCATA TATACTCATT TGAACCAGAC TGTCAATGGT TACGAATTAG TCACTCCGTG GATAGAGTCG CTAGACAGAT AAGCAAGTA
         7390       7400       7410       7420       7430       7440       7450       7460       7470
    CCATAGTTGC CTGACTCCCC GTCGTGTAGA TAACTACGAT ACGGGAGGGC TTACCATCTG GCCCCAGTGC TGCAATGATA CCGGAGACC
    GGTATCAACG GACTGAGGGG CAGCACATCT ATTGATGCTA TGCCCTCCCG AATGGTAGAC CGGGGTCACG ACGTTACTAT GGCGCTCTGG
         7480       7490       7500       7510       7520       7530       7540       7550       7560
    CACGCTCACC GGCTCCAGAT TTATCAGCAA TAAACCAGCC AGCCGGAAGG GCCGAGCGCA GAAGTGGTCC TGCAACTTTA TCCGCCTCCA
    GTGCGAGTGG CCGAGGTCTA AATAGTCGTT ATTTGGTCGG TCGGCCTTCC CGGCTCGCGT CTTCACCAGG ACGTTGAAAT AGGCGGAGGT
         7570       7580       7590       7600       7610       7620       7630       7640       7650
    TCCAGTCTAT TAATTGTTGC CGGGAAGCTA GAGTAAGTAG TTCGCCAGTT AATAGTTTGC GCAACGTTGT TGCCATTGCT ACAGGCATCG
    AGGTCAGATA ATTAACAACG GCCCTTCGAT CTCATTCATC AAGCGGTCAA TTATCAAACG CGTTGCAACA ACGGTAACGA TGTCCGTAGC
         7660       7670       7680       7690       7700       7710       7720       7730       7740
    TGGTGTCACG CTCGTCGTTT GGTATGGCTT CATTCAGCTC CGGTTCCCAA CGATCAAGGC GAGTACATG ATCCCCCATG TTGTGCAAAA
    ACCACAGTGC GAGCAGCAAA CCATACCGAA GTAAGTCGAG GCCAAGGGTT GCTAGTTCCG CTCAATGTAC TAGGGGTAC AACACGTTTT
         7750       7760       7770       7780       7790       7800       7810       7820       7830
    AAGCGGTTAG CTCCTTCGGT TTGTCAGAAG TTGTCAGATCG TAAGTTGGCC GCAGTGTTAT CACTCATGGT TATGGCAGCA CTGCATAATT
    TTCGCCAATC GAGGAAGCCA AACAGTCTTC AACAGTCTAGC ATTCAACCGG CGTCACAATA GTGAGTACCA ATACCGTCGT GACGTATTAA
         7840       7850       7860       7870       7880       7890       7900       7910       7920
    CTCTTACTGT CATGCCATCC GTAAGATGCT TTTCTGTGAC TGGTGAGTAC TCAACCAAGT CATTCTGAGA ATAGTGTATG CGGCGACCGA
    GAGAATGACA GTACGGTAGG CATTCTACGA AAAGACACTG ACCACTCATG AGTTGGTTCA GTAAGACTCT TATCACATAC GCCGCTGGCT
         7930       7940       7950       7960       7970       7980       7990       8000       8010
    GTTGCTCTTG CCCGGCGTCA ATACGGGATA ATACCGCGCC ACATAGCAGA ACTTTAAAAG TGCTCATCAT TGGAAAACGT TCTTCGGGGC
    CAACGAGAAC GGGCCGCAGT TATGCCCTAT TATGGCGCGG TGTATCGTCT TGAAATTTTC ACGAGTAGTA ACCTTTTGCA AGAAGCCCCG
         8020       8030       8040       8050       8060       8070       8080       8090       8100
    GAAAACTCTC AAGGATCTTA CCGCTGTTGA GATCCAGTTC GATGTAACCC ACTCGTGCAC CCAACTGATC TTCAGCATCT TTTACTTTCA
    CTTTGAGAG TTCCTAGAAT GGCGACAACT CTAGGTCAAG CTACATTGGG GTGAGCACGTG GGTTGACTAG AAGTCGTAGA AAATGAAAGT
```

FIG. 14J
Primary Sequence = SEQ ID NO:10
Complementary Sequence = SEQ ID NO:28 pD17-cJ-dCH2.H1

```
        8110       8120       8130       8140       8150       8160       8170       8180       8190
CCAGCGTTTC TGGGTGAGCA AAAACAGGAA GGCAAAATGC CGCAAAAAAG GGAATAAGGG CGACACGGAA ATGTTGAATA CTCATACTCT
GGTCGCAAAG ACCCACTCGT TTTTGTCCTT CCGTTTTACG GCGTTTTTTC CCTTATTCCC GCTGTGCCTT TACAACTTAT GAGTATGAGA 8200       8210       8220       8230       8240       8250       8260       8270       8280
TCCTTTTTCA ATATTATTGA AGCATTTATC AGGGTTATTG TCTCATGAGC GGATACATAT TTGAATGTAT TTAGAAAAAT AAACAAATAG
AGGAAAAAGT TATAATAACT TCGTAAATAG TCCCAATAAC AGAGTACTCG CCTATGTATA AACTTACATA AATCTTTTTA TTTGTTTATC 8290       8300       8310       8320       8330
GGGTTCCGCG CACATTTCCC CGAAAAGTGC CACCTGACGT C
CCCAAGGCGC GTGTAAAGGG GCTTTTTCACG GTGGACTGCA G
```

FIG. 16 hBR96-2B:L235 to A235 and G237 to A237 hBR96-2C:E318 to S318, K320 to S320, and K322 to S322 hBR96-2D:P331 to A331 hBR96-2E:L235 to A235, G237 to A237, E318 to S318, K320 to S320, and K322 to S322 hBR96-2F:L235 to A235, G237 to A237, and P331 to A331 hBR96-2G:E318 to S318, K320 to S320, K322 to S322, and P331 to A331 hBR96-2H: L235 to A235, G237 to A237, E318 to S318, K320 to S320, K322 to S322, and P331 to A331

FIG. 18A (SEQ ID NO:22)

```
   1 GGTACCAATT TAAATTGATA TCTCCTTAGG TCTCGAGTCT CTAGATAACC
  51 GGTCAATCGA TTGGAATTCT TGCGGCCGCT TGCTAGCCAC CATGGAGTTG
 101 TGGTTAAGCT TGGTCTTCCT TGTCCTTGTT TTAAAAGGTG TCCAGTGTGA
 151 AGTGCAACTG GTGGAGTCTG GGGGAGGCTT AGTGCAGCCT GGAGGGTCCC
 201 TGCGACTTTC CTGTGCTGCA TCTGGATTCC CGTTCAGTGA CTATTACATG
 251 TATTGGGTTC GCCAGGCTCC AGGCAAGGGA CTGGAGTGGG TCTCATACAT
 301 TAGTCAAGAT GGTGATATAA CCGACTATGC AGACTCCGTA AAGGGTCGAT
 351 TCACCATCTC CAGAGACAAT GCAAAGAACA GCCTGTACCT GCAAATGAAC
 401 AGCCTGAGGG ACGAGGACAC AGCCGTGTAT TACTGTGCAA GAGGCCTGGC
 451 GGACGGGGCC TGGTTTGCTT ACTGGGGCCA AGGGACTCTG GTCACGGTCT
 501 CTTCCGCTAG CACCAAGGGC CCATCGGTCT TCCCCCTGGC ACCCTCCTCC
 551 AAGAGCACCT CTGGGGGCAC AGCGGCCCTG GGCTGCCTGG TCAAGGACTA
 601 CTTCCCCGAA CCGGTGACGG TGTCGTGGAA CTCAGGCGCC CTGACCAGCG
 651 GCGTGCACAC CTTCCCGGCT GTCCTACAGT CCTCAGGACT CTACTCCCTC
 701 AGCAGCGTGG TCACCGTGCC CTCCAGCAGC TTGGGCACCC AGACCTACAT
 751 CTGCAACGTG AATCACAAGC CCAGCAACAC CAAGGTGGAC AAGAAAGTTG
 801 GTGAGAGGCC AGCACAGGGA GGGAGGGTGT CTGCTGGAAG CCAGGCTCAG
 851 CGCTCCTGCC TGGACGCATC CCGGCTATGC AGCCCCAGTC CAGGGCAGCA
 901 AGGCAGGCCC CGTCTGCCTC TTCACCCGGA GGCCTCTGCC CGCCCCACTC
 951 ATGCTCAGGG AGAGGGTCTT CTGGCTTTTT CCCCAGGCTC TGGGCAGGCA
1001 CAGGCTAGGT GCCCCTAACC CAGGCCCTGC ACACAAAGGG GCAGGTGCTG
1051 GGCTCAGACC TGCCAAGAGC CATATCCGGG AGGACCCTGC CCCTGACCTA
1101 AGCCCACCCC AAAGGCCAAA CTCTCCACTC CCTCAGCTCG GACACCTTCT
1151 CTCCTCCCAG ATTCCAGTAA CTCCCAATCT TCTCTCTGCA GAGCCCAAAT
1201 CTTGTGACAA AACTCACACA TGCCCACCGT GCCCAGGTAA GCCAGCCCAG
1251 GCCTCGCCCT CCAGCTCAAG GCGGGACAGG TGCCCTAGAG TAGCCTGCAT
1301 CCAGGGACAG GCCCCAGCCG GGTGCTGACA CGTCCACCTC CATCTCTTCC
```

FIG. 18B
(SEQ ID NO:22)

```
                        235         237
1351  TCAGCACCTG  AACTCCTGGG  GGGACCGTCA  GTCTTCCTCT  TCCCCCCAAA
1401  ACCCAAGGAC  ACCCTCATGA  TCTCCCGGAC  CCCTGAGGTC  ACATGCGTGG
1451  TGGTGGACGT  GAGCCACGAA  GACCCTGAGG  TCAAGTTCAA  CTGGTACGTG
1501  GACGGCGTGG  AGGTGCATAA  TGCCAAGACA  AAGCCGCGGG  AGGAGCAGTA
1551  CAACAGCACG  TACCGTGTGG  TCAGCGTCCT  CACCGTCCTG  CACCAGGACT
                       318         320   322
1601  GGCTGAATGG  CAAGGAGTAC  AAGTGCAAGG  TCTCCAACAA  AGCCCTCCCA
      331
1651  GCCCCCATCG  AGAAAACCAT  CTCCAAAGCC  AAAGGTGGGA  CCCGTGGGGT
1701  GCGAGGGCCA  CATGGACAGA  GGCCGGCTCG  GCCCACCCTC  TGCCCTGAGA
1751  GTGACCGCTG  TACCAACCTC  TGTCCCTACA  GGGCAGCCCC  GAGAACCACA
1801  GGTGTACACC  CTGCCCCCAT  CCCGGGATGA  GCTGACCAAG  AACCAGGTCA
1851  GCCTGACCTG  CCTGGTCAAA  GGCTTCTATC  CCAGCGACAT  CGCCGTGGAG
1901  TGGGAGAGCA  ATGGGCAGCC  GGAGAACAAC  TACAAGACCA  CGCCTCCCGT
1951  GCTGGACTCC  GACGGCTCCT  TCTTCCTCTA  CAGCAAGCTC  ACCGTGGACA
2001  AGAGCAGGTG  GCAGCAGGGG  AACGTCTTCT  CATGCTCCGT  GATGCATGAG
2051  GCTCTGCACA  ACCACTACAC  GCAGAAGAGC  CTCTCCCTGT  CTCCGGGTAA
2101  ATGAGTGCGA  CGGCCGGCAA  GCCCCGCTC   CCGGGCTCT   CGCGGTCGCA
2151  CGAGGATGCT  TGGCACGTAC  CCCCTGTACA  TACTTCCCGG  GCGCCCAGCA
2201  TGGAAATAAA  GCACCCAGCG  CTGCCCTGGG  CCCCTGCGAG  ACTGTGATGG
2251  TTCTTTCCAC  GGGTCAGGCC  GAGTCTGAGG  CCTGAGTGGC  ATGAGGGAGG
2301  CAGAGCGGGT  CCCACTGTCC  CCACACTGGC  CCAGGCTGTG  CAGGTGTGCC
2351  TGGGCCCCCT  AGGGTGGGGC  TCAGCCAGGG  GCTGCCCTCG  GCAGGGTGGG
2401  GGATTTGCCA  GCGTGGCCCT  CCCTCCAGCA  GCACCTGCCC  TGGGCTGGGC
2451  CACGGGAAGC  CCTAGGAGCC  CCTGGGGACA  GACACACAGC  CCCTGCCTCT
2501  GTAGGAGACT  GTCCTGTTCT  GTGAGCGCCC  CTGTCCTCCC  GACCTCCATG
2551  CCCACTCGGG  GGCATGCCTA  GTCCATGTGC  GTAGGGACAG  GCCCTCCCTC
2601  ACCCATCTAC  CCCCACGGCA  CTAACCCCTG  GCTGCCCTGC  CCAGCCTCGC
2651  ACCCGCATGG  GGACACAACC  GACTCCGGGG  ACATGCACTC  TCGGGCCCTG
2701  TGGAGGGACT  GGTGCAGATG  CCCACACACA  CACTCAGCCC  AGACCCGTTC
2751  AACAAACCCC  GCACTGAGGT  TGGCCGGCCA  CACGGCCACC  ACACACACAC
2801  GTGCACGCCT  CACACACGGA  GCCTCACCCG  GGCGAACTGC  ACAGCACCCA
```

FIG. 18C
(SEQ ID NO:22)

```
2851 GACCAGAGCA AGGTCCTCGC ACACGTGAAC ACTCCTCGGA CACAGGCCCC
2901 CACGAGCCCC ACGCGGCACC TCAAGGCCCA CGAGCCTCTC GGCAGCTTCT
2951 CCACATGCTG ACCTGCTCAG ACAAACCCAG CCCTCCTCTC ACAAGGGTGC
3001 CCCTGCAGCC GCCACACACA CACAGGGGAT CACACACCAC GTCACGTCCC
3051 TGGCCCTGGC CCACTTCCCA GTGCCGCCCT TCCCTGCAGG ACGGATCAGC
3101 CTCGACTGTG CCTTCTAGTT GCCAGCCATC TGTTGTTTGC CCCTCCCCCG
3151 TGCCTTCCTT GACCCTGGAA GGTGCCACTC CCACTGTCCT TTCCTAATAA
3201 AATGAGGAAA TTGCATCGCA TTGTCTGAGT AGGTGTCATT CTATTCTGGG
3251 GGGTGGGGTG GGGCAGGACA GCAAGGGGGA GGATTGGGAA GACAATAGCA
3301 GGCATGCTGG GGATGCGGTG GGCTCTATGG CTTCTGAGGC GGAAAGAACC
3351 AGCTGGGGCT CTAGGGGGTA TCCCCACGCG CCCTGTAGCG GCGCATTAAG
3401 CGCGGCGGGT GTGGTGGTTA CGCGCAGCGT GACCGCTACA CTTGCCAGCG
3451 CCCTAGCGCC CGCTCCTTTC GCTTTCTTCC CTTCCTTTCT CGCCACGTTC
3501 GCCGGGCCTC TCAAAAAGG GAAAAAAAGC ATGCATCTCA ATTAGTCAGC
3551 AACCATAGTC CCGCCCCTAA CTCCGCCCAT CCCGCCCCTA ACTCCGCCCA
3601 GTTCCGCCCA TTCTCCGCCC CATGGCTGAC TAATTTTTTT TATTTATGCA
3651 GAGGCCGAGG CCGCCTCGGC CTCTGAGCTA TTCCAGAAGT AGTGAGGAGG
3701 CTTTTTTGGA GGCCTAGGCT TTTGCAAAAA GCTTGGACAG CTCAGGGCTG
3751 CGATTTCGCG CCAAACTTGA CGGCAATCCT AGCGTGAAGG CTGGTAGGAT
3801 TTTATCCCCG CTGCCATCAT GGTTCGACCA TTGAACTGCA TCGTCGCCGT
3851 GTCCCAAAAT ATGGGGATTG GCAAGAACGG AGACCTACCC TGGCCTCCGC
3901 TCAGGAACGA GTTCAAGTAC TTCCAAAGAA TGACCACAAC CTCTTCAGTG
3951 GAAGGTAAAC AGAATCTGGT GATTATGGGT AGGAAAACCT GGTTCTCCAT
4001 TCCTGAGAAG AATCGACCTT TAAAGGACAG AATTAATATA GTTCTCAGTA
4051 GAGAACTCAA AGAACCACCA CGAGGAGCTC ATTTTCTTGC CAAAAGTTTG
4101 GATGATGCCT TAAGACTTAT TGAACAACCG GAATTGGCAA GTAAAGTAGA
4151 CATGGTTTGG ATAGTCGGAG GCAGTTCTGT TTACCAGGAA GCCATGAATC
4201 AACCAGGCCA CCTTAGACTC TTTGTGACAA GGATCATGCA GGAATTTGAA
4251 AGTGACACGT TTTTCCCAGA AATTGATTTG GGGAAATATA AACTTCTCCC
4301 AGAATACCCA GGCGTCCTCT CTGAGGTCCA GGAGGAAAAA GGCATCAAGT
```

FIG. 18D
(SEQ ID NO:22)

```
4351   ATAAGTTTGA  AGTCTACGAG  AAGAAAGACT  AACAGGAAGA  TGCTTTCAAG
4401   TTCTCTGCTC  CCCTCCTAAA  GCTATGCATT  TTTATAAGAC  CATGGGACTT
4451   TTGCTGGCTT  TAGATCTCTT  TGTGAAGGAA  CCTTACTTCT  GTGGTGTGAC
4501   ATAATTGGAC  AAACTACCTA  CAGAGATTTA  AAGCTCTAAG  GTAAATATAA
4551   AATTTTTAAG  TGTATAATGT  GTTAAACTAC  TGATTCTAAT  TGTTTGTGTA
4601   TTTTAGATTC  CAACCTATGG  AACTGATGAA  TGGGAGCAGT  GGTGGAATGC
4651   CTTTAATGAG  GAAAACCTGT  TTTGCTCAGA  AGAAATGCCA  TCTAGTGATG
4701   ATGAGGCTAC  TGCTGACTCT  CAACATTCTA  CTCCTCCAAA  AAAGAAGAGA
4751   AAGGTAGAAG  ACCCCAAGGA  CTTTCCTTCA  GAATTGCTAA  GTTTTTTGAG
4801   TCATGCTGTG  TTTAGTAATA  GAACTCTTGC  TTGCTTTGCT  ATTTACACCA
4851   CAAAGGAAAA  AGCTGCACTG  CTATACAAGA  AAATTATGGA  AAAATATTCT
4901   GTAACCTTTA  TAAGTAGGCA  TAACAGTTAT  AATCATAACA  TACTGTTTTT
4951   TCTTACTCCA  CACAGGCATA  GAGTGTCTGC  TATTAATAAC  TATGCTCAAA
5001   AATTGTGTAC  CTTTAGCTTT  TTAATTTGTA  AAGGGGTTAA  TAAGGAATAT
5051   TTGATGTATA  GTGCCTTGAC  TAGAGATCAT  AATCAGCCAT  ACCACATTTG
5101   TAGAGGTTTT  ACTTGCTTTA  AAAAACCTCC  CACACCTCCC  CCTGAACCTG
5151   AAACATAAAA  TGAATGCAAT  TGTTGTTGTT  AACTTGTTTA  TTGCAGCTTA
5201   TAATGGTTAC  AAATAAAGCA  ATAGCATCAC  AAATTTCACA  AATAAAGCAT
5251   TTTTTTCACT  GCATTCTAGT  TGTGGTTTGT  CCAAACTCAT  CAATGTATCT
5301   TATCATGTCT  GGATCGGCTG  GATGATCCTC  CAGCGCGGGG  ATCTCATGCT
5351   GGAGTTCTTC  GCCCACCCCA  ACTTGTTTAT  TGCAGCTTAT  AATGGTTACA
5401   AATAAAGCAA  TAGCATCACA  AATTTCACAA  ATAAAGCATT  TTTTTCACTG
5451   CATTCTAGTT  GTGGTTTGTC  CAAACTCATC  AATGTATCTT  ATCATGTCTG
5501   TATACCGTCG  ACCTCTAGCT  AGAGCTTGGC  GTAATCATGG  TCATAGCTGT
5551   TTCCTGTGTG  AAATTGTTAT  CCGCTCACAA  TTCCACACAA  CATACGAGCC
5601   GGAAGCATAA  AGTGTAAAGC  CTGGGGTGCC  TAATGAGTGA  GCTAACTCAC
5651   ATTAATTGCG  TTGCGCTCAC  TGCCCGCTTT  CCAGTCGGGA  AACCTGTCGT
5701   GCCAGCTGCA  TTAATGAATC  GGCCAACGCG  CGGGGAGAGG  CGGTTTGCGT
5751   ATTGGGCGCT  CTTCCGCTTC  CTCGCTCACT  GACTCGCTGC  GCTCGGTCGT
5801   TCGGCTGCGG  CGAGCGGTAT  CAGCTCACTC  AAAGGCGGTA  ATACGGTTAT
```

FIG. 18E
(SEQ ID NO:22)

```
5851   CCACAGAATC   AGGGGATAAC   GCAGGAAAGA   ACATGTGAGC   AAAAGGCCAG
5901   CAAAAGGCCA   GGAACCGTAA   AAAGGCCGCG   TTGCTGGCGT   TTTTCCATAG
5951   GCTCCGCCCC   CCTGACGAGC   ATCACAAAAA   TCGACGCTCA   AGTCAGAGGT
6001   GGCGAAACCC   GACAGGACTA   TAAAGATACC   AGGCGTTTCC   CCCTGGAAGC
6051   TCCCTCGTGC   GCTCTCCTGT   TCCGACCCTG   CCGCTTACCG   GATACCTGTC
6101   CGCCTTTCTC   CCTTCGGGAA   GCGTGGCGCT   TTCTCAATGC   TCACGCTGTA
6151   GGTATCTCAG   TTCGGTGTAG   GTCGTTCGCT   CCAAGCTGGG   CTGTGTGCAC
6201   GAACCCCCCG   TTCAGCCCGA   CCGCTGCGCC   TTATCCGGTA   ACTATCGTCT
6251   TGAGTCCAAC   CCGGTAAGAC   ACGACTTATC   GCCACTGGCA   GCAGCCACTG
6301   GTAACAGGAT   TAGCAGAGCG   AGGTATGTAG   GCGGTGCTAC   AGAGTTCTTG
6351   AAGTGGTGGC   CTAACTACGG   CTACACTAGA   AGGACAGTAT   TTGGTATCTG
6401   CGCTCTGCTG   AAGCCAGTTA   CCTTCGGAAA   AAGAGTTGGT   AGCTCTTGAT
6451   CCGGCAAACA   AACCACCGCT   GGTAGCGGTG   GTTTTTTTGT   TTGCAAGCAG
6501   CAGATTACGC   GCAGAAAAAA   AGGATCTCAA   GAAGATCCTT   TGATCTTTTC
6551   TACGGGGTCT   GACGCTCAGT   GGAACGAAAA   CTCACGTTAA   GGGATTTTGG
6601   TCATGAGATT   ATCAAAAGG    ATCTTCACCT   AGATCCTTTT   AAATTAAAAA
6651   TGAAGTTTTA   AATCAATCTA   AAGTATATAT   GAGTAAACTT   GGTCTGACAG
6701   TTACCAATGC   TTAATCAGTG   AGGCACCTAT   CTCAGCGATC   TGTCTATTTC
6751   GTTCATCCAT   AGTTGCCTGA   CTCCCCGTCG   TGTAGATAAC   TACGATACGG
6801   GAGGGCTTAC   CATCTGGCCC   CAGTGCTGCA   ATGATACCGC   GAGACCCACG
6851   CTCACCGGCT   CCAGATTTAT   CAGCAATAAA   CCAGCCAGCC   GGAAGGGCCG
6901   AGCGCAGAAG   TGGTCCTGCA   ACTTTATCCG   CCTCCATCCA   GTCTATTAAT
6951   TGTTGCCGGG   AAGCTAGAGT   AAGTAGTTCG   CCAGTTAATA   GTTTGCGCAA
7001   CGTTGTTGCC   ATTGCTACAG   GCATCGTGGT   GTCACGCTCG   TCGTTTGGTA
7051   TGGCTTCATT   CAGCTCCGGT   TCCCAACGAT   CAAGGCGAGT   TACATGATCC
7101   CCCATGTTGT   GCAAAAAAGC   GGTTAGCTCC   TTCGGTCCTC   CGATCGTTGT
7151   CAGAAGTAAG   TTGGCCGCAG   TGTTATCACT   CATGGTTATG   GCAGCACTGC
7201   ATAATTCTCT   TACTGTCATG   CCATCCGTAA   GATGCTTTTC   TGTGACTGGT
7251   GAGTACTCAA   CCAAGTCATT   CTGAGAATAG   TGTATGCGGC   GACCGAGTTG
7301   CTCTTGCCCG   GCGTCAATAC   GGGATAATAC   CGCGCCACAT   AGCAGAACTT
```

FIG. 18F (SEQ ID NO:22)

```
7351  TAAAAGTGCT  CATCATTGGA  AAACGTTCTT  CGGGGCGAAA  ACTCTCAAGG
7401  ATCTTACCGC  TGTTGAGATC  CAGTTCGATG  TAACCCACTC  GTGCACCCAA
7451  CTGATCTTCA  GCATCTTTTA  CTTTCACCAG  CGTTTCTGGG  TGAGCAAAAA
7501  CAGGAAGGCA  AAATGCCGCA  AAAAAGGGAA  TAAGGGCGAC  ACGGAAATGT
7551  TGAATACTCA  TACTCTTCCT  TTTTCAATAT  TATTGAAGCA  TTTATCAGGG
7601  TTATTGTCTC  ATGAGCGGAT  ACATATTTGA  ATGTATTTAG  AAAAATAAAC
7651  AAATAGGGGT  TCCGCGCACA  TTTCCCCGAA  AAGTGCCACC  TGACGTCGAC
7701  GGATCGGGAG  ATCTGCTAGG  TGACCTGAGG  CGCGCCGGCT  TCGAATAGCC
7751  AGAGTAACCT  TTTTTTTTAA  TTTTATTTTA  TTTTATTTTT  GAGATGGAGT
7801  TTGGCGCCGA  TCTCCCGATC  CCCTATGGTC  GACTCTCAGT  ACAATCTGCT
7851  CTGATGCCGC  ATAGTTAAGC  CAGTATCTGC  TCCCTGCTTG  TGTGTTGGAG
7901  GTCGCTGAGT  AGTGCGCGAG  CAAAATTTAA  GCTACAACAA  GGCAAGGCTT
7951  GACCGACAAT  TGCATGAAGA  ATCTGCTTAG  GGTTAGGCGT  TTTGCGCTGC
8001  TTCGCGATGT  ACGGGCCAGA  TATACGCGTT  GACATTGATT  ATTGACTAGT
8051  TATTAATAGT  AATCAATTAC  GGGGTCATTA  GTTCATAGCC  CATATATGGA
8101  GTTCCGCGTT  ACATAACTTA  CGGTAAATGG  CCCGCCTGGC  TGACCGCCCA
8151  ACGACCCCCG  CCCATTGACG  TCAATAATGA  CGTATGTTCC  CATAGTAACG
8201  CCAATAGGGA  CTTTCCATTG  ACGTCAATGG  GTGGACTATT  TACGGTAAAC
8251  TGCCCACTTG  GCAGTACATC  AAGTGTATCA  TATGCCAAGT  ACGCCCCTA
8301  TTGACGTCAA  TGACGGTAAA  TGGCCCGCCT  GGCATTATGC  CCAGTACATG
8351  ACCTTATGGG  ACTTTCCTAC  TTGGCAGTAC  ATCTACGTAT  TAGTCATCGC
8401  TATTACCATG  GTGATGCGGT  TTTGGCAGTA  CATCAATGGG  CGTGGATAGC
8451  GGTTTGACTC  ACGGGGATTT  CCAAGTCTCC  ACCCCATTGA  CGTCAATGGG
8501  AGTTTGTTTT  GGCACCAAAA  TCAACGGGAC  TTTCCAAAAT  GTCGTAACAA
8551  CTCCGCCCCA  TTGACGCAAA  TGGGCGGTAG  GCGTGTACGG  TGGGAGGTCT
8601  ATATAAGCAG  AGCTCTCTGG  CTAACTAGAG  AACCCACTGC  TTACTGGCTT
8651  ATCGAAATTA  ATACGACTCA  CTATAGGGAG  ACCCAAGCTT
```

Figure 19E:
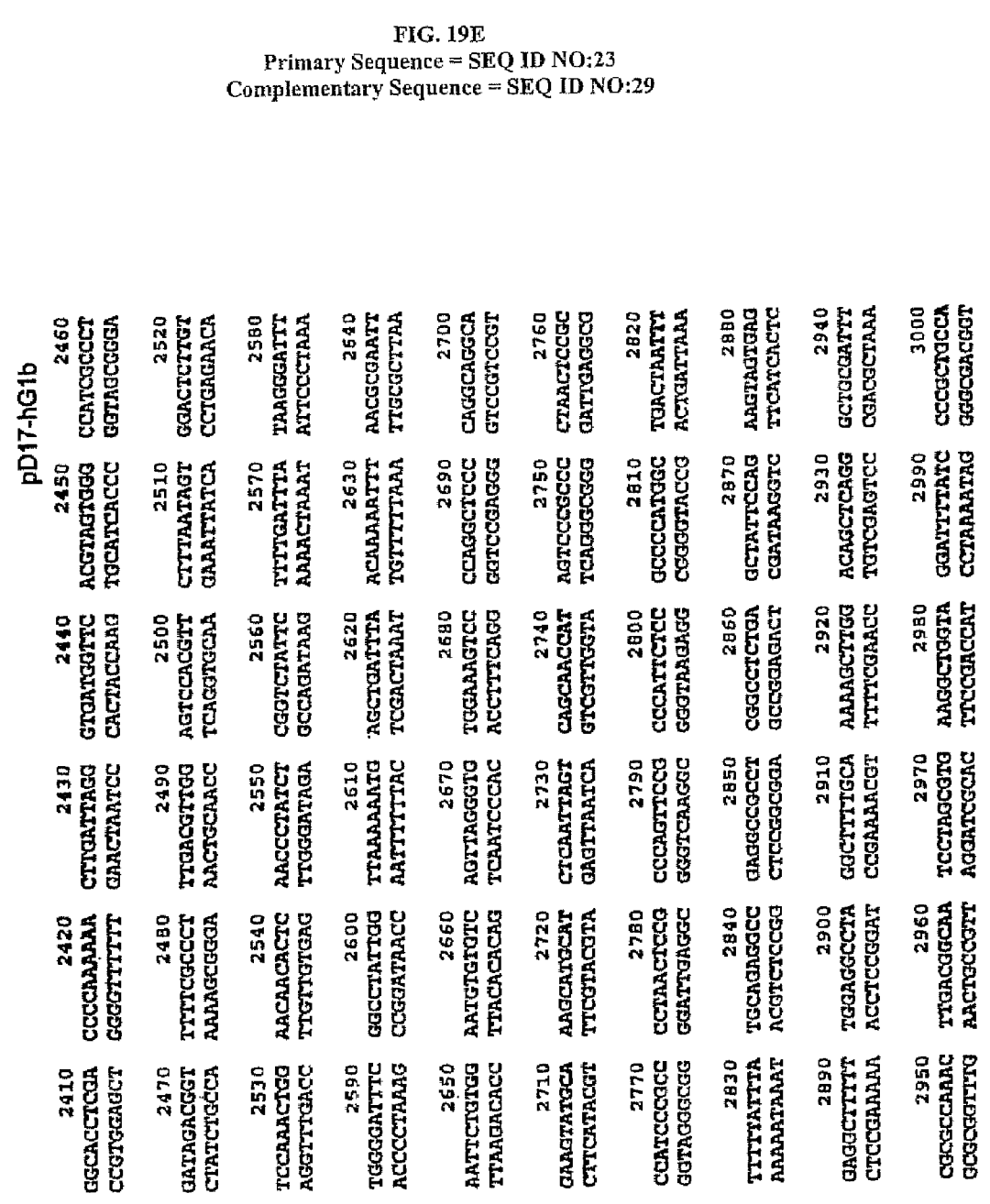
Figure 19J:
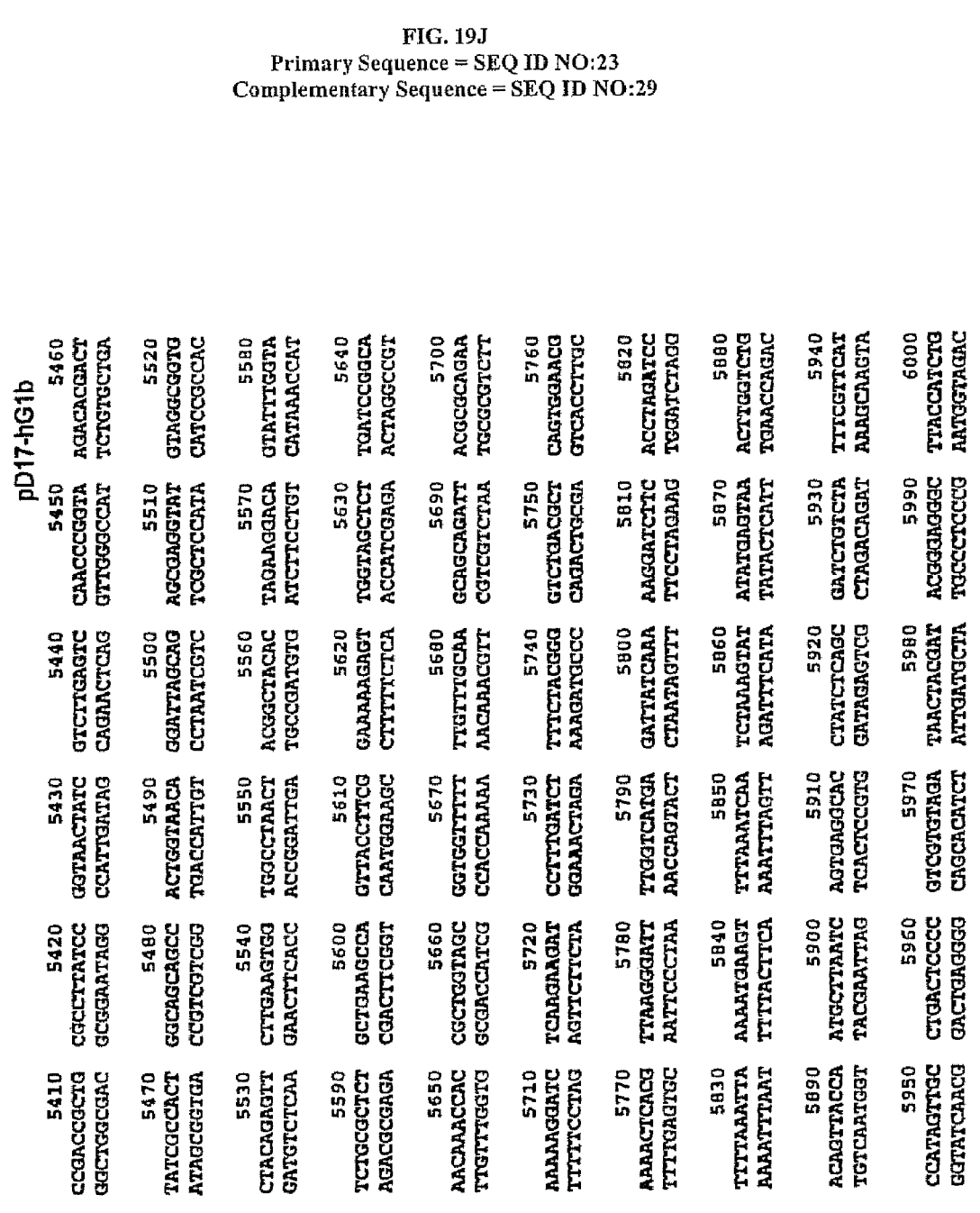

FIG. 19A
Primary Sequence = SEQ ID NO:23
Complementary Sequence = SEQ ID NO:29 pD17-hG1b

```
         10         20         30         40         50         60
   GGTACCAATT TAAATTGATA TCTCCTTAGG TCTCGAGTCT CTAGATAACC GGTCAATCGA
   CCATGGTTAA ATTTAACTAT AGAGGAATCC AGAGCTCAGA GATCTATTGG CCAGTTAGCT 70         80         90        100        110        120
   TTGGAATTCT TGCGGCCGCT TGCTAGCACC AAGGGCCCAT CGGTCTTCCC CCTGGCACCC
   AACCTTAAGA ACGCCGGCGA ACGATCGTGG TTCCCGGGTA GCCAGAAGGG GGACCGTGGG 130        140        150        160        170        180
   TCCTCCAAGA GCACCTCTGG GGGCACAGCG GCCCTGGGCT GCCTGGTCAA GGACTACTTC
   AGGAGGTTCT CGTGGAGACC CCCGTGTCGC CGGGACCCGA CGGACCAGTT CCTGATGAAG 190        200        210        220        230        240
   CCCGAACCGG TGACGGTGTC GTGGAACTCA GGCGCCCTGA CCAGCGGCGT GCACACCTTC
   GGGCTTGGCC ACTGCCACAG CACCTTGAGT CCGCGGGACT GGTCGCCGCA CGTGTGGAAG 250        260        270        280        290        300
   CCCGCTGTCC TACAGTCCTC AGGACTCTAC TCCCTCAGCA GCGTGGTCAC CGTGCCCTCC
   GGCCGACAGG ATGTCAGGAG TCCTGAGATG AGGGAGTCGT GCACCAGTG GCACGGGAGG 310        320        330        340        350        360
   AGCAGCTTGG GCACCCAGAC CTACATCTGC AACGTGAATC ACAAGCCCAG CAACACCAAG
   TCGTCGAACC CGTGGGTCTG GATGTAGACG TTGCACTTAG TGTTCGGGTC GTTGTGGTTC 370        380        390        400        410        420
   GTGGACAAGA AAGTTGGTGA GAGGCCAGCA CAGGAGGGA GGGTGTCTGC TGGAAGCCAG
   CACCTGTTCT TTCAACCACT CTCCGGTCGT GTCCTCCCT CCCACAGACG ACCTTCGGTC 430        440        450        460        470        480
   GCTCAGCGCT CCTGCCTGGA CGCATCCCGG CTATGCAGCC CCAGTCCAGG GCAGCAAGGC
   CGAGTCGCGA GGACGGACCT GCGTAGGGCC GATACGTCGG GGTCAGGTCC CGTCGTTCCG 490        500        510        520        530        540
   AGGCCCCGTC TGCCTCTTCA CCCGGAGGCC TCTGCCCGCC CCACTCATGC TCAGGAGAAG
   TCCGGGGCAG ACGGAGAAGT GGGCCTCCGG AGACGGGCGG GGTGAGTACG AGTCCTCTTC 550        560        570        580        590        600
   GGTCTTCTGG CTTTTTCCCC AGGCTCTGGG CAGGCACAGG CTAGGTGCCC CTAACCCAGG
   CCAGAAGACC GAAAAAGGGG TCCGAGACCC GTCCGTGTCC GATCCACGGG GATTGGGTCC
```

FIG. 19B
Primary Sequence = SEQ ID NO:23
Complementary Sequence = SEQ ID NO:29 pD17-hG1b

```
       610        620        630        640        650        660
CCCTGCACAC AAGGGGCAG GTGCTGGCT CAGACCTGCC AAGAGCCATA TCCGGAGGA
GGGACGTGTG TTTCCCCGTC CACGACCCGA GTCTGGACGG TTCTCGGTAT AGGCCCTCCT 670        680        690        700        710        720
CCCTGCCCT GACCTAAGCC CACCCCAAAG GCCAAACTCT CCACTCCCTC AGCTCGGACA
GGGACGGGGA CTGGATTCGG GTGGGGTTTC CGGTTTGAGA GGTGAGGGAG TCGAGCCTGT 730        740        750        760        770        780
CCTTCTCTCC TCCCAGATTC CAGTAACTCC CAATCTTCTC TCTGCAGAGC CCAAATCTTG
GGAAGAGAGG AGGGTCTAAG GTCATTGAGG GTTAGAAGAG AGACGTCTCG GGTTTAGAAC 790        800        810        820        830        840
TGACAAAACT CACACATGCC CACCGTGCCC AGGTAAGCCA GCCCAGGCCT CGCCCTCCAG
ACTGTTTTGA GTGTGTACGG GTGGCACGGG TCCATTCGGT CGGGTCCGGA GCGGGAGGTC 850        860        870        880        890        900
CTCAAGCGG GACAGGTGCC CTAGAGTAGC CTGCATCCAG GGACAGGCCC CAGCCGGGTG
GAGTTCGCCC CTGTCCACGG GATCTCATCG GACGTAGGTC CCTGTCCGGG GTCGGCCCAC 910        920   235     940        950        237
CTGACACGTC CACCTCCATC TCTTCCTCAG CACCTGAACT CCTGGGGGA CCGTCAGTCT
GACTGTGCAG GTGGAGGTAG AGAAGGAGTC GTGGACTTGA GGACCCCCT GGCAGTCAGA 970        980        990       1000       1010       1020
TCCTCTTCCC CCCAAAACCC AAGGACACCC TCATGATCTC CCGGACCCCT GAGGTCACAT
AGGAGAAGGG GGGTTTTGGG TTCCTGTGGG AGTACTAGAG GGCCTGGGGA CTCCAGTGTA 1030       1040       1050       1060       1070       1080
GCGTGGTGGT GGACGTGAGC CACGAAGACC CTGAGGTCAA GTTCAACTGG TACGTGGACG
CGCACCACCA CCTGCACTCG GTGCTTCTGG GACTCCAGTT CAAGTTGACC ATGCACCTGC 1090       1100       1110       1120       1130       1140
GCGTGGAGGT GCATAATGCC AAGACAAAGC CGCGGGAGGA GCAGTACAAC AGCACGTACC
CGCACCTCCA CGTATTACGG TTCTGTTTCG GCGCCCCTCCT CGTCATGTTG TCGTGCATGG
                                                              320
      1150       1160       1170       1180       1190    318 1200
GTGTGGTCAG CGTCCTCACC GTCCTGCAGT AGGACTGGCT GAATGGCAAG GAGTACAAGT
CACACCAGTC GCAGGAGTGG CAGGACGTCA TCCTGACCGA CTTACCGTTC CTCATGTTCA
```

FIG. 19C
Primary Sequence = SEQ ID NO:23
Complementary Sequence = SEQ ID NO:29

```
                                              pD17-hG1b
      322   1210        1220        1230 331  1240        1250        1260
            GCAAGGTCTC  CAACAAAGCC  CTCCCAGCCC CCATGGAGAA  AACCATCTCC  AAAGCCAAAG
            CGTTCCAGAG  GTTGTTTCGG  GAGGGTCGGG GGTAGTCTT   TTGGTAGAGG  TTTCGGTTTC 1270        1280        1290        1300        1310        1320
            GTGGGACCCG  TGGGGTGCGA  GGGCCACATG  GACAGAGGCC  GGCTCGGCCC  ACCCTCTGCC
            CACCCTGGGC  ACCCCACGCT  CCCGGTGTAC  CTGTCTCCGG  CCGAGCCGGG  TGGGAGACGG 1330        1340        1350        1360        1370        1380
            CTGAGAGTGA  CCGCTGTACC  AACCTCTGTC  CCTACAGGGC  AGCCCCGAGA  ACCACAGGTG
            GACTCTCACT  GGCGACATGG  TTGGAGACAG  GGATGTCCCG  TCGGGGCTCT  TGGTGTCCAC 1390        1400        1410        1420        1430        1440
            TACACCCTGC  CCCATCCCG   GGATGAGCTG  ACCAAGAACC  AGGTCAGCCT  GACCTGCCTG
            ATGTGGGACG  GGGGTAGGGC  CCTACTCGAC  TGGTTCTTGG  TCCAGTCGGA  CTGGACGGAC 1450        1460        1470        1480        1490        1500
            GTCAAAGGCT  TCTATCCCAG  CGACATCGCC  GTGGAGTGGG  AGAGCAATGG  GCAGCCGGAG
            CAGTTCCGA   AGATAGGGTC  GCTGTAGCGG  CACCTCACCC  TCTCGTTACC  CGTCGGCCTC 1510        1520        1530        1540        1550        1560
            AACAACTACA  AGACCACGCC  TCCCGTGCTG  GACTCCGACG  GCTCCTTCTT  CCTCTACAGC
            TTGTTGATGT  TCTGGTGCGG  AGGGCACGAC  CTGAGGCTGC  CGAGGAAGAA  GGAGATGTCG 1570        1580        1590        1600        1610        1620
            AAGCTCACCG  TGGACAAGAG  CAGGTGGCAG  CAGGGGAACG  TCTTCTCATG  CTCCGTGATG
            TTCGAGTGGC  ACCTGTTCTC  GTCCACCGTC  GTCCCCTTGC  AGAAGAGTAC  GAGGCACTAC 1630        1640        1650        1660        1670        1680
            CATGAGGCTC  TGCACAACCA  CTACACGCAG  AAGAGCCTCT  CCCTGTCTCC  GGGTAAATGA
            GTACTCCGAG  ACGTGTTGGT  GATGTGCGTC  TTCTCGGAGA  GGGACAGAGG  CCCATTTACT 1690        1700        1710        1720        1730        1740
            GTGCGACGGC  CGGCAAGCCC  CCGCTCCCGG  GGCTCTCGCG  GTCGCACGAG  GATGCTTGGC
            CACGCTGCCG  GCCGTTCGGG  GGCGAGGGCC  CCGAGAGCGC  CAGCGTGCTC  CTACGAACCG 1750        1760        1770        1780        1790        1800
            ACGTACCCCC  TGTACATACT  TCCCGGGCGC  CCAGCATGGA  AATAAAGCAC  CCAGGCGCTGC
            TGCATGGGGG  ACATGTATGA  AGGGCCCGCG  GGTCGTACCT  TTATTTCGTG  GGTCGCGACG
```

FIG. 19D
Primary Sequence = SEQ ID NO:23
Complementary Sequence = SEQ ID NO:29 pD17-hG1b

```
         1810       1820       1830       1840       1850       1860
    CCTGGGCCCC TCCGAGACTG TGATGGTCT TTCCACGGGT CAGGCCGAGT CTGAGGCCTG
    GGACCCGGGG ACGCTCTGAC ACTACCAAGA AAGGTGCCCA GTCCGGCTCA GACTCCGGAC 1870       1880       1890       1900       1910       1920
    AGTGGCATGA GGGAGGCAGA GCGGGTCCCA CTGTCCCCAC ACTGGCCCAG GCTGTGCAGG
    TCACCGTACT CCCTCCGTCT CGCCCAGGGT GACAGGGGTG TGACCGGGTC CGACACGTCC 1930       1940       1950       1960       1970       1980
    TGTGCCTGGG CCCCTAGGG TGGGGCTCAG CCAGGGGCTG CCCTCGGCAG GGTGGGGAT
    ACACGGACCC GGGGGATCCC ACCCCGAGTC GGTCCCCGAC GGGAGCCGTC CCACCCCTA 1990       2000       2010       2020       2030       2040
    TTGCCAGCGT GGCCCTCCCT CCAGCAGCAC CTGCCCTGGG CTGGGCCACG GGAAGCCCTA
    AACGGTCGCA CCGGGAGGGA GGTCGTCGTG GACGGGACCC GACCCGGTGC CCTTCGGGAT 2050       2060       2070       2080       2090       2100
    GGAGCCCCTG GGAGACAGACA CACAGCCCCT GCCTCTGTAG GAGACTGTCC TGTTCTGTGA
    CCTCGGGGAC CCCTGTCTGT GTGTCGGGGA CGGAGACATC CTCTGACAGG ACAAGACACT 2110       2120       2130       2140       2150       2160
    GCGCCCCTGT CCTCCCGACC TCCATGCCCA CTCGGGGGCA TGCTGGGAT GCGGTGGCT
    CGCGGGGACA GGAGGGCTGG AGGTACGGGT GAGCCCCCGT ACGACCCTA CGCCACCCGA 2170       2180       2190       2200       2210       2220
    CTATGGCTTC TGAGGCGGAA AGAACCAGCT GGGGCTCTAG GGGTATCCC CACGCGCCCT
    GATACCGAAG ACTCCGCCTT TCTTGGTCGA CCCCGAGATC CCCCATAGGG GTGCGCGGGA 2230       2240       2250       2260       2270       2280
    GTAGGGCGC ATTAAGCGCG GCGGGTGTGG TGGTTACGCG CAGCGTGACC GCTACACTG
    CATCGCCCG TAATTCGCGC CGCCCACACC ACCAATGCGC GTCGCACTGG CGATGTGAAC 2290       2300       2310       2320       2330       2340
    CCAGCGCCCT AGCGCCCGCT CCTTTCGCTT TCTTCCCTTC CTTTCTCGCC ACGGTTCGCCG
    GGTCGCGGGA TCGCGGGCGA GGAAAGCGAA AGAAGGGAAG GAAAGAGCGG TGCCAAGCGGC 2350       2360       2370       2380       2390       2400
    GCTTTCCCCG TCAAGCTCTA AATCGGGGGCA TCCCTTTAGG GTTCCGATTT AGTGCTTTAC
    CGAAAGGGGC AGTTCGAGAT TTAGCCCCGT AGGGAAATCC CAAGGCTAAA TCACGAAATG
```

FIG. 19E
Primary Sequence = SEQ ID NO:23
Complementary Sequence = SEQ ID NO:29

FIG. 19F
Primary Sequence = SEQ ID NO:23
Complementary Sequence = SEQ ID NO:29 pD17-hG1b

```
      3010        3020        3030        3040        3050        3060
TCATGGTTCG  ACCATTGAAC  TGCATCGTCG  CCGTGTCCCA  AAATATGGGG  ATTGGCAAGA
AGTACCAAGC  TGGTAACTTG  ACGTAGCAGC  GGCACAGGGT  TTTATACCCC  TAACCGTTCT 3070        3080        3090        3100        3110        3120
ACGGAGACCT  ACCCTGGCCT  CCGCTCAGGA  ACGAGTTCAA  GTACTTCCAA  AGAATGACCA
TGCCTCTGGA  TGGGACCGGA  GGCGAGTCCT  TGCTCAAGTT  CATGAAGGTT  TCTTACTGGT 3130        3140        3150        3160        3170        3180
CAACCTCTTC  AGTGGAAGGT  AAACAGAATC  TGGTGATTAT  GGGTAGGAAA  ACCTGGTTCT
GTTGGAGAAG  TCACCTTCCA  TTTGTCTTAG  ACCACTAATA  CCCATCCTTT  TGGACCAAGA 3190        3200        3210        3220        3230        3240
CCATTCCTGA  GAAGAATCGA  CCTTAAAGG   ACAGAATTAA  TATAGTTCTC  AGTAGAGAAC
GGTAAGGACT  CTTCTTAGCT  GGAAATTCC   TGTCTTAATT  ATATCAAGAG  TCATCTCTTG 3250        3260        3270        3280        3290        3300
TCAAAGAACC  ACCACGAGGA  GCTCATTTTC  TTGCCAAAAG  TTTGGATGAT  GCCTAAGGAC
AGTTTCTTGG  TGGTGCTCCT  CGAGTAAAAG  AACGGTTTTC  AAACCTACTA  CGGATTCCTG 3310        3320        3330        3340        3350        3360
TTATTGAACA  ACCGGAATTG  GCAAGTAAAG  TAGACATGGT  TTGGATAGTC  GGAGGCAGTT
AATAACTTGT  TGGCCTTAAC  CGTTCATTTC  ATCTGTACCA  AACCTATCAG  CCTCCGTCAA 3370        3380        3390        3400        3410        3420
CTGTTACCA   GGAAGCCATG  AATCAACCAG  GCCACCTTAG  ACTCCTTGTG  ACAAGGATCA
GACAAATGGT  CCTTCGGTAC  TTAGTTGGTC  CGGTGGAATC  TGAGAAACAC  TGTTCCTAGT 3430        3440        3450        3460        3470        3480
TGCAGGAATT  TGAAAGTGAC  ACGTTTTTCC  CAGAAATTGA  TTTGGGAAAA  TATAAACTTC
ACGTCCTTAA  ACTTTCACTG  TGCAAAAAGG  GTCTTTAACT  AAACCCTTTT  ATATTTGAAG 3490        3500        3510        3520        3530        3540
TCCCAGAATA  CCCAGGCGTC  CTCTCTGAGG  TCCAGGAGGA  AAAAGGCATC  AAGTATAAGT
AGGGTCTTAT  GGGTCCGCAG  GAGAGACTCC  AGGTCCTCCT  TTTTCCGTAG  TTCATATTCA 3550        3560        3570        3580        3590        3600
TTGAAGTCTA  CGAGAAGAAA  GACTAACAGG  AAGATGCTTT  CAAGTGCTTCT  GCTCCCCTCC
AACTTCAGAT  GCTCTTCTTT  CTGATTGTCC  TTCTACGAAA  GTTCACGAAA  CGAGGGGAGG
```

FIG. 19G
Primary Sequence = SEQ ID NO:23
Complementary Sequence = SEQ ID NO:29 pD17-hG1b

```
        3610        3620        3630        3640        3650        3660
TAAAGCTATG  CATTTTATA   AGACCATGGG  ACTTTGCTG   GCTTAGATC   TCTTTGTGAA
ATTCGATAC   GTAAAAATAT  TCTGGTACCC  TGAAACGAC   CGAAATCTAG  AGAAACACTT 3670        3680        3690        3700        3710        3720
GGAACCTTAC  TTCTGTGGTG  TGACTAATT   GGACAAACTA  CCTACAGAGA  TTTAAAGCTC
CCTTGGAATG  AAGACACCAC  ACTGTATTAA  CCTGTTTGAT  GGATGTCTCT  AAATTTCGAG 3730        3740        3750        3760        3770        3780
TAAGTAAAT   ATAAAATTTT  TAAGTGTATA  ATGTGTTAAA  CTACTGATTC  TAATTGTTTG
ATTCCATTTA  TATTTTAAAA  ATTCACATAT  TACACAATTT  GATGACTAAG  ATTAACAAAC 3790        3800        3810        3820        3830        3840
TGTATTTTAG  ATTCCAACCT  ATGGAACTGA  TGAATGGGAG  CAGTGGTGAA  ATGCCTTTAA
ACATAAAATC  TAAGGTTGGA  TACCTTGACT  ACTTACCCTC  GTCACCACTT  TACGGAAATT 3850        3860        3870        3880        3890        3900
TGAGGAAAAC  CTGTTTTGCT  CAGAAGAAAT  GCCATCTAGT  GATGATGAGG  CTACTGCTGA
ACTCCTTTTG  GACAAAACGA  GTCTTCTTTA  CGGTAGATCA  CTACTACTCC  GATGACGACT 3910        3920        3930        3940        3950        3960
CTCTCAACAT  TCTACTCCTC  CAAAAAAGAA  GAGAAAGGTA  GAAGACCCCA  AGGACTTTCC
GAGAGTTGTA  AGATGAGGAG  GTTTTTCTT   CTCTTTCCAT  CTTCTGGGGT  TCCTGAAAGG 3970        3980        3990        4000        4010        4020
TTCAGAATTG  CTAAGTTTTT  TGAGTCATGC  TGTGTTTAGT  AATAGAACTC  TTGCTTGCTT
AAGTCTTAAC  GATTCAAAAA  ACTCAGTACG  ACACAAATCA  TTATCTTGAG  AACGAACGAA 4030        4040        4050        4060        4070        4080
TGTCTATTAC  ACCACAAAGG  AAAAAGCTGC  ACTGCTATAC  AAGAAAATTA  TGGAAAAATA
ACGATAAATG  TGGTGTTTCC  TTTTTCGACG  TGACGATATG  TTCTTTTAAT  ACCTTTTTAT 4090        4100        4110        4120        4130        4140
TTCTGTAACC  TTTATAAGTA  GGCATAACAG  TTATAATCAT  AACATACTC   TTTTCTTAC
AAGACATTGG  AAATATTCAT  CCGTATTGTC  AATATTAGTA  TTGTATGACA  AAAAGAATG 4150        4160        4170        4180        4190        4200
TCCACACAGG  CATAGAGTGT  CTGCTATTAA  TAACTATGCT  CAAAAATTGT  GTACCTTTAG
AGGTGTGTCC  GTATCTCACA  GACGATAATT  ATTGATACGA  GTTTTTAACA  CATGGAAATC
```

FIG. 19H
Primary Sequence = SEQ ID NO:23
Complementary Sequence = SEQ ID NO:29 pD17-hG1b

| 4210 | 4220 | 4230 | 4240 | 4250 | 4260 |
|------|------|------|------|------|------|
| CTTTTAATT | TGTAAAGGGG | TTAATAAGGA | ATATTTGATG | TATAGTGCCT | TGACTAGAGA |
| GAAAATTAA | ACATTTCCCC | AATTATTCCT | TATAAACTAC | ATATCACGGA | ACTGATCTCT |

| 4270 | 4280 | 4290 | 4300 | 4310 | 4320 |
| TCATAATCAG | CCATACCACA | TTTGTAGAGG | TTTTACTTGC | TTTAAAAAAC | CTCCCACACC |
| AGTATTAGTC | GGTATGGTGT | AAACATCTCC | AAAATGAACG | AAATTTTTG | GAGGGTGTGG |

| 4330 | 4340 | 4350 | 4360 | 4370 | 4380 |
| TCCCCCTGAA | CCTGAAACAT | AAAATGAATG | CAATTGTTGT | TGTTAACTTG | TTTATTGCAG |
| AGGGGGACTT | GGACTTTGTA | TTTTACTTAC | GTTAACAACA | ACAATTGAAC | AAATAACGTC |

| 4390 | 4400 | 4410 | 4420 | 4430 | 4440 |
| CTTATAATGG | TTACAAATAA | AGCAATAGCA | TCACAAATTT | CACAAATAAA | GCATTTTTT |
| GAATATTACC | AATGTTTATT | TCGTTATCGT | AGTGTTTAAA | GTGTTTATTT | CGTAAAAAAA |

| 4450 | 4460 | 4470 | 4480 | 4490 | 4500 |
| CACTGCATTC | TAGTTGTGGT | TTGTCCAAAC | TCATCAATGT | ATCTTATCAT | GTCTGGATCG |
| GTGACGTAAG | ATCAACACCA | AACAGGTTTG | AGTAGTTACA | TAGAATAGTA | CAGACCTAGC |

| 4510 | 4520 | 4530 | 4540 | 4550 | 4560 |
| GCTGGATGAT | CCTCCAGCGC | GGGGATCTCA | TGCTGGAGTT | CTTCGCCCAC | CCCAACTTGT |
| CGACCTACTA | GGAGGTCGCG | CCCCTAGAGT | ACGACCTCAA | GAAGCGGGTG | GGGTTGAACA |

| 4570 | 4580 | 4590 | 4600 | 4610 | 4620 |
| TTATTGCAGC | TTATAATGGT | TACAAATAAA | GCAATAGCAT | CACAAATTTC | ACAAATAAAG |
| AATAACGTCG | AATATTACCA | ATGTTTATTT | CGTTATCGTA | GTGTTTAAAG | TGTTTATTTC |

| 4630 | 4640 | 4650 | 4660 | 4670 | 4680 |
| CATTTTTTC | ACTGCATTCT | AGTTGTGGTT | TGTCCAAACT | CATCAATGTA | TCTTATCATG |
| GTAAAAAAAG | TGACGTAAGA | TCAACACCAA | ACAGGTTTGA | GTAGTTACAT | AGAATAGTAC |

| 4690 | 4700 | 4710 | 4720 | 4730 | 4740 |
| TCTGTATACC | GTCGACCTCT | AGCTAGAGCT | TGGCGTAATC | ATGGTCATAG | CTGTTCCTG |
| AGACATATGG | CAGCTGGAGA | TCGATCTCGA | ACCGCATTAG | TACCAGTATC | GACAAGGAC |

| 4750 | 4760 | 4770 | 4780 | 4790 | 4800 |
| TGTGAAATTG | TTATCCGCTC | ACAATTCCAC | ACAACATACG | AGCCGGAAGC | ATAAAGTGTA |
| ACACTTTAAC | AATAGGCGAG | TGTTAAGGTG | TGTTGTATGC | TCGGCCTTCG | TATTTCACAT |

FIG. 19I
Primary Sequence = SEQ ID NO:23
Complementary Sequence = SEQ ID NO:29 pD17-hG1b

```
        4810       4820       4830       4840       4850       4860
   AAGCCTGGGG TGCCTAATGA GTGAGCTAAC TCACATTAAT TGGCGTTGCG TCACTGCCCG
   TTCGGACCCC ACGGATTACT CACTCGATTG AGTGTAATTA ACGCAACGCG AGTGACGGGC 4870       4880       4890       4900       4910       4920
   CTTTCCAGTC GGGAAACCTG TCGTGCCAGC TGCATTAATG AATCGGCCAA CGCGCGGGGA
   GAAAGGTCAG CCCTTTGGAC AGCACGGTCG ACGTAATTAC TTAGCCGGTT GCGCGCCCCT 4930       4940       4950       4960       4970       4980
   GAGGCGGTTT GCGTATTGGG CGCTCTTCCG CTTCCTCGCT CACTGACTCG CTGCGCTCGG
   CTCCGCCAAA CGCATAACCC GCGAGAAGGC GAAGGAGCGA GTGACTGAGC GACGCGAGCC 4990       5000       5010       5020       5030       5040
   TCGTTCGGCT GCGGCGAGCG GTATCAGCTC ACTCAAAGGC GGTAATACGG TTATCCACAG
   AGCAAGCCGA CGCCGCTCGC CATAGTCGAG TGAGTTTCCG CCATTATGCC AATAGGTGTC 5050       5060       5070       5080       5090       5100
   AATCAGGGGA TAACGCAGGA AAGAACATGT GAGCAAAAGG CCAGCAAAAG GCCAGGAACC
   TTAGTCCCCT ATTGCGTCCT TTCTTGTACA CTCGTTTTCC GGTCGTTTTC CGGTCCTTGG 5110       5120       5130       5140       5150       5160
   GTAAAAAGGC CGCGTTGCTG GCGTTTTTCC ATAGGCTCCG CCCCCCTGAC GAGCATCACA
   CATTTTTCCG GCGCAACGAC CGCAAAAAGG TATCCGAGGC GGGGGGACTG CTCGTAGTGT 5170       5180       5190       5200       5210       5220
   AAAATCGACG CTCAAGTCAG AGGTGGCGAA ACCCGACAGG ACTATAAAGA TACCAGGCGT
   TTTTAGCTGC GAGTTCAGTC TCCACCGCTT TGGGCTGTCC TGATATTTCT ATGGTCCGCA 5230       5240       5250       5260       5270       5280
   TTCCCCCTGG AAGCTCCCTC GTGCGCTCTC CTGTTCCGAC CCTGCCGCTT ACCGGATACC
   AAGGGGGACC TTCGAGGGAG CACGCGAGAG GACAAGGCTG GGACGGCGAA TGGCCTATGG 5290       5300       5310       5320       5330       5340
   TGTCCGCCTT TCTCCCTTCG GGAAGCGTGG CGCTTTCTCA ATGCTCACGC TGTAGGTATC
   ACAGGCGGAA AGAGGGAAGC CCTTCGCACC GCGAAAGAGT TACGAGTGCG ACATCCATAG 5350       5360       5370       5380       5390       5400
   TCAGTTCGGT GTAGGTCGTT CGCTCCAAGC TGGGCTGTGT GCACGAACCC CCCGTTCAGC
   AGTCAAGCCA CATCCAGCAA GCGAGGTTCG ACCCGACACA CGTGCTTGGG GGGCAAGTCG
```

FIG. 19J
Primary Sequence = SEQ ID NO:23
Complementary Sequence = SEQ ID NO:29

FIG. 19K
Primary Sequence = SEQ ID NO:23
Complementary Sequence = SEQ ID NO:29 pD17-hG1b

```
        6010       6020       6030       6040       6050       6060
        GCCCCAGTGC TGAATGATA  CCGGAGACC  CACGCTCACC GGCTCCAGAT TTATCAGCAA
        CGGGGTCACG ACGTTACTAT GGCGTCTGG  GTGCGAGTGG CCGAGGTCTA AATAGTCGTT 6070       6080       6090       6100       6110       6120
        TAAACCAGCC AGCCGGAAGG GCCGAGCGCA GAAGTGGTCC TGCAACTTTA TCCGCCTCCA
        ATTTGGTCGG TCGGCCTTCC CGGCTCGCGT CTTCACCAGG ACGTTGAAAT AGGCGGAGGT 6130       6140       6150       6160       6170       6180
        TCCAGTCTAT TAATGTTGC  CGGGAAGCTA GAGTAGTAG  TTCGCCAGTT AATAGTTGC
        AGGTCAGATA ATTAACAACG GCCCTTCGAT CTCATTCATC AAGCGGTCAA TTATCAAACG 6190       6200       6210       6220       6230       6240
        GCAACGTTGT TGCCATTGCT ACAGGCATCG TGTGTCACG  CTCGTCGTTT GGTATGGCTT
        CGTTGCAACA ACGGTAACGA TGTCCGTAGC ACCACAGTGC GAGCAGCAAA CCATACCGAA 6250       6260       6270       6280       6290       6300
        CATTCAGCTC CGGTTCCCAA CGATCAAGGC GAGTTACATG ATCCCCATG  TTGTGCAAAA
        GTAAGTCGAG GCCAAGGGTT GCTAGTTCCG CTCAATGTAC TAGGGGTAC  AACACGTTTT 6310       6320       6330       6340       6350       6360
        AAGCGGTTAG CTCCTTCGGT CCTCCGATCG TTGTCAGAAG TAAGTTGGCC GCAGTGTTAT
        TTCGCCAATC GAGGAAGCCA GGAGGCTAGC AACAGTCTTC ATTCAACCGG CGTCACAATA 6370       6380       6390       6400       6410       6420
        CACTCATGGT TATGGCAGCA CTGCATAATT CTCCTACTGT CATGCCATCC GTAAGATGCT
        GTGAGTACCA ATACCGTCGT GACGTATTAA GAGAATGACA GTACGGTAGG CATTCTACGA 6430       6440       6450       6460       6470       6480
        TTTCTGTGAC TGGTGAGTAC TCAACCAAGT CATTCTGAGA ATATGTATG  CGGGACCGA
        AAAGACACTG ACCACTCATG AGTTGGTTCA GTAAGACTCT TATACATAC  GCCCTGGCT 6490       6500       6510       6520       6530       6540
        GTTGCTCTG  CCCGGCGTCA ATACGGGATA ATACCGCGCC ACATAGCAGA ACTTAAAAG
        CAACGAGAAC GGGCCGCAGT TATGCCCTAT TATGGCGCGG TGTATCGTCT TGAAATTTTC 6550       6560       6570       6580       6590       6600
        TGCTCATCAT TGGAAAACGT TCTTCGGGGC GAAAACTCTC AAGGATCTTA CCGCTGTGA
        ACGAGTAGTA ACCTTTTGCA AGAAGCCCCG CTTTTGAGAG TTCCTAGAAT GGCGACAACT
```

FIG. 19L
Primary Sequence = SEQ ID NO:23
Complementary Sequence = SEQ ID NO:29 pD17-hG1b

| 6610 | 6620 | 6630 | 6640 | 6650 | 6660 |
|------|------|------|------|------|------|
| GATCCAGTTC | GATGTAACCC | ACTCGTGCAC | CCAACTGATC | TTCAGCATCT | TTTACTTTCA |
| CTAGGTCAAG | CTACATTGGG | TGAGCACGTG | GGTTGACTAG | AAGTCGTAGA | AAATGAAAGT |

| 6670 | 6680 | 6690 | 6700 | 6710 | 6720 |
|------|------|------|------|------|------|
| CCAGCGTTTC | TGGGTGAGCA | AAAACAGGAA | GGCAAAATGC | CGCAAAAAAG | GGAATAAGGG |
| GGTCGCAAAG | ACCCACTCGT | TTTTGTCCTT | CCGTTTTACG | GCGTTTTTTC | CCTTATTCCC |

| 6730 | 6740 | 6750 | 6760 | 6770 | 6780 |
|------|------|------|------|------|------|
| CGACACGGAA | ATGTTGATA | CTCATACTCT | TCCTTTTTCA | ATATTATTGA | AGCATTTATC |
| GCTGTGCCTT | TACAACTTAT | GAGTATGAGA | AGGAAAAAGT | TATAATAACT | TCGTAAATAG |

| 6790 | 6800 | 6810 | 6820 | 6830 | 6840 |
|------|------|------|------|------|------|
| AGGGTTATG | TCTCATGAGC | GGATACATAT | TTGAATGTAT | TTAGAAAAAT | AAACAAATAG |
| TCCCAATAAC | AGAGTACTCG | CCTATGTATA | AACTTACATA | AATCTTTTTA | TTTGTTTATC |

| 6850 | 6860 | 6870 | 6880 | 6890 | 6900 |
|------|------|------|------|------|------|
| GGGTTCCGCG | CACATTTCCC | CGAAAAGTGC | CACCTGACGT | CGACGGATCG | GGAGATCTGC |
| CCCAAGGCGC | GTGTAAAGGG | GCTTTTCACG | GTGGACTGCA | GCTGCCTAGC | CCTCTAGACG |

| 6910 | 6920 | 6930 | 6940 | 6950 | 6960 |
|------|------|------|------|------|------|
| TAGGTGACCT | GAGGCGCCC | GGCTTCGAAT | AGCCAGAGTA | ACCTTTTTTT | TTAATTTTAT |
| ATCCACTGGA | CTCCGCGCGG | CCGAAGCTTA | TCGGTCTCAT | TGGAAAAAAA | AATTAAAATA |

| 6970 | 6980 | 6990 | 7000 | 7010 | 7020 |
|------|------|------|------|------|------|
| TTTATTTAT | TTTTGAGATG | GAGTTTGGCG | CCGATCTCCC | GATCCCTAT | GGTCGACTCT |
| AAATAAATA | AAAACTCTAC | CTCAACCGC | GGCTAGAGGG | CTAGGGATA | CCAGCTGAGA |

| 7030 | 7040 | 7050 | 7060 | 7070 | 7080 |
|------|------|------|------|------|------|
| CAGTACAATC | TGCTCTGATG | CCGCATAGTT | AAGCCAGTAT | CTGCTCCCTG | CTGTGTGTT |
| GTCATGTTAG | ACGAGACTAC | GGCGTATCAA | TTCGGTCATA | GACGAGGGAC | GACACACAA |

| 7090 | 7100 | 7110 | 7120 | 7130 | 7140 |
|------|------|------|------|------|------|
| GGAGGTCGCT | GAGTAGTGCG | CGAGCAAAAT | TTAAGCTACA | ACAAGGCAAG | GCTTGACCGA |
| CCTCCAGCGA | CTCATCACGC | GCTCGTTTTA | AATTCGATGT | TGTTCCGTTC | CGAACTGGCT |

| 7150 | 7160 | 7170 | 7180 | 7190 | 7200 |
|------|------|------|------|------|------|
| CAATTGCATG | AAGAATCTGC | TTAGGGTTAG | GCGTTTTGCG | CTGCTTCGCG | ATGTACGGGC |
| GTTAACGTAC | TTCTTAGACG | AATCCCAATC | CGCAAAACGC | GACGAAGCGC | TACATGCCCG |

FIG. 19M
Primary Sequence = SEQ ID NO:23
Complementary Sequence = SEQ ID NO:29 pD17-hG1b

```
        7210       7220       7230       7240       7250       7260
        CAGATATACG CGTTGACATT GATTATTGAC TAGTTATTAA TAGTAATCAA TTACGGGGTC
        GTCTATATGC GCAACTGTAA CTAATAACTG ATCAATAATT ATCATTAGTT AATGCCCCAG 7270       7280       7290       7300       7310       7320
        ATTAGTTCAT AGCCCATATA TGGAGTTCCG CGTTACATAA CTTACGGTAA ATGGCCCGCC
        TAATCAAGTA TCGGGTATAT ACCTCAAGGC GCAATGTATT GAATGCCATT TACCGGGCGG 7330       7340       7350       7360       7370       7380
        TGGCTGACCG CCCAACGACC CCCGCCCATT GACGTCAATA ATGACGTATG TTCCCATAGT
        ACCGACTGGC GGGTTGCTGG GGGCGGGTAA CTGCAGTTAT TACTGCATAC AAGGGTATCA 7390       7400       7410       7420       7430       7440
        AACGCCAATA GGGACTTTCC ATTGACGTCA ATGGGTGGAC TATTTACGGT AAACTGCCCA
        TTGCGGTTAT CCCTGAAAGG TAACTGCAGT TACCCACCTG ATAAATGCCA TTTGACGGGT 7450       7460       7470       7480       7490       7500
        CTTGGCAGTA CATCAAGTGT ATCATATGCC AAGTACGCCC CCTATTGACG TCAATGACGG
        GAACCGTCAT GTAGTTCACA TAGTATACGG TTCATGCGGG GGATAACTGC AGTTACTGCC 7510       7520       7530       7540       7550       7560
        TAAATGGCCC GCCTGGCATT ATGCCCAGTA CATGACCTTA TGGGACTTTC CTACTTGGCA
        ATTTACCGGG CGGACCGTAA TACGGGTCAT GTACTGGAAT ACCCTGAAAG GATGAACCGT 7570       7580       7590       7600       7610       7620
        GTACATCTAC GTATTAGTCA TCGCTATTAC CATGGTGATG CGGTTTTGGC AGTACATCAA
        CATGTAGATG CATAATCAGT AGCGATAATG GTACCACTAC GCCAAAACCG TCATGTAGTT 7630       7640       7650       7660       7670       7680
        TGGGCGTGGA TAGCGGTTTG ACTCACGGGG ATTTCCAAGT CTCCACCCCA TTGACGTCAA
        ACCCGCACCT ATCGCCAAAC TGAGTGCCCC TAAAGGTTCA GAGGTGGGGT AACTGCAGTT 7690       7700       7710       7720       7730       7740
        TGGGAGTTTG TTTTGGCACC AAAATCAACG GGACTTTCCA AAATGTCGTA ACAACTCCGC
        ACCCTCAAAC AAAACCGTGG TTTTAGTTGC CCTGAAAGGT TTTACAGCAT TGTTGAGGCG 7750       7760       7770       7780       7790       7800
        CCCATTGACG CAAATGGGCG GTAGGCGTGT ACGGTGGGAG GTCTATATAA GCAGAGCTCT
        GGGTAACTGC GTTTACCCGC CATCCGCACA TGCCACCCTC CAGATATATT CGTCTCGAGA
```

FIG. 19N
Primary Sequence = SEQ ID NO:23
Complementary Sequence = SEQ ID NO:29 pD17-hG1b

```
        7810       7820       7830       7840       7850       7860
CTGGCTAACT AGAGAACCCA CTGCTTACTG GCTTATCGAA ATTAATACGA CTCACTATAG
GACCGATTGA TCTCTTGGGT GACGAATGAC CGAATAGCTT TAATTATGCT GAGTGATATC 7870       7880
GGAGACCCAA GCTT
CCTCTGGGTT CGAA
```

FIG. 26 hBR96-2 Heavy Chain Variable Region (V$_H$)

(SEQ ID NO:24)

```
1          11         21         31         41
EVQLVESGGG LVQPGGSLRL SCAASGFPFS DYYMYWVRQA PGKGLEWVSY 51         61         71         81         91
ISQDGDITDY ADSVKGRFTI SRDNAKNSLY LQMNSLRDED TAVYYCARGL 101        111
ADGAWFAYWG QGTLVTVSS
```

Human IgG1 Constant (SEQ ID NO:25)

CH1

```
           A STKGPSVFPL APSSKSTSGG TAALGCLVKD

YFPEPVTVSW NSGALTSGVH TFPAVLQSSG LYSLSSVVTV PSSSLGTQTY
                                     CH2 235  237
ICNVNHKPSN TKVDKKVEPK SCDKTHTCPP CHAPELLGGP SVFLFPPKPK

DTLMISRTPE VTCVVVDVSH EDPEVKFNWY VDGVEVHNAK TKPREEQYNS
              318 320 322           331       CH3
TYRVVSVLTV LHQDWLNGKE YKDKVSNKAL PAPIEKTISK AKGQPREPQV

YTLPPSRDEL TKNQVSLTCL VKGFYPSDIA VEWESNGQPE NNYKTTPPVL

DSDGSFFLYS KLTVDKSRWQ QGNVFSCSVM HEALHNHYTQ KSLSLSPGK
```

FIG. 27 hBR96-2A: Heavy Chain Variable Region ($V_H$)

(SEQ ID NO:24)

```
1          11         21         31         41
EVQLVESGGG LVQPGGSLRL SCAASGFPFS DYYMYWVRQA PGKGLEWVSY 51         61         71         81         91
ISQDGDITDY ADSVKGRFTI SRDNAKNSLY LQMNSLRDED TAVYYCARGL 101        111
ADGAWFAYWG QGTLVTVSS
``` hBR96-2A: Human Heavy Chain IgG1 Constant Region ΔCH2

(SEQ ID NO:26)

```
A STKGPSVFPL APSSKSTSGG TAALGCLVKD YFPEPVTVSW NSGALTSGVH

TFPAVLQSSG LYSLSSVVTV PSSSLGTQTY ICNVNHKPSN TKVDKKVEPK

SCDKTHTCPP CP     GQPREPQV YTLPPSRDEL TKNQVSLTCL VKGFYPSDIA

VEWESNGQPE NNYKTTPPVL DSDGSFFLYS KLTVDKSRWQ QGNVFSCSVM

HEALHNHYTQ KSLSLSPGK
```

FIG. 28

(SEQ ID NO:27)

This sequence is the chi BR96 IgG1 with CH2 deleted.

```
    VH
  1 EVNLVESGGG LVQPGGSLKV SCVTSGFTFS DYYMYWVRQT PEKRLEWVAY

51 ISQGGDITDY PDTVKGRFTI SRDNAKNTLY LQMSRLKSED TAMYYCARGL
                    CH1
101 DDGAWFAYWG QGTLVTVSVA STKGPSVFPL APSSKSTSGG TAALGCLVKD

151 YFPEPVTVSW NSGALTSGVH TFPAVLQSSG LYSLSSVVTV PSSSLGTQTY
                                              CH3
201 ICNVNHKPSN TKVDKKVEPK SCDKTHTCPP CPGQPREPQV YTLPPSRDEL

251 TKNQVSLTCL VKGFYPSDIA VEWESNGQPE NNYKTTPPVL DSDGSFFLYS

301 KLTVDKSRWQ QGNVFSCSVM HEALHNHYTQ KSLSLSPGK
```

US 7,247,302 B1

METHOD FOR INHIBITING IMMUNOGLOBULIN-INDUCED TOXICITY RESULTING FROM THE USE OF IMMUNOGLOBULINS IN THERAPY AND IN VIVO DIAGNOSIS

This application is based on U.S. provisional patent application Ser. No. 60/023,033, filed Aug. 2, 1996.

Throughout this application various publications are referenced. The disclosures of these publications in their entireties are hereby incorporated by reference into this application in order to more fully describe the state of the art to which this invention pertains.

TECHNICAL FIELD OF THE INVENTION

The present invention relates to methods for inhibiting or reducing immunoglobulin-induced toxicity resulting from therapy or in vivo diagnosis. Specifically, in lieu of using unmodified antibodies or recombinant binding proteins for in vivo use, the invention provides the use of modified antibodies or recombinant binding proteins which have been structurally altered in the constant domain so that upon administration immunoglobulin-induced toxicity is reduced or inhibited.

BACKGROUND OF THE INVENTION

Over the years investigators have attempted to harness the immune system for therapeutic use. Immunoglobulin (Ig) molecules which constitute an important part of the immune system are of great interest because they (1) react with a diverse family of ligands, (2) possess different effector functions and (3) are of great biological importance. Despite its potential, a persistent problem with immunoglobulin immunotherapy has been, among other problems, the toxic effect to normal cells of using antibodies which recognize both normal and diseased cells. This problem is far-reaching because the majority of antibodies presently available recognize a target located on both normal and diseased cells (Slavin-Chiorini, et al., Int. J. Cancer 53: 97–103 (1993)).

The constant region can promote cell death through antibody dependent cell medicated cytotoxicity (ADCC) or by complement dependent cytotoxicity (CDC). Despite the deletion of portions of the constant region, particularly the $CH_2$ domain, the antigen binding function can be retained (D. Yelton, M. Scharf, Mutant monoclonal antibody with alterations in biological functions, J. Exp. Methods 156: 1131–1148 (1982)).

Others have generated a $CH_2$-deleted antibody (Mueller et al., Proc. Natl. Acad. Sci. USA 87: 5702–5705 (1990)). Their findings provide that the $CH_2$-deleted antibody was cleared from the blood of tumor-bearing mice much faster than the corresponding intact antibody. Other in vivo findings also confirmed that a $CH_2$-deleted antibody, designated ch14.18DCH2, is a potentially useful reagent for radioimmunodetection of human tumors because of its reduced immunogenicity, increased target specificity, and rapid clearance from circulation (Mueller et al., Proc. Natl. Acad. Sci. USA 87: 5702–5705 (1990).

Generally, whole antibody molecules are composed of two heavy (H) and two light (L) chains which are held together by covalent bonds (disulfide) and non-covalent interactions. Each chain contains a variable region (V) and a constant region (C). The variable regions at the amino termini of the two chains form the antigen binding region. The constant region of the H chain has three components or domains. The first constant region domain ($CH_1$) interacts with the C region of the L chain through hydrophobic interactions and generally a disulfide bond, depending on isotype. The next C region stretch is the hinge-acting disulfide bonds stably introduced between two H chains. The second constant region domain ($CH_2$) is adjacent to the hinge region. $CH_2$ contains sequences important for effector functions of the antibody, such as the sequences responsible for complement fixation and Fc receptor binding. The third constant region domain ($CH_3$) is located at the carboxyl terminus of the H chain, and is considered to play an important role in H chain assembly as well as some C region functions.

Today many antibodies in clinical trials are directed against tumor associated antigens. Most tumor associated antigens are not tumor specific but are also generally found on the cell surface of some normal, non-tumorigenic cells. The clinical use of some antibodies directed against tumor associated antigens are limited because of the toxicity associated with their use. Therefore, there is a need for methods of inhibiting toxicity associated with immunoglobulin use in the field of disease therapy (e.g., therapy for tumors, kidney disease, and the like) and in vivo diagnosis.

We addressed this need by discovering methods for inhibiting or reducing toxicity to normal cells generally associated with immunoglobulin immunotherapy or in vivo diagnosis, wherein the immunoglobulin recognizes both diseased and normal cells. Our discovery involves generating immunoglobulin molecules or Ig fusion proteins having structurally altered constant regions which inhibit or reduce immunoglobulin-induced toxicity.

SUMMARY OF THE INVENTION

The present invention provides methods for inhibiting immunoglobulin-induced toxicity by using known immunoglobulin or Ig fusion protein molecules which are structurally altered in their constant regions so that the resulting structurally altered immunoglobulin or Ig fusion protein molecules exhibit reduced or inhibited toxicity in vivo compared to their original unmodified counterparts.

Structural alteration of the constant region may be effected in a number of ways as long as it results in reducing or inhibiting immunoglobulin-induced toxicity.

In accordance with the practice of the invention, structural alteration of the constant region is effected by deletion of the entire constant region. In another embodiment, only the $CH_2$ domain is deleted. In another embodiment, only that portion of the $CH_2$ domain that binds the Fc receptor is deleted. In yet another embodiment, only that portion of the $CH_2$ domain that binds the complement component C1q is deleted. Alternatively, in another embodiment, multiple deletions in discrete Fc receptor and complement component binding domains are effected.

Alternatively, structural alteration is effected by single or multiple mutations in the $CH_2$ domain such as amino acid insertions and substitutions. The mutation or mutations must result in inhibiting immunoglobulin-induced toxicity. By way of example, the amino acids in multiple toxicity associated domains in the constant region can be altered so as to render the constant region unable to mediate a ADCC response or activate complement thereby inhibiting immunoglobulin induced toxicity resulting from immunotherapy. Alternatively, multiple amino acids in a single toxicity associated domain in the constant region can be altered.

Further alternatively, structural alteration can be effected by isotype switching resulting in an altered immunoglobulin molecule that either does not induce toxicity or induces some limited toxicity but does not cause a harmful effect. For example, isotype switching can result in the constant region being unable to mediate a CDC or ADCC response or some other activity which mediates toxicity.

BRIEF DESCRIPTION OF THE FIGURES

FIGS. 10a–c are schematic diagrams showing the constructions of BR96 IgG1 CH$_2$ domain point mutations.

FIGS. 14A–14J are the nucleic acid sequence of pD17-cJ-dCH2.H1 (SEQ ID NO: 10), the plasmid shown in FIG. 5, chimeric BR96 having the CH2 detection.

FIG. 16 is a description of the seven structural alterations.

FIGS. 18A–18F are the nucleic acid sequence of pD17-hJm14.H1 (SEQ ID NO: 22).

FIGS. 19A–19N are the nucleic acid sequence of pD17-hG1b (SEQ ID NO: 23).

FIG. 26 provides the amino acid sequence for hBR96-2 heavy-chain variable region (SEQ ID NO. 24) and the human IgG1 constant region (SEQ ID NO. 25).

FIG. 27 provides the amino acid sequence for hBR96-2A heavy-chain variable region (SEQ ID NO. 24) and the human IgG1 constant region without the CH$_2$ domain (SEQ ID NO. 26).

FIG. 28 provides the amino acid sequence for chi BR96 heavy-chain variable region and the human IgG1 constant region without the CH$_2$ domain (SEQ ID NO. 27).

DETAILED DESCRIPTION OF THE INVENTION

Definitions

Figure 1:
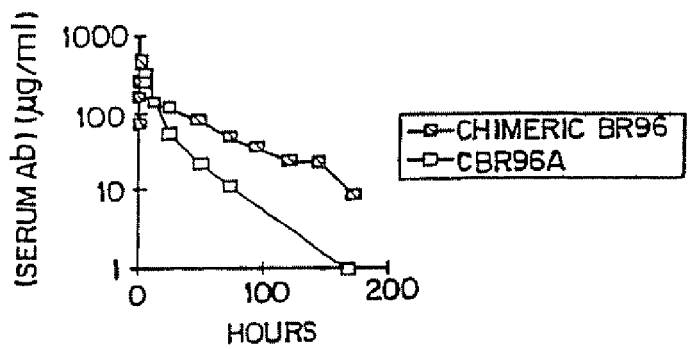
FIG. 1 is a line graph showing plasma clearance in high Le$^y$ expressing dogs using chimeric BR96 versus constant region mutant of cBR96-A.
Figure 2:
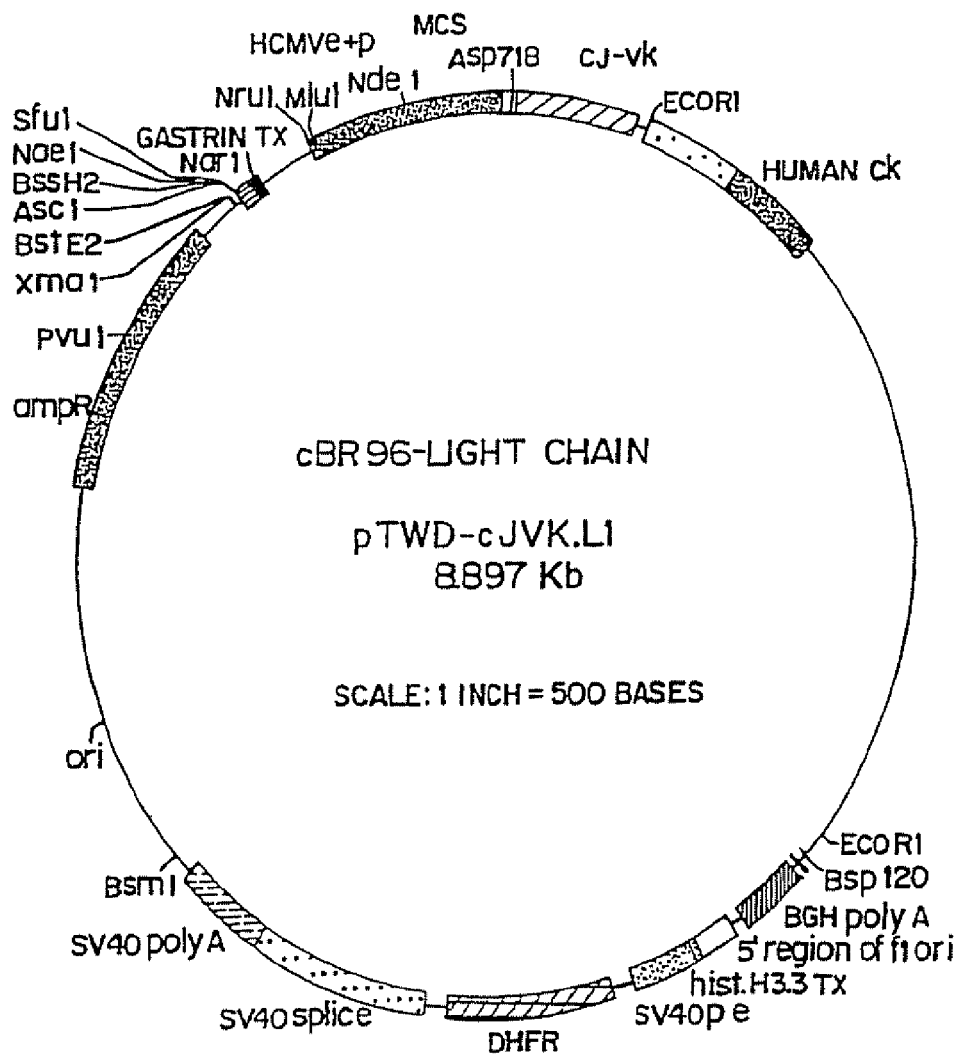
FIG. 2 is a schematic diagram of a plasmid designated pTWD-cJVK.L1 including the chimeric (c)BR96-light chain (SEQ ID NO. 11).
Figure 3:
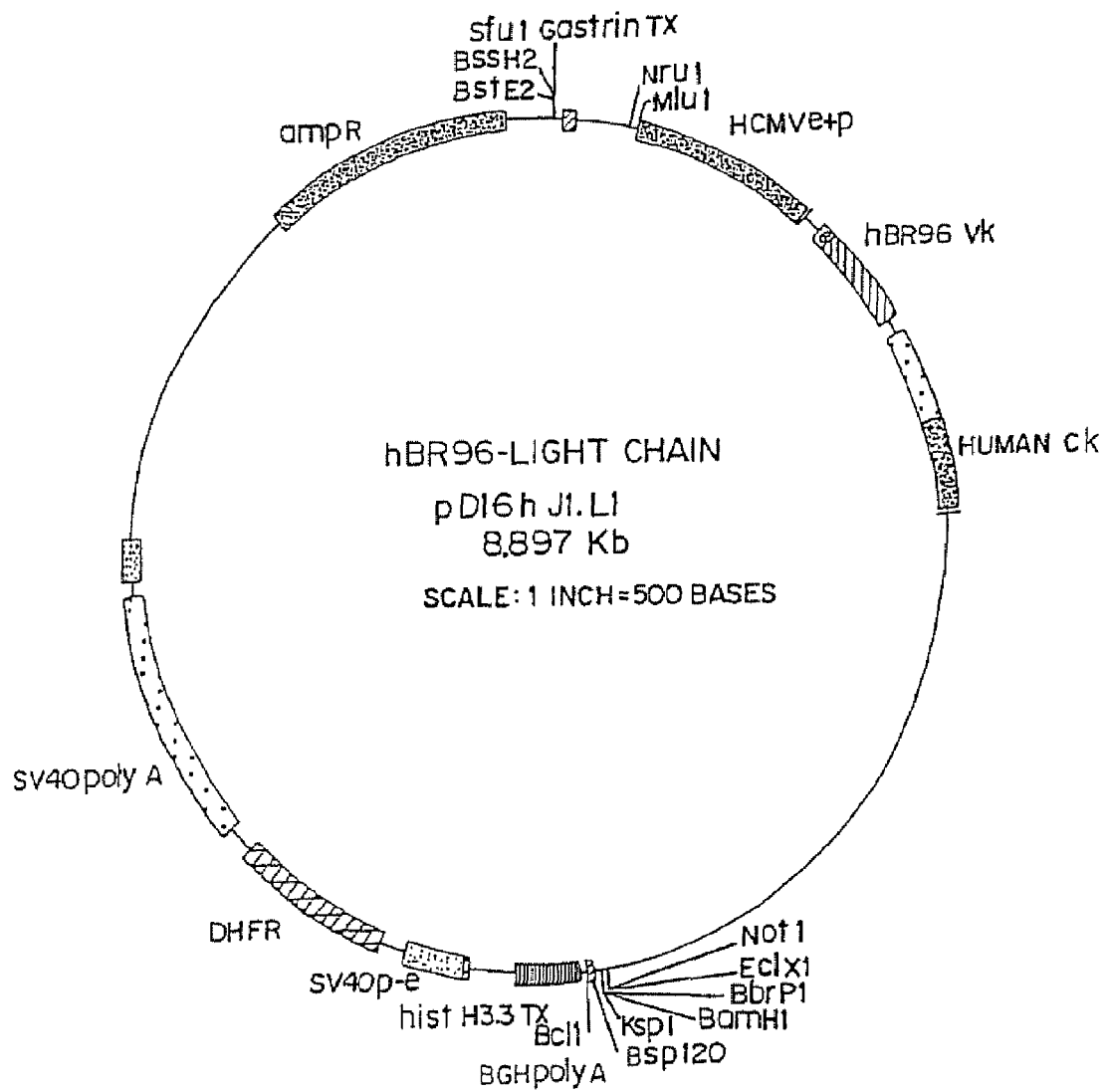
FIG. 3 is a schematic diagram of a plasmid designated pD16hJ1.L1 including the human (h)BR96-light chain (SEQ ID NO. 13).

As used herein the term "inhibiting immunoglobulin-induced toxicity" means to reduce or alleviate symptoms generally associated with toxicity caused by immunoglobulin or Ig fusion protein therapy, e.g., toxicity mediated by effector functions of the Fc portion. For example, BR96 antibody recognizes and binds BR96 antigen which is found at some levels in the gastrointestinal tract and at elevated levels in tumors (as compared to normal gastrointestinal tract tissues). The binding of BR96 antibody to BR96 antigen in vivo causes symptoms associated with gastrointestinal toxicity. These symptoms include rapid onset of vomiting, often with blood, and nausea. In humans the bleeding is limited to the fundus of the stomach, causing erosion of the superficial mucosa of the stomach.

The pathology of the wound is limited and resolves. However, the extreme nature of the nausea and vomiting, unrelieved by anti-emetics, defines it as the dose-limiting toxicity. For highly elevated levels of other antigens found in the central nervous system (CNS), liver, and other locations, the toxicity will be characterized by symptoms other than those described above.

As used herein the term "immunoglobulin molecule" can be produced by B cells or be generated through recombinant engineering or chemical synthetic means. Examples of immunoglobulin molecules include (1) antibodies, e.g., polyclonal and monoclonal antibodies, chimeric or humanized, and (2) recombinant Ig containing binding proteins, e.g., Ig fusion proteins. Recombinant Ig containing binding proteins include cell surface proteins, e.g., CD antigens (in one embodiment, CTLA4), to which an Ig tail is joined.

As used herein the terms "structurally altered" or "structural alteration" means manipulating the constant region so that the resulting molecule or protein exhibits a diminished ability to induce toxicity. Structural alteration can be by chemical modification, proteolytic alteration, or by recombinant genetic means. Recombinant genetic means may include, but is not limited to, the deletion, insertion and substitution of amino acid moieties.

As used herein the term "multiple toxicity associated domains" or "multiple toxicity associated regions" means more than one discrete toxicity associated domain or region. As there appear to be at least two toxicity associated domains or regions in the immunoglobulin molecule, one roughly localized to amino acids 231–238 and the other roughly localized to amino acid 310–331, an example of the structural alteration of multiple toxicity associated domains or regions comprises the insertion, substitution or deletion of amino acid residues in both of these domains or regions. This definition excludes structural alterations targeting a single toxicity associated domain or region.

Merely by way of example, the constant region of the immunoglobulin molecule can be structurally altered so that the molecule no longer mediates a CDC or ADCC response. However, the methods of the invention encompass the use of structurally altered immunoglobulin molecules regardless of whether it mediates a CDC or ADCC response. The underlying requirement is that the altered molecule must inhibit immunoglobulin-induced toxicity.

Structural alteration can be effected in a number of ways. For example, structural alteration can be effected by deletion of the entire constant region.

Alternatively, structural alteration can be effected by deletion of the entire $CH_2$ domain of the constant region. In this instance, deletion of the entire $CH_2$ domain may render the molecule unable to (1) bind an Fc receptor thereby eliminating the molecule's possibility of mediating antibody-dependent cellular cytotoxicity (ADCC), (2) bind C1q, or (3) activate complement.

Alternatively, structural alternation can be effected by deletion of only that portion of the $CH_2$ domain that binds the Fc receptor or complement.

Further alternatively, a single mutation or multiple mutations such as substitutions and insertions in the $CH_2$ domain can be made. The underlying requirement of any mutation is that it must inhibit, diminish, or block immunoglobulin-induced toxicity. For example, this can be achieved by mutating the constant region such that the altered molecule is rendered unable to mediate a CDC response or an ADCC response, or to activate complement.

Alternatively, structural alteration can be effected by isotype switching (also known as class switching) so that the altered molecule does not induce toxicity in the subject. In one embodiment, the constant region of the immunoglobulin is structurally altered so that it no longer binds the Fc receptor or a complement component, e.g., switching a molecule's original IgG isotype from IgG1 to IgG4. Isotype switching can be effected regardless of species, i.e., an isotype from a non-human being can be switched with an isotype from a human being (E. D. Finkleman et al. (1990) Annu. Rev. Immunol. 8:303–333; T. Honjo et al. (1979) Cell 18: 559–568; T. Honjo et al. In "Immunoglobulin Genes" pp. 124–149 Academic Press, London)).

As used herein the term "Ig fusion protein" means any recombinantly produced antigen or ligand binding domain having a constant region which can be structurally altered.

As used herein "cytotoxic agent" includes antimetabolites, alkylating agents, anthracyclines, antibiotics, anti-mitotic agents, and chemotherapeutic agents. Specific examples within these groups include but are not limited to ricin, doxorubicin, daunorubicin, taxol, ethidium bromide, mitomycin, etoposide, tenoposide, vincristine, vinblastine, colchicine, supporin, gelonin, PE40, bryodin, dihydroxy anthracin dione, actinomycin D, and 1-dehydrotestosterone.

As used herein the term "BR96" refers to (1) the whole BR96 monoclonal antibody disclosed in EP No. 95/305444, published Mar. 6, 1996, (2) chimeric BR96 monoclonal antibody disclosed in EP No. 95/305444, published Mar. 6, 1996, or (3) BR96 mutant molecules disclosed in EP No. 95/305444, published Mar. 6, 1996.

As used herein, "treating" means to (1) provide tumor regression so that the tumor is not palpable for a period of time (standard tumor measurement procedures may be followed (A. B. Miller et al. "Reporting results of cancer treatment" Cancer 47:207–214 (1981)); (2) stabilize the disease; or (3) provide any clinically beneficial effects.

As used herein, an "effective amount" is an amount of the antibody, immunoconjugate, or recombinant molecule which kills cells or inhibits the proliferation thereof.

As used herein, "administering" means oral administration, administration as a suppository, topical contact, intravenous, intraperitoneal, intramuscular or subcutaneous administration, or the implantation of a slow-release device such as a miniosmotic pump, to the subject.

As used herein, "pharmaceutically acceptable carrier" includes any material which when combined with the antibody retains the antibody's specificity or efficacy and is non-reactive with the subject's immune system. Examples include, but are not limited to, any of the standard pharmaceutical carriers such as a phosphate buffered saline solution, water, emulsions such as oil/water emulsion, and various types of wetting agents. Other carriers may also include sterile solutions, tablets including coated tablets and capsules.

Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well known conventional methods.

As used herein, "mutation" means a single amino acid or nucleic acid mutation or multiple mutations by whatever means, e.g., homologous recombination, error prone PCR, or site directed mutagenesis.

In order that the invention herein described may be more fully understood, the following description is set forth.

Methods of the Present Invention

The present invention provides a method for inhibiting immunoglobulin-induced toxicity resulting from the use of immunoglobulin during therapy or in vivo diagnosis. For example, the methods of the invention would be useful to minimize the toxicity associated with prolonged clinical exposure to immunoglobulin use during or after tumor imaging with radiolabeled antibodies.

In accordance with the practice of this invention, the subject includes, but is not limited to, human, equine, porcine, bovine, murine, canine, feline, and avian subjects. Other warm blooded animals are also included in this invention.

This method comprises administering an immunoglobulin molecule to the subject. The immunoglobulin can be IgG, IgM, or IgA. IgG is preferred.

In one embodiment of the invention, the immunoglobulin molecule recognizes and binds $Le^y$. In another embodiment, the immunoglobulin recognizes and binds $Le^x$. In a further embodiment, the immunoglobulin is a monoclonal antibody BR96 produced by the hybridoma deposited on Feb. 22, 1989 with the American Type Culture Collection (ATCC), 10801 University Boulevard, Manassas, Va., 20110-2209 USA and accorded ATCC Accession No.: HB 10036. In yet another embodiment, the immunoglobulin is a chimeric antibody ChiBR96 produced by the hybridoma deposited on May 23, 1990, with the ATCC, 10801 University Boulevard, Manassas, Va., 20110-2209 USA and accorded ATCC Accession No.: HB 10460.

In accordance with the practice of the invention, the immunoglobulin can be a bispecific antibody with a binding specificity for two different antigens, one of the antigens being that with which the monoclonal antibody BR96 produced by the hybridoma having the identifying characteristics of HB 10036 as deposited with the ATCC binds. Also, in accordance with the practice of the invention, the immunoglobulin can be an anti-idiotypic antibody.

As required by the invention, at least a portion of the constant region of the immunoglobulin molecule is structurally altered. Structural alteration can be effected by a number of means. In one embodiment, the entire constant region, i.e., $CH_1$, $CH_2$, and $CH_3$ domains, can be deleted.

Figure 4:
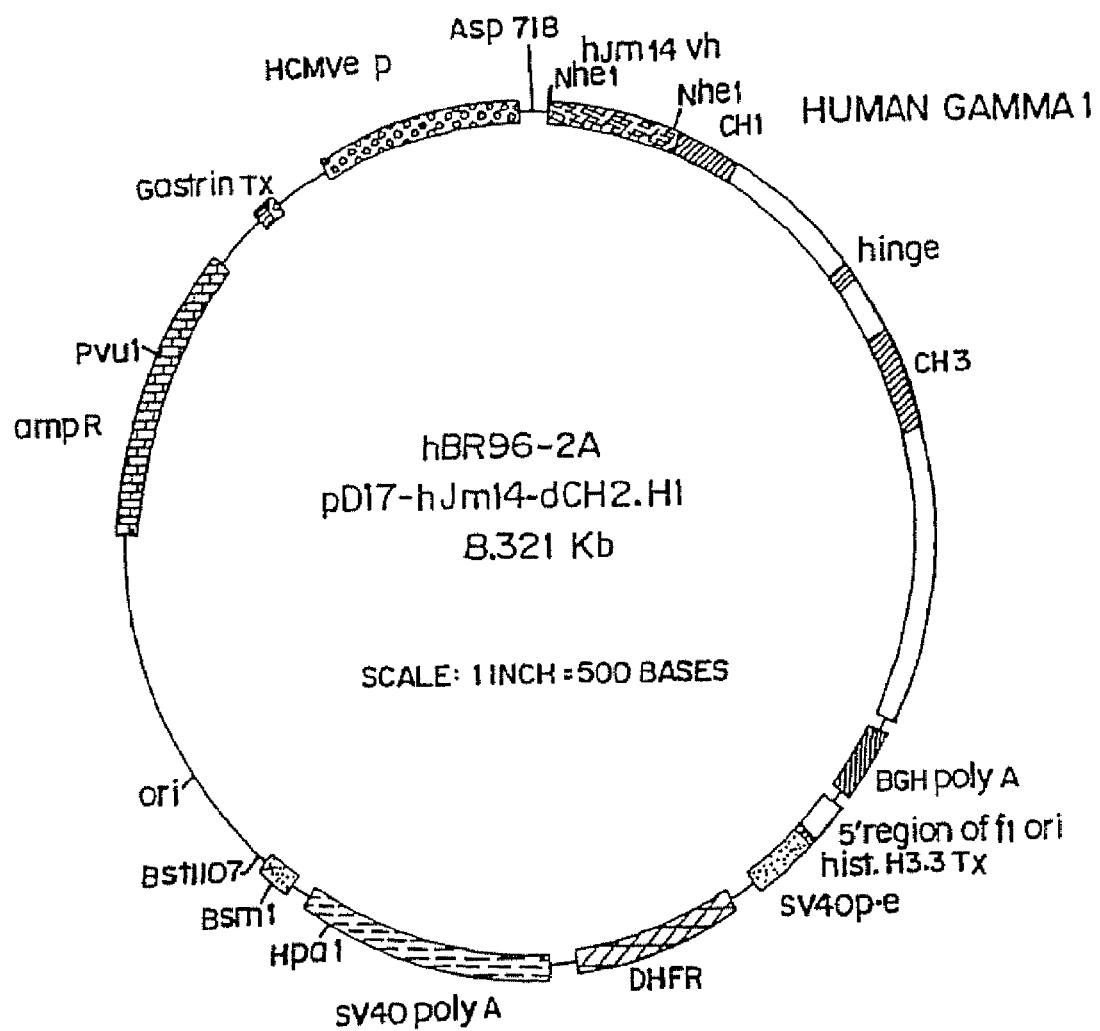
FIG. 4 is a schematic diagram of a plasmid, designated pD17-hJm14-dCH2.H1, of hBR96-2A (i.e., human mutant BR96 having the H1, H2, and H3 mutations and the CH$_2$ deletion (EP Application No. 95/305444, published Mar. 6, 1996)).
Figure 5:
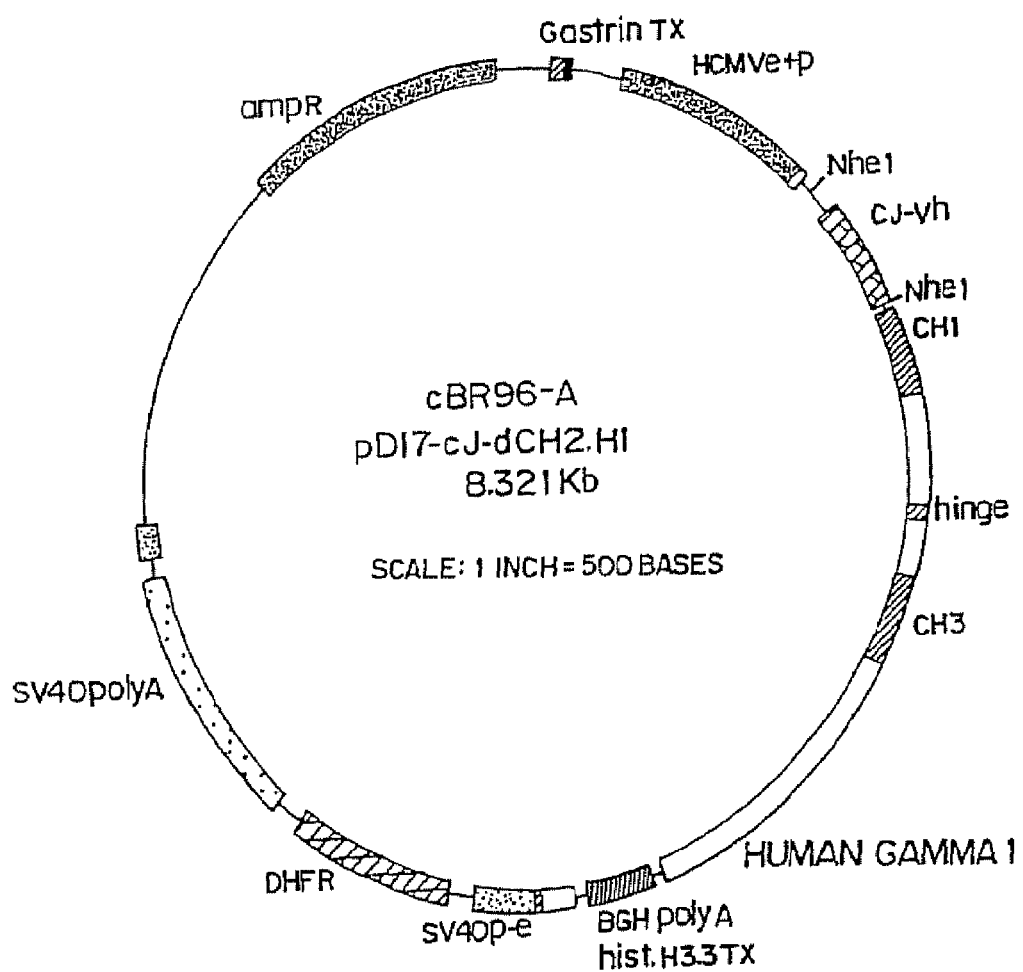
FIG. 5 is a schematic diagram of a plasmid, designated pD17-cJ-dCH2.H1, of cBR96-A (SEQ ID NO. 10) (i.e., chimeric BR96 having the CH$_2$ deletion (EP Application No. 95/305444, published Mar. 6, 1996)).
Figure 6:
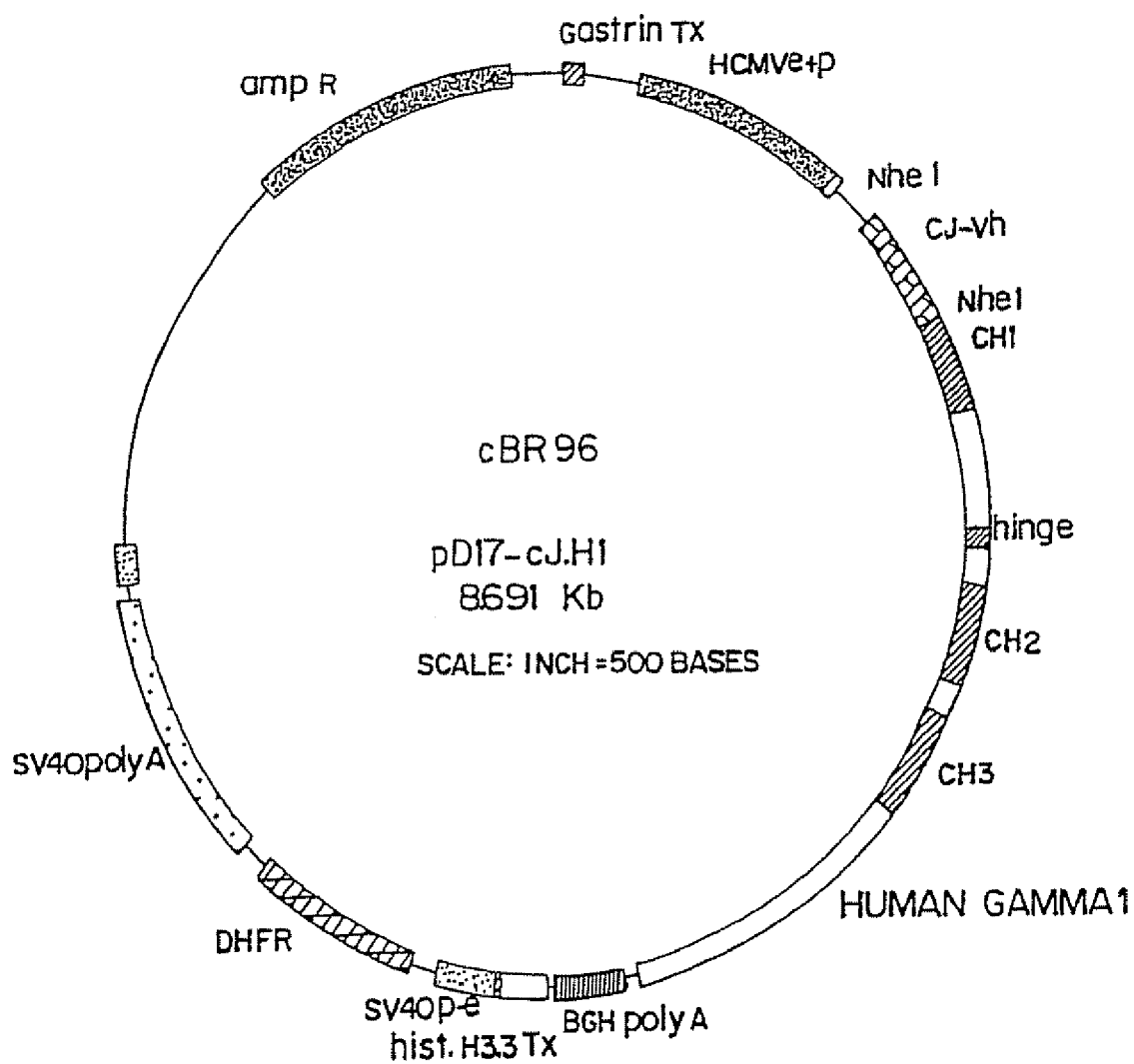
FIG. 6 is a schematic diagram of a plasmid, designated pD17-cJ.H1, of cBR96.
Figure 7:
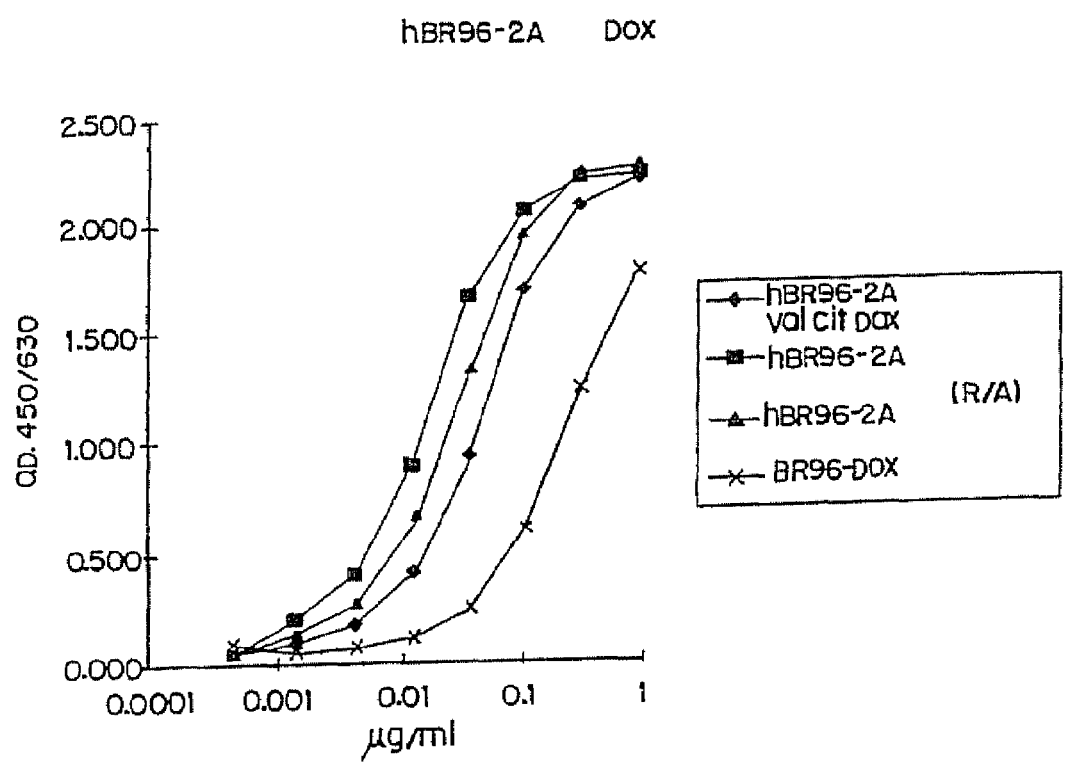
FIG. 7 is a line graph showing the results of an ELISA assay of (1) hBR96-2A-Dox to Le$^y$ (closed diamond), (2) hBR96-2A to Le$^y$ (96:0006A2 R/A)(closed square), (3) hBR96-2A to Le$^y$ (96:0006B R/A)(closed triangle), and BR96-Dox to Le$^y$ (X).
Figure 8:
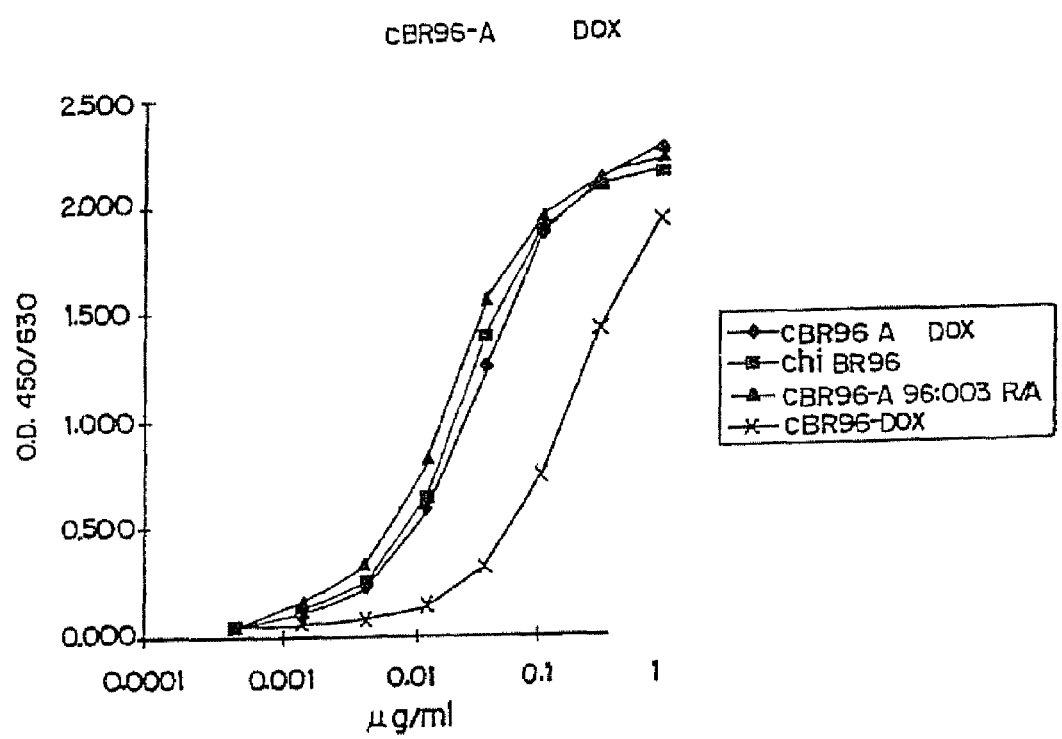
FIG. 8 is a line graph showing the results of an ELISA assay of (1) cBR96-A-Dox to Le$^y$ (closed diamond), (2) chiBR96 to Le$^y$ (closed square), (3) cBR96-A to Le$^y$ (96: 0003 R/A)(closed triangle), and cBR96-Dox to Le$^y$ (X).
Figure 9A:
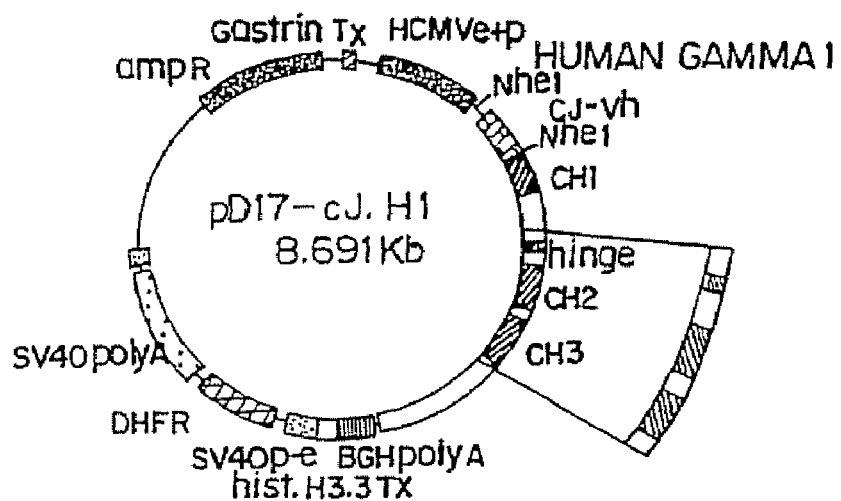
FIGS. 9a–c are schematic diagrams showing the steps for deleting a CH$_2$ domain.
Figure 9B:
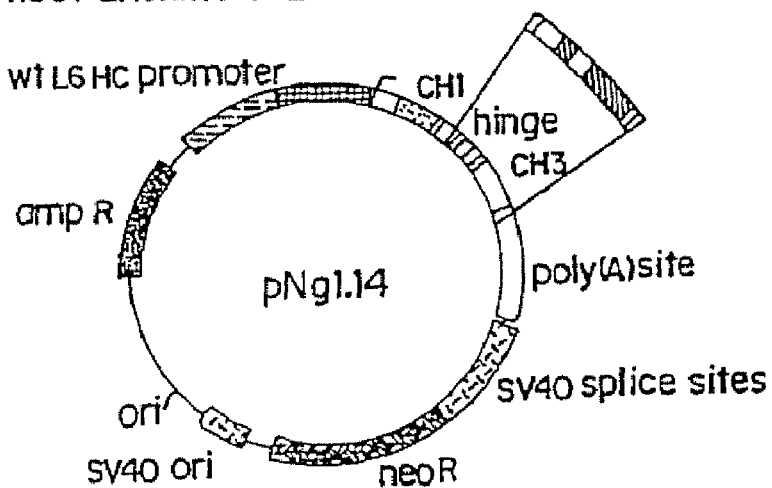
Figure 9C:
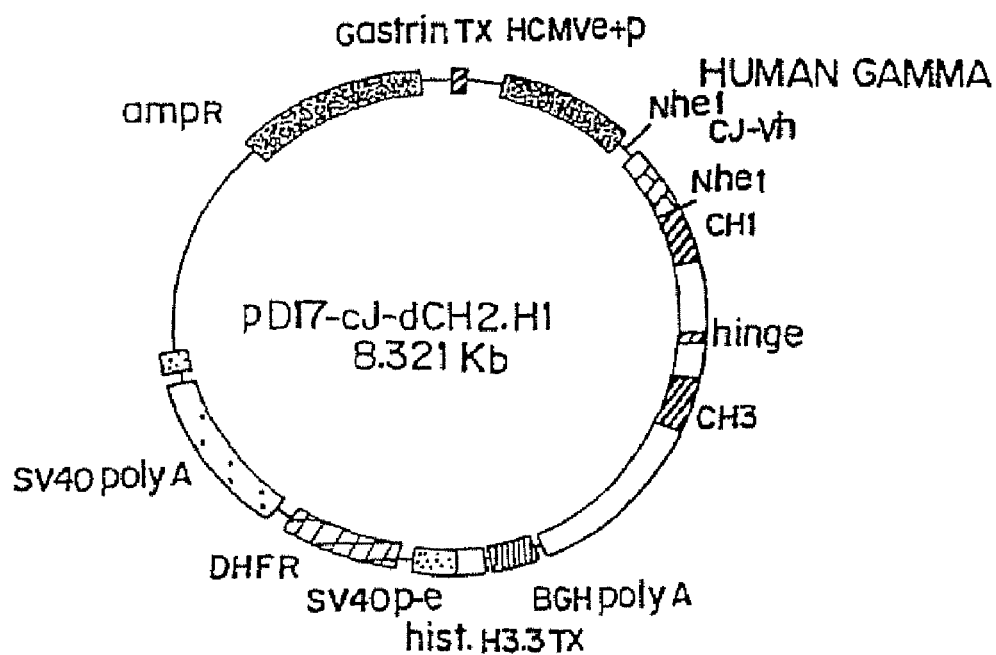

In another embodiment, only the $CH_2$ domain is deleted from the immunoglobulin molecule (e.g., cBR96-A (FIG. 5), hBR96-2A (FIG. 4). In this embodiment, the $CH_2$ deletion may result in a molecule unable to bind the Fc receptor or a complement component.

In another embodiment, only that portion of the $CH_2$ domain which binds the complement component C1q is deleted. In yet another embodiment, mutations in specific portions of the $CH_2$ domain are made. For example, the immunoglobulin molecule may be modified by structurally altering multiple toxicity associated domains in the constant region so that immunoglobulin-induced toxicity is inhibited. A discussion of such mutations are further found hereinafter.

Regardless of the means, the underlying requirement for any structural alteration of the constant region is that immunoglobulin-induced toxicity is substantially reduced or inhibited. In one embodiment, immunoglobulin-induced toxicity is inhibited by structurally altering the constant region such the the molecule's ability to mediate a CDC response or ADCC response and/or activate the complement cascade is prevented or inhibited. Methods for determining whether the molecule is able to inhibit a CDC response are well known, e.g., one method involves a $^{51}$Cr-release test (H. Garrigues et al. Int. J. Cancer 29:511 (1982); I. Hellström et al. PNAS 82:1499 (1985)). Methods for determining whether the molecule is able to inhibit an ADCC response are well known (I. Hellström et al. PNAS 82:1499 (1985)). Methods for determining whether the molecule is able to activate a complement cascade are well known.

In another embodiment of the invention, the method comprises administering to the subject an Ig fusion protein having a structurally altered constant region. Structural alteration of the constant region may include deletion of the entire C region or portions thereof, e.g., alteration of the $CH_2$ domain so that the altered molecule no longer binds the Fc receptor or a complement component.

The invention further provides a method for inhibiting immunoglobulin-induced toxicity resulting from immunotherapy in a subject. The method comprises administering to the subject an antibody which has been modified so that at least a portion of the constant region has been structurally altered as discussed supra. In one embodiment, the antibody recognizes and binds $Le^y$. In another embodiment, the antibody recognizes and binds to $Le^x$.

In accordance with the practice of this invention, the antibody can be monoclonal antibody BR96 produced by the hybridoma having the identifying characteristics of HB 10036 as deposited with the ATCC. Alternatively, the antibody can be chimeric antibody ChiBR96 produced by the hybridoma having the identifying characteristics of HB 10460 as deposited with the ATCC. Further, the antibody can be a bispecific antibody with a binding specificity for two different antigens, one of the antigens being that with which the monoclonal antibody BR96 produced by the hybridoma having the identifying characteristics of HB 10036 as deposited with the ATCC binds.

Additionally, the present invention provides a method for inhibiting immunoglobulin-induced toxicity resulting from immunotherapy for a disease in a subject. The antigen will vary with the disease. Examples of diseases include but are not limited to immunological diseases, cancer, cardiovascular diseases, neurological diseases, dermatological diseases or kidney disease.

This method comprises the following steps. Step one provides selecting an antibody for a target. Generally, the target is associated with the disease and the antibody directed to the target is known. For example, the target can be the BR96 antigen and the antibody selected is BR96.

Step two of this method provides structurally altering the constant region of the antibody so selected so that immunoglobulin induced toxicity is inhibited. Inactivation can include any of the means discussed above. For example, inactivation can be effected by structurally altering multiple toxicity associated domains in the $CH_2$ domain of the constant region of the Ig protein so selected.

Step three of this method provides administering the structurally altered antibody of step two to the subject under conditions that the structurally altered antibody recognizes and binds the target and that such binding directly or indirectly alleviates symptoms associated with the disease.

In accordance with the invention, in one embodiment step one provides selecting an Ig fusion protein for a target. Further, the method provides mutating the Ig fusion protein so selected by structurally altering the $CH_2$ domain of the constant region of the Ig protein by the same means discussed above.

The invention further provides methods to treat human carcinoma. For example, the immunoglobulin, antibody, or Ig fusion protein discussed above can be used in combination with standard or conventional treatment methods such as chemotherapy, radiation therapy or can be conjugated or linked to a therapeutic drug, or toxin, as well as to a lymphokine or a tumor-inhibitory growth factor, for delivery of the therapeutic agent to the site of the carcinoma.

Techniques for conjugating therapeutic agents to immunoglobulins are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellström et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); and Thorpe et al., "The Preparation And Cytotoxic Properties Of Antibody-Toxin Conjugates", Immunol. Rev., 62:119–58 (1982)).

Alternatively, the structurally altered antibody or Ig fusion protein can be coupled to high-energy radiative agents, e.g., a radioisotope such as $^{131}I$; which, when localized at the tumor site, results in a killing of several cell diameters (see, e.g., Order, "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985)). According to yet another embodiment, the structurally altered BR96 antibody can be conjugated to a second antibody to form an antibody heteroconjugate for the treatment of tumor cells as described by Segal in U.S. Pat. No. 4,676,980.

Still other therapeutic applications for the structurally altered antibody or Ig fusion protein of the invention include conjugation or linkage, e.g., by recombinant DNA techniques or protein chemical techniques, to an enzyme capable of converting a prodrug into a cytotoxic drug and the use of that antibody-enzyme conjugate in combination with the prodrug to convert the prodrug to a cytotoxic agent at the tumor site (see, e.g., Senter et al., "Anti-Tumor Effects Of Antibody-alkaline Phosphatase", Proc. Natl. Acad. Sci. USA, 85:4842–46 (1988); "Enhancement of the in vitro and in vivo Antitumor Activities of Phosphorylated Mitomycin C and Etoposide Derivatives by Monoclonal Antibody-Alkaline Phosphatase Conjugates", Cancer Research 49:5789–5792 (1989); and Senter, "Activation of Prodrugs by Antibody-Enzyme Conjugates: A New Approach to Cancer Therapy," FASEB J. 4:188–193 (1990)).

It is apparent therefore that the present invention encompasses pharmaceutical compositions including immunoglobulin molecules, antibodies, and Ig fusion proteins all having structurally altered $CH_2$ domains, and their use in methods for treating human carcinomas. For example, the invention includes pharmaceutical compositions for use in the treatment of human carcinomas comprising a pharmaceutically effective amount of a structurally altered BR96 and a pharmaceutically acceptable carrier.

The compositions may contain the structurally altered antibody or Ig fusion protein or antibody fragments, either unmodified, conjugated to a therapeutic agent (e.g., drug, toxin, enzyme or second antibody). The compositions may additionally include other antibodies or conjugates for treating carcinomas (e.g., an antibody cocktail).

The compositions of the invention can be administered using conventional modes of administration including, but not limited to, intrathecal, intravenous, intraperitoneal, oral, intralymphatic or administration directly into the tumor. Intravenous administration is preferred.

The composition of the invention can be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The compositions of the invention also preferably include conventional pharmaceutically acceptable carriers and adjuvants known in the art such as human serum albumin, ion exchangers, alumina, lecithin, buffer substances such as phosphates, glycine, sorbic acid, potassium sorbate, and salts or electrolytes such as protamine sulfate.

In accordance with the practice of the invention, the pharmaceutical carrier can be a lipid carrier. The lipid carrier can be a phospholipid. Further, the lipid carrier can be a fatty acid. Also, the lipid carrier can be a detergent. As used herein, a detergent is any substance that alters the surface tension of a liquid, generally lowering it.

In one example of the invention, the detergent can be a nonionic detergent. Examples of noionic detergents include, but are not limited to, polysorbate 80 (also known as TWEEN 80) or polyoxyethylenesorbitan monooleate (also known as BRIJ) and tetramethylbutylphenyl polymer with formaldehyde and oxirane (for example TRITON WR-1339 and TRITON A-20).

Alternatively, the detergent can be an ionic detergent. An example of an ionic detergent includes, but is not limited to, alkyltrimethylammonium bromide.

Additionally, in accordance with the invention, the lipid carrier can be a liposome. As used in this application, a "liposome" is any membrane bound vesicle which contains any molecules of the invention or combinations thereof.

The most effective mode of administration and dosage regimen for the compositions of this invention depends upon the severity and course of the disease, the patient's health and response to treatment and the judgment of the treating physician.

The interrelationship of dosages for animals of various sizes and species and humans based on $mg/m^2$ of surface area is described by Freireich, E. J., et al. Cancer Chemother., Rep. 50 (4): 219–244 (1966). Adjustments in the dosage regimen can be made to optimize the tumor cell growth inhibiting and killing response, e.g., doses can be divided and administered on a daily basis or the dose reduced proportionally depending upon the situation (e.g., several divided doses can be administered daily or proportionally reduced depending on the specific therapeutic situation).

The Molecules of the Invention

The present invention provides structurally altered BR96 or BR96 Ig fusion proteins. Structurally altered BR96 antibodies or Ig fusion proteins have the variable region of BR96 and a modified constant region. This modification provides structurally altered BR96 antibodies or Ig fusion proteins with the ability to inhibit immunoglobulin-induced toxicity.

Various embodiments of structurally altered BR96 or BR96 Ig fusion proteins have been made.

In one embodiment, designated cBR96-A, the entire $CH_2$ domain of cBR96 was deleted. CBR96-A is expressed by the plasmid having the sequence shown in SEQ. ID. NO. 10. cBR96 is expressed by a plasmid having the sequence in SEQ ID NO. 9.

In another embodiment, designated hBR96-2A, the entire $CH_2$ domain of hBR96 was deleted. hBR96-2A is expressed by the plasmid having the sequence shown in SEQ. ID. NO. 12. hBR96-2 is a mutant BR96 having the H1, H2, and H3 mutations described in EP Application No. 95/305444, published Mar. 6, 1996.

In yet another embodiment, designated hBR96-2B, the leucine residue located at amino acid position 235 is mutated to alanine. Additionally, the glycine residue located at amino acid position 237 is mutated to alanine. The amino acid position numbering used is described in Kabat et al. Sequences of Proteins of Immunological Interest 5th Edition (1991) United States Department of Health and Human Services.

In a further embodiment, designated hBR96-2C, the glutamic acid residue at position 318 is mutated to serine; the lysine residue located at position 320 is mutated to serine; and the lysine residue located at position 322 is mutated to serine using standard protocols (Alexander R. Duncan and Greg Winter "The binding site for C1q on IgG" Nature 332:738 (1988)).

In another embodiment, designated hBR96-2D, the proline residue at position 331 is mutated to alanine (M-H. Tao et al., "Structural features of human immunoglobulin G that determine isotype-specific differences in complement activation" J. Exp. Med. 178:661–667 (1993); Y. Xu et al., "Residue at position 31 in the IgG1 and IgG4 domains contributes to their differential ability to bind and activate complement" J. Biol. Chem. 269:3469–3474 (1994)).

In an additional embodiment, designated hBR96-2E, the leucine residue at position 235 is mutated to alanine; the glycine residue located at position 237 is mutated to alanine; the glutamic acid residue located at position 318 is mutated to serine; the lysine residue located at position 320 is mutated to serine; and the lysine residue located at position 322 is mutated to serine (A. Morgan et al., "The N-terminal end of the $CH_2$ domain of chimeric human IgG1 anti-HLA-DR is necessary for C1q, Fc(gamma)RI and Fc(gamma)RIII binding" Immunol. 86:319–324 (1995)).

In yet a further embodiment, designated hBR96-2F, the leucine residue located at position 235 is mutated to alanine; the glycine residue located at position 237 is mutated to alanine; and the proline residue located at position 331 is mutated to alanine.

In yet another embodiment, designated hBR96-2G, the glutamic acid residue located at position 318 is mutated to serine; the lysine residue located at position 320 is mutated to serine; the lysine residue located at position 322 is mutated to serine; and the proline residue located at position 331 is mutated to alanine.

In another embodiment, designated hBR96-2H, the leucine residue located at position 235 is mutated to alanine; the glycine residue located at position 237 is mutated to alanine; the glutamic acid residue at position 318 is mutated to serine; the lysine residue located at position 320 is mutated to serine; the lysine residue located at position 322 is mutated to serine; and the proline residue located at position 331 is mutated to alanine.

Depending on its form, a structurally altered BR96 antibody or fusion protein can be a monofunctional antibody, such as a monoclonal antibody, or bifunctional antibody, such as a bispecific antibody or a heteroantibody. The uses of structurally altered BR96, i.e., as a therapeutic or diagnostic agent, will determine the different forms of structurally altered BR96 which is made.

Several options exists for antibody expression. Immunoexpression libraries can be combined with transfectoma technology, i.e., the genes for the Fab molecules derived from the immunoglobulin gene expression library can be connected to the desired constant-domain exons. These recombinant genes can then be transfected and expressed in a transfectoma that would secrete an antibody molecule.

Once produced, the polypeptides of the invention can be modified, i.e., by amino acid modifications within the molecule, so as to produce derivative molecules. Such derivative molecules would retain the functional property of the polypeptide, namely, the molecule having such substitutions will still permit the binding of the polypeptide to the BR96 antigen or portions thereof.

It is a well-established principle of protein chemistry that certain amino acid substitutions, entitled "conservative amino acid substitutions," can frequently be made in a protein without altering either the conformation or the function of the protein.

Amino acid substitutions include, but are not necessarily limited to, amino acid substitutions known in the art as "conservative".

Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa.

Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

In one embodiment of the present invention, the polypeptide is substantially pure, i.e., free of other amino acid residues which would inhibit or diminish binding of the polypeptide to its target and would inhibit or reduce gastrointestinal toxicity which are normally exhibited during or after antibody therapy.

Nucleic Acid Molecules Encoding the Present Invention

The nucleotide sequences and the amino acid sequences of the variable and constant regions of BR96 are known. The sequence for the immunoglobulin constant region is known and provided in FIG. 18. Specific mutations in the constant region of the BR96 antibody were made. Nucleic acid molecules encoding the seven mutants described above (hBR96-2B through hBR96-2H) are as follows.

In hBR96-2B, alanine at amino acid positions 235 and 237 is encoded by codons GCU, GCC, GCA, or GCG.

In hBR96-2C, serine at positions 318, 320, and 322 is encoded by UCU, UCC, UCA, or UGG.

In hBR96-2D, alanine at position 331 is encoded by codons GCU, GCC, GCA, or GCG.

In hBR96-2E, alanine at positions 235 and 237 is encoded by condons GCU, GCC, GCA, or GCG. Serine at positions 318, 320, and 322 is encoded by UCU, UCC, UCA, or UGG.

In hBR96-2F, alanine at positions 235, 237, and 331 is encoded by condons GCU, GCC, GCA, or GCG.

In hBR96-2G, serine at positions 318, 320, 322 is encoded by UCU, UCC, UCA, or UGG. Further, the alanine at position 331 is encoded by codons GCU, GCC, GCA, or GCG.

In hBR96-2H, alanine at positions 235, 237, and 331 is encoded by condons GCU, GCC, GCA, or GCG. Additionally, serine at positions 318, 320, 322 is encoded by UCU, UCC, UCA, or UGG.

Any of the above can be deoxyribonucleic acid (DNA), e.g., complementary DNA (cDNA), or ribonucleic acid (RNA).

Immunoconjugates

Immunoconjugates (having whole antibody or Ig fusion proteins) may be constructed using a wide variety of chemotherapeutic agents such as folic acid and anthracyclines (Peterson et al., "Transport And Storage Of Anthracyclines In Experimental Systems And Human Leukemia", in Anthracycline Antibiotics In Cancer Therapy, Muggia et al. (Eds.), p. 132 (Martinus Nijhoff Publishers (1982); Smyth et al., "Specific Targeting of Chlorambucil to Tumors With the Use of Monoclonal Antibodies", J. Natl. Cancer Inst., 76:503–510 (1986)), including doxorubicin (DOX) (Yang and Reisfeld "Doxorubicin Conjugated with a Monoclonal Antibody Directed to a Human Melanoma-Associated Proteoglycan Suppresses Growth of Established Tumor xenografts in Nude Mice PNAS (USA)" 85:1189–1193 (1988)), Daunomycin (Arnon and Sela "In Vitro and in vivo Efficacy of Conjugates of Daunomycin With Anti-Tumor Antibodies" Immunol. Rev., 65:5–27 (1982)), and morpholinodoxorubicin (Mueller et al., "Antibody Conjugates With Morpholinodoxorubicin and Acid-Cleavable Linkers", Bioconjugate Chem., 1:325–330 (1990)).

BR96 has been conjugated to doxorubicin and has been shown to be effective in therapy of certain cancers or carcinomas (Trail, P. A., Willner, D., Lasch, S. J., Henderson, A. J., Casazza, A. M., Firestone, R. A., Hellström, I., and Hellström, K. E. Cure of xenografted human carcinomas by BR96-doxorubicin immunoconjugates. Science, 261:212–215, 1993).

In accordance with the practice of the invention, structurally altered BR96 can be used in forms including unreduced IgG, reduced structurally altered IgG, and fusion proteins (EP Application No. 95/305444, published Mar. 6, 1996).

Suitable therapeutic agents for use in making the immunoconjugate includes Pseudomonas exotoxin A (PE) in either the native PE or LysPE40 form. LysPE40 is a truncated form containing a genetically modified amino terminus that includes a lysine residue for conjugation purposes. Doxorubicin is also a suitable therapeutic agent.

Additional examples of therapeutic agents include, but are not limited to, antimetabolites, alkylating agents, anthracyclines, antibiotics, and anti-mitotic agents.

Antimetabolites include methotrexate, 6-mercaptopurine, 6-thioguanine, cytarabine, 5-fluorouracil decarbazine.

Alkylating agents include mechlorethamine, thiotepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin.

Anthracyclines include daunorubicin (formerly daunomycin) and doxorubicin (also referred to herein as ADRIAMYCIN (doxorubicin HCl). Additional examples include mitozantrone and bisantrene.

Antibiotics include dactinomycin (formerly actinomycin), bleomycin, mithramycin, and anthramycin (AMC).

Antimitotic agents include vincristine and vinblastine (which are commonly referred to as vinca alkaloids).

Other cytotoxic agents include procarbazine, hydroxyurea, asparaginase, corticosteroids, mytotane (O,P'-(DDD)), interferons.

Further examples of cytotoxic agents include, but are not limited to, ricin, bryodin, gelonin, supporin, doxorubicin, TAXOL, cytochalasin B, gramicidin D, ethidium bromide, etoposide, tenoposide, colchicine, digyhdroxy antracin dione, 1-dehydrotesteosterone, and glucocoticoid.

Clearly analogs and homologs of such therapeutic and cytotoxic agents are encompassed by the present invention. For example, the chemotherapeutic agent aminopterin has a correlative improved analog namely methotrexate.

Further, the improved analog of doxorubicin is an Fe-chelate. Also, the improved analog for 1-methylnitrosourea is lomustine. Further, the improved analog of vinblastine is vincristine. Also, the improved analog of mechlorethamine is cyclophosphamide.

Methods for Making Molecules of the Invention

There are multiple approaches to making site specific mutations in the $CH_2$ domain of an immunoglobulin molecule. One approach entails PCR amplification of the $CH_2$ domain with the mutations followed by homologous recombination of the mutated $CH_2$ into the vector containing the desired immunoglobulin, e.g., hBR96-2. For example, hBR96-2B, hBR96-2D, hBR96-2F, and hBR96-2H have been made by this method.

Another approach would be to introduce mutations by site-directed mutagenesis of single-stranded DNA. For example, vector pD17-hG1b, which contains only the constant region of IgG1 and not the V domain of hBR96, has the f1 origin of replication. This gives the vector the properties of a phagemid and site-directed mutagenesis experiments can be performed according to the methods of Kunkel, et al. (Kunkel, T. A., J. D. Roberts, and R. A. Zakour, 1987 Methods Enzymol. 154:367–383) as provided in the Bio-Rad Muta-Gene® phagemid in vitro mutagenesis kit, version 2. For example, hBR96-C, -E and -G were made by this method.

In order that the invention described herein may be more fully understood, the following examples are set forth. It should be understood that these examples are for illustrative purposes only and are not to be construed as limiting the scope of this invention in any manner.

EXAMPLE 1

The following standard ELISA protocol was used.

Materials: Immulon2 96 well plates and Genetic Systems Specimen Diluent Concentrate (10x); antibody conjugate was Goat Anti Human Kappa-HRP Mouse Adsorbed, Southern Biotech. at 1:10,000 in Genetic Systems Conjugate Diluent (1x); Genetic Systems EIA Chromogen Reagent (TMB) (1:100); Genetic Systems EIA Buffered Substrate (1x); plate coat antibody or antigen were AffiniPure F(ab')$_2$ Fragment Goat Anti Human IgG Fc Fragment specific (Jackson Immuno Research), Goat Anti Human Kappa-UNLB (Southern Biotechnology Associates), Le$^y$-HSA (Alberta Research Council).

Methods: Dilute plate coat antibody or antigen to 1.0 µg/ml in 0.05 M Carb/Bicarb buffer. Add 100 µl of the diluted solution per well in Immulon 2 plates. Seal plates are incubate O.N. at 4° C.

Block plates by flicking them and blotting on paper towels. Add 200 µl/well of Genetic Systems, Specimen Diluent Concentrate (1x). Incubate at least 1 hour at room temperature and then dump the contents of the plates. Wash the plates 3x in saline/Tween. Blot to dry. Allow the plates to dry at R.T. (45 min. to 1 hour). Seal and store the plates at 4° C.

Test samples as follows. Dilute samples and standards in Specimen Diluent at 1:10. Perform serial dilutions in separate round bottom plates. Transfer 100 µl/well of final dilutions to antigen coated assay plates; then incubate O.N. at 4° C. Wash plates 3x with saline/Tween.

Add 100 µl/well of antibody-HRP conjugate in Genetic Systems Conjugate Diluent (1x). Incubate plates at Room Temp. for 60 min. Wash plates 3x in saline/Tween.

Add 100 µl/well of Genetic Systems EIA Chromogen Reagent (TMB) 1:100 in EIA Buffered Substrate (1x). Incubate at R.T. for 15 min. and stop with 1 N H$_2$SO$_4$, 100 µl/well. Read plate at 450/630 nm in EIA plate reader.

EXAMPLE 2

Construction of CH$_2$ deleted BR96 molecules

Strategy for Deleting CH$_2$ Domains: To construct CH$_2$ deleted BR96 molecules, the hinge, CH$_2$ and CH$_3$ domains were removed from chimeric BR96 and humanized BR96-2 IgG1 molecules by an Eco47-III restriction digestion in non-coding regions. The hinge and CH$_3$ domains were amplified by polymerase chain reaction (PCR) from a human IgG1 (pNγ1.14) molecule lacking the CH$_2$ domain. Two oligonucleotides (Sense 49 mer, Antisense 50 mer) homologous to the sequences of IgG1 constant region at both 3' and 5' ends preserving Eco47-III sites were synthesized. The amplified hinge and CH$_3$ domain PCR fragments were added into Eco47-III sites on BR96 IgG1 molecules by in vivo homologous recombination (P. Bubeck et al., Nucleic Acid Research (1993) 21:3601–3602). The new BR96 IgG1 molecules were verified by restriction mapping and sequencing.

A sewing PCR strategy was used for the construction of CH$_2$ deleted human IgG1 (pNγ1.14) (Robert M. Horton, et al. (1990) Biotech 8 (5)P, 528).

The CH$_1$ domain was amplified as a 580 bp fragment with a sense oligonucleotide (5' TGG CAC CGA AAG CTT TCT GGG GCA GGC CAG GCC TGA 3'), (SEQ ID NO. 1), (primer A) and an antisense oligonucleotide (5' TCC GGA CAT GTT GGT ACC CAC GTG GTG GTC GAC GCT GAG CCT GGC TTC GAG CAG ACA 3'), (SEQ ID NO. 2), (primer B) from a lineraized human IgG1 constant region vector (pNγ1.7). The PCR fragment extends from the 5' end of the Hind-III site (in bold) through the Cel-II, Sal-I, Dra-III, Kpn-I, 6 bp nucleotide spacer and Mro-I sites (in bold) at the 3' end of the CH$_1$ domain.

The CH$_3$ domain was then partially amplified (to the Xba-I site) with a sense primer (5' GTC GAC CAC CAC GTG GGT ACC AAC ATG TCC GGA GCC ACA TGG ACA GAG GCC GGC T 3'), (SEQ ID NO. 3), (primer C) and an antisense primer (5' CTG GTT CTT GGT CAT CTC CTC TCT AGA TGG 3'), (SEQ ID NO. 4), (primer D) from a linearized human IgG1 constant region vector (pNγ1.7). A PCR fragment (about 150 bp) with Sal-I, Dra-III, Kpn-I, 6 nucleotide spacer and Mro-I sites (in bold) on its 5' end, extends only through the Xba-I site (in bold) within the CH$_3$ domain.

The CH$_1$ and CH$_3$ partial PCR fragments were combined in a PCR without any primer. The reaction was run through two full cycles of denaturation and reannealing to allow the fragments to combine at the homologous region at the 3' ends. Primers A and D (described above) were added to the reaction and the PCR cycle was completed. The polymerase extends the DNA with primer A and primer D, yielding a full-length (660 bp) PCR fragment. The newly extended PCR fragment is arranged from the 5' end to the 3' end in the following order: Hind-III-CH$_1$-Cel-II-Sal-I-Dra-III-Kpn-I-6 bp spacer-Mro-I-CH$_3$ partial-Xba-1.

The combined PCR fragment, with the CH$_1$ and partial CH$_3$ domains, was then cloned by a blunt end ligation into a Sma-I site on a pEMBL18 vector and the sequence was confirmed by dideoxy sequencing (Sanger et al. (1977) PNAS (USA) 74:5463–5466).

To transfer the CH$_1$ and partial CH$_3$ into a mammalian expression vector, both the pEMBL18 and pNγ1.7 vectors were digested with Hind-III and Xba-I. The Hind-III and Xba-I fragment was ligated into the same sites on a linearized pNγ1.7 vector. The new construct, with CH$_1$ and a full CH$_3$ domain, was designated the pNγ1.10 vector.

The hinge fragment was amplified from a Hind-III digested pNγ1.7 vector with the primers designed to flank the hinge exon with a Sal-I and a Dra-III cloning site at each end. These sites also exist between the CH$_1$ and CH$_3$ domains of the pNγ1.10 construct. The sense oligonucleotide (5' ACC ATG GTC GAC CTC AGA CCT GCC AAG AGC CAT ATC 3') with a 6 bp spacer and a Sal-I cloning site (in bold) and the antisense oligonucleotide (5' CAT GGT CAC GTG GTG TGT CCC TGG ATG CAG GCT ACT CTA G 3') with a 6 bp spacer and a Dra-III cloning site (in bold) were used for the amplification of the hinge fragment (250 bp).

The hinge region PCR fragment was cloned into a Sma-I site on pEMBL18 by blunt end ligation. Both the pEMBL18 with the hinge domain and the pNγ1.10 with the CH$_1$ and CH$_3$ domains were digested with Sal-I and Dra-III. The digested hinge fragment was cloned into the Sal-I and Dra-III lineraized sites on the pNγ1.10 vector. The new construct, now carrying the CH$_1$, hinge and CH$_3$ domains, was designated pNγ1.11.

Figure 11:
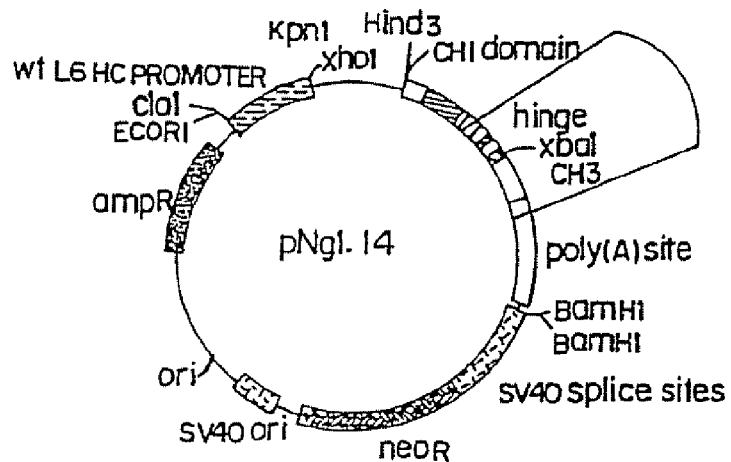
FIG. 11 is a schematic diagram showing the construction of the pNq1.14 vector.

To make the final CH$_2$ deleted human IgG1 construct, both the pNγ1.11 construct and pNγ1.11 vector were digested with BamH1 and HindIII. A fragment containing the CH$_1$, hinge and CH$_3$ domains was cloned into the lineraized pNγ1.11 vector. The new constant region IgG1 construct lacks the CH$_2$ domain and is designated pNγ1.14 (FIG. 11).

Figure 12:
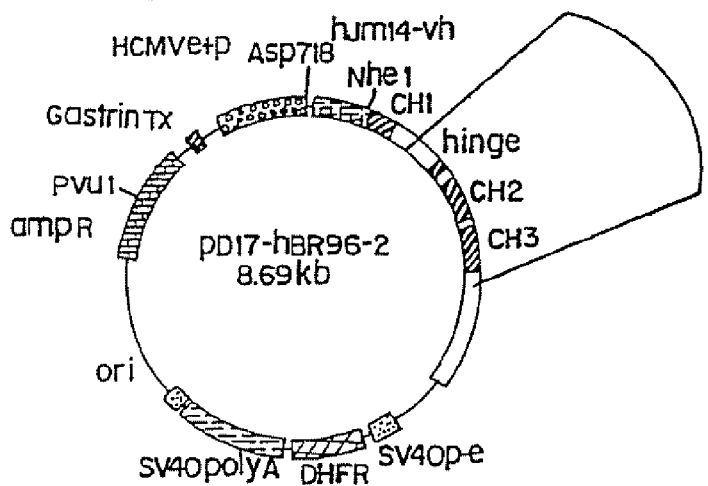
FIG. 12 is a schematic diagram showing the construction of pD17-hBR96-2.

Digestion of the BR96 IgG1 vector with Eco47-III, generates a restriction fragment with hinge, CH$_2$ and CH$_3$ domains in both chimeric and humanized molecules. The 5' end of this fragment lies inside the intron between CH$_1$ and hinge and the 3' end is located inside the CH$_3$ intron of the BR96 IgG1 molecule. The hinge, CH$_2$ and CH$_3$ domains (1.368 kb fragment) were removed from BR96 IgG1 molecules by Eco47-III restriction digestion. The Eco47-III is a blunt end cutter. The BR96 IgG1 DNA digested with this enzyme does not require any pretreatment before cloning. FIG. 12 is a diagrammatic representation of the pD17-hBR96-2 vector showing the Eco47-III sites used in cloning.

The $CH_2$ deleted BR96 IgG1 was then constructed as follows. The hinge and $CH_3$ domains were amplified from the pNγ1.14 vector construct with a sense oligonucleotide (5' CAGGGAGGGAGGGTGTCTGCTGGAAGC-CAGGCTCAGCGCTGACCTCAGA 3'), (SEQ ID NO. 7), homologous to the constant region sequence of IgG1 at the 5' end of the Eco47-III site (in bold) and an antisense oligonucleotide (5'GGAAAGAACCATCACAGTCTCG-CAGGGG CCCAGGGCAGCGCTGGGTGCTT 3'), (SEQ ID NO. 8), homologous to the constant region sequence of IgG1 at the 3' end of the Eco47-III site (in bold). The Eco47-III site at the 3' end of the pNγ1.14 construct is modified in the cloning process. The Eco47-III site is thus introduced into an antisense primer and used in amplification of the hinge and $CH_3$ domains.

Figure 13:
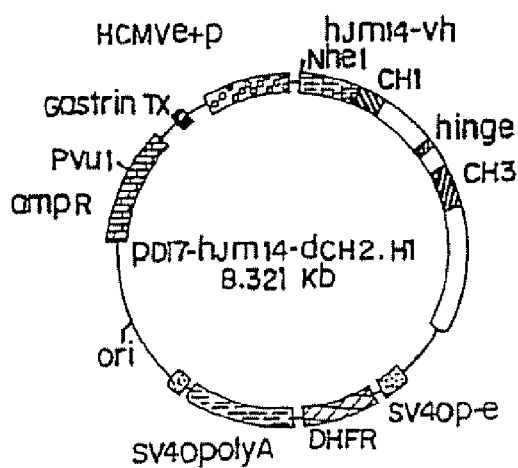
FIG. 13 is a schematic diagram showing the construction of pD17-hJm14-dCH2.H1.
Figure 15:
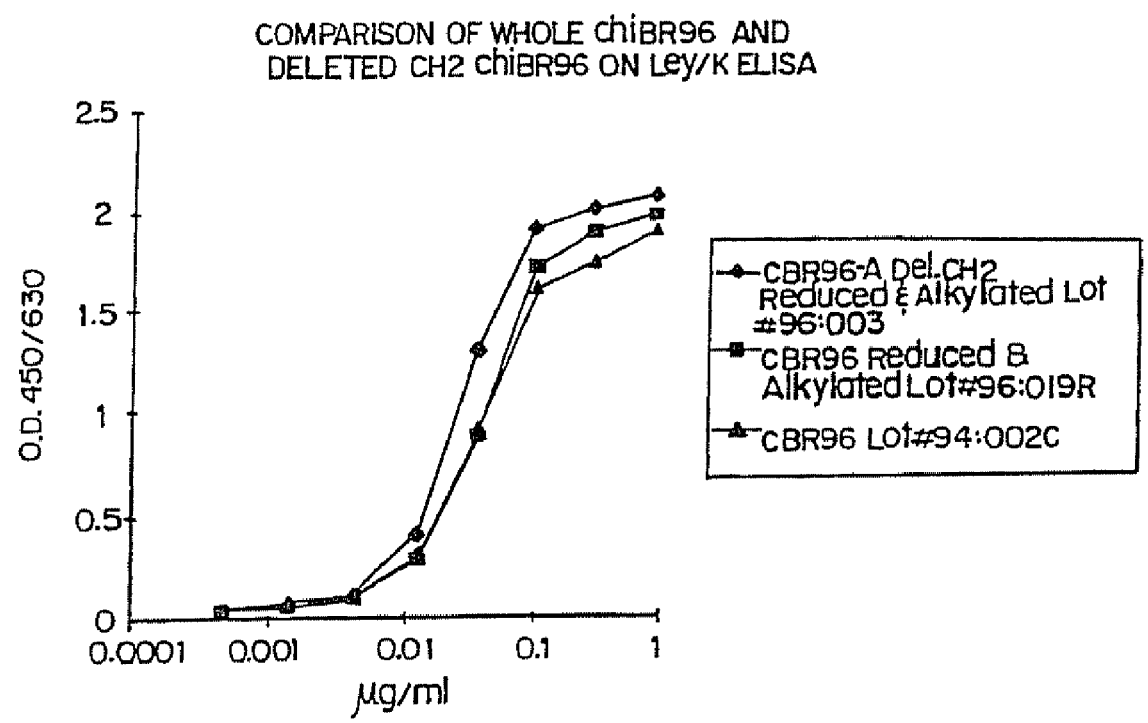
FIG. 15 is a line graph showing the results of an ELISA assay comparing whole chiBR96 and deleted CH$_2$ chiBR96 on Le$^y$.
Figure 17:
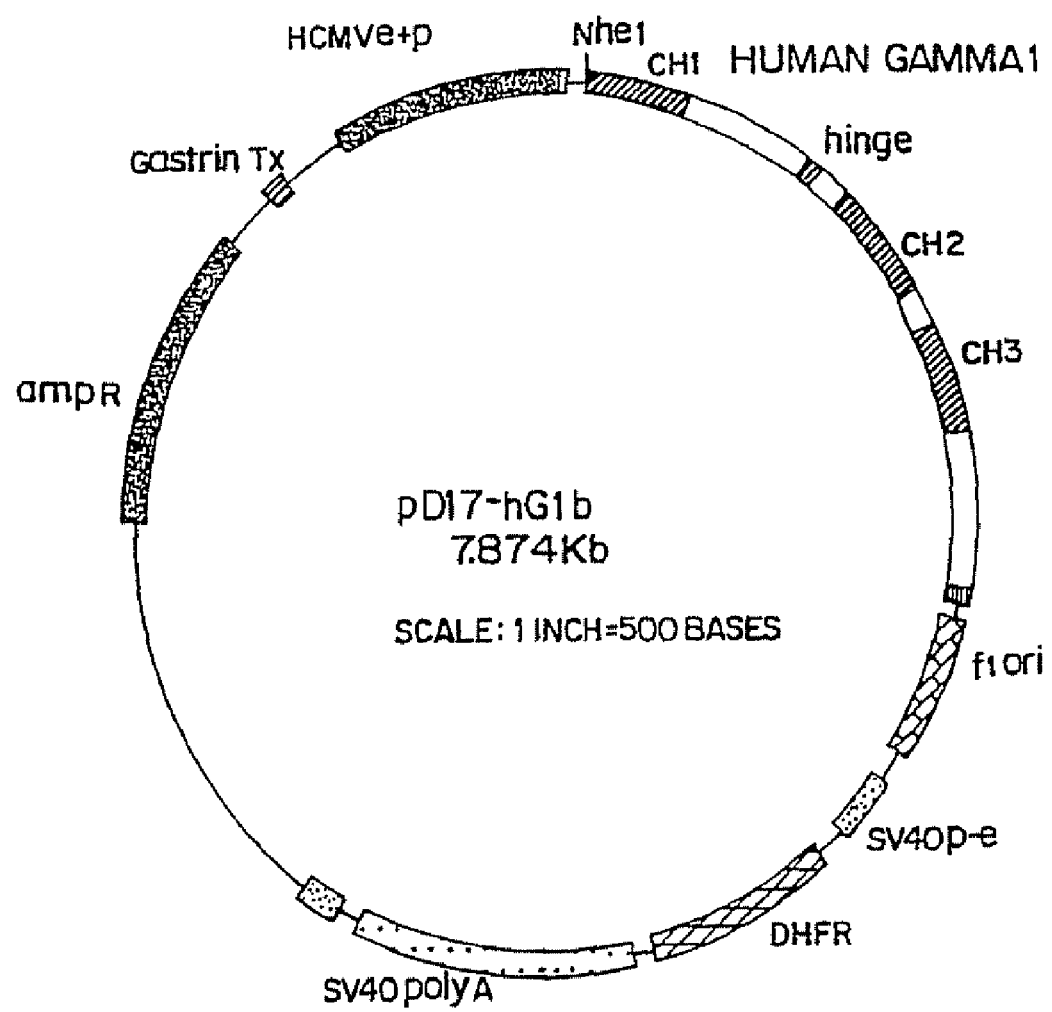
FIG. 17 is a schematic diagram of a plasmid designated pD17-hG1b.
Figure 20:
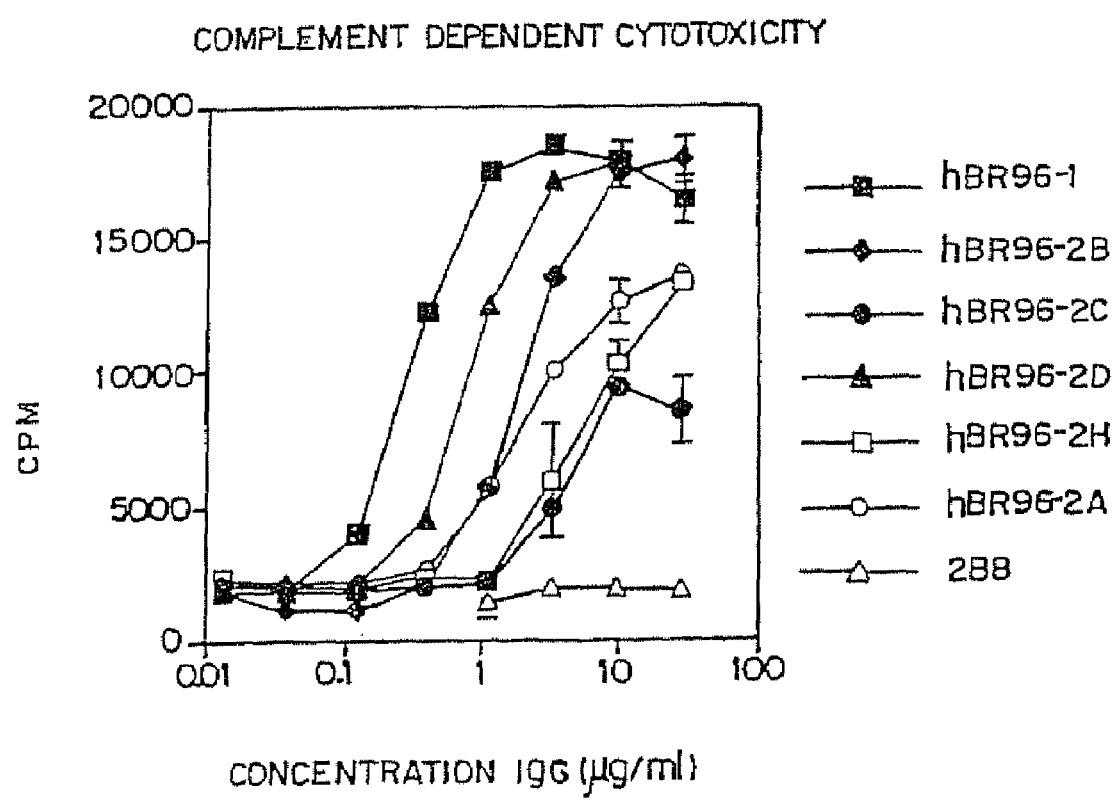
FIG. 20 is a line graph showing complement dependent cytotoxicity. In the legend, the closed square is hBR96-1; closed diamond is hBR96-2B; closed circle is hBR96-2C; closed triangle is hBR96-2D; open square is hBR96-2H; open circle is hBR96-2A and open triangle is 2B8, anti-Pseudonomas aeruginosa flagella type b mAb, negative control.
Figure 21:
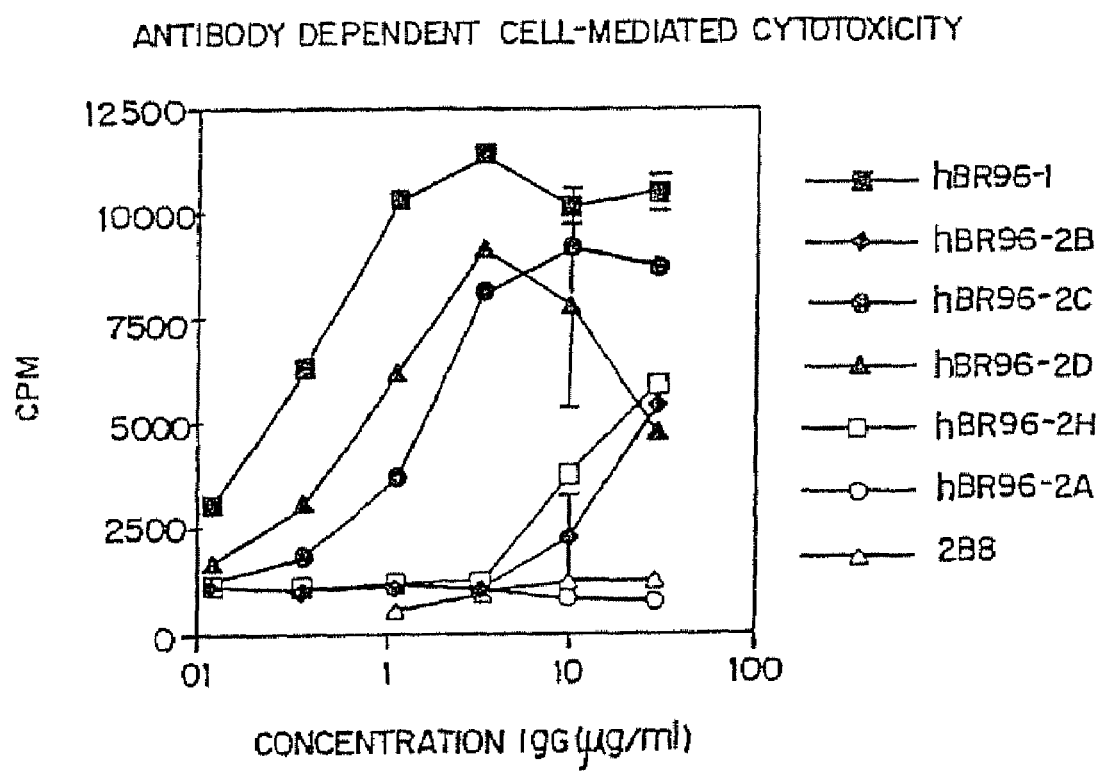
FIG. 21 is a line graph showing antibody dependent cell-mediated cytotoxity. In the legend, the closed square is hBR96-1; closed diamond is hBR96-2B; closed circle is hBR96-2C; closed triangle is hBR96-2D; open square is hBR96-2H; open circle is hBR96-2A and open triangle is 2B8, anti-Pseudonomas aeruginosa flagella type b monoclonal antibody (mAb), negative control.
Figure 22:
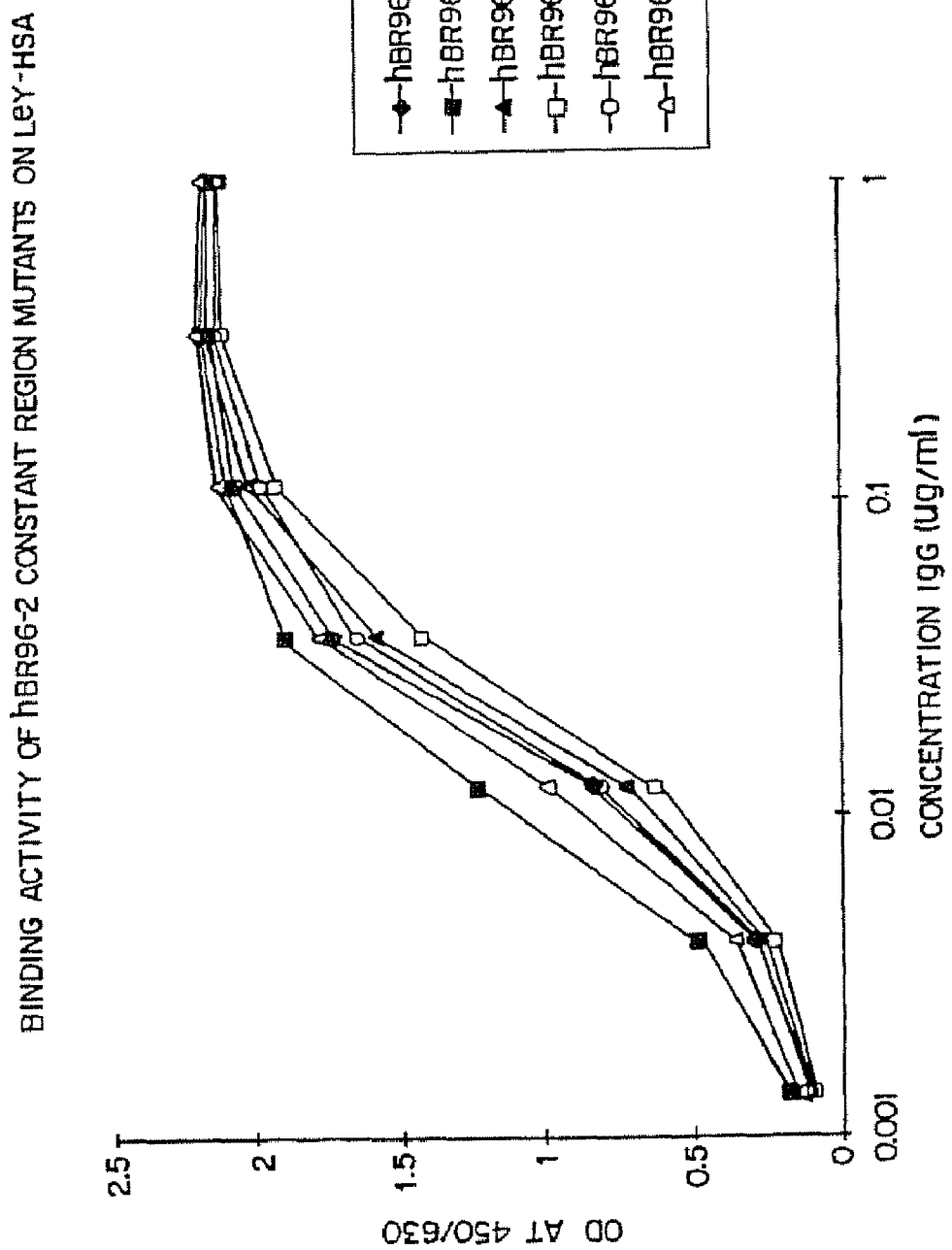
FIG. 22 is a line graph showing binding activity of hBR96-2 constant region mutants on LeY-HSA. In the legend, the solid diamond is hBR96-1; solid square is hBR96-2A (CH2 deletion); solid triangle is hBR96-2B (235, 237 mutations); open square is hBR96-2C (318, 320, 322 mutations); open circle is hBR96-2D (331 mutation); and open triangle is hBR96-2H (235, 237, 318, 320, 322, 331 mutations).
Figure 23:
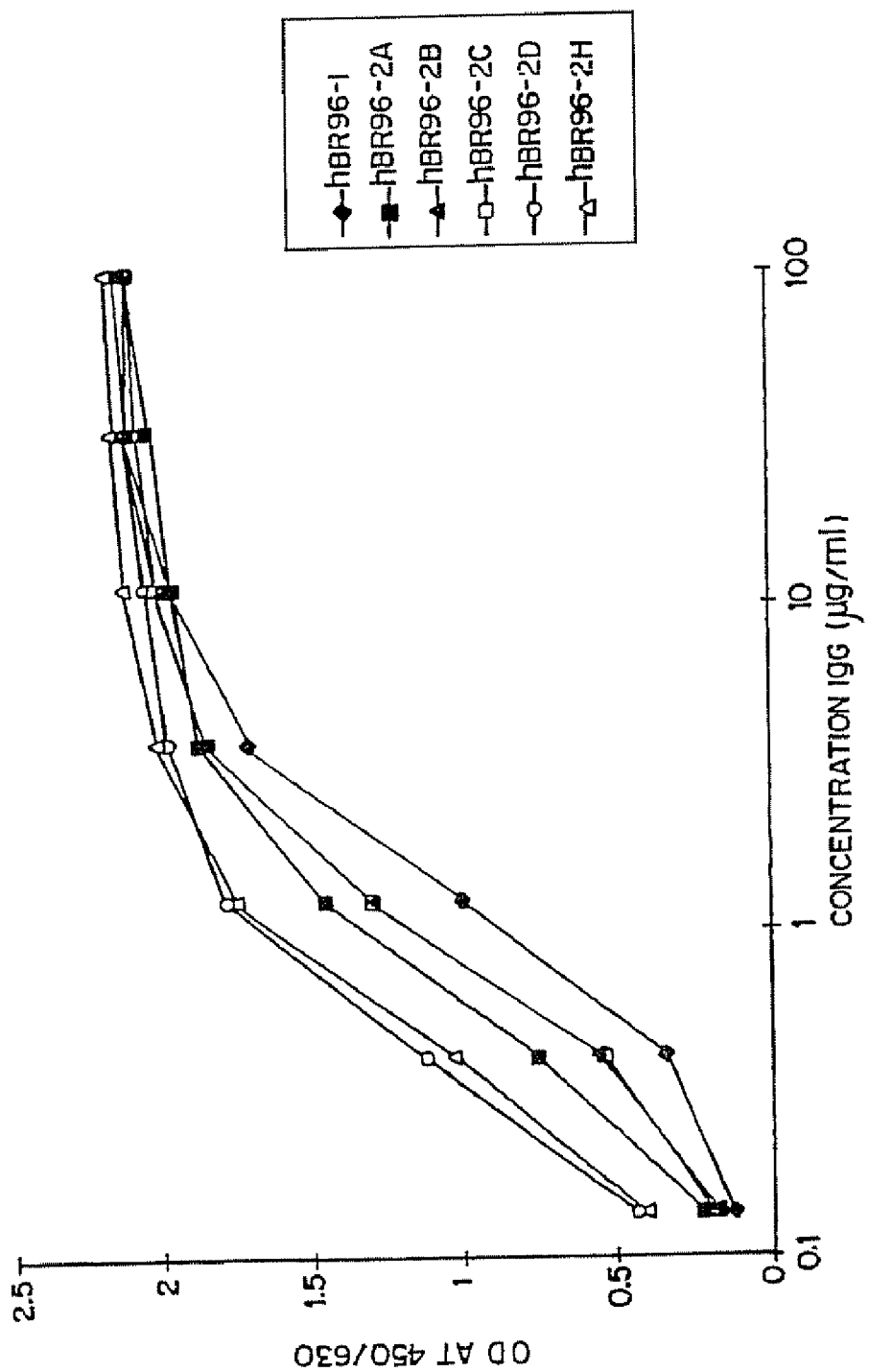
FIG. 23 is a line graph showing binding activity of hBR96-2 constant region mutants on LNFPIII-BSA. LNFPIII is a lacto-N-fucopentasose, a Lewis X trisaccharide with an additional lactose spacer (V Labs, Covington, La.). In the legend, the solid diamond is hBR96-1; solid square is hBR96-2A (CH2 deletion); solid triangle is hBR96-2B (235, 237 mutations); open square is hBR96-2C (318, 320, 322 mutations); open circle is hBR96-2D (331 mutation); and open triangle is hBR96-2H (235, 237, 318, 320, 322, 331 mutations).
Figure 24A:
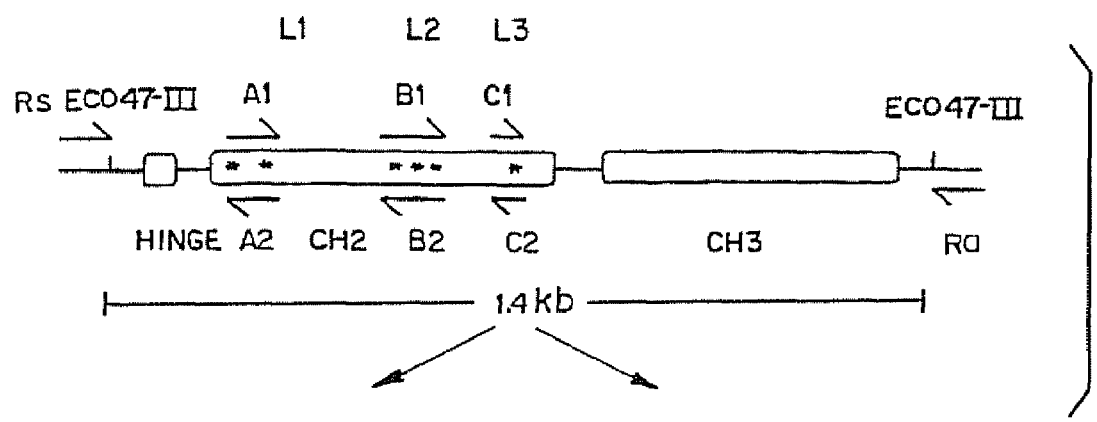
FIGS. 24A and 24B provide a strategy for introducing multiple mutations by RPCR. (A) Diagram of he 1.4 kpb IgG heavy chain region showing the hinge CH$_2$ and CH$_3$ domains as boxed regions. Site-specific mutations to be introduced into CH2 positions L1, L2, and L3 are encoded by complementary sets of mutant PCR primers (A1 and A2; B1 and B2; and C1 and C2). The asterisks (*) indicate the number of amino acid changes introduced at each L position. The two PCR primers, Rs (Recombination-sense) and Ra (Recombination-antisense), flank the Eco-47-III restriction sites and mediate homologous recombination with vector ends. The 3' ends of the oligonucleotides are represented by arrowheads. (B) A three-way homologous recombination event between fragments RsA2, A1Ra and the linearized vector produces the L1 mutant IgG. Two distally located sets of mutations (L1 and L2) are simultaneously introduced by increasing the number of recombining PCR produces as is shown in the four-way recombination of RsA2, A1B1, B1Ra with vector.
Figure 24B:
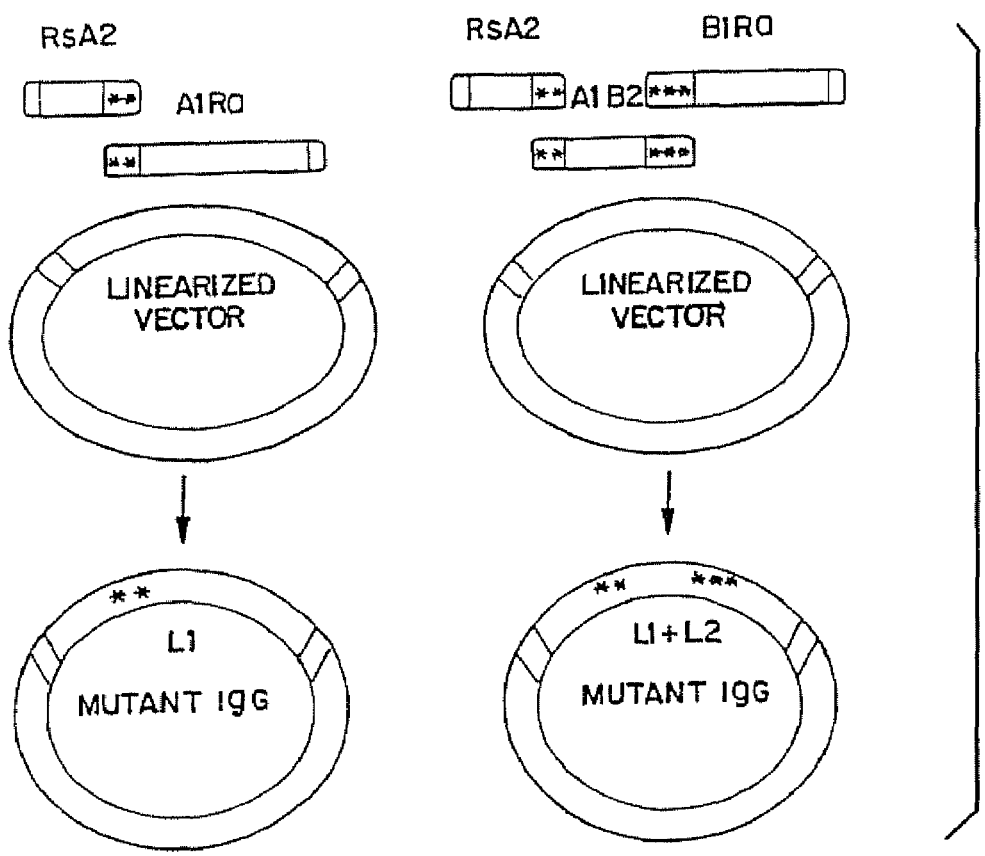

The pD17-BR96 IgG1 vector was digested with Eco47-III and the hinge, $CH_2$ and $CH_3$ domains were removed. The linearized pD17-BR96 IgG1 vector was mixed with equimolar amounts of hinge and $CH_3$ PCR fragments. Cotransformation of the PCR fragment with linearized DNA into E.coli DH5α competent cells resulted in a recombinant molecule, mediated by homologous recombination in bacteria. This construct lacks the $CH_2$ domain of BR96 IgG1 molecules, and is designated pD17-BR96-dCH2 (FIG. 13).

1.9 grams of $CH_2$-deleted chimeric BR96 was obtained as raw material from 89L of culture supernatant.

EXAMPLE 3

Toxicity, localization and clearance of $CH_2$-deleted chimeric BR96 was tested in vivo as follows.

Three dogs received 400 mg/m² of cBR96-A, the $CH_2$ deletion mutant of chimeric BR96, and two received chimeric BR96. Both molecules had been mildly reduced and alkylated. This is required to prevent dimerization of the deletion mutant into a tetravalent form. Both control dogs experienced the typical GI toxicity and none of the three receiving the mutant displayed any toxicity. The control dogs and two of the test dogs were sacrificed at 1 hr to obtain duodenal tissue to measure antibody localization. Both control dogs had grossly visible GI pathology, and the test dogs had normal appearing GI tissue. The third dog has continued to show no signs of toxicity.

Results: A significant amount of localization of the $CH_2$ deleted cBR96 (cBR96-A) occurred to the GI tract in dogs treated with 400 mg/m², although the intact chiBR96 localized slightly better. The levels of localization indicate that roughly equivalent amounts of intact and $CH_2$ deleted cBR96 was delivered to the GI tract in these dogs.

TABLE 1

Localization of cBR96 to GI tissue.

| Group | Animal | Specific Localization | mean |
|---|---|---|---|
| cBR96 | #271 | 155 | 135 |
|  | #272 | 114 |  |
| cBR96-A | #273 | 126 | 89 |
|  | #274 | 52 |  |

Using the mean level of specific localization, an amount of cBR96-A equivalent to at least 66% of the amount of cBR96 was delivered to the target organ of toxicity, the duodenum. Based on the dose ranging done with cBR96 in dogs (some clinical sings of toxicity seen at doses of 10 mg/m²), even if this difference is real, it could not explain the difference between significant toxicity and no toxicity. Evaluation to date indicated that dogs treated with cBR96-A had no toxicity, pending microscopic histopathologic examination. This evaluation was based on analysis of 2 frozen blocks per dog and 2 sections per block. Replicates were quite good. We also ran historical frozen tissues from dogs treated with native cBR96 or F(ab)2/BR96 and the levels of localization for those tissues were 110 and 0, respectively, consistent with our previous data.

Assuming that there is no toxicity at marginally higher (2×) doses of cBR96-A, these data indicate that the $CH_2$ domain is associated with the induction of acute gastroenteropathy, and that the removal of this domain prevents the induction of gastroenteropathy mediated by BR96.

This study confirms the results showing that F(ab')2 is not toxic in the dog model and that the toxicity is medicated by the constant region. The $CH_2$ deletion mutant is a candidate for targeting agents clinically. Because of the very long half-life of chimeric BR96, some decrease in the mutant's half-life should be acceptable.

FIG. 1 shows the measurement of the clearance of the cBR96-A in high Le$^y$ expressing dogs. The study used chimeric versus constant region mutant of cBR96-A.

CBR96-A did clear faster than the chimeric BR96. The localization of cBR96-A to the gastrointestinal epithelium is not significantly affected by this more rapid clearance. More than enough of the cBR96-A localized to have cause toxicity.

Discussion: The constant region of chimeric IgG is responsible for the GI toxicity seen in clinical trials, i.e. with chiBR96-dox. The GI toxicity seen in the dog model is very similar to the clinical toxicity. Both in man and dog, administration of the unconjugated antibody mediated an acute GI toxicity characterized by rapid onset of vomiting, often with blood.

In man the bleeding is limited to the fundus of the stomach, causing erosion of the superficial mucosa of the stomach. Although the pathology of the wound is limited and resolves, the extreme nature of the nausea and vomiting, unrelieved by anti-emetics, defines it as the dose-limiting toxicity.

This toxicity is mediated in man and dog by the antibody molecule alone. At higher doses of the antibody-dox conjugate, additional toxicity is seen in the dog model, probably due to doxorubicin. Although the intact IgG of BR96 causes toxicity in dog and man, the F(ab')2 molecule (divalent and lacking only in the constant region) is not toxic in dogs.

The $CH_2$ domain is known to mediate complement and FcR binding. It was not known that structural alteration of the $CH_2$ domain would result in immunoglobulin-induced toxicity inhibition.

Toxicology Study of hBR96-2B

The toxicology study of hBR96-2B in high Lewis Y expresser dogs (n=2) showed that a dose of 400 mg/m² did not cause hematemesis nor bloody stools, in contrast to BR96 which consistently causes one or both signs. A dog sacrificed at 24 hrs had normal gross appearance of the GI tract, again in marked contrast to chimeric BR96 which causes hemorrhagic lesions and mucosal erosions.

EXAMPLE 4

(PCR) is a widely used and versatile technique for the amplification and subsequent modification of immunoglobulin genes. The rapidity and accuracy with which antibody genes can be modified in vitro has produced an assortment of novel antibody genes. For example, PCR methods have been used for engineering antibodies with increased affinity to antigen, for "humanizing" antibodies, and for modulating effector function (Marks, J. D., A. D. Griffiths, M. Malmqvist, T. Clackson, J. M. Bye and G. Winter. 1992. Bypassing immunization: high affinity human antibodies by chain shuffling. Bio/Technology 10:779–783; Rosok, M. J., D. E. Yelton, L. J. Harris, J. Bajorath, K.-E. Hellstrom, I. Hellstrom, G. A. Cruz, K. Kristensson, H. Lin, W. D. Huse and S. M. Glaser. 1996. A combinatorial library strategy for the rapid humanization of anticarcinoma BR96 Fab. J. Biol. Chem. 271:22611–22618; Morgan, A. N., D. Jones, A. M. Nesbitt, L. Chaplin, M. W. Bodmer and S. Emtage. 1995. The N-terminal end of the CH2 domain of chimeric human IgG1 anti-HLA-DR is necessary for C1q, FcγRI and FcγRIII binding. Immunology. 86:319–324).

We introduced various site specific mutations in the $CH_2$ constant domain of human $IgG_1$. Six specific amino acid residues distributed throughout the CH2 domain previously identified to play a role in immune effector function were marked as targets for mutagenesis (Morgan, A. N., D. Jones, A. M. Nesbitt, L. Chaplin, M. W. Bodmer and S. Emtage. 1995. The N-terminal end of the CH2 domain of chimeric human IgG1 anti-HLA-DR is necessary for C1q, FcγRI and FcγRIII binding. Immunology. 86:319–324; Duncan, A. R. and G. Winter. 1988. The binding site for C1q on IgG. Nature 332:738–740; Tao, M.-H., R. I. F. Smith and S. L. Morrison. 1993. Structural features of human immunoglobulin G that determine isotype-specific differences in complement activation. J.Exp.Med. 178:661–667). Five of the six residues were grouped into two cluster. One cluster consisted of two residues, two amino acids apart (Location 1, or L1), and a second cluster consisted of three residues spanning a sequence of five amino acids (L2). The remaining amino acid position (L3) made for the total of six residues. We constructed a panel of mutant $CH_2$ domain IgGs consisting of each L mutation by itself as well as in combination with other L mutants (e.g., L1; L1; and L2; L1, L2 and L3; etc.).

Various in vitro methods have been described where PCR is used to simultaneously introduce distally located site-specific mutations within a gene sequence (Ho, S. N., H. D. Hunt, R. M. Horton, J. K. Pullen and L. R. Pease. 1989. Site-directed mutagenesis by overlap extension. Gene 77:51–59; Ge, L. and P. Rudolpf. 1996. Simultaneous introduction of multiple mutations using overlap extension PCR. BioTechniques 22:28–30). Alternatively, an in vivo procedure termed recombination PCR (RPCR) has also successfully been used for rapidly and efficiently generating distally located site-specific mutations (Jones, D. H. and S. C. Winistorfer. 1993. Use of polymerase chain reaction for making recombinant constructs. p.241–250. In B. A. White (Ed.), Methods in Molecular Biology, Vol. 15. Humana Press Inc., Totowa, NJ, Jones, D. H. And B. H. Howard. 1991. A rapid method for recombination and site-specific mutagenesis by placing homologous ends on DNA using polymerase chain reaction. BioTechniques 10:62–66). RPCR uses *E. coli's* recombination machinery to generate intact circular recombinant plasmids from a transfected mixture of linear PCR-generated product and lineraized vector. In vivo recombination is mediated through the joining of nucleotide sequences designed into the 5' ends of both PCR primers that are homologous to DNA sequences encoded by the vector. In this report we describe an extension of the RPCR procedure for simultaneously introducing complex combinations of mutations into an antibody $CH_2$ domain.

Humanized BR96 variable region heavy and light chain genes, previously cloned and co-expressed as an assembled active Fab fragment in an M13 phage expression vector, provided the starting material (Rosok, M. J., D. E. Yelton, L. J. Harris, J. Bajorath, K.-E. Hellstrom, I. Hellstrom, G. A. Cruz, K. Kristensson, H. Lin, W. D. Huse and S. M. Glaser. 1996. A combinatorial library strategy for the rapid humanization of anticarcinoma BR96 Fab. J. Biol. Chem. 271:22611–22618). The heavy and light chain V genes were amplified by PCR from a single-stranded M13 DNA template and subcloned by in vivo recombination (Jones, D. H. And B. H. Howard. 1991. A rapid method for recombination and site-specific mutagenesis by placing homologous ends on DNA using polymerase chain reaction. BioTechniques 10:62–66) into vectors pD17-hG1a and pD16-hCκ, to form pBR96-hG1a and pBR96-hCκ respectively. pD17-hG1a and pD16-hCκ are eukaryotic immunoglobulin expression vectors derived from pcDNA3 (Invitrogen, San Diego, Calif.). The plasmid pBR96-hG1a was further modified by site-directed mutagenesis to introduce two Eco47-III restriction sites flanking the immunoglobulin hinge-$CH_2$-$CH_3$ domains using standard procedures. The recipient vector was then prepared by digesting pBR96-hG1a with Eco47-III, isolating the vector backbone by agarose gel electrophoresis followed by extracting the vector DNA from the excised gel slice using the Qiagen Gel Extraction kit (Qiagen, Chatsworth, Calif.).

The strategy for introducing multiple mutations within the immunoglobulin $CH_2$ gene, shown in FIG. 24, relies on the in vivo homologous recombination of several independently amplified PCR products with each other as well as with the pBR96-hG1a vector DNA. For introducing mutations at two distal locations two PCR products are synthesized (FIG. 24B). One end of each PCR product is for recombining with an homologous end of the linear vector, and the other end, encoding the mutation(s) of interest, is for recombining with the neighboring PCR product. As shown in FIG. 24B, additional distally-located mutations can be introduced into a target sequence by increasing the number of PCR products proportionately. The recombination of neighboring PCR products always occurs across the regions containing the desired mutations, therefore the oligonucleotide primers encoding these ends (e.g., A1, A2) contain complementary mutant residues. The mutagenic PCR primers contain at least 15 nucleotides of wild-type sequence flanking each side of the mutant residue for either priming the polymerization reaction or mediating recombination. Two 49-nucleotide long PCR sense and anti-sense primers (Rs and Ra) contain sequences for recombining with the end regions of the Eco47-III digested pBR96-hG1a vector.

Each L mutation was amplified in a separate PCR reaction. The reaction conditions were 250 ng intact pBR96-hG1a DNA template, 10 ul of 1× Pfu buffer (Stratagene, Inc. San Diego, Calif.), 10 nmol dNTPs, 200 ng each of the appropriate PCR primers, 10% dimethysulfoxide (ATCC, Manassas, Va.) and 2.5 units cloned Pfu DNA polymerase in a 100 ul reaction volume. Samples were first denatured at 95° C. for 5 min, cooled to 45° C. for 5 min, and extended at 72° C. for 1 min followed by 25 cycles of denaturation at 94° C. for 45 sec, annealing at 45° C. for 45 sec, extension at 72° C. for 1 min/kb, followed by a final extension at 72°

C. for 7 min in a Perkin-Elmer DNA Thermal Cycler (Norwalk, Conn.). The amplified products were purified from a 1% agarose gel, extracted with Qiagen Gel Extraction kit and the recovered DNA quantitated. 50 ng of each PCR product was mixed with 25 ng of the Eco47-III digested pBR96-hG1a vector, transfected into Max competent E. coli DH5α according to the manufacturer's procedure (GIBCO BRL/Life Technologies, Gaithersburg, Md.), and the entire transfection reaction plated onto selection LB agar plates containing 100 ug/ml ampicillin.

The results of several cloning experiments are summarized in the Table that follows. Typically the transformations produced from 80 to 200 bacterial colonies. Individual colonies were selected and grown overnight in 2 ml liquid cultures for isolation of miniprep plasmid DNA (Qiagen) and analysis by Eco47-III restriction endonuclease mapping. Among 24 independent transformants analyzed from triple homologous recombination events (two PCR products plus vector) 11 clones contained the predicted 1.4 kb DNA insert.

Figure 25:
FIG. 25 is a gel showing Eco-47-III restriction endonuclease analysis of DNAs prepared from colonies generated by multiple PCR fragment RPCR. Lane M: 1 kb ladder DNA marker (GIBCO/BRL Life Science Technology). Lanes 1–12: Twelve randomly selected colonies resulting from quadruple homologous recombination events were used to prepare plasmid and digested with Eco47-III. Clones 1, 2, 6 and 9 contain the fully assembled 1.4 kpb insert.

FIG. 25 shows a sample diagnostic restriction analysis of DNA prepared from clones derived from quadruple homologous recombination events (three PCR products plus vector). Additional sampling of clones resulting from quadruple recombination yielded a cloning efficiency of 29% (7 clones containing inserts/24 clones sampled). At this point, due to the small sampling sizes, we do not know whether the differences in the cloning efficiencies observed between the triple and quadruple recombination events are meaningful.

To evaluate the expression of $Le^y$-binding activity of the $CH_2$ mutant IgGs, miniprep DNAs from 6 clones derived from the triple recombination reaction and 6 clones derived from the quadruple recombination reaction exhibiting the predicted diagnostic Eco47-III restriction patterns were isolated, mixed with pBR96-hCκ DNA and used to co-transfect COS7 cells. 48 hours spent supernatants from 3 ml cultures were assayed for total IgG production and for $Le^y$-binding activity by enzyme-linked immunosorbent assay (EIA) as described (Yelton, D. E., M. J. Rosok, G. A. Cruz, W. L. Cosand, J. Bajorath, I. Hellstom, K.-E. Hellstorm, W. D. Huse and S. M. Glaser. 1995. Affinity maturation of the BR96 anti-carcinoma antibody by codon-based mutagenesis. J.Immunol. 155:1994–2004). All twelve cultures were found to secrete approximately 2–3 ug/ml $Le^y$-reactive IgG. The spectrum of $Le^y$ binding activities were all similar to that of native humanized BR96 IgG indicating that the homologously recombined antibodies did not acquire any gross mutations that affected antigen binding. To confirm that the desired $CH_2$ mutations had been incorporated, and to evaluate the recombined genes for misincorporated nucleotides, four of the clones producing functional antibody were sequenced using Sequenase Version 2 DNA Sequencing Kit (United States Biochemical). One clone was found to contain a single nucleotide change within the forward PCR primer used for mediating recombination with vector DNA. We are uncertain whether this error occurred during chemical synthesis of the oligonucleotide primer or is a result of misincorporation during the PCR reaction, despite the fact that we used a thermostable polymerase with proofreading activity.

A RPCR procedure for homologously recombining up to three separate PCR-generated mutated antibody sequence products into a eukaryotic expression vector for the rapid construction of engineered IgG molecules is described herein. The advantage of this approach is the ability to simultaneously introduce multiple distally-located mutations with PCR products synthesized by a single round of PCR. Recombinant DNAs are produced with a reasonably high cloning efficiency and fidelity of correct nucleotide sequences. The ability to efficiently rejoin several distinct PCR products should permit combinatorial strategies for constructing complexly mutated protein domains as well as broadening the number and location of desired mutations.

Analysis of transformants generated by multiple-fragment RPCR.

| Mutant IgGs Constructed | PCR Fragments in reaction | HR[a] events | Colonies Analyzed | Cloning Efficiency[b] |
|---|---|---|---|---|
| 2 | 2 | triple | 24 | 45% |
| 2 | 3 | quadruple | 24 | 33% |

[a]HR-homologous recombination
[b]Cloning efficiency (number of clones containing 1.4 kbp insert/total number of colonies

EXAMPLE 5

This example provides two methods for introducing site specific mutations into the $CH_2$ domain of human IgG1 constant region containing vectors.

One method involves PCR amplification of a segment or segments of the constant region, wherein mutations are introduced using appropriately constructed oligonucleotides. The vector receiving the fragment(s) is digested with a restriction enzyme to linearize the vector. PCR amplification primers are designed so that the 5' ends of the PCR fragments can hybridize to the DNA sequence of the vectors. If more than one PCR fragment is amplified, then common sequences to the two fragments are introduced by oligonucleotide. Bacteria are transfected with the PCR fragments and with the digested vector. The fragments and vector can recombine by homologous recombination using the bacteria's recombination machinery. Bacterial colonies are selected and the DNA is analyzed by size and restriction map as a preliminary determination that the vector and fragment(s) recombined correctly. Correct insertion of fragments with the mutations is confirmed by dideoxynucleotide sequence analysis. DNA is then introduced into mammalian cells as described for the CH2 deleted antibody, and the expressed antibody analyzed for binding and functional activity.

By way of example, mutations Leu to Ala at residue 235 in CH2 and Gly to Ala at residue 237 were introduced by the procedure disclosed in Example 4. The heavy chain vector used for this procedure was pD17-hG1a, similar to pD17-BR96 vector described herein except that humanized V regions (Rosok, M. J., D. E. Yelton, L. J. Harris, J. Bajorath, K-E. Hellstrom, I, Hellstrom, G. A. Cruz, K. Kristensson, H. Lin, W. D. Huse, and S. M. Glaser, 1996. J. Biol. Chem 271 37:22611–22618) with three affinity mutations (H1, H2, and H3 mutations) were substituted.

pBR96-hG1a contains two Eco47-III restriction sites flanking the Ig hinge-CH2-CH3 domains. The recipient vector was prepared by (1) digesting pBR96-hG1a with Eco47-III, (2) isolating the vector by agarose gel electrophoresis, and (3) extracting the vector DNA from the excised gel slice using the Qiagen Gel Extraction kit (Qiagen, Chatsworth, Calif.). To introduce mutations at a single location, such as for positions 235 and 237, two PCR products were synthesized.

To introduce two distally located mutations, such as for mutant F (also referred to herein as hBR96-2F) with mutations at 235, 237, 331, requires 3 PCR products. The recombination of neighboring PCR products occurs across the regions containing the desired mutations, therefore the oligonucleotide primers encoding these ends contain complementary mutant residues. The mutagenic PCR primers contain at least 15 nucleotides of wild-type sequence flanking each side of the mutant residues for either priming the polymerization reaction or mediating recombination. Two 49-nucleotide long PCR sense and anti-sense primers containing sequences for recombining with the end regions of the Eco47-III digested pBR96-hG1a vector.

PCR amplification used 250 ng intact pBR96-hG1a DNA template, 10 μl of 10× Pfu buffer (Stratagene, Inc., San Diego, Calif.), 10 nmol dNTPs, 200 ng each of the appropriate PCR primers, 10% dimethylsufoxide (ATCC, Manassas, Va.) and 2.5 units cloned Pfu DNA polymerase (Stratagen, Inc. San Diego, Calif.) in 100 μl reaction. Samples were denatured at 95° C. for 5 min, annealed at 45° C. for 5 min, and extended at 72° C. for 1 min followed by 25 cycles of denaturation at 94° C. for 45 sec, annealing at 45° C. for 45 sec, extension at 72° C. for 1 min/kb, and a final extension at 72° C. for 7 min. The amplified products were purified from a 1% agarose gel, extracted with the Qiagen Gel Extraction kit and quantitated. 50 ng of each PCR product was mixed with 25 ng of the Eco47-III digested pBR96-hG1a vector and transfected in E.coli MAX Efficiency DH5α™ according to the manufacturer's instructions (GIBCO BRL/Life Technologies, Gaithersburg, Md.). The entire transaction reaction was plated onto LB agar plated containing 100 μg/ml ampicillin.

Bacterial colonies were selected and grown overnight at 37° C. in 2 ml liquid cultures. DNA was isolated and analyzed by Eco47-III restriction endonuclease mapping. Clones with the correct size insert were sequenced (Sequenase Version 2, U.S. Biochemiccal Corp., Cleveland, Ohio).

The second method for introducing site specific mutations into the $CH_2$ domain of human IgG1 involved the method of Kunkel (1987 Methods Enzymology, supra). For this procedure pD17-hG1b DNA with the F1 origin of replication was introduced into electrocompetent E. coli CJ236 dut-ung-(Bio-Rad Laboratories, Hercules, Calif.) by electroporation according to manufacturer's instructions. PD17-hG1b is a vector having a constant region but no variable region. The F1 ori site allows treatment of this vector as a phagemid.

Bacteria containing the plasmid were selected by ampicillin resistance. Single stranded uridinylated DNA was prepared using the Muta-Gene Phagemid In Vitro Mutagenesis Version 2 protocol (Bio-Rad). Mutations were introduced by site-directed mutagenesis with the appropriate antisense oligonucleotide. For molecules with mutations at more than one location, mutations were introduced by either of the two methods discussed above. One method would be to (1) prepare one mutant, for example, mutant 2C (also referred to herein as BR96-2C) with the mutations at residues 318, 320, 322, (2) isolate ssDNA, and (3) introduce a second mutation set with the appropriate anti-sense oligonucleotide. The second method would be to anneal two antisense oligonucleotides with the same uridinylated ssDNA and screen for mutants with both sets of changes.

The V region of humanized BR96-2 heavy chain was introduced by the homologous recombination method described above in pD17-hJm14.H1. The pD17-hJm14.H1 plasmid contains the BR96 humanized variable region with the H1/H2/H3 mutations and the plasmid was used to transfect mutant sequences into mammalian cells. The pD17G1b vector containing the Fc mutation(s) was digested with NheI for 3 hr at 37° C. and the DNA isolated by methods described above. Insertion of the V region into the vector was determined by size and restriction enzyme mapping and confirmed by sequence analysis.

Transient expression of whole antibodies was performed by transfection of COS cells. For production of antibody, stable transfections of CHO cells were performed (see description of deleted CH2 mutant). All mutants were purified from CHO culture supernatants by protein A chromatography.

The oligonucleotide primers homologous to the vector and used to introduce the constant regions mutations were as follows:

Oligonucleotides homologous to vector sequences:

Sens(sense)CH2 E47-3-5: CAG GGA GGG AGG GTG TCT GCT GGA AGC CAG GCT CAG CGC TGA CCT CAGA, (SEQ ID NO. 7).

D CH2 E47-3 A (antisense): GGA AAG AAC CAT CAC AGT CTC GCA GGG GCC CAG GGC AGC GCT GGG TGC TT, (SEQ ID NO. 8).

Oligonucleotides to mutate Leu235 to Ala and Gly237 to Ala (underlined sequences show sites of mutation):

Antisense CH2 L235-G237/aa: GAA GAG GAA GAC TGA CGG TGC CCC CGC GAG TTC AGG TGC TGA GG, (SEQ ID NO. 14).

SensCH2 L235-G237/AA: CCT CAG CAC CTG AAC TC G CGG GGG CAC CGT CAG TCT TCC TCT TC, (SEQ ID NO. 15).

Oligonucleotides to mutate Glu318, Lys320, Lys322 to Ser

Antis(antisense)CH2 EKK/SSS-2: CTG GGA GGG CTT TGT TGG AGA CCG AGC ACG AGT ACG ACT TGC CAT TCA GCC, (SEQ ID NO. 16).

Oligonucleotides to mutate Pro331 to Ala:

Antis CH2 P331/A/3: GAT GGT TTT CTC GAT GGC GGC TGG GAG GGC, (SEQ ID NO. 17).

Sense CH2 P33/A: GCC CTC CCA GCC GCC ATC GAG AAA ACC ATC, (SEQ ID NO. 18).

Alternative antisense oligo to introduce Ala at 331 by site-directed mutation:

CH2P331A: GAT GGT TTT CTC GAT AGC GGC TGG GAG GGC TTT G, (SEQ ID NO. 19).

Oligonucleotides to mutate Glu318 to Ser, Lys320 to Ser, Lys322 to Ser, and Pro331 to Ala:

Antis CH2 EKKP/SSA-6: GAT GGT TTT CTC GAT GGC GGC TGG GAG GGC TTT GTT GGA GAC CGA GCA CGA GTA CGA CTT GCC ATT CAG CCA GTC CTG GTG, (SEQ ID NO. 20).

Sense CH2 EKKP/SSA-6: CAC CAG GAC TGG CTG AAT GGC AAG TCG TAC TCG TGC TCG GTC TCC AAC AAA GCC CTC CCA GCC GCC ATC GAG AAA ACC ATC, (SEQ ID NO. 21).

In Vitro Assays of the Mutants

Results of the CDC demonstrate that mutant hBR96-2B has approximately 10 fold less activity than the control hBR96-1 (which has two affinity mutations, one in H2 and one in H3, as shown in provisional patent application Ser. No. 60/023,033 filed Aug. 2, 1996 (FIG. 20)). The mutants that have the least ability to kill cells in the presence of complement is hBR96-2C with the triple mutations at positions 318, 320 and 322 and the hBR96-2H mutant (least cytotoxic antibodies in the panel) which contains all six mutations at the three different locations. ADCC activity was most affected by the CH2 deleted hBR96-2 molecule (FIG. 21). hBR96-2B and -2H lost between 100 and 1000 fold activity to kill in the presence of effector cells. In the ADCC assay the hBR96-2B molecule also lost approximately 10 fold activity (FIG. 21).

FIGS. 26–28 provide the amino acid sequences for the heavy chain variable region for both chimeric and humanized BR96 having the H1, H2, and H3 mutations. The amino acid sequence for the light chain variable region is known and methods for generating it are found in PCT Application No. 95/305444. Additionally provided is the amino acid sequence for the IgG1 constant region. Mutations in the constant region are marked.

What is claimed is:

1. A method of inhibiting IgG immunoglobulin-induced toxicity in a subject, said toxicity resulting from immunotherapy for a disease or in vivo diagnosis of a disease comprising administering to said subject an IgG immunoglobulin that binds to a target antigen associated with said disease, said IgG immunoglobulin having a variable region and a constant region comprising the $CH_2$ domain of said IgG, wherein said IgG is modified prior to the administration by structurally altering multiple toxicity-associated regions in the $CH_2$ domain of said constant region so that said administration inhibits said toxicity in said subject, wherein said multiple toxicity-associated regions are localized to amino acids 231–238 and amino acids 310–331 of the $CH_2$ domain, wherein the numbering of said amino acids is according to the 1991 Kabat amino acid numbering system.

2. A method of inhibiting IgG immunoglobulin-induced toxicity in a subject, said toxicity resulting from immunotherapy for a disease or in vivo diagnosis of a disease comprising administering to said subject a structurally altered IgG antibody that binds to a target antigen associated with said disease, said structurally altered IgG antibody comprising a variable region and a constant region comprising the $CH_2$ domain of said IgG, wherein multiple toxicity-associated regions in the $CH_2$ domain of said constant region are modified prior to the administration so as to render said constant region unable to mediate an antibody dependent cellular cytotoxicity response or activate complement, whereby said administration inhibits said toxicity in said subject, wherein said multiple toxicity-associated regions are localized to amino acids 231–238 and amino acids 310–331 of the $CH_2$ domain, wherein the numbering of said amino acids is according to the 1991 Kabat amino acid numbering system.

3. A method of inhibiting IgG immunoglobulin-induced toxicity in a subject resulting from IgG fusion protein immunotherapy for a disease or in vivo diagnosis of a disease comprising administering to said subject an IgG fusion protein, wherein the IgG in the fusion protein binds to a target antigen specific to said disease and has a variable region and a constant region comprising the $CH_2$ domain, wherein said IgG in the fusion protein is modified prior to the administration by structurally altering multiple toxicity-associated regions in the $CH_2$ domain of said constant region so that said administration inhibits said toxicity in said subject, wherein said multiple toxicity-associated regions are localized to amino acids 231–238 and amino acids 310–331 of the $CH_2$ domain, wherein the numbering of said amino acids is according to the 1991 Kabat amino acid numbering system.

4. A method for inhibiting IgG immunoglobulin-induced toxicity in a subject comprising:

(a) selecting an IgG which recognizes and binds to a target antigen, said target antigen being associated with a disease;

(b) mutating said IgG so selected by structurally altering multiple toxicity-associated regions in the $CH_2$ domain of the constant region of said IgG, thereby creating a structurally altered IgG having the modified $CH_2$ domain; and (c) administering said structurally altered IgG of step (b) to said subject under conditions so that said structurally altered IgG recognizes and binds said target antigen, wherein said multiple toxicity-associated regions are localized to amino acids 231–238 and amino acids 310–331 of the $CH_2$ domain wherein the numbering of said amino acids is according to the 1991 Kabat amino acid numbering system.

5. A method for inhibiting IgG immunoglobulin-induced toxicity in a subject comprising:

(a) selecting an IgG fusion protein which recognizes and binds to a target antigen, said target antigen being associated with a disease;

(b) structurally altering multiple toxicity-associated regions in the $CH_2$ domain of the constant region of the IgG in said fusion protein so selected, thereby creating a structurally altered IgG fusion protein having the modified $CH_2$ domain; and (c) administering said structurally altered IgG fusion protein of step (b) to said subject under conditions so that said structurally altered IgG fusion protein recognizes and binds said target antigen, wherein said multiple toxicity-associated regions are localized to amino acids 231–238 and amino acids 310–331 of the $CH_2$ domain wherein the numbering of said amino acids is according to the 1991 Kabat amino acid numbering system.

6. The method of claim 2, wherein said antibody recognizes and binds $Le^y$.

7. The method of claim 2, wherein said antibody recognizes and binds $Le^x$.

8. The method of claim 1 or 4, wherein said immunoglobulin recognizes and binds $Le^x$.

9. The method of claim 1 or 4, wherein said immunoglobulin recognizes and binds $Le^y$.

10. The method of claim 2, wherein said antibody is monoclonal antibody BR96 produced by the hybridoma HB 10036 as deposited with the ATCC.

11. The method of claim 2, wherein said antibody is chimeric antibody ChiBR96 produced by the hybridoma HB 10460 as deposited with the ATCC.

12. The method of claim 1 or 4, wherein said immunoglobulin is monoclonal BR96 produced by the hybridoma HB 10036 as deposited with the ATCC.

13. The method of claim 1 or 4, wherein said immunoglobulin is chimeric ChiBR96 produced by the hybridoma HB 10460 as deposited with the ATCC.

14. The method of claim 3 or 5, wherein said IgG fusion protein recognizes and binds $Le^y$.

15. The method of claim 3 or 5, wherein said IgG fusion protein recognizes and binds $Le^x$.

16. The method of claim 3 or 5, wherein said IgG fusion protein comprises the antigen binding site of monoclonal antibody BR96 produced by the hybridoma HB 10036 as deposited with the ATCC.

17. The method of claim 3 or 5, wherein said IgG fusion protein comprises the antigen binding site of chimeric antibody ChiBR96 produced by the hybridoma HB 10460 as deposited with the ATCC.

18. The method of claim 2, wherein said antibody is conjugated to a cytotoxic agent.

19. The method of claim 1 or 4, wherein said immunoglobulin is conjugated to a cytotoxic agent.

20. The method of claim 3 or 5, wherein said IgG fusion protein is conjugated to a cytotoxic agent.

21. The method of claim 18, wherein the cytotoxic agent is selected from the group consisting of antimetabolites, alkylating agents, anthracyclines, antibiotics, anti-mitotic agents, and chemotherapeutic agents.

22. The method of claim 1, 2, 3, 4 or 5 wherein said immunoglobulin-induced toxicity is gastrointestinal toxicity.

* * * * *

```
                             SEQUENCE LISTING

<160> NUMBER OF SEQ ID NOS: 29

<210> SEQ ID NO 1
<211> LENGTH: 36
<212> TYPE: DNA
<213> ORGANISM: Homo sapiens

<400> SEQUENCE: 1
tggcaccgaa agctttctgg ggcaggccag gcctga                             36

<210> SEQ ID NO 2
<211> LENGTH: 57
<212> TYPE: DNA
<213> ORGANISM: Homo sapiens

<400> SEQUENCE: 2
tccggacatg ttggtaccca cgtggtggtc gacgctgagc ctggcttcga gcagaca     57

<210> SEQ ID NO 3
<211> LENGTH: 55
<212> TYPE: DNA
<213> ORGANISM: Homo sapiens

<400> SEQUENCE: 3
gtcgaccacc acgtgggtac caacatgtcc ggagccacat ggacagaggc cggct       55

<210> SEQ ID NO 4
<211> LENGTH: 30
<212> TYPE: DNA
<213> ORGANISM: Homo sapiens

<400> SEQUENCE: 4
ctggttcttg ttcatctcct ctctagatgg                                   30

<210> SEQ ID NO 5
<211> LENGTH: 36
<212> TYPE: DNA
<213> ORGANISM: Homo sapiens

<400> SEQUENCE: 5
accatggtcg acctcagacc tgccaagagc catatc                            36

<210> SEQ ID NO 6
<211> LENGTH: 40
<212> TYPE: DNA
<213> ORGANISM: Homo sapiens

<400> SEQUENCE: 6
catggtcacg tggtgtgtcc ctggatgcag gctactctag                        40

<210> SEQ ID NO 7
<211> LENGTH: 49
<212> TYPE: DNA
<213> ORGANISM: Homo sapiens

<400> SEQUENCE: 7
cagggaggga gggtgtctgc tggaagccag gctcagcgct gacctcaga              49
```

<210> SEQ ID NO 8
<211> LENGTH: 50
<212> TYPE: DNA
<213> ORGANISM: Homo sapiens

<400> SEQUENCE: 8

| | | | | |
|---|---|---|---|---|
| ggaaagaacc atcacagtct cgcaggggcc cagggcagcg ctgggtgctt | | | | 50 |

<210> SEQ ID NO 9
<211> LENGTH: 8691
<212> TYPE: DNA
<213> ORGANISM: Homo sapiens

<400> SEQUENCE: 9

| | | | | | |
|---|---|---|---|---|---|
| gacggatcgg gagatctgct aggtgacctg aggcgcgccg gcttcgaata gccagagtaa | | | | | 60 |
| cctttttttt taattttatt ttatttttatt tttgagatgg agtttggcgc cgatctcccg | | | | | 120 |
| atccccctatg gtcgactctc agtacaatct gctctgatgc cgcatagtta agccagtatc | | | | | 180 |
| tgctccctgc ttgtgtgttg gaggtcgctg agtagtgcgc gagcaaaatt taagctacaa | | | | | 240 |
| caaggcaagg cttgaccgac aattgcatga agaatctgct tagggttagg cgttttgcgc | | | | | 300 |
| tgcttcgcga tgtacgggcc agatatacgc gttgacattg attattgact agttattaat | | | | | 360 |
| agtaatcaat tacgggtca ttagttcata gcccatatat ggagttccgc gttacataac | | | | | 420 |
| ttacggtaaa tggcccgcct ggctgaccgc ccaacgaccc ccgcccattg acgtcaataa | | | | | 480 |
| tgacgtatgt tcccatagta acgccaatag ggactttcca ttgacgtcaa tgggtggact | | | | | 540 |
| atttacggta aactgcccac ttggcagtac atcaagtgta tcatatgcca agtacgcccc | | | | | 600 |
| ctattgacgt caatgacggt aaatggcccg cctggcatta tgcccagtac atgaccttat | | | | | 660 |
| gggactttcc tacttggcag tacatctacg tattagtcat cgctattacc atggtgatgc | | | | | 720 |
| ggttttggca gtacatcaat gggcgtggat agcggtttga ctcacgggga tttccaagtc | | | | | 780 |
| tccaccccat tgacgtcaat gggagtttgt tttggcacca aaatcaacgg gactttccaa | | | | | 840 |
| aatgtcgtaa caactccgcc ccattgacgc aaatgggcgg taggcgtgta cggtgggagg | | | | | 900 |
| tctatataag cagagctctc tggctaacta gagaacccac tgcttactgg cttatcgaaa | | | | | 960 |
| ttaatacgac tcactatagg gagacccaag cttggtacca attttaaattg atatctcctt | | | | | 1020 |
| aggtctcgag tctctagata accggtcaat cgattggaat tcttgcggcc gcttgctagc | | | | | 1080 |
| caccatggag ttgtggttaa gcttggtcct tccttgtcct tgttttaaaa ggtgtccagt | | | | | 1140 |
| gtgaagtgaa tctggtggag tctgggggag gcttagtgca gcctggaggg tccctgaaag | | | | | 1200 |
| tctcctgtgt aacctctgga ttcactttca gtgactatta catgtattgg ttcgccaga | | | | | 1260 |
| ctccagagaa gaggctggag tgggtcgcat acattagtca aggtggtgat ataaccgact | | | | | 1320 |
| atccagacac tgtaaagggt cgattcacca tctccagaga caatgccaag aacaccctgt | | | | | 1380 |
| acctgcaaat gagccgtctg aagtctgagg acacagccat gtattactgt gcaagaggcc | | | | | 1440 |
| tggacgacgg ggcctggttt gcttactggg gccaagggac tctggtcacg gtctctgtag | | | | | 1500 |
| ctagcaccaa gggcccatcg gtcttccccc tggcaccctc ctccaagagc acctctgggg | | | | | 1560 |
| gcacagcggc cctgggctgc ctggtcaagg actacttccc cgaaccggtg acggtgtcgt | | | | | 1620 |
| ggaactcagg cgccctgacc agcggcgtgc acaccttccc ggctgtccta cagtcctcag | | | | | 1680 |
| gactctactc cctcagcagc gtggtcaccg tgccctccag cagcttgggc acccagacct | | | | | 1740 |
| acatctgcaa cgtgaatcac aagcccagca acaccaaggt ggacaagaaa gttggtgaga | | | | | 1800 |

```
ggccagcaca gggagggagg gtgtctgctg gaagccaggc tcagcgctcc tgcctggacg   1860
catcccggct atgcagcccc agtccagggc agcaaggcag gccccgtctg cctcttcacc   1920
cggaggcctc tgcccgcccc actcatgctc agggagaggg tcttctggct ttttccccag   1980
gctctgggca ggcacaggct aggtgcccct aacccaggcc ctgcacacaa agggcaggt    2040
gctgggctca gacctgccaa gagccatatc cgggaggacc ctgcccctga cctaagccca   2100
ccccaaaggc caaactctcc actccctcag ctcggacacc ttctctcctc ccagattcca   2160
gtaactccca atcttctctc tgcagagccc aaatcttgtg acaaaactca cacatgccca   2220
ccgtgcccag gtaagccagc ccaggcctcg ccctccagct caaggcggga caggtgccct   2280
agagtagcct gcatccaggg acaggcccca gccgggtgct gacacgtcca cctccatctc   2340
ttcctcagca cctgaactcc tggggggacc gtcagtcttc ctcttccccc caaacccaa    2400
ggacaccctc atgatctccc ggacccctga ggtcacatgc gtggtggtgg acgtgagcca   2460
cgaagaccct gaggtcaagt tcaactggta cgtggacggc gtggaggtgc ataatgccaa   2520
gacaaagccg cgggaggagc agtacaacag cacgtaccgt gtggtcagcg tcctcaccgt   2580
cctgcaccag gactggctga atggcaagga gtacaagtgc aaggtctcca acaaagccct   2640
cccagccccc atcgagaaaa ccatctccaa agccaaaggt gggacccgtg gggtgcgagg   2700
gccacatgga cagaggccgg ctcggcccac cctctgccct gagagtgacc gctgtaccaa   2760
cctctgtccc tacagggcag ccccgagaac acaggtgta caccctgccc ccatcccggg   2820
atgagctgac caagaaccag gtcagcctga cctgcctggt caaaggcttc tatcccagcg   2880
acatcgccgt ggagtgggag agcaatgggc agccggagaa caactacaag accacgcctc   2940
ccgtgctgga ctccgacggc tccttcttcc tctacagcaa gctcaccgtg gacaagagca   3000
ggtggcagca ggggaacgtc ttctcatgct ccgtgatgca tgaggctctg cacaaccact   3060
acacgcagaa gagcctctcc ctgtctccgg gtaaatgagt gcgacggccg gcaagccccc   3120
gctccccggg ctctcgcggt cgcacgagga tgcttggcac gtaccccctg tacatacttc   3180
ccgggcgccc agcatggaaa taaagcaccc agcgctgccc tgggcccctg cgagactgtg   3240
atggttcttt ccacgggtca ggccgagtct gaggcctgag tggcatgagg gaggcagagc   3300
gggtcccact gtccccacac tggcccaggc tgtgcaggtg tgcctgggcc cctaggtg    3360
gggctcagcc aggggctgcc ctcggcaggg tgggggattt gccagcgtgg ccctccctcc   3420
agcagcacct gccctgggct gggcacggg aagccctagg agccctggg acagacaca     3480
cagcccctgc ctctgtagga gactgtcctg ttctgtgagc gcccctgtcc tcccgacctc   3540
catgcccact cggggcatg cctagtccat gtgcgtaggg acaggccctc cctcacccat   3600
ctaccccac ggcactaacc cctggctgcc ctgcccagcc tcgcacccgc atggggacac    3660
aaccgactcc ggggacatgc actctcgggc cctgtggagg gactggtgca gatgcccaca   3720
cacacactca gcccagaccc gttcaacaaa ccccgcactg aggttggccg gccacacggc   3780
caccacacac acacgtgcac gcctcacaca cggagcctca cccgggcgaa ctgcacagca   3840
cccagaccag agcaaggtcc tcgcacacgt gaacactcct cggacacagg cccccacgag   3900
ccccacgcgg cacctcaagg cccacgagcc tctcggcagc ttctccacat gctgacctgc   3960
tcagacaaac ccagccctcc tctcacaagg gtgcccctgc agccgccaca cacacacagg   4020
ggatcacaca ccacgtcacg tccctggccc tggcccactt cccagtgccg cccttccctg   4080
caggacggat cagcctcgac tgtgccttct agttgccagc catctgttgt ttgcccctcc   4140
cccgtgcctt ccttgaccct ggaaggtgcc actcccactg tcctttccta ataaaatgag   4200
```

-continued

```
gaaattgcat cgcattgtct gagtaggtgt cattctattc tgggggggtgg ggtggggcag    4260 gacagcaagg gggaggattg ggaagacaat agcaggcatg ctggggatgc ggtgggctct    4320
atggcttctg aggcggaaag aaccagctgg ggctctaggg ggtatcccca cgcgccctgt    4380
agcggcgcat taagcgcggc gggtgtggtg gttacgcgca gcgtgaccgc tacacttgcc    4440
agcgccctag cgcccgctcc tttcgctttc ttcccttcct ttctcgccac gttcgccggg    4500
cctctcaaaa aagggaaaaa agcatgcat ctcaattagt cagcaaccat agtcccgccc    4560
ctaactccgc ccatcccgcc cctaactccg cccagttccg cccattctcc gccccatggc    4620
tgactaattt ttttttattta tgcagaggcc gaggccgcct cggcctctga gctattccag    4680
aagtagtgag gaggctttttt tggaggccta ggcttttgca aaaagcttgg acagctcagg    4740
gctgcgattt cgcgccaaac ttgacggcaa tcctagcgtg aaggctggta ggattttatc    4800
cccgctgcca tcatggttcg accattgaac tgcatcgtcg ccgtgtccca aaatatgggg    4860
attggcaaga acggagacct accctggcct ccgctcagga acgagttcaa gtacttccaa    4920
agaatgacca caacctcttc agtggaaggt aaacagaatc tggtgattat gggtaggaaa    4980
acctggttct ccattcctga gaagaatcga cctttaaagg acagaattaa tatagttctc    5040
agtagagaac tcaaagaacc accacgagga gctcattttc ttgccaaaag tttggatgat    5100
gccttaagac ttattgaaca accggaattg gcaagtaaag tagacatggt ttggatagtc    5160
ggaggcagtt ctgtttacca ggaagccatg aatcaaccag gccaccttag actctttgtg    5220
acaaggatca tgcaggaatt tgaaagtgac acgttttttcc cagaaattga tttggggaaa    5280
tataaacttc tcccagaata cccaggcgtc ctctctgagg tccaggagga aaaaggcatc    5340
aagtataagt ttgaagtcta cgagaagaaa gactaacagg aagatgcttt caagttctct    5400 gctccccttcc taaagctatg cattttttata agaccatggg acttttgctg gctttagatc    5460
tctttgtgaa ggaaccttac ttctgtggtg tgacataatt ggacaaacta cctacagaga    5520
tttaaagctc taaggtaaat ataaaatttt taagtgtata atgtgttaaa ctactgattc    5580
taattgtttg tgtattttag attccaacct atggaactga tgaatgggag cagtggtgga    5640
atgcctttaa tgaggaaaac ctgttttgct cagaagaaat gccatctagt gatgatgagg    5700
ctactgctga ctctcaacat tctactcctc caaaaaagaa gagaaaggta gaagaccccca    5760 aggactttcc ttcagaattg ctaagttttt tgagtcatgc tgtgtttagt aatagaactc    5820
ttgcttgctt tgctatttac accacaaagg aaaaagctgc actgctatac aagaaaatta    5880
tggaaaaata ttctgtaacc tttataagta ggcataacag ttataatcat aacatactgt    5940
tttttcttac tccacacagg catagagtgt ctgctattaa taactatgct caaaaattgt    6000
gtacctttag cttttaatt tgtaaagggg ttaataagga atatttgatg tatagtgcct    6060
tgactagaga tcataatcag ccataccaca tttgtagagg ttttacttgc tttaaaaaac    6120
ctcccacacc tcccctgaa cctgaaacat aaaatgaatg caattgttgt tgttaacttg    6180
tttattgcag cttataatgg ttacaaataa agcaatagca tcacaaattt cacaaataaa    6240 gcatttttttt cactgcattc tagttgtggt ttgtccaaac tcatcaatgt atcttatcat    6300
gtctggatcg gctggatgat cctccagcgc ggggatctca tgctggagtt cttcgcccac    6360
cccaacttgt ttattgcagc ttataatggt tacaaataaa gcaatagcat cacaaatttc    6420
acaaataaag cattttttttc actgcattct agttgtggtt tgtccaaact catcaatgta    6480
tcttatcatg tctgtatacc gtcgacctct agctagagct tggcgtaatc atggtcatag    6540
```

```
ctgtttcctg tgtgaaattg ttatccgctc acaattccac acaacatacg agccggaagc    6600
ataaagtgta aagcctgggg tgcctaatga gtgagctaac tcacattaat tgcgttgcgc    6660
tcactgcccg ctttccagtc gggaaacctg tcgtgccagc tgcattaatg aatcggccaa    6720
cgcgcgggga gaggcggttt gcgtattggg cgctcttccg cttcctcgct cactgactcg    6780
ctgcgctcgg tcgttcggct gcggcgagcg gtatcagctc actcaaaggc ggtaatacgg    6840
ttatccacag aatcagggga taacgcagga agaacatgt gagcaaaagg ccagcaaaag    6900
gccaggaacc gtaaaaaggc cgcgttgctg gcgtttttcc ataggctccg ccccctgac    6960 gagcatcaca aaaatcgacg ctcaagtcag aggtggcgaa acccgacagg actataaaga    7020
taccaggcgt ttccccctgg aagctccctc gtgcgctctc ctgttccgac cctgccgctt    7080
accggatacc tgtccgcctt tctcccttcg ggaagcgtgg cgctttctca atgctcacgc    7140
tgtaggtatc tcagttcggt gtaggtcgtt cgctccaagc tgggctgtgt gcacgaaccc    7200
cccgttcagc ccgaccgctg cgccttatcc ggtaactatc gtcttgagtc caacccggta    7260
agacacgact tatcgccact ggcagcagcc actggtaaca ggattagcag agcgaggtat    7320
gtaggcggtg ctacagagtt cttgaagtgg tggcctaact acggctacac tagaaggaca    7380
gtatttggta tctgcgctct gctgaagcca gttaccttcg gaaaaagagt tggtagctct    7440
tgatccggca aacaaaccac cgctggtagc ggtggttttt ttgtttgcaa gcagcagatt    7500
acgcgcagaa aaaaggatc tcaagaagat cctttgatct tttctacggg gtctgacgct    7560
cagtggaacg aaaactcacg ttaagggatt ttggtcatga gattatcaaa aaggatcttc    7620
acctagatcc ttttaaatta aaaatgaagt tttaaatcaa tctaaagtat atatgagtaa    7680
acttggtctg acagttacca atgcttaatc agtgaggcac ctatctcagc gatctgtcta    7740
tttcgttcat ccatagttgc ctgactcccc gtcgtgtaga taactacgat acgggagggc    7800
ttaccatctg gccccagtgc tgcaatgata ccgcgagacc cacgctcacc ggctccagat    7860
ttatcagcaa taaaccagcc agccggaagg gccgagcgca gaagtggtcc tgcaacttta    7920
tccgcctcca tccagtctat taattgttgc cgggaagcta gagtaagtag ttcgccagtt    7980
aatagtttgc gcaacgttgt tgccattgct acaggcatcg tggtgtcacg ctcgtcgttt    8040
ggtatggctt cattcagctc cggttcccaa cgatcaaggc gagttacatg atcccccatg    8100
ttgtgcaaaa aagcggttag ctccttcggt cctccgatcg ttgtcagaag taagttggcc    8160
gcagtgttat cactcatggt tatggcagca ctgcataatt ctcttactgt catgccatcc    8220
gtaagatgct tttctgtgac tggtgagtac tcaaccaagt cattctgaga atagtgtatg    8280
cggcgaccga gttgctcttg cccggcgtca atacgggata ataccgcgcc acatagcaga    8340
actttaaaag tgctcatcat tggaaaacgt tcttcggggc gaaaactctc aaggatctta    8400
ccgctgttga tccagttc gatgtaaccc actcgtgcac ccaactgatc ttcagcatct    8460
tttactttca ccagcgtttc tgggtgagca aaaacaggaa ggcaaaatgc cgcaaaaaag    8520
ggaataaggg cgacacggaa atgttgaata ctcatactct tcctttttca atattattga    8580
agcatttatc agggttattg tctcatgagc ggatacatat ttgaatgtat ttagaaaaat    8640
aaacaaatag gggttccgcg cacatttccc cgaaaagtgc cacctgacgt c             8691
```

<210> SEQ ID NO 10
<211> LENGTH: 8321
<212> TYPE: DNA
<213> ORGANISM: Homo sapiens

<400> SEQUENCE: 10

-continued

```
gacggatcgg gagatctgct aggtgacctg aggcgcgccg gcttcgaata gccagagtaa      60
cctttttttt taattttatt ttattttatt tttgagatgg agtttggcgc cgatctcccg     120
atccccctatg gtcgactctc agtacaatct gctctgatgc cgcatagtta agccagtatc    180
tgctccctgc ttgtgtgttg gaggtcgctg agtagtgcgc gagcaaaatt taagctacaa    240
caaggcaagg cttgaccgac aattgcatga agaatctgct tagggttagg cgttttgcgc    300
tgcttcgcga tgtacgggcc agatatacgc gttgacattg attattgact agttattaat    360
agtaatcaat tacggggtca ttagttcata gcccatatat ggagttccgc gttacataac    420
ttacggtaaa tggcccgcct ggctgaccgc ccaacgaccc ccgcccattg acgtcaataa    480
tgacgtatgt tcccatagta acgccaatag ggactttcca ttgacgtcaa tgggtggact    540
atttacggta aactgcccac ttggcagtac atcaagtgta tcatatgcca agtacgcccc    600
ctattgacgt caatgacggt aaatggcccg cctggcatta tgcccagtac atgaccttat    660
gggactttcc tacttggcag tacatctacg tattagtcat cgctattacc atggtgatgc    720
ggttttggca gtacatcaat gggcgtggat agcggtttga ctcacgggga tttccaagtc    780
tccacccccat tgacgtcaat gggagtttgt tttggcacca aaatcaacgg gactttccaa    840
aatgtcgtaa caactccgcc ccattgacgc aaatgggcgg taggcgtgta cggtgggagg    900
tctatataag cagagctctc tggctaacta gagaacccac tgcttactgg cttatcgaaa    960
ttaatacgac tcactatagg gagacccaag cttggtacca atttaaattg atatctcctt   1020
aggtctcgag tctctagata accggtcaat cgattggaat tcttgcggcc gcttgctagc   1080
caccatggag ttgtggttaa gcttggtcct tccttgtcct tgttttaaaa ggtgtccagt   1140
gtgaagtgaa tctggtggag tctggggggag gcttagtgca gcctggaggg tccctgaaag   1200
tctcctgtgt aacctctgga ttcactttca gtgactatta catgtattgg gttcgccaga   1260
ctccagagaa gaggctggag tgggtcgcat acattagtca aggtggtgat ataaccgact   1320
atccagacac tgtaaagggt cgattcacca tctccagaga caatgccaag aacaccctgt   1380
acctgcaaat gagccgtctg aagtctgagg acacagccat gtattactgt gcaagaggcc   1440
tggacgacgg ggcctggttt gcttactggg gccaagggac tctggtcacg gtctctgtag   1500
ctagcaccaa gggcccatcg gtcttccccc tggcaccctc ctccaagagc acctctgggg   1560
gcacagcggc cctgggctgc ctggtcaagg actacttccc cgaaccggtg acggtgtcgt   1620
ggaactcagg cgccctgacc agcggcgtgc acaccttccc ggctgtccta cagtcctcag   1680
gactctactc cctcagcagc gtggtcaccg tgccctccag cagcttgggc acccagacct   1740
acatctgcaa cgtgaatcac aagcccagca acaccaaggt ggacaagaaa gttggtgaga   1800
ggccagcaca gggagggagg gtgtctgctg gaagccaggc tcagcgctcc tgcctggacg   1860
catcccggct atgcagcccc agtccagggc agcaaggcag gccccgtctg cctcttcacc   1920
cggaggcctc tgcccgcccc actcatgctc agggagaggg tcttctggct ttttccccag   1980
gctctgggca ggcacaggct aggtgcccct aacccaggcc ctgcacacaa aggggcaggt   2040
gctgggctca gacctgccaa gagccatatc cgggaggacc ctgcccctga cctaagccca   2100
ccccaaaggc caaactctcc actccctcag ctccggacacc ttctctcctc ccagattcca   2160
gtaactccca atcttctctc tgcagagccc aaatcttgtg acaaaactca cacatgccca   2220
ccgtgcccag gtaagccagc ccaggcctcg ccctccagct caaggcggga caggtgccct   2280
agagtagcct gcatccaggg acacaccacg tgggtaccaa catgtccgga gccacatgga   2340
```

```
cagaggccgg ctcggcccac cctctgccct gagagtgacc gctgtaccaa cctctgtccc   2400
tacagggcag ccccgagaac cacaggtgta caccctgccc ccatcccggg atgagctgac   2460
caagaaccag gtcagcctga cctgcctggt caaaggcttc tatcccagcg acatcgccgt   2520
ggagtgggag agcaatgggc agccggagaa caactacaag accacgcctc ccgtgctgga   2580
ctccgacggc tccttcttcc tctacagcaa gctcaccgtg gacaagagca ggtggcagca   2640
ggggaacgtc ttctcatgct ccgtgatgca tgaggctctg cacaaccact acacgcagaa   2700
gagcctctcc ctgtctccgg gtaaatgagt gcgacggccg gcaagccccc gctccccggg   2760
ctctcgcggt cgcacgagga tgcttggcac gtacccctg tacatacttc ccgggcgccc   2820
agcatggaaa taaagcaccc agcgctgccc tgggcccctg cgagactgtg atggttcttt   2880
ccacgggtca ggccgagtct gaggcctgag tggcatgagg gaggcagagc gggtcccact   2940
gtccccacac tggcccaggc tgtgcaggtg tgcctgggcc ccctagggtg gggctcagcc   3000
aggggctgcc ctcggcaggg tgggggattt gccagcgtgg ccctccctcc agcagcacct   3060
gccctgggct gggccacggg aagccctagg agccctggg gacagacaca cagcccctgc   3120
ctctgtagga gactgtcctg ttctgtgagc gccctgtcc tcccgacctc catgcccact   3180
cgggggcatg cctagtccat gtgcgtaggg acaggccctc cctcacccat ctaccccac   3240 ggcactaacc cctggctgcc ctgcccagcc tcgcacccgc atggggacac aaccgactcc   3300
ggggacatgc actctcgggc cctgtggagg gactggtgca gatgcccaca cacacactca   3360
gcccagaccc gttcaacaaa ccccgcactg aggttggccg gccacacggc caccacacac   3420
acacgtgcac gcctcacaca cggagcctca cccgggcgaa ctgcacagca cccagaccag   3480
agcaaggtcc tcgcacacgt gaacactcct cggacacagg ccccacgag ccccacgcgg    3540 cacctcaagg cccacgagcc tctcggcagc ttctccacat gctgacctgc tcagacaaac   3600
ccagccctcc tctcacaagg gtgccctgc agccgccaca cacacacagg ggatcacaca    3660
ccacgtcacg tccctggccc tggcccactt cccagtgccg ccttccctg caggacggat    3720 cagcctcgac tgtgccttct agttgccagc catctgttgt ttgcccctcc cccgtgcctt   3780 ccttgacccct ggaaggtgcc actcccactg tcctttccta ataaaatgag gaaattgcat  3840
cgcattgtct gagtaggtgt cattctattc tgggggtgg ggtgggcag acagcaagg      3900 gggaggattg ggaagacaat agcaggcatg ctggggatgc ggtgggctct atggcttctg   3960
aggcggaaag aaccagctgg ggctctaggg ggtatcccca cgcgccctgt agcggcgcat   4020
taagcgcggc gggtgtggtg gttacgcgca gcgtgaccgc tacacttgcc agcgccctag   4080
cgcccgctcc tttcgctttc ttcccttcct ttctcgccac gttcgccggg cctctcaaaa   4140
aagggaaaaa aagcatgcat ctcaattagt cagcaaccat agtcccgccc ctaactccgc   4200
ccatcccgcc cctaactccg cccagttccg cccattctcc gccccatggc tgactaattt   4260
tttttattta tgcagaggcc gaggccgcct cggcctctga gctattccag aagtagtgag   4320
gaggcttttt tggaggccta ggcttttgca aaaagcttgg acagtcagg gctgcgattt    4380 cgcgccaaac ttgacggcaa tcctagcgtg aaggctggta ggattttatc cccgctgcca   4440
tcatggttcg accattgaac tgcatcgtcg ccgtgtccca aaatatgggg attggcaaga   4500
acggagacct accctggcct ccgctcagga acgagttcaa gtacttccaa gaatgaccca  4560
caacctcttc agtggaaggt aaacagaatc tggtgattat gggtaggaaa acctggttct   4620
ccattcctga gaagaatcga cctttaaagg acagaattaa tatagttctc agtagagaac   4680
tcaaagaacc accacgagga gctcattttc ttgccaaaag tttggatgat gccttaagac   4740
```

```
ttattgaaca accggaattg gcaagtaaag tagacatggt ttggatagtc ggaggcagtt    4800
ctgtttacca ggaagccatg aatcaaccag gccaccttag actctttgtg acaaggatca    4860
tgcaggaatt tgaaagtgac acgttttttcc cagaaattga tttggggaaa tataaacttc   4920
tcccagaata cccaggcgtc ctctctgagg tccaggagga aaaaggcatc aagtataagt    4980
ttgaagtcta cgagaagaaa gactaacagg aagatgcttt caagttctct gctcccctcc    5040
taaagctatg cattttata agaccatggg acttttgctg gctttagatc tctttgtgaa     5100
ggaaccttac ttctgtggtg tgacataatt ggacaaacta cctacagaga tttaaagctc    5160
taaggtaaat ataaaatttt taagtgtata atgtgttaaa ctactgattc taattgtttg    5220
tgtattttag attccaacct atggaactga tgaatgggag cagtggtgga atgcctttaa    5280
tgaggaaaac ctgttttgct cagaagaaat gccatctagt gatgatgagg ctactgctga    5340
ctctcaacat tctactcctc caaaaaagaa gagaaaggta aagaccccca aggactttcc    5400
ttcagaattg ctaagttttt tgagtcatgc tgtgtttagt aatagaactc ttgcttgctt    5460
tgctatttac accacaaagg aaaaagctgc actgctatac aagaaaatta tggaaaaata    5520
ttctgtaacc tttataagta ggcataacag ttataatcat aacatactgt tttttcttac    5580
tccacacagg catagagtgt ctgctattaa taactatgct caaaaattgt gtaccttag     5640 cttttttaatt tgtaaagggg ttaataagga atatttgatg tatagtgcct tgactagaga   5700
tcataatcag ccataccaca tttgtagagg ttttacttgc tttaaaaaac ctcccacacc    5760 tcccctgaa cctgaaacat aaaatgaatg caattgttgt tgttaacttg tttattgcag     5820
cttataatgg ttacaaataa agcaatagca tcacaaattt cacaaataaa gcattttttt    5880
cactgcattc tagttgtggt ttgtccaaac tcatcaatgt atcttatcat gtctggatcg    5940
gctggatgat cctccagcgc ggggatctca tgctggagtt cttcgccac cccaacttgt     6000 ttattgcagc ttataatggt tacaaataaa gcaatagcat cacaaatttc acaaataaag    6060
catttttttc actgcattct agttgtggtt tgtccaaact catcaatgta tcttatcatg    6120
tctgtatacc gtcgacctct agctagagct tggcgtaatc atggtcatag ctgtttcctg    6180
tgtgaaattg ttatccgctc acaattccac acaacatacg agccgaagc ataaagtgta     6240 aagcctgggg tgcctaatga gtgagctaac tcacattaat tgcgttgcgc tcactgcccg    6300
ctttccagtc gggaaacctg tcgtgccagc tgcattaatg aatcggccaa cgcgcgggga    6360
gaggcggttt gcgtattggg cgctcttccg cttcctcgct cactgactcg ctgcgctcgg    6420
tcgttcggct gcggcgagcg gtatcagctc actcaaaggc ggtaatacgg ttatccacag    6480
aatcagggga taacgcagga aagaacatgt gagcaaaagg ccagcaaaag gccaggaacc    6540
gtaaaaaggc cgcgttgctg gcgtttttcc ataggctccg ccccctgac gagcatcaca     6600 aaaatcgacg ctcaagtcag aggtggcgaa acccgacagg actataaaga taccaggcgt    6660
ttccccctgg aagctccctc gtgcgctctc ctgttccgac cctgccgctt accggatacc    6720
tgtccgcctt tctcccttcg ggaagcgtgg cgctttctca atgctcacgc tgtaggtatc    6780
tcagttcggt gtaggtcgtt cgctccaagc tgggctgtgt gcacgaaccc cccgttcagc    6840
ccgaccgctg cgccttatcc ggtaactatc gtcttgagtc aacccggta agacacgact     6900 tatcgccact ggcagcagcc actggtaaca ggattagcag agcgaggtat gtaggcggtg    6960
ctacagagtt cttgaagtgg tggcctaact acggctacac tagaaggaca gtatttggta    7020
tctgcgctct gctgaagcca gttaccttcg gaaaaagagt tggtagctct tgatccggca    7080
```

-continued

```
aacaaaccac cgctggtagc ggtggttttt ttgtttgcaa gcagcagatt acgcgcagaa    7140
aaaaaggatc tcaagaagat cctttgatct tttctacggg gtctgacgct cagtggaacg    7200
aaaactcacg ttaagggatt ttggtcatga gattatcaaa aaggatcttc acctagatcc    7260 tttttaaatta aaaatgaagt tttaaatcaa tctaaagtat atatgagtaa acttggtctg    7320
acagttacca atgcttaatc agtgaggcac ctatctcagc gatctgtcta tttcgttcat    7380
ccatagttgc ctgactcccc gtcgtgtaga taactacgat acgggagggc ttaccatctg    7440
gccccagtgc tgcaatgata ccgcgagacc cacgctcacc ggctccagat ttatcagcaa    7500
taaaccagcc agccggaagg gccgagcgca gaagtggtcc tgcaacttta tccgcctcca    7560
tccagtctat taattgttgc cgggaagcta gagtaagtag ttcgccagtt aatagtttgc    7620
gcaacgttgt tgccattgct acaggcatcg tggtgtcacg ctcgtcgttt ggtatggctt    7680
cattcagctc cggttcccaa cgatcaaggc gagttacatg atcccccatg ttgtgcaaaa    7740
aagcggttag ctccttcggt cctccgatcg ttgtcagaag taagttggcc gcagtgttat    7800
cactcatggt tatggcagca ctgcataatt ctcttactgt catgccatcc gtaagatgct    7860
tttctgtgac tggtgagtac tcaaccaagt cattctgaga atagtgtatg cggcgaccga    7920
gttgctcttg cccggcgtca atacgggata ataccgcgcc acatagcaga actttaaaag    7980
tgctcatcat tggaaaacgt tcttcggggc gaaaactctc aaggatctta ccgctgttga    8040
gatccagttc gatgtaaccc actcgtgcac ccaactgatc ttcagcatct tttactttca    8100
ccagcgtttc tgggtgagca aaaacaggaa ggcaaaatgc cgcaaaaaag ggaataaggg    8160
cgacacggaa atgttgaata ctcatactct tcctttttca atattattga agcatttatc    8220
agggttattg tctcatgagc ggatacatat ttgaatgtat ttagaaaaat aaacaaatag    8280
gggttccgcg cacatttccc cgaaaagtgc cacctgacgt c                       8321
```

<210> SEQ ID NO 11
<211> LENGTH: 8897
<212> TYPE: DNA
<213> ORGANISM: Homo sapiens

<400> SEQUENCE: 11

```
ggtaccaatt taaattgata tctccttagg tctcgagcac catgaagttg cctgttaggc      60
tgttggtgct gatgttctgg attcctgctt ccagcagtga tgttttgatg acccaaattc     120
cagtctccct gcctgtcagt cttggagatc aagcgtccat ctcttgcaga tctagtcaga     180
tcattgtaca taataatggc aacacctatt tagaatggta cctgcagaaa ccaggccagt     240
ctccacagct cctgatctac aaagtttcca accgattttc tggggtccca gacaggttca     300
gcggcagtgg atcagggaca gatttcacac tcaagatcag cagagtggag ctgaggatc      360 tgggagtttta ttactgcttt caaggttcac atgttccatt cacgttcggc tcggggacaa     420
agttggaaat aaaacgtaag tctcgagtct ctagataacc ggtcaatcga ttggaattct     480
aaactctgag ggggtcggat gacgtggcca ttctttgcct aaagcattga gtttactgca     540
aggtcagaaa agcatgcaaa gccctcagaa tggctgcaaa gagctccaac aaaacaattt     600
agaactttat taaggaatag ggggaagcta ggaagaaact caaaacatca agattttaaa     660
tacgcttctt ggtctccttg ctataattat ctgggataag catgctgttt tctgtctgtc     720
cctaacatgc cttatccgc aaacaacaca cccaagggca gaactttgtt acttaaacac      780
catcctgttt gcttctttcc tcaggaactg tggctgcacc atctgtcttc atcttcccgc     840
catctgatga gcagttgaaa tctggaactg cctctgttgt gtgcctgctg aataacttct     900
```

-continued

```
atcccagaga ggccaaagta cagtggaagg tggataacgc cctccaatcg ggtaactccc        960
aggagagtgt cacagagcag gagagcaagg acagcaccta cagcctcagc agcaccctga       1020
cgctgagcaa agcagactac gagaaacaca agtctacgc ctgcgaagtc acccatcagg        1080
gcctgagctc gcccgtcaca aagagcttca caggggaga gtgttagagg gagaagtgcc       1140
cccacctgct cctcagttcc agcctgaccc cctcccatcc tttggcctct gaccctttt        1200
ccacagggga cctaccccta ttgcggtcct ccagctcatc tttcacctca ccccctcct       1260
cctccttggc tttaattatg ctaatgttgg aggagaatga ataaataaag tgaatctttg       1320
cacctgtggt ttctctcttt cctcatttaa taattattat ctgttgtttt accaactact       1380
caatttctct tataagggac taaatatgta gtcatcctaa ggcacgtaac catttataaa       1440
aatcatcctt cattctattt taccctatca tcctctgcaa gacagtcctc cctcaaaccc       1500
acaagccttc tgtcctcaca gtcccctggg ccatggtagg agagacttgc ttccttgttt       1560
tcccctcctc agcaagccct catagtcctt tttaagggtg acaggtctta cagtcatata       1620
tcctttgatt caattcctg agaatcaacc aaagcaaatt tttcaaaaga gaaacctgc        1680
tataaagaga atcattcatt gcaacatgat ataaaataac aacacaataa aagcaattaa       1740
ataaacaaac aatagggaaa tgtttaagtt catcatggta cttagactta atggaatgtc       1800
atgccttatt tacattttta aacaggtact gagggactcc tgtctgccaa gggccgtatt       1860
gagtactttc cacaacctaa tttaatccac actatactgt gagattaaaa acattcatta       1920
aaatgttgca aaggttctat aaagctgaga gacaaatata ttctataact cagcaatccc       1980
acttctagat gactgagtgt ccccacccac caaaaaacta tgcaagaatg ttcaaagcag       2040
ctttatttac aaaagccaaa aattggaaat agcccgattg tccaacaata gaatgagtta       2100
ttaaactgtg gtatgtttat acattagaat acccaatgag gagaattaac aagctacaac       2160
tatacctact cacacagatg aatctcataa aaataatgtt acataagaga aactcaatgc       2220
aaaagatatg ttctgtatgt tttcatccat ataaagttca aaaccaggta aaaataaagt       2280
tagaaatttg gatggaaatt actcttagct gggggtgggc gagttagtgc ctggagaag        2340
acaagaaggg gcttctgggg tcttggtaat gttctgttcc tcgtgtgggg ttgtgcagtt       2400
atgatctgtg cactgttctg tatacacatt atgcttcaaa ataacttcac ataaagaaca       2460
tcttataccc agttaataga tagaagagga ataagtaata ggtcaagacc aacgcagctg       2520
gtaagtgggg gcctgggatc aaatagctac ctgcctaatc ctgcccwctt gagccctgaa       2580
tgagtctgcc ttccagggct caaggtgctc aacaaaacaa caggcctgct attttcctgg       2640
catctgtgcc ctgtttggct agctaggagc acacatacat agaaattaaa tgaaacagac       2700
cttcagcaag gggacagagg acagaattaa ccttgcccag acactggaaa cccatgtatg       2760
aacactcaca tgtttgggaa gggggaaggg cacatgtaaa tgaggactct tcctcattct       2820
atggggcact ctggccctgc ccctctcagc tactcatcca tccaacacac ctttctaagt       2880
acctctctct gcctacactc tgaagggggt caggagtaac taacacagca tcccttccct       2940
caaatgactg acaatcccttt tgtcctgctt tgttttctt tccagtcagt actgggaaag       3000
tggggaagga cagtcatgga gaaactacat aaggaagcac cttgcccttc tgcctcttga       3060
gaatgttgat gagtatcaaa tctttcaaac tttggaggtt tgagtagggg tgagactcag       3120
taatgtccct tccaatgaca tgaacttgct cactcatccc tggggccaa attgaacaat        3180
caaaggcagg cataatccag ttatgaattc ttgcggccgc ttgctagctt cacgtgttgg       3240
```

-continued

```
atccaaccgc ggaagggccc tattctatag tgtcacctaa atgctagagc tcgctgatca    3300
gcctcgactg tgccttctag ttgccagcca tctgttgttt gcccctcccc cgtgccttcc    3360
ttgaccctgg aagtgccac  tcccactgtc ctttcctaat aaaatgagga aattgcatcg    3420
cattgtctga gtaggtgtca ttctattctg gggggtgggg tggggcagga cagcaagggg    3480
gaggattggg aagacaatag caggcatgct ggggatgcgg tgggctctat ggcttctgag    3540
gcggaaagaa ccagctgggg ctctaggggg tatcccacg  cgccctgtag cggcgcatta    3600
agcgcggcgg gtgtggtggt tacgcgcagc gtgaccgcta cacttgccag cgccctagcg    3660
cccgctcctt tcgctttctt cccttccttt ctcgccacgt tcgccgggcc tctcaaaaaa    3720
gggaaaaaaa gcatgcatct caattagtca gcaaccatag tcccgcccct aactccgccc    3780
atcccgcccc taactccgcc cagttccgcc cattctccgc cccatggctg actaattttt    3840
tttatttatg cagaggccga ggccgcctcg gcctctgagc tattccagaa gtagtgagga    3900
ggcttttttg gaggcctagg cttttgcaaa aagcttggac agctcagggc tgcgatttcg    3960
cgccaaactt gacggcaatc ctagcgtgaa ggctggtagg attttatccc cgctgccatc    4020
atggttcgac cattgaactg catcgtcgcc gtgtcccaaa atatggggat tggcaagaac    4080
ggagacctac cctggcctcc gctcaggaac gagttcaagt acttccaaag aatgaccaca    4140
acctcttcag tggaaggtaa acagaatctg gtgattatgg gtaggaaaac ctggttctcc    4200
attcctgaga agaatcgacc tttaaaggac agaattaata tagttctcag tagagaactc    4260
aaagaaccac cacgaggagc tcattttctt gccaaaagtt tggatgatgc cttaagactt    4320
attgaacaac cggaattggc aagtaaagta gacatggttt ggatagtcgg aggcagttct    4380
gtttaccagg aagccatgaa tcaaccaggc caccttagac tctttgtgac aaggatcatg    4440
caggaatttg aaagtgacac gttttttccca gaaattgatt tggggaaata taaacttctc    4500
ccagaatacc caggcgtcct ctctgaggtc caggaggaaa aaggcatcaa gtataagttt    4560
gaagtctacg agaagaaaga ctaacaggaa gatgctttca agttctctgc tccctccta    4620 aagctatgca ttttttataag accatgggac ttttgctggc tttagatctc tttgtgaagg    4680
aaccttactt ctgtggtgtg acataattgg acaaactacc tacagagatt taaagctcta    4740
aggtaaatat aaaatttta agtgtataat gtgttaaact actgattcta attgtttgtg    4800
tattttagat tccaacctat ggaactgatg aatgggagca gtggtggaat gcctttaatg    4860
aggaaaacct gttttgctca gaagaaatgc catctagtga tgatgaggct actgctgact    4920
ctcaacattc tactcctcca aaaagaaga gaaaggtaga agaccccaag gactttcctt    4980
cagaattgct aagttttttg agtcatgctg tgtttagtaa tagaactctt gcttgctttg    5040
ctatttacac cacaaaggaa aaagctgcac tgctatacaa gaaaattatg gaaaaatatt    5100
ctgtaacctt tataagtagg cataacagtt ataatcataa catactgttt tttcttactc    5160
cacacaggca tagagtgtct gctattaata actatgctca aaaattgtgt acctttagct    5220
ttttaatttg taaggggtt  aataaggaat atttgatgta tagtgccttg actagagatc    5280
ataatcagcc ataccacatt tgtagaggtt ttacttgctt taaaaaacct cccacacctc    5340 ccctgaacc  tgaaacataa aatgaatgca attgttgttg ttaacttgtt tattgcagct    5400
tataatggtt acaaataaag caatagcatc acaaatttca caaataaagc atttttttca    5460
ctgcattcta gttgtggttt gtccaaactc atcaatgtat cttatcatgt ctggatcggc    5520
tggatgatcc tccagcgcgg ggatctcatg ctggagttct tcgcccaccc caacttgttt    5580
attgcagctt ataatggtta caaataaagc aatagcatca caaatttcac aaataaagca    5640
```

-continued

```
ttttttttcac tgcattctag ttgtggtttg tccaaactca tcaatgtatc ttatcatgtc    5700
tgtataccgt cgacctctag ctagagcttg gcgtaatcat ggtcatagct gtttcctgtg    5760
tgaaattgtt atccgctcac aattccacac aacatacgag ccggaagcat aaagtgtaaa    5820
gcctggggtg cctaatgagt gagctaactc acattaattg cgttgcgctc actgcccgct    5880
ttccagtcgg gaaacctgtc gtgccagctg cattaatgaa tcggccaacg cgcgggaga    5940
ggcggtttgc gtattgggcg ctcttccgct tcctcgctca ctgactcgct gcgctcggtc    6000
gttcggctgc ggcgagcggt atcagctcac tcaaaggcgg taatacggtt atccacagaa    6060
tcagggata acgcaggaaa gaacatgtga gcaaaaggcc agcaaaaggc caggaaccgt    6120
aaaaaggccg cgttgctggc gttttccat aggctccgcc cccctgacga gcatcacaaa    6180
aatcgacgct caagtcagag gtggcgaaac ccgacaggac tataaagata ccaggcgttt    6240
ccccctggaa gctccctcgt gcgctctcct gttccgaccc tgccgcttac cggatacctg    6300
tccgcctttc tcccttcggg aagcgtggcg ctttctcaat gctcacgctg taggtatctc    6360
agttcggtgt aggtcgttcg ctccaagctg ggctgtgtgc acgaaccccc cgttcagccc    6420
gaccgctgcg ccttatccgg taactatcgt cttgagtcca acccggtaag acacgactta    6480
tcgccactgg cagcagccac tggtaacagg attagcagag cgaggtatgt aggcggtgct    6540
acagagttct tgaagtggtg gcctaactac ggctacacta aggacagt atttggtatc    6600
tgcgctctgc tgaagccagt taccttcgga aaaagagttg gtagctcttg atccggcaaa    6660
caaaccaccg ctggtagcgg tggtttttt gtttgcaagc agcagattac gcgcagaaaa    6720
aaaggatctc aagaagatcc tttgatcttt tctacgggt ctgacgctca gtggaacgaa    6780
aactcacgtt aagggatttt ggtcatgaga ttatcaaaaa ggatcttcac ctagatcctt    6840
ttaaattaaa aatgaagttt taaatcaatc taaagtatat atgagtaaac ttggtctgac    6900
agttaccaat gcttaatcag tgaggcacct atctcagcga tctgtctatt tcgttcatcc    6960
atagttgcct gactccccgt cgtgtagata actacgatac gggagggctt accatctggc    7020
cccagtgctg caatgatacc gcgagaccca cgctcaccgg ctccagattt atcagcaata    7080
aaccagccag ccggaagggc cgagcgcaga agtggtcctg caactttatc cgcctccatc    7140
cagtctatta attgttgccg ggaagctaga gtaagtagtt cgccagttaa tagtttgcgc    7200
aacgttgttg ccattgctac aggcatcgtg gtgtcacgct cgtcgtttgg tatggcttca    7260
ttcagctccg gttcccaacg atcaaggcga gttacatgat cccccatgtt gtgcaaaaaa    7320
gcggttagct ccttcggtcc tccgatcgtt gtcagaagta agttggccgc agtgttatca    7380
ctcatggtta tggcagcact gcataattct cttactgtca tgccatccgt aagatgcttt    7440
tctgtgactg gtgagtactc aaccaagtca ttctgagaat agtgtatgcg gcgaccgagt    7500
tgctcttgcc cggcgtcaat acgggataat accgcgccac atagcagaac tttaaaagtg    7560
ctcatcattg gaaaacgttc ttcggggcga aaactctcaa ggatcttacc gctgttgaga    7620
tccagttcga tgtaacccac tcgtgcaccc aactgatctt cagcatcttt tactttcacc    7680
agcgtttctg ggtgagcaaa aacaggaagg caaaatgccg caaaaaaggg aataagggcg    7740
acacggaaat gttgaatact catactcttc cttttcaat attattgaag catttatcag    7800
ggttattgtc tcatgagcgg atacatattt gaatgtattt agaaaaataa acaaataggg    7860
gttccgcgca catttccccg aaaagtgcca cctgacgtcg acggatcggg agatctgcta    7920
gcccgggtga cctgaggcgc gccggcttcg aatagccaga gtaaccttt tttttaattt    7980
```

-continued

```
tattttatttt tatttttgag atggagtttg gcgccgatct cccgatcccc tatggtcgac     8040
tctcagtaca atctgctctg atgccgcata gttaagccag tatctgctcc ctgcttgtgt     8100
gttggaggtc gctgagtagt gcgcgagcaa aatttaagct acaacaaggc aaggcttgac     8160
cgacaattgc atgaagaatc tgcttagggt taggcgtttt gcgctgcttc gcgatgtacg     8220
ggccagatat acgcgttgac attgattatt gactagttat taatagtaat caattacggg     8280
gtcattagtt catagcccat atatggagtt ccgcgttaca taacttacgg taaatggccc     8340
gcctggctga ccgcccaacg accccgccc attgacgtca ataatgacgt atgttcccat      8400
agtaacgcca atagggactt tccattgacg tcaatgggtg gactatttac ggtaaactgc     8460
ccacttggca gtacatcaag tgtatcatat gccaagtacg cccctattg acgtcaatga      8520 cggtaaatgg cccgcctggc attatgccca gtacatgacc ttatgggact ttcctacttg     8580
gcagtacatc tacgtattag tcatcgctat taccatggtg atgcggtttt ggcagtacat     8640
caatgggcgt ggatagcggt ttgactcacg gggatttcca gtctccacc ccattgacgt      8700 caatgggagt ttgttttggc accaaaatca acgggacttt ccaaaatgtc gtaacaactc     8760
cgccccattg acgcaaatgg gcggtaggcg tgtacggtgg gaggtctata taagcagagc     8820
tctctggcta actagagaac ccactgctta ctggcttatc gaaattaata cgactcacta     8880
tagggagacc caagctt                                                    8897
```

<210> SEQ ID NO 12
<211> LENGTH: 8321
<212> TYPE: DNA
<213> ORGANISM: Homo sapiens

<400> SEQUENCE: 12

```
ggtaccaatt taaattgata tctccttagg tctcgagtct ctagataacc ggtcaatcga       60
ttggaattct tgcggccgct tgctagccac catggagttg tggttaagct tggtcttcct      120
tgtccttgtt ttaaaaggtg tccagtgtga agtgcaactg gtggagtctg ggggaggctt      180
agtgcagcct ggagggtccc tgcgactttc ctgtgctgca tctggattcc cgttcagtga      240
ctattacatg tattgggttc gccaggctcc aggcaaggga ctggagtggg tctcatacat      300
tagtcaagat ggtgatataa ccgactatgc agactccgta aagggtcgat tcaccatctc      360
cagagacaat gcaaagaaca gcctgtacct gcaaatgaac agcctgaggg acgaggacac      420
agccgtgtat tactgtgcaa gaggcctggc ggacggggcc tggtttgctt actggggcca      480
agggactctg gtcacggtct cttccgctag caccaagggc ccatcggtct tccccctggc      540
accctcctcc aagagcacct ctgggggcac agcggccctg ggctgcctgg tcaaggacta      600
cttccccgaa ccggtgacgg tgtcgtggaa ctcaggcgcc ctgaccagcg gcgtgcacac      660
cttcccggct gtcctacagt cctcaggact ctactccctc agcagcgtgg tcaccgtgcc      720
ctccagcagc ttgggcaccc agacctacat ctgcaacgtg aatcacaagc ccagcaacac      780
caaggtggac aagaaagttg gtgagaggcc agcacaggga gggagggtgt ctgctggaag      840
ccaggctcag cgctcctgcc tggacgcatc ccggctatgc agccccagtc agggcagca      900 aggcaggccc cgtctgcctc ttcacccgga ggcctctgcc cgccccactc atgctcaggg      960
agagggtctt ctggcttttt ccccaggctc tgggcaggca caggctaggt gccctaacc      1020 caggccctgc acacaagggg gcaggtgctg ggctcagacc tgccaagagc catatccggg     1080
aggaccctgc cctgaccta agcccacccc aaaggccaaa ctctccactc cctcagctcg      1140
gacaccttct ctcctcccag attccagtaa ctcccaatct tctctctgca gagcccaaat     1200
```

```
cttgtgacaa aactcacaca tgcccaccgt gcccaggtaa gccagccag gcctcgccct    1260 ccagctcaag gcgggacagg tgccctagag tagcctgcat ccagggacac accacgtggg    1320
taccaacatg tccggagcca catggacaga ggccggctcg gcccaccctc tgccctgaga    1380
gtgaccgctg taccaacctc tgtccctaca gggcagcccc gagaaccaca ggtgtacacc    1440
ctgcccccat cccgggatga gctgaccaag aaccaggtca gcctgacctg cctggtcaaa    1500
ggcttctatc ccagcgacat cgccgtggag tgggagagca atgggcagcc ggagaacaac    1560
tacaagacca cgcctcccgt gctggactcc gacggctcct tcttcctcta cagcaagctc    1620
accgtggaca agagcaggtg gcagcagggg aacgtcttct catgctccgt gatgcatgag    1680
gctctgcaca accactacac gcagaagagc ctctccctgt ctccgggtaa atgagtgcga    1740
cggccggcaa gcccccgctc cccgggctct cgcggtcgca cgaggatgct tggcacgtac    1800
cccctgtaca tacttcccgg gcgcccagca tggaaataaa gcacccagcg ctgccctggg    1860
cccctgcgag actgtgatgg ttctttccac gggtcaggcc gagtctgagg cctgagtggc    1920 atgaggagg cagagcgggt cccactgtcc ccacactggc ccaggctgtg caggtgtgcc    1980 tgggcccct agggtggggc tcagccaggg gctgccctcg gcagggtggg ggatttgcca    2040
gcgtggccct ccctccagca gcacctgccc tgggctgggc cacgggaagc cctaggagcc    2100
cctggggaca gacacacagc ccctgcctct gtaggagact gtcctgttct gtgagcgccc    2160
ctgtcctccc gacctccatg cccactcggg ggcatgccta gtccatgtgc gtagggacag    2220
gccctccctc acccatctac ccccacgca ctaaccctg gctgccctgc cagcctcgc    2280 acccgcatgg ggacacaacc gactccgggg acatgcactc tcgggccctg tggagggact    2340
ggtgcagatg cccacacaca cactcagccc agacccgttc aacaaacccc gcactgaggt    2400
tggccggcca cacggccacc acacacacac gtgcacgcct cacacacgga gcctcacccg    2460
ggcgaactgc acagcaccca gaccagagca aggtcctcgc acacgtgaac actcctcgga    2520
cacaggcccc cacgagcccc acgcggcacc tcaaggccca cgagcctctc ggcagcttct    2580
ccacatgctg acctgctcag acaaacccag ccctcctctc acaagggtgc ccctgcagcc    2640
gccacacaca cacaggggat cacacaccac gtcacgtccc tggccctggc ccacttccca    2700
gtgccgccct tccctgcagg acggatcagc ctcgactgtg ccttctagtt gccagccatc    2760
tgttgtttgc ccctcccccg tgccttcctt gaccctggaa ggtgccactc ccactgtcct    2820
ttcctaataa aatgaggaaa ttgcatcgca ttgtctgagt aggtgtcatt ctattctggg    2880
gggtggggtg gggcaggaca gcaaggggga ggattgggaa gacaatagca ggcatgctgg    2940
ggatgcggtg ggctctatgg cttctgaggc ggaaagaacc agctggggct ctaggggta    3000 tccccacgcg ccctgtagcg gcgcattaag gcggcgggt gtggtggtta cgcgcagcgt    3060
gaccgctaca cttgccagcg ccctagcgcc cgctcctttc gctttcttcc cttcctttct    3120
cgccacgttc gccgggcctc tcaaaaaagg gaaaaaagc atgcatctca attagtcagc    3180
aaccatagtc ccgcccctaa ctccgcccat cccgcccta actccgccca gttccgccca    3240
ttctccgccc catggctgac taatttttttt tatttatgca gaggccgagg ccgcctcggc    3300
ctctgagcta ttccagaagt agtgaggagg cttttttgga ggcctaggct tttgcaaaaa    3360
gcttggacag ctcagggctg cgatttcgcg ccaaacttga cggcaatcct agcgtgaagg    3420
ctggtaggat tttatccccg ctgccatcat ggttcgacca ttgaactgca tcgtcgccgt    3480
gtcccaaaat atggggattg gcaagaacgg agacctaccc tggcctccgc tcaggaacga    3540
```

-continued

```
gttcaagtac ttccaaagaa tgaccacaac ctcttcagtg gaaggtaaac agaatctggt    3600
gattatgggt aggaaaacct ggttctccat tcctgagaag aatcgacctt taaaggacag    3660
aattaatata gttctcagta gagaactcaa agaaccacca cgaggagctc attttcttgc    3720
caaaagtttg gatgatgcct taagacttat tgaacaaccg gaattggcaa gtaaagtaga    3780
catggtttgg atagtcggag gcagttctgt ttaccaggaa gccatgaatc aaccaggcca    3840
ccttagactc tttgtgacaa ggatcatgca ggaatttgaa agtgacacgt tttcccaga    3900 aattgatttg gggaaatata aacttctccc agaatccca ggcgtcctct ctgaggtcca    3960
ggaggaaaaa ggcatcaagt ataagtttga agtctacgag aagaaagact aacaggaaga    4020
tgctttcaag ttctctgctc ccctcctaaa gctatgcatt tttataagac catgggactt    4080
ttgctggctt tagatctctt tgtgaaggaa ccttacttct gtggtgtgac ataattggac    4140
aaactaccta cagagattta aagctctaag gtaaatataa aattttttaag tgtataatgt    4200 gttaaactac tgattctaat tgtttgtgta ttttagattc caacctatgg aactgatgaa    4260
tgggagcagt ggtggaatgc ctttaatgag gaaaacctgt tttgctcaga agaaatgcca    4320
tctagtgatg atgaggctac tgctgactct caacattcta ctcctccaaa aaagaagaga    4380
aaggtagaag acccccaagga ctttccttca gaattgctaa gttttttgag tcatgctgtg    4440
tttagtaata gaactcttgc ttgctttgct atttacacca caaggaaaa agctgcactg    4500 ctatacaaga aaattatgga aaaatattct gtaacctta taagtaggca taacagttat    4560
aatcataaca tactgttttt tcttactcca cacaggcata gagtgtctgc tattaataac    4620
tatgctcaaa aattgtgtac ctttagcttt ttaatttgta aaggggttaa taaggaatat    4680
ttgatgtata gtgccttgac tagagatcat aatcagccat accacatttg tagaggtttt    4740
acttgcttta aaaaacctcc cacacctccc cctgaacctg aaacataaaa tgaatgcaat    4800
tgttgttgtt aacttgttta ttgcagctta taatggttac aaataaagca atagcatcac    4860
aaatttcaca aataaagcat ttttttcact gcattctagt tgtggtttgt ccaaactcat    4920
caatgtatct tatcatgtct ggatcggctg atgatcctc cagcgcgggg atctcatgct    4980
ggagttcttc gcccacccca acttgtttat tgcagcttat aatggttaca aataaagcaa    5040
tagcatcaca aatttcacaa ataaagcatt ttttcactg cattctagtt gtggtttgtc    5100
caaactcatc aatgtatctt atcatgtctg tataccgtcg acctctagct agagcttggc    5160
gtaatcatgg tcatagctgt ttcctgtgtg aaattgttat ccgctcacaa ttccacacaa    5220
catacgagcc ggaagcataa agtgtaaagc ctggggtgcc taatgagtga gctaactcac    5280
attaattgcg ttgcgctcac tgcccgcttt ccagtcggga acctgtcgt gccagctgca    5340 ttaatgaatc ggccaacgcg cggggagagg cggtttgcgt attgggcgct cttccgcttc    5400
ctcgctcact gactcgctgc gctcggtcgt tcggctgcgg cgagcggtat cagctcactc    5460
aaaggcggta atacggttat ccacagaatc aggggataac gcaggaaaga acatgtgagc    5520
aaaaggccag caaaaggcca ggaaccgtaa aaaggccgcg ttgctggcgt ttttccatag    5580
gctccgcccc cctgacgagc atcacaaaaa tcgacgctca gtcagaggt ggcgaaaccc    5640 gacaggacta taaagatacc aggcgtttcc ccctggaagc tccctcgtgc gctctcctgt    5700
tccgaccctg ccgcttaccg gatacctgtc cgcctttctc ccttcgggaa gcgtggcgct    5760
ttctcaatgc tcacgctgta ggtatctcag ttcggtgtag tcgttcgct ccaagctggg    5820 ctgtgtgcac gaaccccccg ttcagcccga ccgctgcgcc ttatccggta actatcgtct    5880
tgagtccaac ccggtaagac acgacttatc gccactggca gcagccactg gtaacaggat    5940
```

```
tagcagagcg aggtatgtag gcggtgctac agagttcttg aagtggtggc ctaactacgg    6000
ctacactaga aggacagtat ttggtatctg cgctctgctg aagccagtta ccttcggaaa    6060
aagagttggt agctcttgat ccggcaaaca aaccaccgct ggtagcggtg gtttttttgt    6120
ttgcaagcag cagattacgc gcagaaaaaa aggatctcaa gaagatcctt tgatcttttc    6180 tacgggtct gacgctcagt ggaacgaaaa ctcacgttaa gggattttgg tcatgagatt    6240
atcaaaaagg atcttcacct agatcctttt aaattaaaaa tgaagtttta atcaatcta    6300 aagtatatat gagtaaactt ggtctgacag ttaccaatgc ttaatcagtg aggcaccta    6360 ctcagcgatc tgtctatttc gttcatccat agttgcctga ctccccgtcg tgtagataac    6420
tacgatacgg gagggcttac catctggccc cagtgctgca atgataccgc gagacccacg    6480
ctcaccggct ccagatttat cagcaataaa ccagccagcc ggaagggccg agcgcagaag    6540
tggtcctgca actttatccg cctccatcca gtctattaat tgttgccggg aagctagagt    6600
aagtagttcg ccagttaata gtttgcgcaa cgttgttgcc attgctacag gcatcgtggt    6660
gtcacgctcg tcgtttggta tggcttcatt cagctccggt tcccaacgat caaggcgagt    6720
tacatgatcc cccatgttgt gcaaaaaagc ggttagctcc ttcggtcctc cgatcgttgt    6780
cagaagtaag ttggccgcag tgttatcact catggttatg gcagcactgc ataattctct    6840
tactgtcatg ccatccgtaa gatgcttttc tgtgactggt gagtactcaa ccaagtcatt    6900
ctgagaatag tgtatgcggc gaccgagttg ctcttgcccg gcgtcaatac gggataatac    6960
cgcgccacat agcagaactt taaaagtgct catcattgga aaacgttctt cggggcgaaa    7020
actctcaagg atcttaccgc tgttgagatc cagttcgatg taacccactc gtgcacccaa    7080
ctgatcttca gcatctttta ctttcaccag cgtttctggg tgagcaaaaa caggaaggca    7140
aaatgccgca aaaaagggaa taagggcgac acggaaatgt tgaatactca tactcttcct    7200
ttttcaatat tattgaagca tttatcaggg ttattgtctc atgagcggat acatatttga    7260
atgtatttag aaaaataaac aaataggggt tccgcgcaca tttccccgaa aagtgccacc    7320
tgacgtcgac ggatcgggag atctgctagg tgacctgagg cgcgccggct tcgaatagcc    7380
agagtaacct ttttttttaa ttttatttta ttttattttt gagatggagt ttggcgccga    7440
tctcccgatc ccctatggtc gactctcagt acaatctgct ctgatgccgc atagttaagc    7500
cagtatctgc tccctgcttg tgtgttggag gtcgctgagt agtgcgcgag caaaatttaa    7560
gctacaacaa ggcaaggctt gaccgacaat tgcatgaaga atctgcttag ggttaggcgt    7620
tttgcgctgc ttcgcgatgt acgggccaga tatacgcgtt gacattgatt attgactagt    7680
tattaatagt aatcaattac ggggtcatta gttcatagcc catatatgga gttccgcgtt    7740
acataactta cggtaaatgg cccgcctggc tgaccgccca acgacccccg cccattgacg    7800
tcaataatga cgtatgttcc catagtaacg ccaataggga ctttccattg acgtcaatgg    7860
gtggactatt tacggtaaac tgcccacttg gcagtacatc aagtgtatca tatgccaagt    7920
acgcccccta ttgacgtcaa tgacggtaaa tggcccgcct ggcattatgc ccagtacatg    7980
accttatggg actttcctac ttggcagtac atctacgtat tagtcatcgc tattaccatg    8040
gtgatgcggt tttggcagta catcaatggg cgtggatagc ggtttgactc acggggattt    8100
ccaagtctcc accccattga cgtcaatggg agtttgtttt ggcaccaaaa tcaacgggac    8160
tttccaaaat gtcgtaacaa ctccgcccca ttgacgcaaa tgggcggtag gcgtgtacgg    8220
tgggaggtct atataagcag agctctctgg ctaactagag aacccactgc ttactggctt    8280
```

-continued

```
atcgaaatta atacgactca ctatagggag acccaagctt g              8321
```

<210> SEQ ID NO 13
<211> LENGTH: 8897
<212> TYPE: DNA
<213> ORGANISM: Homo sapiens

<400> SEQUENCE: 13

```
gacggatcgg gagatctgct agcccgggtg acctgaggcg cgccggcttc gaatagccag     60
agtaaccttt ttttttaatt ttattttatt ttattttttga gatggagttt ggcgccgatc   120
tcccgatccc ctatggtcga ctctcagtac aatctgctct gatgccgcat agttaagcca   180
gtatctgctc cctgcttgtg tgttggaggt cgctgagtag tgcgcgagca aaatttaagc   240
tacaacaagg caaggcttga ccgacaattg catgaagaat ctgcttaggg ttaggcgttt   300
tgcgctgctt cgcgatgtac gggccagata tacgcgttga cattgattat tgactagtta   360
ttaatagtaa tcaattacgg ggtcattagt tcatagccca tatatggagt tccgcgttac   420
ataacttacg gtaaatggcc cgcctggctg accgcccaac gacccccgcc cattgacgtc   480
aataatgacg tatgttccca tagtaacgcc aatagggact ttccattgac gtcaatgggt   540
ggactattta cggtaaactg cccacttggc agtacatcaa gtgtatcata tgccaagtac   600
gccccctatt gacgtcaatg acggtaaatg gcccgcctgg cattatgccc agtacatgac   660
cttatgggac tttcctactt ggcagtacat ctacgtatta gtcatcgcta ttaccatggt   720
gatgcggttt tggcagtaca tcaatgggcg tggatagcgg tttgactcac ggggatttcc   780
aagtctccac cccattgacg tcaatgggag tttgttttgg caccaaaatc aacgggactt   840
tccaaaatgt cgtaacaact ccgccccatt gacgcaaatg ggcggtaggc gtgtacggtg   900
ggaggtctat ataagcagag ctctctggct aactagagaa cccactgctt actggcttat   960
cgaaattaat acgactcact atagggagac ccaagcttgg taccaattta aattgatatc  1020
tccttaggtc tcgagcacca tgaagttgcc tgttaggctg ttggtgctga tgttctggat  1080
tcctgcttcc agcagtgatg ttgtcatgac ccaaaccccca ctgtccagtc tgtcacgct  1140
tggacaacct gcgtccatct cttgcagatc tagtcagatc attgtacata ataatggcaa  1200
cacctatctg gaatggtacc agcagagacc agggcagtct ccacggctcc tgatctacaa  1260
agtttccaac cgatttttctg gggtcccaga caggttcagc ggcagtggag ctgggacaga  1320
tttcacactc aagatcagca gagtggaggc tgaggatgtg ggagtttact actgcttcca  1380
gggttcacat gttccattca cgttcggcca agggacaaag ttggaaatca aacgtaagtc  1440
tcgagtctct agataaccgg tcaatcgatt ggaattctaa actctgaggg ggtcggatga  1500
cgtggccatt ctttgcctaa agcattgagt ttactgcaag gtcagaaaag catgcaaagc  1560
cctcagaatg gctgcaaaga gctccaacaa acaatttag aactttatta aggaataggg  1620
ggaagctagg aagaaactca aaacatcaag attttaaata cgcttcttgg tctccttgct  1680
ataattatct gggataagca tgctgttttc tgtctgtccc taacatgccc ttatccgcaa  1740
acaacacacc caagggcaga actttgttac ttaaacacca tcctgtttgc ttctttcctc  1800
aggaactgtg gctgcaccat ctgtcttcat cttcccgcca tctgatgagc agttgaaatc  1860
tggaactgcc tctgttgtgt gcctgctgaa taacttctat cccagagagg ccaaagtaca  1920
gtggaaggtg gataacgccc tccaatcggg taactcccag gagagtgtca cagagcagga  1980
gagcaaggac agcacctaca gcctcagcag caccctgacg ctgagcaaag cagactacga  2040
gaaacacaaa gtctacgcct gcgaagtcac ccatcagggc ctgagctcgc ccgtcacaaa  2100
```

```
gagcttcaac agggagagt gttagaggga gaagtgcccc cacctgctcc tcagttccag    2160
cctgacccc tcccatcctt tggcctctga ccctttttcc acaggggacc taccctatt     2220
gcggtcctcc agctcatctt tcacctcacc cccctcctcc tccttggctt taattatgct   2280
aatgttggag gagaatgaat aaataaagtg aatctttgca cctgtggttt ctctcttttcc  2340
tcatttaata attattatct gttgttttac caactactca atttctctta taagggacta   2400
aatatgtagt catcctaagg cacgtaacca tttataaaaa tcatccttca ttctatttta   2460
ccctatcatc ctctgcaaga cagtcctccc tcaaacccac aagccttctg tcctcacagt   2520
ccccctgggcc atggtaggag agacttgctt ccttgttttc ccctcctcag caagccctca  2580
tagtcctttt taagggtgac aggtcttaca gtcatatatc ctttgattca attccctgag   2640
aatcaaccaa agcaaatttt tcaaaagaag aaacctgcta taagagaat cattcattgc    2700
aacatgatat aaaataacaa cacaataaaa gcaattaaat aaacaaacaa tagggaaatg   2760
tttaagttca tcatggtact tagacttaat ggaatgtcat gccttattta catttttaaa   2820
caggtactga gggactcctg tctgccaagg gccgtattga gtactttcca caacctaatt   2880
taatccacac tatactgtga gattaaaaac attcattaaa atgttgcaaa ggttctataa   2940
agctgagaga caaatatatt ctataactca gcaatcccac ttctagatga ctgagtgtcc   3000
ccacccacca aaaactatg caagaatgtt caaagcagct ttatttacaa agccaaaaa     3060
ttggaaatag cccgattgtc caacaataga atgagttatt aaactgtggt atgtttatac   3120
attagaatac ccaatgagga gaattaacaa gctacaacta tacctactca cacagatgaa   3180
tctcataaaa ataatgttac ataagagaaa ctcaatgcaa agatatgtt ctgtatgttt     3240
tcatccatat aaagttcaaa accaggtaaa ataaagtta gaaatttgga tggaaattac    3300
tcttagctgg gggtgggcga gttagtgcct gggagaagac aagaagggc ttctggggtc    3360
ttggtaatgt tctgttcctc gtgtgggggtt gtgcagttat gatctgtgca ctgttctgta  3420
tacacattat gcttcaaaat aacttcacat aaagaacatc ttatacccag ttaatagata   3480
gaagaggaat aagtaatagg tcaagaccaa cgcagctggt aagtggggc ctgggatcaa    3540
atagctacct gcctaatcct gcccwcttga gccctgaatg agtctgcctt ccagggctca   3600
aggtgctcaa caaacaaca ggcctgctat tttcctggca tctgtgccct gtttggctag    3660
ctaggagcac acatacatag aaattaaatg aaacagacct tcagcaaggg gacagaggac   3720
agaattaacc ttgcccagac actggaaacc catgtatgaa cactcacatg tttgggaagg   3780
gggaagggca catgtaaatg aggactcttc ctcattctat ggggcactct ggccctgccc   3840
ctctcagcta ctcatccatc caacacacct ttctaagtac ctctctctgc ctacactctg   3900
aaggggttca ggagtaacta acacagcatc ccttccctca aatgactgac aatcccttg    3960
tcctgctttg ttttttcttc cagtcagtac tgggaaagtg gggaaggaca gtcatggaga   4020
aactacataa ggaagcacct tgcccttctg cctcttgaga atgttgatga gtatcaaatc   4080
tttcaaactt tggaggtttg agtaggggtg agactcagta atgtcccttc caatgacatg   4140
aacttgctca ctcatccctg ggggccaaat tgaacaatca aaggcaggca taatccagtt   4200
atgaattctt gcggccgctt gctagcttca cgtgttggat ccaaccgcgg aagggcccta   4260
ttctatagtg tcacctaaat gctagagctc gctgatcagc ctcgactgtg ccttctagtt   4320
gccagccatc tgttgtttgc ccctccccg tgccttcctt gacccctggaa ggtgccactc   4380
ccactgtcct ttcctaataa aatgaggaaa ttgcatcgca ttgtctgagt aggtgtcatt   4440
```

-continued

```
ctattctggg gggtggggtg gggcaggaca gcaaggggga ggattgggaa gacaatagca      4500
ggcatgctgg ggatgcggtg ggctctatgg cttctgaggc ggaaagaacc agctggggct      4560
ctagggggta tccccacgcg ccctgtagcg gcgcattaag cgcggcgggt gtggtggtta      4620
cgcgcagcgt gaccgctaca cttgccagcg ccctagcgcc cgctcctttc gctttcttcc      4680
cttcctttct cgccacgttc gccgggcctc tcaaaaaagg gaaaaaaagc atgcatctca      4740
attagtcagc aaccatagtc ccgcccctaa ctccgcccat cccgcccta actccgccca       4800 gttccgccca ttctccgccc catggctgac taatttttt tatttatgca gaggccgagg       4860
ccgcctcggc ctctgagcta ttccagaagt agtgaggagg ctttttttgga ggcctaggct     4920 tttgcaaaaa gcttggacag ctcagggctg cgatttcgcg ccaaacttga cggcaatcct      4980
agcgtgaagg ctggtaggat tttatccccg ctgccatcat ggttcgacca ttgaactgca     5040
tcgtcgccgt gtcccaaaat atggggattg gcaagaacgg agacctaccc tggcctccgc     5100
tcaggaacga gttcaagtac ttccaaagaa tgaccacaac ctcttcagtg gaaggtaaac     5160
agaatctggt gattatgggt aggaaaacct ggttctccat tcctgagaag aatcgacctt     5220
taaaggacag aattaatata gttctcagta gagaactcaa agaaccacca cgaggagctc     5280
attttcttgc caaaagtttg gatgatgcct taagacttat tgaacaaccg gaattggcaa     5340
gtaaagtaga catggtttgg atagtcggag gcagttctgt ttaccaggaa gccatgaatc     5400
aaccaggcca ccttagactc tttgtgacaa ggatcatgca ggaatttgaa agtgacacgt     5460
ttttcccaga aattgatttg gggaaatata aacttctccc agaataccca ggcgtcctct     5520
ctgaggtcca ggaggaaaaa ggcatcaagt ataagtttga agtctacgag aagaaagact     5580
aacaggaaga tgctttcaag ttctctgctc ccctcctaaa gctatgcatt tttataagac     5640
catgggactt tgctggcttt tagatctctt tgtgaaggaa ccttacttct gtggtgtgac     5700
ataattggac aaaactaccta cagagattta aagctctaag gtaaatataa aattttaag     5760 tgtataatgt gttaaactac tgattctaat tgtttgtgta ttttagattc caacctatgg     5820
aactgatgaa tgggagcagt ggtggaatgc ctttaatgag gaaaacctgt tttgctcaga     5880
agaaatgcca tctagtgatg atgaggctac tgctgactct caacattcta ctcctccaaa     5940
aaagaagaga aagtagaag accccaagga ctttccttca gaattgctaa gtttttgag      6000 tcatgctgtg tttagtaata gaactcttgc ttgctttgct atttacacca caaaggaaaa     6060
agctgcactg ctatacaaga aaattatgga aaaatattct gtaacctta taagtaggca      6120 taacagttat aatcataaca tactgttttt tcttactcca cacaggcata gagtgtctgc     6180
tattaataac tatgctcaaa aattgtgtac ctttagcttt ttaatttgta aaggggttaa     6240
taaggaatat ttgatgtata gtgccttgac tagagatcat aatcagccat accacatttg     6300
tagaggtttt acttgcttta aaaaacctcc cacacctccc cctgaacctg aaacataaaa     6360
tgaatgcaat tgttgttgtt aacttgttta ttgcagctta taatggttac aaataaagca     6420
atagcatcac aaatttcaca aataaagcat ttttttcact gcattctagt tgtggtttgt     6480
ccaaactcat caatgtatct tatcatgtct ggatcggctg gatgatcctc cagcgcgggg     6540
atctcatgct ggagttcttc gcccacccca acttgtttat tgcagcttat aatggttaca     6600
aataaagcaa tagcatcaca aatttcacaa ataaagcatt tttttcactg cattctagtt     6660
gtggtttgtc caaactcatc aatgtatctt atcatgtctg tataccgtcg acctctagct     6720
agagcttggc gtaatcatgg tcatagctgt ttcctgtgtg aaattgttat ccgctcacaa     6780
ttccacacaa catacgagcc ggaagcataa agtgtaaagc ctggggtgcc taatgagtga     6840
```

-continued

```
gctaactcac attaattgcg ttgcgctcac tgcccgcttt ccagtcggga aacctgtcgt    6900
gccagctgca ttaatgaatc ggccaacgcg cggggagagg cggtttgcgt attgggcgct    6960
cttccgcttc ctcgctcact gactcgctgc gctcggtcgt tcggctgcgg cgagcggtat    7020
cagctcactc aaaggcggta atacggttat ccacagaatc aggggataac gcaggaaaga    7080
acatgtgagc aaaaggccag caaaaggcca ggaaccgtaa aaaggccgcg ttgctggcgt    7140
ttttccatag gctccgcccc cctgacgagc atcacaaaaa tcgacgctca agtcagaggt    7200
ggcgaaaccc gacaggacta taaagatacc aggcgtttcc ccctggaagc tccctcgtgc    7260
gctctcctgt tccgaccctg ccgcttaccg gatacctgtc cgcctttctc ccttcgggaa    7320
gcgtggcgct ttctcaatgc tcacgctgta ggtatctcag ttcggtgtag gtcgttcgct    7380
ccaagctggg ctgtgtgcac gaaccccccg ttcagcccga ccgctgcgcc ttatccggta    7440
actatcgtct tgagtccaac ccggtaagac acgacttatc gccactggca gcagccactg    7500
gtaacaggat tagcagagcg aggtatgtag gcggtgctac agagttcttg aagtggtggc    7560
ctaactacgg ctacactaga aggacagtat ttggtatctg cgctctgctg aagccagtta    7620
ccttcggaaa aagagttggt agctcttgat ccggcaaaca accaccgct  ggtagcggtg    7680 gtttttttgt ttgcaagcag cagattacgc gcagaaaaaa aggatctcaa gaagatcctt    7740
tgatcttttc tacgggtct  gacgctcagt ggaacgaaaa ctcacgttaa gggattttgg    7800
tcatgagatt atcaaaaagg atcttcacct agatcctttt aaattaaaaa tgaagtttta    7860
aatcaatcta agtatatat  gagtaaactt ggtctgacag ttaccaatgc ttaatcagtg    7920
aggcacctat ctcagcgatc tgtctatttc gttcatccat agttgcctga ctccccgtcg    7980
tgtagataac tacgatacgg gagggcttac catctggccc cagtgctgca atgataccgc    8040
gagacccacg ctcaccggct ccagatttat cagcaataaa ccagccagcc ggaagggccg    8100
agcgcagaag tggtcctgca actttatccg cctccatcca gtctattaat tgttgccggg    8160
aagctagagt aagtagttcg ccagttaata gtttgcgcaa cgttgttgcc attgctacag    8220
gcatcgtggt gtcacgctcg tcgtttggta tggcttcatt cagctccggt tcccaacgat    8280
caaggcgagt tacatgatcc cccatgttgt gcaaaaaagc ggttagctcc ttcggtcctc    8340
cgatcgttgt cagaagtaag ttggccgcag tgttatcact catggttatg gcagcactgc    8400
ataattctct tactgtcatg ccatccgtaa gatgcttttc tgtgactggt gagtactcaa    8460
ccaagtcatt ctgagaatag tgtatgcggc gaccgagttg ctcttgcccg gcgtcaatac    8520
gggataatac cgcgccacat agcagaactt taaaagtgct catcattgga aaacgttctt    8580
cggggcgaaa actctcaagg atcttaccgc tgttgagatc cagttcgatg taacccactc    8640
gtgcacccaa ctgatcttca gcatctttta ctttcaccag cgtttctggg tgagcaaaaa    8700
caggaaggca aaatgccgca aaaaagggaa taagggcgac acggaaatgt tgaatactca    8760
tactcttcct ttttcaatat tattgaagca tttatcaggg ttattgtctc atgagcggat    8820
acatatttga atgtatttag aaaaataaac aatagggt  tccgcgcaca tttccccgaa    8880
aagtgccacc tgacgtc                                                   8897
```

<210> SEQ ID NO 14
<211> LENGTH: 44
<212> TYPE: DNA
<213> ORGANISM: Homo sapiens

<400> SEQUENCE: 14

```
gaagaggaag actgacggtg cccccgcgag ttcaggtgct gagg            44
```

<210> SEQ ID NO 15
<211> LENGTH: 44
<212> TYPE: DNA
<213> ORGANISM: Homo sapiens

<400> SEQUENCE: 15

```
cctcagcacc tgaactcgcg ggggcaccgt cagtcttcct cttc            44
```

<210> SEQ ID NO 16
<211> LENGTH: 51
<212> TYPE: DNA
<213> ORGANISM: Homo sapiens

<400> SEQUENCE: 16

```
ctgggagggc tttgttggag accgagcacg agtacgactt gccattcagc c    51
```

<210> SEQ ID NO 17
<211> LENGTH: 30
<212> TYPE: DNA
<213> ORGANISM: Homo sapiens

<400> SEQUENCE: 17

```
gatggttttc tcgatggcgg ctgggagggc                            30
```

<210> SEQ ID NO 18
<211> LENGTH: 30
<212> TYPE: DNA
<213> ORGANISM: Homo sapiens

<400> SEQUENCE: 18

```
gccctcccag ccgccatcga gaaaaccatc                            30
```

<210> SEQ ID NO 19
<211> LENGTH: 34
<212> TYPE: DNA
<213> ORGANISM: Homo sapiens

<400> SEQUENCE: 19

```
gatggttttc tcgatagcgg ctgggagggc tttg                       34
```

<210> SEQ ID NO 20
<211> LENGTH: 81
<212> TYPE: DNA
<213> ORGANISM: Homo sapiens

<400> SEQUENCE: 20

```
gatggttttc tcgatggcgg ctgggagggc tttgttggag accgagcacg agtacgactt   60
gccattcagc cagtcctggt g                                            81
```

<210> SEQ ID NO 21
<211> LENGTH: 81
<212> TYPE: DNA
<213> ORGANISM: Homo sapiens

<400> SEQUENCE: 21

```
caccaggact ggctgaatgg caagtcgtac tcgtgctcgg tctccaacaa agccctccca   60
gccgccatcg agaaaaccat c                                            81
```

<210> SEQ ID NO 22
<211> LENGTH: 8690

<210> TYPE: DNA
<213> ORGANISM: Homo sapiens

<400> SEQUENCE: 22

| | | | | | |
|---|---|---|---|---|---|
| ggtaccaatt | taaattgata | tctccttagg | tctcgagtct | ctagataacc | ggtcaatcga | 60 |
| ttggaattct | tgcggccgct | tgctagccac | catggagttg | tggttaagct | tggtcttcct | 120 |
| tgtccttgtt | ttaaaaggtg | tccagtgtga | agtgcaactg | gtggagtctg | ggggaggctt | 180 |
| agtgcagcct | ggagggtccc | tgcgactttc | ctgtgctgca | tctggattcc | cgttcagtga | 240 |
| ctattacatg | tattgggttc | gccaggctcc | aggcaaggga | ctggagtggg | tctcatacat | 300 |
| tagtcaagat | ggtgatataa | ccgactatgc | agactccgta | aagggtcgat | tcaccatctc | 360 |
| cagagacaat | gcaaagaaca | gcctgtacct | gcaaatgaac | agcctgaggg | acgaggacac | 420 |
| agccgtgtat | tactgtgcaa | gaggcctggc | ggacggggcc | tggtttgctt | actggggcca | 480 |
| agggactctg | gtcacggtct | cttccgctag | caccaagggc | ccatcggtct | tccccctggc | 540 |
| accctcctcc | aagagcacct | ctgggggcac | agcggccctg | ggctgcctgg | tcaaggacta | 600 |
| cttccccgaa | ccggtgacgg | tgtcgtggaa | ctcaggcgcc | ctgaccagcg | gcgtgcacac | 660 |
| cttcccggct | gtcctacagt | cctcaggact | ctactccctc | agcagcgtgg | tcaccgtgcc | 720 |
| ctccagcagc | ttgggcaccc | agacctacat | ctgcaacgtg | aatcacaagc | ccagcaacac | 780 |
| caaggtggac | aagaaagttg | gtgagaggcc | agcacaggga | gggaggtgt | ctgctggaag | 840 |
| ccaggctcag | cgctcctgcc | tggacgcatc | ccggctatgc | agccccagtc | cagggcagca | 900 |
| aggcaggccc | cgtctgcctc | ttcacccgga | ggcctctgcc | cgcccactc | atgctcaggg | 960 |
| agagggtctt | ctggctttt | ccccaggctc | tgggcaggca | caggctaggt | gcccctaacc | 1020 |
| caggccctgc | acacaaaggg | gcaggtgctg | ggctcagacc | tgccaagagc | catatccggg | 1080 |
| aggaccctgc | ccctgaccta | agcccacccc | aaaggccaaa | ctctccactc | cctcagctcg | 1140 |
| gacaccttct | ctcctcccag | attccagtaa | ctcccaatct | tctctctgca | gagcccaaat | 1200 |
| cttgtgacaa | aactcacaca | tgcccaccgt | gcccaggtaa | gccagcccag | gcctcgccct | 1260 |
| ccagctcaag | gcgggacagg | tgccctagag | tagcctgcat | ccaggacag | gccccagccg | 1320 |
| ggtgctgaca | cgtccacctc | catctcttcc | tcagcacctg | aactcctggg | gggaccgtca | 1380 |
| gtcttcctct | tccccccaaa | acccaaggac | accctcatga | tctcccggac | ccctgaggtc | 1440 |
| acatgcgtgg | tggtggacgt | gagccacgaa | gaccctgagg | tcaagttcaa | ctggtacgtg | 1500 |
| gacggcgtgg | aggtgcataa | tgccaagaca | aagccgcggg | aggagcagta | caacagcacg | 1560 |
| taccgtgtgg | tcagcgtcct | caccgtcctg | caccaggact | ggctgaatgg | caaggagtac | 1620 |
| aagtgcaagg | tctccaacaa | agccctccca | gcccccatcg | agaaaaccat | ctccaaagcc | 1680 |
| aaaggtggga | cccgtggggt | gcgagggcca | catggacaga | ggccggctcg | gcccaccctc | 1740 |
| tgccctgaga | gtgaccgctg | taccaacctc | tgtccctaca | gggcagcccc | gagaaccaca | 1800 |
| ggtgtacacc | ctgcccccat | cccgggatga | gctgaccaag | aaccaggtca | gcctgacctg | 1860 |
| cctggtcaaa | ggcttctatc | ccagcgacat | cgccgtggag | tgggagagca | atgggcagcc | 1920 |
| ggagaacaac | tacaagacca | cgcctcccgt | gctggactcc | gacggctcct | tcttcctcta | 1980 |
| cagcaagctc | accgtggaca | agagcaggtg | gcagcagggg | aacgtcttct | catgctccgt | 2040 |
| gatgcatgag | gctctgcaca | accactacac | gcagaagagc | ctctccctgt | ctccgggtaa | 2100 |
| atgagtgcga | cggccggcaa | gccccgctc | ccgggctct | cgcggtcgca | cgaggatgct | 2160 |
| tggcacgtac | cccctgtaca | tacttcccgg | gcgcccagca | tggaaataaa | gcacccagcg | 2220 |

```
ctgccctggg cccctgcgag actgtgatgg ttctttccac gggtcaggcc gagtctgagg    2280
cctgagtggc atgagggagg cagagcgggt cccactgtcc ccacactggc ccaggctgtg    2340
caggtgtgcc tgggccccct agggtggggc tcagccaggg gctgcccteg gcagggtggg    2400 ggatttgcca gcgtggccct ccctccagca gcacctgccc tgggctgggc cacgggaagc    2460
cctaggagcc cctggggaca gacacacagc ccctgcctct gtaggagact gtcctgttct    2520
gtgagcgccc ctgtcctccc gacctccatg cccactcggg ggcatgccta gtccatgtgc    2580
gtagggacag gccctccctc acccatctac ccccacggca ctaaccgctg gctgccctgc    2640
ccagcctcgc acccgcatgg ggacacaacc gactccgggg acatgcactc tcgggccctg    2700
tggagggact ggtgcagatg cccacacaca cactcagccc agaccgcttc aacaaacccc    2760
gcactgaggt tggccggcca cacggccacc acacacacac gtgcacgcct cacacacgga    2820
gcctcacccg ggcgaactgc acagcaccca gaccagagca aggtcctcgc acacgtgaac    2880
actcctcgga cacaggcccc cacgagcccc acgcggcacc tcaaggccca cgagcctctc    2940
ggcagcttct ccacatgctg acctgctcag acaaacccag ccctcctctc acaagggtgc    3000
ccctgcagcc gccacacaca cacagggat cacacaccac gtcacgtccc tggccctggc    3060
ccacttccca gtgccgccct tccctgcagg acggatcagc ctcgactgtg ccttctagtt    3120
gccagccatc tgttgtttgc ccctccccg tgccttcctt gaccctggaa ggtgccactc    3180
ccactgtcct ttcctaataa aatgaggaaa ttgcatcgca ttgtctgagt aggtgtcatt    3240
ctattctggg gggtggggtg gggcaggaca gcaaggggga ggattgggaa gacaatagca    3300
ggcatgctgg ggatgcggtg ggctctatgg cttctgaggc ggaaagaacc agctggggct    3360 ctaggggta tccccacgcg ccctgtagcg gcgcattaag cgcggcgggt gtggtggtta    3420
cgcgcagcgt gaccgctaca cttgccagcg ccctagcgcc cgctcctttc gctttcttcc    3480
cttcctttct cgccacgttc gccgggcctc tcaaaaaagg gaaaaaaagc atgcatctca    3540
attagtcagc aaccatagtc ccgcccctaa ctccgcccat cccgcccca actccgccca    3600 gttccgccca ttctccgccc catggctgac taattttttt tatttatgca gaggccgagg    3660
ccgcctcggc ctctgagcta ttccagaagt agtgaggagg cttttttgga ggcctaggct    3720
tttgcaaaaa gcttggacag ctcagggctg cgatttcgcg ccaaacttga cggcaatcct    3780
agcgtgaagg ctggtaggat tttatccccg ctgccatcat ggttcgacca ttgaactgca    3840
tcgtcgccgt gtcccaaaat atggggattg gcaagaacgg agacctaccc tggcctccgc    3900
tcaggaacga gttcaagtac ttccaaagaa tgaccacaac ctcttcagtg gaaggtaaac    3960
agaatctggt gattatgggt aggaaaacct ggttctccat tcctgagaag aatcgaccgt    4020
taaaggacag aattaatata gttctcagta gagaactcaa agaaccacca cgaggagctc    4080 atttcttgc caaagtttg gatgatgcct taagacttat tgaacaaccg gaattggcaa    4140
gtaaagtaga catggtttgg atagtcggag gcagttctgt ttaccaggaa gccatgaatc    4200
aaccaggcca ccttagactc tttgtgacaa ggatcatgca ggaatttgaa agtgacacgt    4260
ttttcccaga aattgatttg gggaaatata aacttctccc agaatacccca ggcgtcctct    4320 ctgaggtcca ggaggaaaaa ggcatcaagt ataagtttga agtctacgag aagaaagact    4380
aacaggaaga tgctttcaag ttctctgctc ccctcctaaa gctatgcatt tttataagac    4440
catgggactt tgctggctt tagatctctt tgtgaaggaa ccttacttct gtggtgtgac    4500
ataattggac aaactaccta cagagattta aagctctaag gtaaatataa aatttttaag    4560
tgtataatgt gttaaactac tgattctaat tgtttgtgta tttagattc caacctatgg    4620
```

```
aactgatgaa tgggagcagt ggtggaatgc ctttaatgag gaaaacctgt tttgctcaga    4680
agaaatgcca tctagtgatg atgaggctac tgctgactct caacattcta ctcctccaaa    4740
aaagaagaga aaggtagaag accccaagga ctttccttca gaattgctaa gttttttgag    4800
tcatgctgtg tttagtaata gaactcttgc ttgctttgct atttacacca caaaggaaaa    4860
agctgcactg ctatacaaga aaattatgga aaaatattct gtaacctta  taagtaggca    4920 taacagttat aatcataaca tactgttttt tcttactcca cacaggcata gagtgtctgc    4980
tattaataac tatgctcaaa aattgtgtac ctttagcttt ttaatttgta aagggg ttaa    5040 taaggaatat ttgatgtata gtgccttgac tagagatcat aatcagccat accacatttg    5100
tagaggtttt acttgcttta aaaaacctcc cacacctccc cctgaacctg aaacataaaa    5160
tgaatgcaat tgttgttgtt aacttgttta ttgcagctta taatggttac aaataaagca    5220
atagcatcac aaatttcaca ataaagcat  ttttttcact gcattctagt tgtggtttgt    5280
ccaaactcat caatgtatct tatcatgtct ggatcggctg gatgatcctc cagcgcgggg    5340
atctcatgct ggagttcttc gcccacccca acttgtttat tgcagcttat aatggttaca    5400
aataaagcaa tagcatcaca aatttcacaa ataaagcatt ttttcactg  cattctagtt    5460 gtggtttgtc caaactcatc aatgtatctt atcatgtctg tataccgtcg acctctagct    5520
agagcttggc gtaatcatgg tcatagctgt ttcctgtgtg aaattgttat ccgctcacaa    5580
ttccacacaa catacgagcc ggaagcataa agtgtaaagc ctggggtgcc taatgagtga    5640
gctaactcac attaattgcg ttgcgctcac tgcccgcttt ccagtcggga aacctgtcgt    5700
gccagctgca ttaatgaatc ggccaacgcg cggggagagg cggtttgcgt attgggcgct    5760
cttccgcttc ctcgctcact gactcgctgc gctcggtcgt tcggctgcgg cgagcggtat    5820
cagctcactc aaaggcggta atacggttat ccacagaatc aggggataac gcaggaaaga    5880
acatgtgagc aaaaggccag caaaaggcca ggaaccgtaa aaaggccgcg ttgctggcgt    5940
ttttccatag gctccgcccc cctgacgagc atcacaaaaa tcgacgctca agtcagaggt    6000
ggcgaaaccc gacaggacta taaagatacc aggcgtttcc ccctggaagc tccctcgtgc    6060
gctctcctgt tccgaccctg ccgcttaccg gatacctgtc cgcctttctc ccttcgggaa    6120
gcgtggcgct ttctcaatgc tcacgctgta ggtatctcag ttcggtgtag tcgttcgct     6180 ccaagctggg ctgtgtgcac gaacccccg  ttcagcccga ccgctgcgcc ttatccggta    6240
actatcgtct tgagtccaac ccggtaagac acgacttatc gccactggca gcagccactg    6300
gtaacaggat tagcagagcg aggtatgtag gcggtgctac agagttcttg aagtggtggc    6360
ctaactacgg ctacactaga aggacagtat ttggtatctg cgctctgctg aagccagtta    6420
ccttcggaaa aagagttggt agctcttgat ccggcaaaca aaccaccgct ggtagcggtg    6480 gttttttgt  ttgcaagcag cagattacgc gcagaaaaaa aggatctcaa gaagatcctt    6540
tgatcttttc tacgggg tct gacgctcagt ggaacgaaaa ctcacgttaa gggattttgg    6600
tcatgagatt atcaaaaagg atcttcacct agatcctttt aaattaaaaa tgaagtttta    6660
aatcaatcta aagtatatat gagtaaactt ggtctgacag ttaccaatgc ttaatcagtg    6720
aggcacctat ctcagcgatc tgtctatttc gttcatccat agttgcctga ctccccgtcg    6780
tgtagataac tacgatacgg gagggcttac catctggccc cagtgctgca atgataccgc    6840
gagacccacg ctcaccggct ccagatttat cagcaataaa ccagccagcc ggaagggccg    6900
agcgcagaag tggtcctgca actttatccg cctccatcca gtctattaat tgttgccggg    6960
```

| | |
|---|---:|
| aagctagagt aagtagttcg ccagttaata gtttgcgcaa cgttgttgcc attgctacag | 7020 |
| gcatcgtggt gtcacgctcg tcgtttggta tggcttcatt cagctccggt tcccaacgat | 7080 |
| caaggcgagt tacatgatcc cccatgttgt gcaaaaaagc ggttagctcc ttcggtcctc | 7140 |
| cgatcgttgt cagaagtaag ttggccgcag tgttatcact catggttatg gcagcactgc | 7200 |
| ataattctct tactgtcatg ccatccgtaa gatgcttttc tgtgactggt gagtactcaa | 7260 |
| ccaagtcatt ctgagaatag tgtatgcggc gaccgagttg ctcttgcccg gcgtcaatac | 7320 |
| gggataatac cgcgccacat agcagaactt aaaagtgct catcattgga aaacgttctt | 7380 |
| cggggcgaaa actctcaagg atcttaccgc tgttgagatc cagttcgatg taacccactc | 7440 |
| gtgcacccaa ctgatcttca gcatctttta ctttcaccag cgtttctggg tgagcaaaaa | 7500 |
| caggaaggca aaatgccgca aaaagggaa taagggcgac acggaaatgt tgaatactca | 7560 |
| tactcttcct ttttcaatat tattgaagca tttatcaggg ttattgtctc atgagcggat | 7620 |
| acatatttga atgtatttag aaaaataaac aaataggggg tccgcgcaca tttccccgaa | 7680 |
| aagtgccacc tgacgtcgac ggatcgggag atctgctagg tgacctgagg cgcgccggct | 7740 |
| tcgaatagcc agagtaacct tttttttaa ttttattta ttttatttt gagatggagt | 7800 |
| ttggcgccga tctcccgatc ccctatggtc gactctcagt acaatctgct ctgatgccgc | 7860 |
| atagttaagc cagtatctgc tccctgcttg tgtgttggag gtcgctgagt agtgcgcgag | 7920 |
| caaaatttaa gctacaacaa ggcaaggctt gaccgacaat tgcatgaaga atctgcttag | 7980 |
| ggttaggcgt tttgcgctgc ttcgcgatgt acgggccaga tatacgcgtt gacattgatt | 8040 |
| attgactagt tattaatagt aatcaattac ggggtcatta gttcatagcc catatatgga | 8100 |
| gttccgcgtt acataactta cggtaaatgg cccgcctggc tgaccgccca acgaccccg | 8160 |
| cccattgacg tcaataatga cgtatgttcc catagtaacg ccaatagggga ctttccattg | 8220 |
| acgtcaatgg gtggactatt tacgtaaac tgcccacttg gcagtacatc aagtgtatca | 8280 |
| tatgccaagt acgccccta ttgacgtcaa tgacggtaaa tggcccgcct ggcattatgc | 8340 |
| ccagtacatg accttatggg actttcctac ttggcagtac atctacgtat tagtcatcgc | 8400 |
| tattaccatg gtgatgcggt tttggcagta catcaatggg cgtggatagc ggtttgactc | 8460 |
| acggggattt ccaagtctcc accccattga cgtcaatggg agtttgtttt ggcaccaaaa | 8520 |
| tcaacgggac tttccaaaat gtcgtaacaa ctccgcccca ttgacgcaaa tgggcggtag | 8580 |
| gcgtgtacgg tgggaggtct atataagcag agctctctgg ctaactagag aacccactgc | 8640 |
| ttactggctt atcgaaatta atacgactca ctataggag acccaagctt | 8690 |

<210> SEQ ID NO 23
<211> LENGTH: 7874
<212> TYPE: DNA
<213> ORGANISM: Homo sapiens

<400> SEQUENCE: 23

| | |
|---|---:|
| ggtaccaatt taaattgata tctccttagg tctcgagtct ctagataacc ggtcaatcga | 60 |
| ttggaattct gcggccgct tgctagcacc aagggcccat cggtcttccc cctggcaccc | 120 |
| tcctccaaga gcacctctgg gggcacagcg gccctgggct gcctggtcaa ggactacttc | 180 |
| cccgaaccgg tgacggtgtc gtggaactca ggcgccctga ccagcggcgt gcacaccttc | 240 |
| ccggctgtcc tacagtcctc aggactctac tccctcagca gcgtggtcac cgtgccctcc | 300 |
| agcagcttgg gcacccagac ctacatctgc aacgtgaatc acaagccag caacaccaag | 360 |
| gtggacaaga aagttggtga gaggccagca cagggaggga gggtgtctgc tggaagccag | 420 |

```
gctcagcgct cctgcctgga cgcatcccgg ctatgcagcc ccagtccagg gcagcaaggc      480
aggccccgtc tgcctcttca cccggaggcc tctgcccgcc ccactcatgc tcagggagag      540
ggtcttctgg cttttcccc aggctctggg caggcacagg ctaggtgccc ctaacccagg       600
ccctgcacac aaaggggcag gtgctgggct cagacctgcc aagagccata tccgggagga      660
ccctgcccct gacctaagcc caccccaaag gccaaactct ccactccctc agctcggaca      720
ccttctctcc tcccagattc cagtaactcc caatcttctc tctgcagagc ccaaatcttg      780
tgacaaaact cacacatgcc caccgtgccc aggtaagcca gcccaggcct cgccctccag      840
ctcaaggcgg gacaggtgcc ctagagtagc ctgcatccag ggacaggccc cagccgggtg      900
ctgacacgtc cacctccatc tcttcctcag cacctgaact cctggggggga ccgtcagtct     960 tcctcttccc cccaaaaccc aaggacaccc tcatgatctc ccggacccct gaggtcacat     1020
gcgtggtggt ggacgtgagc cacgaagacc ctgaggtcaa gttcaactgg tacgtggacg     1080
gcgtggaggt gcataatgcc aagacaaagc cgcgggagga gcagtacaac agcacgtacc     1140
gtgtggtcag cgtcctcacc gtcctgcacc aggactggct gaatggcaag gagtacaagt     1200
gcaaggtctc caacaaagcc ctcccagccc ccatcgagaa aaccatctcc aaagccaaag     1260
gtgggacccg tggggtgcga gggccacatg gacagaggcc ggctcggccc accctctgcc     1320
ctgagagtga ccgctgtacc aacctctgtc cctacagggc agccccgaga accacaggtg     1380
tacaccctgc ccccatcccg ggatgagctg accaagaacc aggtcagcct gacctgcctg     1440
gtcaaaggct tctatcccag cgacatcgcc gtggagtggg agagcaatgg gcagccggag     1500
aacaactaca agaccacgcc tcccgtgctg gactccgacg gctccttctt cctctacagc     1560
aagctcaccg tggacaagag caggtggcag caggggaacg tcttctcatg ctccgtgatg     1620
catgaggctc tgcacaacca ctacacgcag aagagcctct ccctgtctcc gggtaaatga     1680
gtgcgacggc cggcaagccc ccgctccccg ggctctcgcg gtcgcacgag gatgcttggc     1740
acgtaccccc tgtacatact tcccgggcgc ccagcatgga aataaagcac ccagcgctgc     1800
cctgggcccc tgcgagactg tgatggttct ttccacgggt caggccgagt ctgaggcctg     1860
agtggcatga gggaggcaga gcgggtccca ctgtccccac actggcccag gctgtgcagg     1920
tgtgcctggg ccccctaggg tggggctcag ccaggggctg ccctcggcag ggtgggggat     1980
ttgccagcgt ggccctccct ccagcagcac ctgccctggg ctgggccacg ggaagcccta     2040 ggagccctg gggacagaca cacagcccct gcctctgtag gagactgtcc tgttctgtga      2100
gcgcccctgt cctcccgacc tccatgccca ctcggggggca tgctggggat gcggtgggct     2160
ctatggcttc tgaggcggaa agaaccagct ggggctctag ggggtatccc cacgcgccct     2220
gtagcggcgc attaagcgcg gcgggtgtgg tggttacgcg cagcgtgacc gctacacttg     2280
ccagcgccct agcgcccgct cctttcgctt tcttcccttc ctttctcgcc acgttcgccg     2340
gctttccccg tcaagctcta atcggggca tccctttagg gttccgattt agtgctttac      2400
ggcacctcga cccaaaaaa cttgattagg gtgatggttc acgtagtggg ccatcgccct      2460
gatagacggt ttttcgccct tgacgttgg agtccacgtt ctttaatagt ggactcttgt      2520
tccaaactgg aacaacactc aaccctatct cggtctattc ttttgattta agggatttt     2580 tgggatttc ggcctattgg ttaaaaaatg agctgattta acaaaaattt aacgcgaatt      2640
aattctgtgg aatgtgtgtc agttagggtg tggaaagtcc ccaggctccc caggcaggca     2700
gaagtatgca aagcatgcat ctcaattagt cagcaaccat agtcccgccc ctaactccgc     2760
```

-continued

```
ccatcccgcc cctaactccg cccagttccg cccattctcc gccccatggc tgactaattt    2820
tttttattta tgcagaggcc gaggccgcct cggcctctga gctattccag aagtagtgag    2880
gaggcttttt tggaggccta ggcttttgca aaaagcttgg acagctcagg gctgcgattt    2940
cgcgccaaac ttgacggcaa tcctagcgtg aaggctggta ggattttatc cccgctgcca    3000
tcatggttcg accattgaac tgcatcgtcg ccgtgtccca aaatatgggg attggcaaga    3060
acggagacct accctggcct ccgctcagga acgagttcaa gtacttccaa agaatgacca    3120
caacctcttc agtggaaggt aaacagaatc tggtgattat gggtaggaaa acctggttct    3180
ccattcctga gaagaatcga cctttaaagg acagaattaa tatagttctc agtagagaac    3240
tcaaagaacc accacgagga gctcattttc ttgccaaaag tttggatgat gccttaagac    3300
ttattgaaca accggaattg gcaagtaaag tagacatggt ttggatagtc ggaggcagtt    3360
ctgtttacca ggaagccatg aatcaaccag gccaccttag actctttgtg acaaggatca    3420
tgcaggaatt tgaaagtgac acgttttttcc cagaaattga tttggggaaa tataaacttc    3480
tcccagaata cccaggcgtc ctctctgagg tccaggagga aaaaggcatc aagtataagt    3540
ttgaagtcta cgagaagaaa gactaacagg aagatgcttt caagttctct gctcccctcc    3600
taaagctatg cattttata agaccatggg acttttgctg gctttagatc tctttgtgaa    3660
ggaaccttac ttctgtggtg tgacataatt ggacaaacta cctacagaga tttaaagctc    3720
taaggtaaat ataaaatttt taagtgtata atgtgttaaa ctactgattc taattgtttg    3780
tgtattttag attccaacct atggaactga tgaatgggag cagtggtgga atgcctttaa    3840
tgaggaaaac ctgttttgct cagaagaaat gccatctagt gatgatgagg ctactgctga    3900
ctctcaacat tctactcctc caaaaaagaa gagaaaggta gaagacccca aggacttttcc    3960
ttcagaattg ctaagttttt tgagtcatgc tgtgtttagt aatagaactc ttgcttgctt    4020
tgctatttac accacaaagg aaaaagctgc actgctatac aagaaaatta tggaaaaata    4080
ttctgtaacc tttataagta ggcataacag ttataatcat aacatactgt tttttcttac    4140
tccacacagg catagagtgt ctgctattaa taactatgct caaaaattgt gtacctttag    4200
ctttttaatt tgtaaagggg ttaataagga atatttgatg tatagtgcct tgactagaga    4260
tcataatcag ccataccaca tttgtagagg ttttacttgc tttaaaaaac ctcccacacc    4320
tccccctgaa cctgaaacat aaaatgaatg caattgttgt tgttaacttg tttattgcag    4380
cttataatgg ttacaaataa agcaatagca tcacaaattt cacaaataaa gcatttttt    4440
cactgcattc tagttgtggt ttgtccaaac tcatcaatgt atcttatcat gtctggatcg    4500
gctggatgat cctccagcgc ggggatctca tgctggagtt cttcgcccac cccaacttgt    4560
ttattgcagc ttataatggt tacaaataaa gcaatagcat cacaaatttc acaaataaag    4620
cattttttc actgcattct agttgtggtt tgtccaaact catcaatgta tcttatcatg    4680
tctgtatacc gtcgacctct agctagagct tggcgtaatc atggtcatag ctgtttcctg    4740
tgtgaaattg ttatccgctc acaattccac acaacatacg agccggaagc ataaagtgta    4800
aagcctgggg tgcctaatga gtgagctaac tcacattaat tgcgttgcgc tcactgcccg    4860
ctttccagtc gggaaacctg tcgtgccagc tgcattaatg aatcggccaa cgcgcgggga    4920
gaggcggttt gcgtattggg cgctcttccg cttcctcgct cactgactcg ctgcgctcgg    4980
tcgttcggct gcggcgagcg gtatcagctc actcaaaggc ggtaatacgg ttatccacag    5040
aatcagggga taacgcagga aagaacatgt gagcaaaagg ccagcaaaag gccaggaacc    5100
gtaaaaaggc cgcgttgctg gcgtttttcc ataggctccg ccccctgac gagcatcaca    5160
```

-continued

```
aaaatcgacg ctcaagtcag aggtggcgaa acccgacagg actataaaga taccaggcgt    5220 ttcccctgg aagctccctc gtgcgctctc ctgttccgac cctgccgctt accggatacc    5280
tgtccgcctt tctcccttcg ggaagcgtgg cgctttctca atgctcacgc tgtaggtatc    5340
tcagttcggt gtaggtcgtt cgctccaagc tgggctgtgt gcacgaaccc cccgttcagc    5400
ccgaccgctg cgccttatcc ggtaactatc gtcttgagtc caacccggta agacacgact    5460
tatcgccact ggcagcagcc actggtaaca ggattagcag agcgaggtat gtaggcggtg    5520
ctacagagtt cttgaagtgg tggcctaact acggctacac tagaaggaca gtatttggta    5580
tctgcgctct gctgaagcca gttaccttcg gaaaaagagt tggtagctct tgatccggca    5640
aacaaaccac cgctggtagc ggtggttttt ttgtttgcaa gcagcagatt acgcgcagaa    5700
aaaaaggatc tcaagaagat cctttgatct tttctacggg gtctgacgct cagtggaacg    5760
aaaactcacg ttaagggatt ttggtcatga gattatcaaa aaggatcttc acctagatcc    5820
ttttaaatta aaaatgaagt tttaaatcaa tctaaagtat atatgagtaa acttggtctg    5880
acagttacca atgcttaatc agtgaggcac ctatctcagc gatctgtcta tttcgttcat    5940
ccatagttgc ctgactcccc gtcgtgtaga taactacgat acgggagggc ttaccatctg    6000
gccccagtgc tgcaatgata ccgcgagacc cacgctcacc ggctccagat ttatcagcaa    6060
taaaccagcc agccggaagg gccgagcgca gaagtggtcc tgcaacttta tccgcctcca    6120
tccagtctat taattgttgc cgggaagcta gagtaagtag ttcgccagtt aatagtttgc    6180
gcaacgttgt tgccattgct acaggcatcg tggtgtcacg ctcgtcgttt ggtatggctt    6240
cattcagctc cggttcccaa cgatcaaggc gagttacatg atcccccatg ttgtgcaaaa    6300
aagcggttag ctccttcggt cctccgatcg ttgtcagaag taagttggcc gcagtgttat    6360
cactcatggt tatggcagca ctgcataatt ctcttactgt catgccatcc gtaagatgct    6420
tttctgtgac tggtgagtac tcaaccaagt cattctgaga atagtgtatg cggcgaccga    6480
gttgctcttg cccggcgtca atacgggata ataccgcgcc acatagcaga actttaaaag    6540
tgctcatcat tggaaaacgt tcttcgggc gaaaactctc aaggatctta ccgctgttga    6600
gatccagttc gatgtaaccc actcgtgcac ccaactgatc ttcagcatct tttactttca    6660
ccagcgtttc tgggtgagca aaaacaggaa ggcaaaatgc cgcaaaaaag ggaataaggg    6720
cgacacggaa atgttgaata ctcatactct tcctttttca atattattga agcatttatc    6780
agggttattg tctcatgagc ggatacatat ttgaatgtat ttagaaaaat aaacaaatag    6840
gggttccgcg cacatttccc cgaaaagtgc cacctgacgt cgacggatcg ggagatctgc    6900
taggtgacct gaggcgcgcc ggcttcgaat agccagagta accttttttt ttaattttat    6960
tttattttat ttttgagatg gagtttggcg ccgatctccc gatccctat ggtcgactct    7020 cagtacaatc tgctctgatg ccgcatagtt aagccagtat ctgctccctg cttgtgtgtt    7080
ggaggtcgct gagtagtgcg cgagcaaaat ttaagctaca acaaggcaag gcttgaccga    7140
caattgcatg aagaatctgc ttagggttag gcgttttgcg ctgcttcgcg atgtacgggc    7200
cagatatacg cgttgacatt gattattgac tagttattaa tagtaatcaa ttacggggtc    7260
attagttcat agcccatata tggagttccg cgttacataa cttacggtaa atggcccgcc    7320
tggctgaccg cccaacgacc cccgcccatt gacgtcaata atgacgtatg ttcccatagt    7380
aacgccaata gggactttcc attgacgtca atgggtggac tatttacggt aaactgccca    7440
cttggcagta catcaagtgt atcatatgcc aagtacgccc cctattgacg tcaatgacgg    7500
```

-continued

```
taaatggccc gcctggcatt atgcccagta catgacctta tgggactttc ctacttggca    7560
gtacatctac gtattagtca tcgctattac catggtgatg cggttttggc agtacatcaa    7620
tgggcgtgga tagcgtttg actcacgggg atttccaagt ctccacccca ttgacgtcaa     7680
tgggagtttg ttttggcacc aaaatcaacg ggactttcca aaatgtcgta caactccgc     7740 cccattgacg caaatgggcg gtaggcgtgt acggtgggag gtctatataa gcagagctct    7800
ctggctaact agagaaccca ctgcttactg gcttatcgaa attaatacga ctcactatag    7860
ggagacccaa gctt                                                     7874
```

<210> SEQ ID NO 24
<211> LENGTH: 119
<212> TYPE: PRT
<213> ORGANISM: Homo sapiens

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Asp Tyr
            20                  25                  30

Tyr Met Tyr Trp Val Arg Gln Ala Pro Gly Lys Gly Leu Glu Trp Val
        35                  40                  45

Ser Tyr Ile Ser Gln Asp Gly Asp Ile Thr Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Gly Leu Ala Asp Gly Ala Trp Phe Ala Tyr Trp Gly Gln Gly
            100                 105                 110

Thr Leu Val Thr Val Ser Ser
        115
```

<210> SEQ ID NO 25
<211> LENGTH: 330
<212> TYPE: PRT
<213> ORGANISM: Homo sapiens

<400> SEQUENCE: 25

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

-continued

```
            130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Asp Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 220
<212> TYPE: PRT
<213> ORGANISM: Homo sapiens

<400> SEQUENCE: 26

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Gly Gln Pro Arg Glu Pro Gln Val Tyr Thr Leu Pro Pro Ser Arg
        115                 120                 125

Asp Glu Leu Thr Lys Asn Gln Val Ser Leu Thr Cys Leu Val Lys Gly
    130                 135                 140

Phe Tyr Pro Ser Asp Ile Ala Val Glu Trp Glu Ser Asn Gly Gln Pro
145                 150                 155                 160

Glu Asn Asn Tyr Lys Thr Thr Pro Pro Val Leu Asp Ser Asp Gly Ser
                165                 170                 175
```

```
Phe Phe Leu Tyr Ser Lys Leu Thr Val Asp Lys Ser Arg Trp Gln Gln
                180                 185                 190

Gly Asn Val Phe Ser Cys Ser Val Met His Glu Ala Leu His Asn His
        195                 200                 205

Tyr Thr Gln Lys Ser Leu Ser Leu Ser Pro Gly Lys
    210                 215                 220

<210> SEQ ID NO 27
<211> LENGTH: 339
<212> TYPE: PRT
<213> ORGANISM: Homo sapiens

<400> SEQUENCE: 27

Glu Val Asn Leu Val Glu Ser Gly Gly Gly Leu Val Gln Pro Gly Gly
1               5                   10                  15

Ser Leu Lys Val Ser Cys Val Thr Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Tyr Ile Ser Gln Gly Gly Asp Ile Thr Asp Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Gly Leu Asp Asp Gly Ala Trp Phe Ala Tyr Trp Gly Gln Gly
            100                 105                 110

Thr Leu Val Thr Val Ser Val Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Gly Gln Pro Arg Glu Pro Gln Val
225                 230                 235                 240

Tyr Thr Leu Pro Pro Ser Arg Asp Glu Leu Thr Lys Asn Gln Val Ser
                245                 250                 255

Leu Thr Cys Leu Val Lys Gly Phe Tyr Pro Ser Asp Ile Ala Val Glu
            260                 265                 270

Trp Glu Ser Asn Gly Gln Pro Glu Asn Asn Tyr Lys Thr Thr Pro Pro
        275                 280                 285

Val Leu Asp Ser Asp Gly Ser Phe Phe Leu Tyr Ser Lys Leu Thr Val
    290                 295                 300

Asp Lys Ser Arg Trp Gln Gln Gly Asn Val Phe Ser Cys Ser Val Met
305                 310                 315                 320

His Glu Ala Leu His Asn His Tyr Thr Gln Lys Ser Leu Ser Leu Ser
                325                 330                 335
```

Pro Gly Lys

<210> SEQ ID NO 28
<211> LENGTH: 8321
<212> TYPE: DNA
<213> ORGANISM: Homo sapiens

<400> SEQUENCE: 28

| | | | | | |
|---|---|---|---|---|---|
| ctgcctagcc | ctctagacga | tccactggac | tccgcgcggc | cgaagcttat | cggtctcatt | 60 |
| ggaaaaaaaa | attaaaataa | aataaaataa | aaactctacc | tcaaaccgcg | gctagagggc | 120 |
| tagggggatac | cagctgagag | tcatgttaga | cgagactacg | gcgtatcaat | tcggtcatag | 180 |
| acgagggacg | aacacacaac | ctccagcgac | tcatcacgcg | ctcgttttaa | attcgatgtt | 240 |
| gttccgttcc | gaactggctg | ttaacgtact | tcttagacga | atcccaatcc | gcaaaacgcg | 300 |
| acgaagcgct | acatgcccgg | tctatatgcg | caactgtaac | taataactga | tcaataatta | 360 |
| tcattagtta | atgccccagt | aatcaagtat | cgggtatata | cctcaaggcg | caatgtattg | 420 |
| aatgccattt | accgggcgga | ccgactggcg | ggttgctggg | ggcgggtaac | tgcagttatt | 480 |
| actgcataca | agggtatcat | tgcggttatc | cctgaaaggt | aactgcagtt | acccacctga | 540 |
| taaatgccat | ttgacgggtg | aaccgtcatg | tagttcacat | agtatacggt | tcatgcgggg | 600 |
| gataactgca | gttactgcca | tttaccgggc | ggaccgtaat | acgggtcatg | tactggaata | 660 |
| ccctgaaagg | atgaaccgtc | atgtagatgc | ataatcagta | gcgataatgg | taccactacg | 720 |
| ccaaaaccgt | catgtagtta | cccgcaccta | tcgccaaact | gagtgcccct | aaaggttcag | 780 |
| aggtggggta | actgcagtta | ccctcaaaca | aaaccgtggt | tttagttgcc | ctgaaaggtt | 840 |
| ttacagcatt | gttgaggcgg | ggtaactgcg | tttacccgcc | atccgcacat | gccaccctcc | 900 |
| agatatattc | gtctcgagag | accgattgat | ctcttgggtg | acgaatgacc | gaatagcttt | 960 |
| aattatgctg | agtgatatcc | ctctgggttc | gaaccatggt | taaatttaac | tatagaggaa | 1020 |
| tccagagctc | agagatctat | tggccagtta | gctaaccttaa | agaacgccgg | cgaacgatcg | 1080 |
| gtggtacctc | aacaccaatt | cgaaccagga | aggaacagga | acaaaatttt | ccacaggtca | 1140 |
| cacttcactt | agaccaccte | agaccccctc | cgaatcacgt | cggacctccc | agggactttc | 1200 |
| agaggacaca | ttgagacct | aagtgaaagt | cactgataat | gtacataacc | caagcggtct | 1260 |
| gaggtctctt | ctccgacctc | acccagcgta | tgtaatcagt | tccaccacta | tattggctga | 1320 |
| taggtctgtg | acatttccca | gctaagtggt | agaggtctct | gttacggttc | ttgtgggaca | 1380 |
| tggacgttta | ctcggcagac | ttcagactcc | tgtgtcggta | cataatgaca | cgttctccgg | 1440 |
| acctgctgcc | ccggaccaaa | cgaatgaccc | cggttccctg | agaccagtgc | cagagacatc | 1500 |
| gatcgtggtt | cccgggtagc | cagaagggg | accgtgggag | gaggttctcg | tggagacccc | 1560 |
| cgtgtcgccg | ggacccgacg | gaccagttcc | tgatgaaggg | gcttggccac | tgccacagca | 1620 |
| ccttgagtcc | gcgggactgg | tcgccgcacg | tgtggaaggg | ccgacaggat | gtcaggagtc | 1680 |
| ctgagatgag | ggagtcgtcg | caccagtggc | acggaggtc | gtcgaacccg | tgggtctgga | 1740 |
| tgtagacgtt | gcacttagtg | ttcgggtcgt | tgtggttcca | cctgttcttt | caaccactct | 1800 |
| ccggtcgtgt | ccctccctcc | cacagacgac | cttcggtccg | agtcgcgagg | acggacctgc | 1860 |
| gtagggccga | tacgtcgggg | tcaggtcccg | tcgttccgtc | cggggcagac | ggagaagtgg | 1920 |
| gcctccggag | acgggcgggg | tgagtacgag | tccctctccc | agaagaccga | aaagggggtc | 1980 |
| cgagacccgt | ccgtgtccga | tccacgggga | ttgggtccgg | gacgtgtgtt | tccccgtcca | 2040 |

```
cgacccgagt ctggacggtt ctcggtatag gccctcctgg gacgggact ggattcgggt      2100 ggggtttccg gtttgagagg tgagggagtc gagcctgtgg aagagaggag ggtctaaggt      2160
cattgagggt tagaagagag acgtctcggg tttagaacac tgttttgagt gtgtacgggt      2220
ggcacgggtc cattcggtcg ggtccggagc gggaggtcga gttccgccct gtccacggga      2280
tctcatcgga cgtaggtccc tgtgtggtgc acccatggtt gtacaggcct cggtgtacct      2340
gtctccggcc gagccgggtg ggagacggga ctctcactgg cgacatggtt ggagacaggg      2400
atgtcccgtc ggggctcttg gtgtccacat gtgggacggg ggtagggccc tactcgactg      2460
gttcttggtc cagtcggact ggacggacca gtttccgaag atagggtcgc tgtagcggca      2520 cctcacccctc tcgttacccg tcggcctctt gttgatgttc tggtgcggag ggcacgacct      2580
gaggctgccg aggaagaagg agatgtcgtt cgagtggcac ctgttctcgt ccaccgtcgt      2640 cccccttgcag aagagtacga ggcactacgt actccgagac gtgttggtga tgtgcgtctt      2700
ctcggagagg gacagaggcc catttactca cgctgccggc cgttcggggg cgaggggccc      2760
gagagcgcca gcgtgctcct acgaaccgtg catgggggac atgtatgaag ggcccgcggg      2820
tcgtaccttt atttcgtggg tcgcgacggg accccgggac gctctgacac taccaagaaa      2880
ggtgcccagt ccggctcaga ctccggactc accgtactcc ctccgtctcg cccagggtga      2940 cagggtgtg accgggtccg acacgtccac acggacccgg gggatcccac cccgagtcgg      3000
tccccgacgg gagccgtccc acccctaaa cggtcgcacc gggagggagg tcgtcgtgga      3060
cgggacccga cccggtgccc ttcgggatcc tcggggaccc ctgtctgtgt gtcggggacg      3120
gagacatcct ctgacaggac aagacactcg cggggacagg agggctggag gtacgggtga      3180
gcccccgtac ggatcaggta cacgcatccc tgtccgggag ggagtgggta gatgggggtg      3240
ccgtgattgg ggaccgacgg gacgggtcgg agcgtgggcg taccctgtg ttggctgagg      3300 cccctgtacg tgagagcccg ggacacctcc ctgaccacgt ctacggggtgt gtgtgtgagt      3360 cgggtctggg caagttgttt ggggcgtgac tccaaccggc cggtgtgccg gtggtgtgtg      3420
tgtgcacgtg cggagtgtgt gcctcggagt gggcccgctt gacgtgtcgt gggtctggtc      3480
tcgttccagg agcgtgtgca cttgtgagga gcctgtgtcc ggggtgctc ggggtgcgcc      3540 gtggagttcc gggtgctcgg agagccgtcg aagaggtgta cgactggacg agtctgtttg      3600
ggtcgggagg agagtgttcc cacgggggacg tcggcggtgt gtgtgtgtcc cctagtgtgt      3660
ggtgcagtgc agggaccggg accgggtgaa gggtcacggc gggaagggac gtcctgccta      3720
gtcggagctg acacggaaga tcaacggtcg gtagacaaca aacggggagg gggcacggaa      3780
ggaactggga ccttccacgg tgaggtgac aggaaaggat tattttactc ctttaacgta      3840
gcgtaacaga ctcatccaca gtaagataag acccccaccc ccaccccgtc ctgtcgttcc      3900
ccctcctaac ccttctgtta tcgtccgtac gaccccctacg ccaccccgaga taccgaagac      3960 tccgccttttc ttggtcgacc ccgagatccc ccataggggt gcgcgggaca tcgccgcgta      4020
attcgcgccg cccacaccac caatgcgcgt cgcactggcg atgtgaacgg tcgcgggatc      4080
gcgggcgagg aaagcgaaag aagggaagga aagagcggtg caagcggccc ggagagttttt     4140 ttccctttttt ttcgtacgta gagttaatca gtcgttggta tcagggcggg gattgaggcg      4200
ggtagggcgg ggattgaggc gggtcaaggc gggtaagagg cggggtaccg actgattaaa      4260
aaaaataaat acgtctccgg ctccggcgga gccggagact cgataaggtc ttcatcactc      4320
ctccgaaaaa acctccggat ccgaaaacgt ttttcgaacc tgtcgagtcc cgacgctaaa      4380
gcgcggtttg aactgccgtt aggatcgcac ttccgaccat cctaaaatag ggcgacggt       4440
```

```
agtaccaagc tggtaacttg acgtagcagc ggcacagggt tttataccccc taaccgttct   4500
tgcctctgga tgggaccgga ggcgagtcct tgctcaagtt catgaaggtt tcttactggt   4560
gttggagaag tcaccttcca tttgtcttag accactaata cccatccttt tggaccaaga   4620
ggtaaggact cttcttagct ggaaatttcc tgtcttaatt atatcaagag tcatctcttg   4680
agtttcttgg tggtgctcct cgagtaaaag aacggttttc aaacctacta cggaattctg   4740
aataacttgt tggccttaac cgttcatttc atctgtacca aacctatcag cctccgtcaa   4800
gacaaatggt ccttcggtac ttagttggtc cggtggaatc tgagaaacac tgttcctagt   4860
acgtccttaa actttcactg tgcaaaaagg gtctttaact aaaccccttt atatttgaag   4920
agggtcttat gggtccgcag gagagactcc aggtcctcct ttttccgtag ttcatattca   4980
aacttcagat gctcttcttt ctgattgtcc ttctacgaaa gttcaagaga cgaggggagg   5040
atttcgatac gtaaaaatat tctggtaccc tgaaaacgac cgaaatctag agaaacactt   5100
ccttggaatg aagacaccac actgtattaa cctgtttgat ggatgtctct aaatttcgag   5160
attccatttta tattttaaaa attcacatat tacacaattt gatgactaag attaacaaac   5220
acataaaatc taaggttgga taccttgact acttaccctc gtcaccacct tacggaaatt   5280
actccttttg gacaaaacga gtcttcttta cggtagatca ctactactcc gatgacgact   5340
gagagttgta agatgaggag gttttttctt ctctttccat cttctgggt tcctgaaagg   5400
aagtcttaac gattcaaaaa actcagtacg acacaaatca ttatcttgag aacgaacgaa   5460
acgataaatg tggtgtttcc ttttcgacg tgacgatatg ttcttttaat acctttttat   5520
aagacattgg aaatattcat ccgtattgtc aatattagta ttgtatgaca aaaaagaatg   5580
aggtgtgtcc gtatctcaca gacgataatt attgatacga gtttttaaca catggaaatc   5640
gaaaaattaa acatttcccc aattattcct tataaactac atatcacgga actgatctct   5700
agtattagtc ggtatggtgt aaacatctcc aaaatgaacg aaatttttttg gagggtgtgg   5760
aggggggactt ggactttgta ttttacttac gttaacaaca acaattgaac aaataacgtc   5820
gaatattacc aatgtttatt tcgttatcgt agtgtttaaa gtgtttatttt cgtaaaaaaa   5880
gtgacgtaag atcaacacca aacaggtttg agtagttaca tagaatagtac   5940
cgacctacta ggaggtcgcg cccctagagt acgacctcaa gaagcgggtg gggttgaaca   6000
aataacgtcg aatattacca atgtttattt cgttatcgta gtgtttaaag tgtttatttc   6060
gtaaaaaaag tgacgtaaga tcaacaccaa acaggtttga gtagttacat agaatagtac   6120
agacatatgg cagctggaga tcgatctcga accgcattag taccagtatc gacaaaggac   6180
acactttaac aataggcgag tgttaaggtg tgttgtatgc tcggccttcg tatttcacat   6240
ttcggaccccc acggattact cactcgattg agtgtaatta acgcaacgcg agtgacgggc   6300
gaaaggtcag ccctttggac agcacggtcg acgtaattac ttagccggtt gcgcgccccct   6360
ctccgccaaa cgcataaccc gcgagaaggc gaaggagcga gtgactgagc gacgcgagcc   6420
agcaagccga cgccgctcgc catagtcgag tgagtttccg ccattatgcc aataggtgtc   6480
ttagtcccct attgcgtcct tccttgtaca ctcgttttcc ggtcgttttc cggtccttgg   6540
catttttccg gcgcaacgac cgcaaaaagg tatccgaggc ggggggactg ctcgtagtgt   6600
ttttagctgc gagttcagtc tccaccgctt tgggctgtcc tgatatttct atggtccgca   6660
aaggggggacc ttcgagggag cacgcgagag gacaaggctg ggacggcgaa tggcctatgg   6720
acaggcggaa agagggaagc ccttcgcacc gcgaaagagt tacgagtgcg acatccatag   6780
```

```
agtcaagcca catccagcaa gcgaggttcg acccgacaca cgtgcttggg gggcaagtcg    6840
ggctggcgac gcggaatagg ccattgatag cagaactcag gttgggccat tctgtgctga    6900
atagcggtga ccgtcgtcgg tgaccattgt cctaatcgtc tcgctccata catccgccac    6960
gatgtctcaa gaacttcacc accggattga tgccgatgtg atcttcctgt cataaaccat    7020
agacgcgaga cgacttcggt caatggaagc cttttctca accatcgaga actaggccgt      7080
ttgtttggtg gcgaccatcg ccaccaaaaa aacaaacgtt cgtcgtctaa tgcgcgtctt    7140
tttttcctag agttcttcta ggaaactaga aagatgccc cagactgcga gtcaccttgc     7200
ttttgagtgc aattccctaa aaccagtact ctaatagttt ttcctagaag tggatctagg    7260
aaaatttaat ttttacttca aaatttagtt agatttcata tatactcatt tgaaccagac    7320
tgtcaatggt tacgaattag tcactccgtg gatagagtcg ctagacagat aaagcaagta    7380
ggtatcaacg gactgagggg cagcacatct attgatgcta tgccctcccg aatggtagac    7440
cggggtcacg acgttactat ggcgctctgg gtgcgagtgg ccgaggtcta aatagtcgtt    7500
atttggtcgg tcggccttcc cggctcgcgt cttcaccagg acgttgaaat aggcggaggt    7560
aggtcagata attaacaacg gcccttcgat ctcattcatc aagcggtcaa ttatcaaacg    7620
cgttgcaaca acggtaacga tgtccgtagc accacagtgc gagcagcaaa ccataccgaa    7680
gtaagtcgag gccaagggtt gctagttccg ctcaatgtac tagggggtac aacacgtttt    7740
ttcgccaatc gaggaagcca ggaggctagc aacagtcttc attcaaccgg cgtcacaata    7800
gtgagtacca ataccgtcgt gacgtattaa gagaatgaca gtacggtagg cattctacga    7860
aaagacactg accactcatg agttggttca gtaagactct tatcacatac gccgctggct    7920
caacgagaac gggccgcagt tatgccctat tatggcgcgg tgtatcgtct tgaaattttc    7980
acgagtagta accttttgca agaagccccg cttttgagag ttcctagaat ggcgacaact    8040
ctaggtcaag ctacattggg tgagcacgtg ggttgactag aagtcgtaga aaatgaaagt    8100
ggtcgcaaag acccactcgt ttttgtcctt ccgttttacg gcgtttttc ccttattccc      8160
gctgtgcctt tacaacttat gagtatgaga aggaaaaagt tataataact tcgtaaatag    8220
tcccaataac agagtactcg cctatgtata aacttacata aatctttta tttgtttatc     8280
cccaaggcgc gtgtaaaggg gcttttcacg gtggactgca g                          8321
```

<210> SEQ ID NO 29
<211> LENGTH: 7874
<212> TYPE: DNA
<213> ORGANISM: Homo sapiens

<400> SEQUENCE: 29

```
ccatggttaa atttaactat agaggaatcc agagctcaga gatctattgg ccagttagct      60
aaccttaaga acgccggcga acgatcgtgg ttcccgggta gccagaaggg ggaccgtggg     120
aggaggttct cgtggagacc cccgtgtcgc cgggacccga cggaccagtt cctgatgaag    180
ggcttggcc actgccacag caccttgagt ccgcgggact ggtcgccgca cgtgtggaag      240
ggccgacagg atgtcaggag tcctgagatg agggagtcgt cgcaccagtg gcacgggagg    300
tcgtcgaacc cgtgggtctg gatgtagacg ttgcacttag tgttcgggtc gttgtggttc    360
cacctgttct ttcaaccact ctccggtcgt gtccctccct cccacagacg accttcggtc    420
cgagtcgcga ggacggacct gcgtagggcc gatacgtcgg ggtcaggtcc cgtcgttccg    480
tccggggcag acgagaagt gggcctccgg agacgggcgg ggtgagtacg agtccctctc       540
ccagaagacc gaaaaagggg tccgagaccc gtccgtgtcc gatccacggg gattgggtcc    600
```

```
gggacgtgtg tttccccgtc cacgacccga gtctggacgg ttctcggtat aggccctcct    660 ggacgggga ctggattcgg gtggggtttc cggtttgaga ggtgagggag tcgagcctgt    720
ggaagagagg agggtctaag gtcattgagg gttagaagag agacgtctcg ggtttagaac    780
actgttttga gtgtgtacgg gtggcacggg tccattcggt cgggtccgga gcgggaggtc    840
gagttccgcc ctgtccacgg gatctcatcg gacgtaggtc cctgtccggg gtcggcccac    900
gactgtgcag gtggaggtag agaaggagtc gtggacttga ggaccccct ggcagtcaga    960 aggagaaggg ggttttggg ttcctgtggg agtactagag ggcctgggga ctccagtgta   1020
cgcaccacca cctgcactcg gtgcttctgg gactccagtt caagttgacc atgcacctgc   1080
cgcacctcca cgtattacgg ttctgtttcg gcgccctcct cgtcatgttg tcgtgcatgg   1140
cacaccagtc gcaggagtgg caggacgtgg tcctgaccga cttaccgttc ctcatgttca   1200
cgttccagag gttgtttcgg gagggtcggg ggtagctctt ttggtagagg tttcggtttc   1260
caccctgggc accccacgct cccggtgtac ctgtctccgg ccgagccggg tgggagacgg   1320
gactctcact ggcgacatgg ttggagacag ggatgtcccg tcggggctct tggtgtccac   1380
atgtgggacg ggggtagggc cctactcgac tggttcttgg tccagtcgga ctggacggac   1440
cagtttccga agataggtc gctgtagcgg cacctcaccc tctcgttacc cgtcggcctc   1500
ttgttgatgt tctggtgcgg agggcacgac ctgaggctgc cgaggaagaa ggagatgtcg   1560
ttcgagtggc acctgttctc gtccaccgtc gtccccttgc agaagagtac gaggcactac   1620
gtactccgag acgtgttggt gatgtgcgtc ttctcggaga gggacagagg cccatttact   1680
cacgctgccg gccgttcggg ggcgagggc ccgagagcgc cagcgtgctc ctacgaaccg   1740
tgcatggggg acatgtatga agggcccgcg ggtcgtacct ttatttcgtg ggtcgcgacg   1800
ggacccgggg acgctctgac actaccaaga aaggtgccca gtccggctca gactccggac   1860
tcaccgtact ccctccgtct cgcccagggt gacaggggtg tgaccgggtc cgacacgtcc   1920
acacggaccc gggggatccc acccgagtc ggtccccgac gggagccgtc ccacccccta   1980 aacgtcgca ccgggaggga ggtcgtcgtg acgggaccc gacccggtgc ccttcgggat   2040
cctcggggac ccctgtctgt gtgtcgggga cggagacatc ctctgacagg acaagacact   2100
cgcggggaca ggagggctgg aggtacgggt gagccccgt acgacccta cgccacccga   2160 gataccgaag actccgcctt tcttggtcga ccccgagatc cccataggg gtgcgcggga   2220 catcgccgcg taattcgcgc cgcccacacc accaatgcgc gtcgcactgg cgatgtgaac   2280
ggtcgcggga tcgcgggcga ggaaagcgaa agaagggaag gaaagagcgg tgcaagcggc   2340
cgaaaggggc agttcgagat ttagccccgt agggaaatcc caaggctaaa tcacgaaatg   2400
ccgtggagct ggggtttttt gaactaatcc cactaccaag tgcatcaccc ggtagcggga   2460
ctatctgcca aaaagcggga aactgcaacc tcaggtgcaa gaattatca cctgagaaca   2520 aggtttgacc ttgttgtgag ttgggataga gccagataag aaaactaaat attccctaaa   2580
acccctaaag ccggataacc aattttttac tcgactaaat tgtttttaaa ttgcgcttaa   2640
ttaagacacc ttacacacag tcaatcccac acctttcagg ggtccgaggg gtccgtccgt   2700
cttcatacgt ttcgtacgta gagttaatca gtcgttggta tcaggcggg gattgaggcg   2760 ggtagggcgg ggattgaggc gggtcaaggc gggtaagagg cggggtaccg actgattaaa   2820
aaaaataaat acgtctccgg ctccggcgga gccggagact cgataaggtc ttcatcactc   2880
ctccgaaaaa acctccggat ccgaaaacgt ttttcgaacc tgtcgagtcc cgacgctaaa   2940
```

```
gcgcggtttg aactgccgtt aggatcgcac ttccgaccat cctaaaatag gggcgacggt   3000
agtaccaagc tggtaacttg acgtagcagc ggcacagggt tttataccccc taaccgttct  3060
tgcctctgga tgggaccgga ggcgagtcct tgctcaagtt catgaaggtt tcttactggt   3120
gttggagaag tcaccttcca tttgtcttag accactaata cccatccttt tggaccaaga   3180
ggtaaggact cttcttagct ggaaatttcc tgtcttaatt atatcaagag tcatctcttg   3240
agtttcttgg tggtgctcct cgagtaaaag aacggttttc aaacctacta cggaattctg   3300
aataacttgt tggccttaac cgttcatttc atctgtacca aacctatcag cctccgtcaa   3360
gacaaatggt ccttcggtac ttagttggtc cggtggaatc tgagaaacac tgttcctagt   3420
acgtccttaa actttcactg tgcaaaaagg gtctttaact aaaccccttt atatttgaag   3480
agggtcttat gggtccgcag gagagactcc aggtcctcct ttttccgtag ttcatattca   3540
aacttcagat gctcttcttt ctgattgtcc ttctacgaaa gttcaagaga cgaggggagg   3600
atttcgatac gtaaaaatat tctggtaccc tgaaaacgac cgaaatctag agaaacactt   3660
ccttggaatg aagacaccac actgtattaa cctgtttgat ggatgtctct aaatttcgag   3720
attccattta tattttaaaa attcacatat tacacaattt gatgactaag attaacaaac   3780
acataaaatc taaggttgga taccttgact acttaccctc gtcaccacct tacggaaatt   3840
actccttttg gacaaaacga gtcttcttta cggtagatca ctactactcc gatgacgact   3900
gagagttgta agatgaggag gttttttctt ctctttccat cttctggggt tcctgaaagg   3960
aagtcttaac gattcaaaaa actcagtacg acacaaatca ttatcttgag aacgaacgaa   4020
acgataaatg tggtgtttcc tttttcgacg tgacgatatg ttcttttaat acctttttat   4080
aagacattgg aaatattcat ccgtattgtc aatattagta ttgtatgaca aaaagaatg    4140
aggtgtgtcc gtatctcaca gacgataatt attgatacga gtttttaaca catggaaatc   4200
gaaaaattaa acatttcccc aattattcct tataaactac atatcacgga actgatctct   4260
agtattagtc ggtatggtgt aaacatctcc aaaatgaacg aaattttttg gagggtgtgg   4320
aggggggactt ggactttgta ttttacttac gttaacaaca acaattgaac aaataacgtc   4380
gaatattacc aatgtttatt tcgttatcgt agtgtttaaa gtgtttattt cgtaaaaaaa   4440
gtgacgtaag atcaacacca aacaggtttg agtagttaca tagaatagta cagacctagc   4500
cgacctacta ggaggtcgcg cccctagagt acgacctcaa gaagcgggtg gggttgaaca   4560
aataacgtcg aatattacca atgtttattt cgttatcgta gtgtttaaag tgtttatttc   4620
gtaaaaaaag tgacgtaaga tcaacaccaa acaggtttga gtagttacat agaatagtac   4680
agacatatgg cagctggaga tcgatctcga accgcattag taccagtatc gacaaaggac   4740
acactttaac aataggcgag tgttaaggtg tgttgtatgc tcggccttcg tatttcacat   4800
ttcggacccc acggattact cactcgattg agtgtaatta acgcaacgcg agtgacgggc   4860
gaaaggtcag ccctttggac agcacggtcg acgtaattac ttagccggtt gcgcgccccct  4920
ctccgccaaa cgcataaccc gcgagaaggc gaaggagcga gtgactgagc gacgcgagcc   4980
agcaagccga cgccgctcgc catagtcgag tgagtttccg ccattatgcc aataggtgtc   5040
ttagtcccct attgcgtcct ttcttgtaca ctcgttttcc ggtcgttttc cggtccttgg   5100
cattttccgg gcgcaacgac cgcaaaaagg tatccgaggc gggggactg  ctcgtagtgt   5160
ttttagctgc gagttcagtc tccaccgctt tgggctgtcc tgatatttct atggtccgca   5220
aagggggacc ttcgagggag cacgcgagag acaaggctg  ggacggcgaa tggcctatgg   5280
acaggcggaa agagggaagc ccttcgcacc gcgaaagagt tacgagtgcg acatccatag   5340
```

-continued

```
agtcaagcca catccagcaa gcgaggttcg acccgacaca cgtgcttggg gggcaagtcg    5400
ggctggcgac gcggaatagg ccattgatag cagaactcag gttgggccat tctgtgctga    5460
atagcggtga ccgtcgtcgg tgaccattgt cctaatcgtc tcgctccata catccgccac    5520
gatgtctcaa gaacttcacc accggattga tgccgatgtg atcttcctgt cataaaccat    5580
agacgcgaga cgacttcggt caatggaagc cttttcctca accatcgaga actaggccgt    5640
ttgtttggtg gcgaccatcg ccaccaaaaa aacaaacgtt cgtcgtctaa tgcgcgtctt    5700
tttttcctag agttcttcta ggaaactaga aaagatgccc cagactgcga gtcaccttgc    5760
ttttgagtgc aattccctaa aaccagtact ctaatagttt ttcctagaag tggatctagg    5820
aaaatttaat ttttacttca aaatttagtt agatttcata tatactcatt tgaaccagac    5880
tgtcaatggt tacgaattag tcactccgtg gatagagtcg ctagacagat aaagcaagta    5940
ggtatcaacg gactgagggg cagcacatct attgatgcta tgccctcccg aatggtagac    6000
cggggtcacg acgttactat ggcgctctgg gtgcgagtgg ccgaggtcta aatagtcgtt    6060
atttggtcgg tcggccttcc cggctcgcgt cttcaccagg acgttgaaat aggcggaggt    6120
aggtcagata attaacaacg gcccttcgat ctcattcatc aagcggtcaa ttatcaaacg    6180
cgttgcaaca acgtaacga tgtccgtagc accacagtgc gagcagcaaa ccataccgaa    6240
gtaagtcgag gccaagggtt gctagttccg ctcaatgtac taggggtac aacacgtttt    6300 ttcgccaatc gaggaagcca ggaggctagc aacagtcttc attcaaccgg cgtcacaata    6360
gtgagtacca ataccgtcgt gacgtattaa gagaatgaca gtacgtagg cattctacga    6420 aaagacactg accactcatg agttggttca gtaagactct tatcacatac gccgctggct    6480
caacgagaac gggccgcagt tatgccctat tatggcgcgg tgtatcgtct tgaaattttc    6540
acgagtagta acctttgca agaagccccg cttttgagag ttcctagaat ggcgacaact    6600
ctaggtcaag ctacattggg tgagcacgtg ggttgactag aagtcgtaga aaatgaaagt    6660
ggtcgcaaag acccactcgt ttttgtcctt ccgttttacg gcgttttttc ccttattccc    6720
gctgtgcctt tacaacttat gagtatgaga aggaaaaagt tataataact tcgtaaatag    6780
tcccaataac agagtactcg cctatgtata aacttacata aatctttta tttgtttatc    6840 cccaaggcgc gtgtaaaggg gcttttcacg gtggactgca gctgcctagc cctctagacg    6900
atccactgga ctccgcgcgg ccgaagctta tcggtctcat tggaaaaaaa aattaaaata    6960
aaataaaata aaaactctac ctcaaaccgc ggctagaggg ctagggata ccagctgaga    7020 gtcatgttag acgagactac ggcgtatcaa ttcggtcata gacgagggac gaacacacaa    7080
cctccagcga ctcatcacgc gctcgtttta aattcgatgt tgttccgttc cgaactggct    7140
gttaacgtac ttcttagacg aatcccaatc cgcaaaacgc gacgaagcgc tacatgcccg    7200
gtctatatgc gcaactgtaa ctaataactg atcaataatt atcattagtt aatgccccag    7260
taatcaagta tcgggtatat acctcaaggc gcaatgtatt gaatgccatt taccgggcgg    7320
accgactggc gggttgctgg gggcgggtaa ctgcagttat tactgcatac aagggtatca    7380
ttgcggttat ccctgaaagg taactgcagt tacccacctg ataaatgcca tttgacgggt    7440
gaaccgtcat gtagttcaca tagtatacgg ttcatgcggg ggataactgc agttactgcc    7500
atttaccggg cggaccgtaa tacgggtcat gtactggaat accctgaaag gatgaaccgt    7560
catgtagatg cataatcagt agcgataatg gtaccactac gccaaaaccg tcatgtagtt    7620
acccgcacct atcgccaaac tgagtgcccc taaaggttca gaggtggggt aactgcagtt    7680
```

-continued

| | |
|---|---|
| accctcaaac aaaaccgtgg ttttagttgc cctgaaaggt tttacagcat tgttgaggcg | 7740 |
| gggtaactgc gtttacccgc catccgcaca tgccaccctc cagatatatt cgtctcgaga | 7800 |
| gaccgattga tctcttgggt gacgaatgac cgaatagctt taattatgct gagtgatatc | 7860 |
| cctctgggtt cgaa | 7874 |